(12) United States Patent
Alitalo et al.

(10) Patent No.: US 7,855,178 B2
(45) Date of Patent: Dec. 21, 2010

(54) GROWTH FACTOR BINDING CONSTRUCTS MATERIALS AND METHODS

(75) Inventors: Kari Alitalo, Helsinki (FI); Markku Michael Jeltsch, Helsinki (FI)

(73) Assignee: Vegenics Limited, Toorak (AU)

( * ) Notice: Subject to any disclaimer, the term of this patent is extended or adjusted under 35 U.S.C. 154(b) by 0 days.

(21) Appl. No.: 12/180,990

(22) Filed: Jul. 28, 2008

(65) Prior Publication Data

US 2009/0155268 A1 Jun. 18, 2009

Related U.S. Application Data

(62) Division of application No. 11/075,047, filed on Mar. 7, 2005, now Pat. No. 7,422,741.

(60) Provisional application No. 60/550,907, filed on Mar. 5, 2004.

(51) Int. Cl.
*A61K 38/18* (2006.01)
*A61K 39/395* (2006.01)
*C12P 21/04* (2006.01)

(52) U.S. Cl. ............ 514/12; 424/130.1; 435/69.7

(58) Field of Classification Search .............. None
See application file for complete search history.

(56) References Cited

U.S. PATENT DOCUMENTS

| | | | |
|---|---|---|---|
| 3,691,016 A | 9/1972 | Patel et al. |
| 3,773,919 A | 11/1973 | Boswell et al. |
| 3,969,287 A | 7/1976 | Jaworek et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,330,440 A | 5/1982 | Ayers et al. |
| 4,342,776 A | 8/1982 | Cragoe, Jr. et al. |
| 4,526,988 A | 7/1985 | Hertel |
| 4,808,614 A | 2/1989 | Hertel |
| 4,861,719 A | 8/1989 | Miller |
| 5,004,758 A | 4/1991 | Boehm et al. |
| 5,139,941 A | 8/1992 | Muzyczka et al. |
| 5,223,608 A | 6/1993 | Chou et al. |
| 5,234,784 A | 8/1993 | Aslam et al. |
| 5,252,479 A | 10/1993 | Srivastava |
| 5,328,688 A | 7/1994 | Roizman |
| 5,474,935 A | 12/1995 | Chatterjee et al. |
| 5,474,982 A | 12/1995 | Murray et al. |
| 5,512,545 A | 4/1996 | Brown et al. |
| 5,585,362 A | 12/1996 | Wilson et al. |
| 5,620,985 A | 4/1997 | Jacquesy et al. |
| 5,622,856 A | 4/1997 | Natsoulis |
| 5,658,776 A | 8/1997 | Flotte et al. |
| 5,661,033 A | 8/1997 | Ho et al. |
| 5,670,488 A | 9/1997 | Gregory et al. |
| 5,686,278 A | 11/1997 | Williams et al. |
| 5,693,509 A | 12/1997 | Cotten et al. |
| 5,707,618 A | 1/1998 | Armentano et al. |
| 5,770,414 A | 6/1998 | Gage et al. |
| 5,773,289 A | 6/1998 | Samulski et al. |
| 5,776,755 A | 7/1998 | Alitalo et al. |
| 5,789,390 A | 8/1998 | Descamps et al. |
| 5,824,544 A | 10/1998 | Armentano et al. |
| 5,830,725 A | 11/1998 | Nolan et al. |
| 5,830,727 A | 11/1998 | Wang et al. |
| 5,834,441 A | 11/1998 | Philip et al. |
| 5,849,571 A | 12/1998 | Glorioso et al. |
| 5,851,521 A | 12/1998 | Branellec et al. |
| 5,856,152 A | 1/1999 | Wilson et al. |
| 5,863,541 A | 1/1999 | Samulski et al. |
| 5,879,934 A | 3/1999 | DeLuca |
| 5,888,502 A | 3/1999 | Guber et al. |
| 5,952,199 A | 9/1999 | Davis-Smyth et al. |
| 6,011,003 A | 1/2000 | Charnock-Jones et al. |
| 6,100,071 A | 8/2000 | Davis-Smyth et al. |
| 6,107,046 A | 8/2000 | Alitalo et al. |
| 6,348,333 B1 | 2/2002 | Niwa et al. |
| 6,375,929 B1 | 4/2002 | Thomas, Jr. et al. |
| 6,383,486 B1 | 5/2002 | Davis-Smyth et al. |
| 6,524,583 B1 * | 2/2003 | Thorpe et al. ............ 424/145.1 |
| 6,630,124 B1 | 10/2003 | Gozes et al. |
| 6,699,843 B2 | 3/2004 | Pietras et al. |
| 6,764,820 B2 | 7/2004 | Ferrell et al. |
| 6,824,777 B1 | 11/2004 | Alitalo et al. |
| 7,034,105 B2 | 4/2006 | Alitalo et al. |

(Continued)

FOREIGN PATENT DOCUMENTS

EP 418099 3/1991

(Continued)

OTHER PUBLICATIONS

U.S. Appl. No. 10/774,802, filed Feb. 9, 2004, Alitalo et al.
U.S. Appl. No. 11/327,075, filed Jan. 6, 2006, Alitalo et al.
Achen et al., "Monoclonal Antibodies to Vascular Endothelial Growth Factor-D Block its Interactions with both VEGF Receptor-2 and VEGF Receptor-3," *Eur. J. Biochem.*, 267:2505-2515 (2000).
Achen et al., "Vascular Endothelial Growth Factor D (VEGF-D) is a Ligang for the Tyrosine Kinases VEGF Receptor 2 (FLK1) and VEGF Receptor 3 (FLT4)," *Proc. Natl. Acad. Sci.* (USA), 95(2):548-553 (1998).
Banerji et al., "LYVE-1, A new homologue of the CD44 glycoprotein, is a lymph-specfic receptor for hyaluronan," *J. Cell Biol.*, 144:789-801 (1999).

(Continued)

*Primary Examiner*—Marianne P Allen
(74) *Attorney, Agent, or Firm*—Marshall, Gerstein & Borun LLP

(57) ABSTRACT

The present invention provides materials and methods for antagonizing the function of vascular endothelial growth factor receptors, platelet derived growth factor receptors and other receptors. Soluble binding constructs able to bind vascular endothelial growth factors, platelet derived growth factors, and other ligands are provided.

12 Claims, 3 Drawing Sheets

U.S. PATENT DOCUMENTS

| | | | |
|---|---|---|---|
| 7,070,959 | B1 | 7/2006 | Papadopoulos et al. |
| 7,422,741 | B2 | 9/2008 | Alitalo et al. |
| 2002/0103345 | A1 | 8/2002 | Zhu |
| 2002/0162126 | A1 | 10/2002 | Beach et al. |
| 2002/0164667 | A1 | 11/2002 | Alitalo et al. |
| 2002/0164687 | A1 | 11/2002 | Eriksson et al. |
| 2002/0164710 | A1 | 11/2002 | Eriksson et al. |
| 2003/0053989 | A1 | 3/2003 | Kovesdi |
| 2003/0055006 | A1 | 3/2003 | Siemeister et al. |
| 2003/0064053 | A1 | 4/2003 | Liu et al. |
| 2003/0092604 | A1 | 5/2003 | Davis-Smyth et al. |
| 2003/0108545 | A1 | 6/2003 | Rockwell et al. |
| 2003/0113324 | A1 | 6/2003 | Alitalo et al. |
| 2004/0014667 | A1 | 1/2004 | Daly et al. |
| 2004/0208879 | A1 | 10/2004 | Alitalo et al. |
| 2005/0282233 | A1 | 12/2005 | Eriksson et al. |
| 2006/0177901 | A1 | 8/2006 | Alitalo et al. |

FOREIGN PATENT DOCUMENTS

| | | |
|---|---|---|
| WO | WO-98/28621 | 7/1998 |
| WO | WO-00/25085 | 5/2000 |
| WO | WO-01/62942 | 8/2001 |
| WO | WO-02/060950 | 8/2002 |
| WO | WO-03/029814 | 4/2003 |

OTHER PUBLICATIONS

Baulcombe, "Gene Silencing: RNA Makes RNA Makes No Protein," *Curr. Biol.*, 9:R599-R601 (1999).

Benz et al., "Estrogen-dependent, tamoxifen-resistant tumorigenic growth of MCF-7 cells transfected with HER2/neu," *Breast Cancer Res. Treat.*, 24:85-95 (1993).

Borg et al., "Biochemical Characterization of Two Isoforms of FLT4, a VEGF Receptor-related Tyrosine Kinase," *Oncogene*, 10(5):973-984 (1995).

Brüggemann et al., "Production fo Human Antibody Repertoires in Transgenic Mice," *Curr. Opin. Biotechnol.*, 8:455-458 (1997).

Brüggemann et al., "Strategies for Expressing Human Antibody Repertoires in Transgenic Mice," *Immunol. Today*, 17(8):391-397 (1996).

Carter et al., "Toward the Production of Bispecific Antibody Fragments for Clinical Applications," *J. Hematotherapy*, 4:463-470 (1995).

Davis-Smyth et al., "The Second Immunoglobulin-like Domain of the VEGF Tyrosine Kinase Receptor Flt-1 Determines Ligang Binding and May Initate a Signal Transduction Cascase," *EMBO J.*, 15(18):4919-4927 (1996).

de Azevedo et al., "Molecular Cloning and Expression of a Functional Snake Venom Vascular Endothelium Growth Factor (VEGF) from the *Bothrops insularis* Pit Viper," *J. Biol. Chem.*, 276:39836-39842 (2001).

De Vries et al., "The *Fins*-like Tyrosine Kinase, a Receptor for Vascular Endothelial Growth Factor," *Science*, 255:989-991 (1992).

Egeblad et al., "Cell Death Induced by TNF or Serum Starvation is Independent of ERbB Receptor Signaling in MCF-7 Breast Carcinoma Cells," *Int. J. Cancer*, 86:617-625 (2000).

Fairbrother et al., "Novel Peptides Selected to Bind Vascular Endothelial Growth Factor Target the Receptor-binding Site," *Biochemistry*, 37:17754-17764 (1998).

Ferrara, "Molecular and Biological Properties of Vascular Endothelial Growth Factor," *J. Mol. Med.*, 77:527-543 (1999).

Fire, "RNA-triggered Gene Silencing," *Trends Genet*, 15:358-363 (1999).

Folkman et al., "Long-term Culture of Capillary Endothelial Cells," *Proc. Natl. Acad. Sci.* (USA), 76:5217-5221 (1979).

Foote et al., "Antibody Framework Residues Affecting the Conformation of the Hypervariable Loops," *J. Mol. Biol.*, 224:487-499 (1992).

Fuh et al., "Requirements for Binding and Signaling of the Kinase Domain Receptor for Vascular Endothelial Growth Factor," *J. Biol. Chem.*, 273(18):11197-11204 (1998).

Gasmi et al., "Complete Structure of an Increasing Capillary Permeability Protein (ICPP) Purified from *Vipera lebetina* Venom," *J. Biol. Chem.*, 277(33):29992-29998 (2002).

Gasmi et al., "Purification and Characterization of a Growth Factor-like Which Increases Capillary Permeability from *Vipera lebetina* Venom," *Biochem. Biophys. Res. Commun.*, 268:69-72 (2002).

Green et al., "Antigen-specific Human Monoclonal Antibodies from Mice Engineered with Human Ig Heavy and Light Chain YACs," *Nature Genetics*, 7:13-21 (1994).

Grimmond et al., "Cloning and Characterization of a Novel Human Gene Related to Vascular Endothelial Growth Factor," *Genome Res.*, 6:124-131 (1996).

Hauser et al., "A Heparin-Binding Form of Placenta Growth Factor (PIGF-2) is Expressed in Human Umbilical Vein Endothelial Cells and in Placenta," *Growth Factors*, 9:259-268 (1993).

Hoogenboom, "Designing and Optimizing Library Selection Strategies for Generating High-affinity Antibodies," *Tibtech*, 15:62-70 (1997).

Hughes et al., "Alternative Splicing of the Human VEGFGR-3/FLT4 Gene as a Consequence of an Integrated Human Endogenous Retrovirus," *J. Mol. Evol.*, 52(2):77-79 (2001).

Hunter, "Genetics: A Touch of Elegance with RNAi," *Curr. Biol.*, 9:R440-R442 (1999).

Jacobs et al., "Surface Modification for Improved Blood Compatibility," *Artif. Organs*, 12:500-501 (1988).

Jones et al., "Replacing the Complementarity-determining Regions in a Human Antibody with those from a Mouse," *Nature*, 321:522-525 (1986).

Joukov et al., "Proteolytic Processing Regulates Receptor Specificity and Activity of VEFG-C,"*EMBO J.*, 16:3898-3911 (1997).

Kaplan et al., "Characterization of a Soluble Vascular Endothelial Growth Factor Receptor-Immunoglobulin Chimera," *Growth Factors*, 14:243-256 (1997).

Karpanen et al., "Vascular Endothelial Growth Factor C Promotes Tumor Lymphangiogensis and Intralymphatic Tumor Growth," *Cancer Res.*, 61:1786-1790 (2001).

Kendall et al., "Inhibition of Vascular Endothelial Cell Growth Factor Activity by an Endogenously Encoded Soluble Receptor," *PNAS USA*, 90:10705-10709 (1993).

Kettleborough et al., "Humanization of a Mouse Monoclonal Antibody by CDR-Grafting: The Importance of Framework Residues on Loop Conformation," *Protein Engin.*, 4:773-783 (1991).

Komori et al., "Vascular Endothelial Growth Factor VEGF-like Heparin-binding Protein from the Venom of *Vipera aspis aspis* (Aspic viper)," *Biochemistry*, 38:11796-803 (1999).

Kudo et al., "Involvement of Vascular Endothelial Growth Factor Receptor-3 in Maintenance of Integrity of Endothelial Cell Lining During Tumor Angiogensis," *Blood*, 96(2):546-553 (2000).

Laitinen et al., "Adenovirus-Mediated Gene Transfer to Lower Limb Artery of Patients with Chronic Critical Leg Ischemia," *Hum. Gene Ther.*, 9:1481-1486 (1998).

Li et al., "Isoform-specific Expression of VEGF-B in Normal Tissues and Tumors," *Growth Factor*, 19:49-59 (2001).

Li et al., "Novel VEGF Family Members: VEGF-B, VEGF-C and VEGF-D," *J. Biochem. Cell. Biol.*, 33(4):421-426 (2001).

Lokker et al., "Functional Importance of Platelet-derived Growth Factor (PDGF) Receptor Extracellular Immunoglobulin-like Domains," *J. Biol. Chem.*, 272:33037-3304 (1997).

Lu et al., "Acquired Antagonistic Activity of a Bispecific Diabody Directed Against Two Different Epitopes on Vascular Endothelial Growth Factor Receptor 2," *J. Immunological Methods*, 230:159-171 (1999).

Lu et al., "Complete Inhibition of Vascular Endothelial Growth Factor (VEGF) Activities with a Bifunctional Diabody Directed Against Both VEGF Kinase Receptors, fms-like Tyrosine Kinase Receptor and Kinase Insert Domain-containing Receptor," *Cancer Research*, 61:7002-7008 (2001).

Lu et al., "Identification of the Residues in the Extracellular Region of KDR Important for Interaction with Vascular Endothelial Growth Factor and Neutralizing Anti-KDR Antibodies," *J. Biol. Chem.*, 275(19):14321-14330 (2000).

Lu et al., "Tailoring in Vitro Selection for a Picomolar Affinity Human Antibody Directed Against Vascular Endothelial Growth Factor Receptor 2 for Enhanced Neutralizing Activity," *J. Biol. Chem.*, 278(44):43496-43507 (2003).

Maglione et al., "Two Alternative mRNAs Coding for the Angiogenic Factor, Placenta Growth Factor (PlGF), are Transcribed from a Single Gene of Chromosome 14," *Oncogene*, 8:925-931 (1993).

Makkinen et al., "Inhibition of Lymphangiogensis with Resulting Lymphedema in Transgenic Mice Expressing Soluble VEGF Receptor-3," *Nature Medicine*, 7(2):199-205 (2001).

Matthews et al., "A Receptor Tyrosine Kinase cDNA Isolated From a Population of Enriched Primitive Hematopoietic Cells and Exhibiting Close Genetic Linkage to *c-kit*," *Proc. Natl. Acad. Sci.* (USA), 88:9026-9030 (1991).

Muller et al., "The Crystal Structure of Vascular Endothelial Growth Factor (VEGF) Refined to 1.93 a Resolution: Multiple Copy Flexibility and Receptor Binding," *Structure*, 5:1325-1338 (1997).

Neufeld et al., "Vascular Endothelial Growth Factor (VEGF) and its Receptor," *FASEB J.*, 13:9-22 (1999).

Olofsson et al., "Genomic Organization of the Mouse and Human Genes for Vascular Endothelial Growth Factor B (VEGF-B) and Characterization of a Second Splice Isoform," *J. Biol. Chem.*, 271:19310-19317 (1996).

Olofsson et al., "Vascular Endothelial Growth Factor B (VEGF-B) Binds to VEGF Receptor-1 and Regulates Plasminogen Activator Activity in Endothelial Cells," *Proc. Natl. Acad. Sci.* (USA), 95:11709-11714 (1998).

Ortega et al., "Signal Relays in the VEGF System," *Fron. Biosci.*, 4:141-152 (1999).

Pajusola et al., "Signalling Properties of FLT4, a Proteolyically Processed Receptor Tyrosine Kinase Related to Two VEGF Receptors," *Oncogene*, 9:3545-3555 (1994).

Pajusola et al., "Two Human FLT4 Receptor Tyrosine Kinase Isoforms with Distinct Carboxy Terminal Tails are Produced by Alternative Processing of Primary Transcripts," *Oncogene*, 8(11):2931-2937 (1993).

Partanen et al., "Lack of Lymphatic Vascular Specificity of Vascular Endothelial Growth Factor Receptor 3 in 185 Vascular Tumors," *Cancer*, 86:2406-2412 (1999).

Pertovaara et al., "Vascular Endothelial Growth Factor is Induced in Response to Transforming Growth Factor-β in Fibroblastic and Epithelial Cells," *J. Biol. Chem.*, 269:6271-6274 (1994).

Petrova et al., "Signaling via Vascular Endothelial Growth Factor Receptors," *Exp. Cell. Res.*, 253:117-130 (1999).

Pietras et al., "PDGF Receptors as Cancer Drug Targets," *Cancer Cell*, 3:439-443 (2003).

Plückthun et al., "New Protein Engineering Approaches to Multivalent and Bispecific Antibody Fragments," *Immunotechnology*, 3:83-105 (1997).

Renner et al., "Tumor Therapy by Immune Recruitment with Bispecific Antibodies," *Immunological Reviews*, 145:179-209 (1995).

Riechmann et al., "Reshaping Human Antibodies for Therapy," *Nature*, 332:323-327 (1988).

Rosen, "Inhibitors of the Vascular Endothelial Growth Factor Receptor," *Hematol. Oncol. Clin. N. Am.*, 16:1173-1187 (2002).

Sambrook et al., *Molecular Cloning: A Laboratory Manual*, 2nd Ed, Cold Spring Harbor Laboratory, Cold Spring Harbor, New York, pp. 9.47-9.51 (1989).

Segal et al., "Alternative Triggering Molecules and Single Chain Bispecific Antibodies," *J. Hematotherapy*, 4:377-382 (1995).

Segal et al., "Targeting of Anti-tumor Responses with Bispecific Antibodies," *Immunobiology*, 185:390-402 (1992).

Sharp "RNAi and Double-strand RNA," *Genes Dev.*, 13:139-141 (1999).

Shinkai et al., "Mapping of the Sites Involved in Ligand Association and Dissociation at the Extracellular Domain of the Kinase Insert Domain-containing Receptor for Vascular Endothelial Growth Factor," *J. Biol. Chem.*, 273(47):31283-31288 (1998).

Stacker et al., "A Mutant Form of Vascular Endothelial Growth Factor (VEGF) That Lacks VEGF Receptor-2 Activation Retains the Ability to Induce Vascular Permeability," *J. Biol. Chem.*, 274:34884-34892 (1999).

Stacker et al., "The Vascular Endothelial Growth Factor Family: Signalling for Vascular Development,"*Growth Factors*, 17:1-11 (1999).

Starovasnik et al., "Solution Structure of the VEGF-binding Domain of Flt-1: Comparison of its Free and Bound States," *J. Mol. Biol.*, 293:531-544 (1999).

Tam, "Recent Advances in Multiple Antigen Peptides," *J. Immunol. Methods*, 196:17-32 (1996).

Tammela et al., "The Biology of Vascular Endothelial Growth Factors," *Cardiovascular Research*, 65(3):550-563 (2005).

Tempest et al., "Reshaping a Human Monoclonal Antibody to Inhibit Human Respiratory Syncytial Virus Infection in Vivo," *Bio/Technology*, 9:266-271 (1991).

Terman et al., "Identification of the KDR Tyrosine Kinase as a Receptor for Vascular Endothelial Cell Growth Factor," *Biochem. Biophys. Res. Comm.*, 187:1579-1586 (1992).

Vaucheret et al., "Transgene-induced Gene Silencing in Plants," *Plant J.*, 16:651-659 (1998).

Veikkola et al., "Regulation of Angiogensis via Vascular Endothelial Growth Factor Receptors," *Cancer Res.*, 60:203-212 (2000).

Wiesmann et al., "Crystal Structure at 1.7 a Resolution of VEGF in Complex with Domain 2 of the Flt-1 Receptor," *Cell*, 91:695-704 (1997).

Zachary, "Vascular Endothelial Growth Factor," *Intl. J. Biochem. Cell. Bio.*, 30:1169-1174 (1998).

Jeltsch, VEGFR-3 Ligands and Lymphangiogenesis (2002).

* cited by examiner

SEQUENCE LISTING

```
<160> NUMBER OF SEQ ID NOS: 128

<210> SEQ ID NO 1
<211> LENGTH: 5777
<212> TYPE: DNA
<213> ORGANISM: Homo sapiens
<220> FEATURE:
<221> NAME/KEY: misc_feature
<223> OTHER INFORMATION: VEGFR-1
<220> FEATURE:
<221> NAME/KEY: CDS
<222> LOCATION: (250)..(4266)

<400> SEQUENCE: 1
gcggacactc ctctcggctc ctccccggca gcggcggcgg ctcggagcgg gctccggggc      60
tcgggtgcag cggccagcgg gcctggcggc gaggattacc cggggaagtg gttgtctcct     120
ggctggagcc gcgagacggg cgctcagggc gcggggccgg cggcggcgaa cgagaggacg     180
gactctggcg gccgggtcgt tggccggggg agcgcgggca ccgggcgagc aggccgcgtc     240 gcgctcacc atg gtc agc tac tgg gac acc ggg gtc ctg ctg tgc gcg ctg     291
          Met Val Ser Tyr Trp Asp Thr Gly Val Leu Leu Cys Ala Leu
          1               5                   10 ctc agc tgt ctg ctt ctc aca gga tct agt tca ggt tca aaa tta aaa       339
Leu Ser Cys Leu Leu Leu Thr Gly Ser Ser Ser Gly Ser Lys Leu Lys
15                  20                  25                  30 gat cct gaa ctg agt tta aaa ggc acc cag cac atc atg caa gca ggc       387
Asp Pro Glu Leu Ser Leu Lys Gly Thr Gln His Ile Met Gln Ala Gly
                35                  40                  45 cag aca ctg cat ctc caa tgc agg ggg gaa gca gcc cat aaa tgg tct       435
Gln Thr Leu His Leu Gln Cys Arg Gly Glu Ala Ala His Lys Trp Ser
            50                  55                  60 ttg cct gaa atg gtg agt aag gaa agc gaa agg ctg agc ata act aaa       483
Leu Pro Glu Met Val Ser Lys Glu Ser Glu Arg Leu Ser Ile Thr Lys
        65                  70                  75 tct gcc tgt gga aga aat ggc aaa caa ttc tgc agt act tta acc ttg       531
Ser Ala Cys Gly Arg Asn Gly Lys Gln Phe Cys Ser Thr Leu Thr Leu
    80                  85                  90 aac aca gct caa gca aac cac act ggc ttc tac agc tgc aaa tat cta       579
Asn Thr Ala Gln Ala Asn His Thr Gly Phe Tyr Ser Cys Lys Tyr Leu
95                  100                 105                 110
```

```
gct gta cct act tca aag aag aag gaa aca gaa tct gca atc tat ata    627
Ala Val Pro Thr Ser Lys Lys Lys Glu Thr Glu Ser Ala Ile Tyr Ile
            115                 120                 125 ttt att agt gat aca ggt aga cct ttc gta gag atg tac agt gaa atc    675
Phe Ile Ser Asp Thr Gly Arg Pro Phe Val Glu Met Tyr Ser Glu Ile
            130                 135                 140 ccc gaa att ata cac atg act gaa gga agg gag ctc gtc att ccc tgc    723
Pro Glu Ile Ile His Met Thr Glu Gly Arg Glu Leu Val Ile Pro Cys
            145                 150                 155 cgg gtt acg tca cct aac atc act gtt act tta aaa aag ttt cca ctt    771
Arg Val Thr Ser Pro Asn Ile Thr Val Thr Leu Lys Lys Phe Pro Leu
    160                 165                 170 gac act ttg atc cct gat gga aaa cgc ata atc tgg gac agt aga aag    819
Asp Thr Leu Ile Pro Asp Gly Lys Arg Ile Ile Trp Asp Ser Arg Lys
175                 180                 185                 190 ggc ttc atc ata tca aat gca acg tac aaa gaa ata ggg ctt ctg acc    867
Gly Phe Ile Ile Ser Asn Ala Thr Tyr Lys Glu Ile Gly Leu Leu Thr
                195                 200                 205 tgt gaa gca aca gtc aat ggg cat ttg tat aag aca aac tat ctc aca    915
Cys Glu Ala Thr Val Asn Gly His Leu Tyr Lys Thr Asn Tyr Leu Thr
            210                 215                 220 cat cga caa acc aat aca atc ata gat gtc caa ata agc aca cca cgc    963
His Arg Gln Thr Asn Thr Ile Ile Asp Val Gln Ile Ser Thr Pro Arg
        225                 230                 235 cca gtc aaa tta ctt aga ggc cat act ctt gtc ctc aat tgt act gct   1011
Pro Val Lys Leu Leu Arg Gly His Thr Leu Val Leu Asn Cys Thr Ala
    240                 245                 250 acc act ccc ttg aac acg aga gtt caa atg acc tgg agt tac cct gat   1059
Thr Thr Pro Leu Asn Thr Arg Val Gln Met Thr Trp Ser Tyr Pro Asp
255                 260                 265                 270 gaa aaa aat aag aga gct tcc gta agg cga cga att gac caa agc aat   1107
Glu Lys Asn Lys Arg Ala Ser Val Arg Arg Arg Ile Asp Gln Ser Asn
                275                 280                 285 tcc cat gcc aac ata ttc tac agt gtt ctt act att gac aaa atg cag   1155
Ser His Ala Asn Ile Phe Tyr Ser Val Leu Thr Ile Asp Lys Met Gln
            290                 295                 300 aac aaa gac aaa gga ctt tat act tgt cgt gta agg agt gga cca tca   1203
Asn Lys Asp Lys Gly Leu Tyr Thr Cys Arg Val Arg Ser Gly Pro Ser
        305                 310                 315 ttc aaa tct gtt aac acc tca gtg cat ata tat gat aaa gca ttc atc   1251
Phe Lys Ser Val Asn Thr Ser Val His Ile Tyr Asp Lys Ala Phe Ile
    320                 325                 330 act gtg aaa cat cga aaa cag cag gtg ctt gaa acc gta gct ggc aag   1299
Thr Val Lys His Arg Lys Gln Gln Val Leu Glu Thr Val Ala Gly Lys
335                 340                 345                 350 cgg tct tac cgg ctc tct atg aaa gtg aag gca ttt ccc tcg ccg gaa   1347
Arg Ser Tyr Arg Leu Ser Met Lys Val Lys Ala Phe Pro Ser Pro Glu
                355                 360                 365 gtt gta tgg tta aaa gat ggg tta cct gcg act gag aaa tct gct cgc   1395
Val Val Trp Leu Lys Asp Gly Leu Pro Ala Thr Glu Lys Ser Ala Arg
            370                 375                 380 tat ttg act cgt ggc tac tcg tta att atc aag gac gta act gaa gag   1443
Tyr Leu Thr Arg Gly Tyr Ser Leu Ile Ile Lys Asp Val Thr Glu Glu
        385                 390                 395 gat gca ggg aat tat aca atc ttg ctg agc ata aaa cag tca aat gtg   1491
Asp Ala Gly Asn Tyr Thr Ile Leu Leu Ser Ile Lys Gln Ser Asn Val
    400                 405                 410 ttt aaa aac ctc act gcc act cta att gtc aat gtg aaa ccc cag att   1539
Phe Lys Asn Leu Thr Ala Thr Leu Ile Val Asn Val Lys Pro Gln Ile
```

-continued

| | | | | | | | | | | | | | | | | |
|---|---|---|---|---|---|---|---|---|---|---|---|---|---|---|---|---|
| | | 415 | | | | 420 | | | | 425 | | | | 430 | | |
| tac | gaa | aag | gcc | gtg | tca | tcg | ttt | cca | gac | ccg | gct | ctc | tac | cca | ctg | 1587 |
| Tyr | Glu | Lys | Ala | Val | Ser | Ser | Phe | Pro | Asp | Pro | Ala | Leu | Tyr | Pro | Leu | |
| | | | | 435 | | | | 440 | | | | 445 | | | | |
| ggc | agc | aga | caa | atc | ctg | act | tgt | acc | gca | tat | ggt | atc | cct | caa | cct | 1635 |
| Gly | Ser | Arg | Gln | Ile | Leu | Thr | Cys | Thr | Ala | Tyr | Gly | Ile | Pro | Gln | Pro | |
| | | | 450 | | | | 455 | | | | 460 | | | | | |
| aca | atc | aag | tgg | ttc | tgg | cac | ccc | tgt | aac | cat | aat | cat | tcc | gaa | gca | 1683 |
| Thr | Ile | Lys | Trp | Phe | Trp | His | Pro | Cys | Asn | His | Asn | His | Ser | Glu | Ala | |
| | | 465 | | | | 470 | | | | 475 | | | | | | |
| agg | tgt | gac | ttt | tgt | tcc | aat | aat | gaa | gag | tcc | ttt | atc | ctg | gat | gct | 1731 |
| Arg | Cys | Asp | Phe | Cys | Ser | Asn | Asn | Glu | Glu | Ser | Phe | Ile | Leu | Asp | Ala | |
| 480 | | | | 485 | | | | 490 | | | | | | | | |
| gac | agc | aac | atg | gga | aac | aga | att | gag | agc | atc | act | cag | cgc | atg | gca | 1779 |
| Asp | Ser | Asn | Met | Gly | Asn | Arg | Ile | Glu | Ser | Ile | Thr | Gln | Arg | Met | Ala | |
| 495 | | | | 500 | | | | 505 | | | | 510 | | | | |
| ata | ata | gaa | gga | aag | aat | aag | atg | gct | agc | acc | ttg | gtt | gtg | gct | gac | 1827 |
| Ile | Ile | Glu | Gly | Lys | Asn | Lys | Met | Ala | Ser | Thr | Leu | Val | Val | Ala | Asp | |
| | | | | 515 | | | | 520 | | | | 525 | | | | |
| tct | aga | att | tct | gga | atc | tac | att | tgc | ata | gct | tcc | aat | aaa | gtt | ggg | 1875 |
| Ser | Arg | Ile | Ser | Gly | Ile | Tyr | Ile | Cys | Ile | Ala | Ser | Asn | Lys | Val | Gly | |
| | | | 530 | | | | 535 | | | | 540 | | | | | |
| act | gtg | gga | aga | aac | ata | agc | ttt | tat | atc | aca | gat | gtg | cca | aat | ggg | 1923 |
| Thr | Val | Gly | Arg | Asn | Ile | Ser | Phe | Tyr | Ile | Thr | Asp | Val | Pro | Asn | Gly | |
| | | 545 | | | | 550 | | | | 555 | | | | | | |
| ttt | cat | gtt | aac | ttg | gaa | aaa | atg | ccg | acg | gaa | gga | gag | gac | ctg | aaa | 1971 |
| Phe | His | Val | Asn | Leu | Glu | Lys | Met | Pro | Thr | Glu | Gly | Glu | Asp | Leu | Lys | |
| | 560 | | | | 565 | | | | 570 | | | | | | | |
| ctg | tct | tgc | aca | gtt | aac | aag | ttc | tta | tac | aga | gac | gtt | act | tgg | att | 2019 |
| Leu | Ser | Cys | Thr | Val | Asn | Lys | Phe | Leu | Tyr | Arg | Asp | Val | Thr | Trp | Ile | |
| 575 | | | | 580 | | | | 585 | | | | | | | 590 | |
| tta | ctg | cgg | aca | gtt | aat | aac | aga | aca | atg | cac | tac | agt | att | agc | aag | 2067 |
| Leu | Leu | Arg | Thr | Val | Asn | Asn | Arg | Thr | Met | His | Tyr | Ser | Ile | Ser | Lys | |
| | | | | 595 | | | | 600 | | | | 605 | | | | |
| caa | aaa | atg | gcc | atc | act | aag | gag | cac | tcc | atc | act | ctt | aat | ctt | acc | 2115 |
| Gln | Lys | Met | Ala | Ile | Thr | Lys | Glu | His | Ser | Ile | Thr | Leu | Asn | Leu | Thr | |
| | | | 610 | | | | 615 | | | | 620 | | | | | |
| atc | atg | aat | gtt | tcc | ctg | caa | gat | tca | ggc | acc | tat | gcc | tgc | aga | gcc | 2163 |
| Ile | Met | Asn | Val | Ser | Leu | Gln | Asp | Ser | Gly | Thr | Tyr | Ala | Cys | Arg | Ala | |
| | | | 625 | | | | 630 | | | | 635 | | | | | |
| agg | aat | gta | tac | aca | ggg | gaa | gaa | atc | ctc | cag | aag | aaa | gaa | att | aca | 2211 |
| Arg | Asn | Val | Tyr | Thr | Gly | Glu | Glu | Ile | Leu | Gln | Lys | Lys | Glu | Ile | Thr | |
| 640 | | | | 645 | | | | 650 | | | | | | | | |
| atc | aga | gat | cag | gaa | gca | cca | tac | ctc | ctg | cga | aac | ctc | agt | gat | cac | 2259 |
| Ile | Arg | Asp | Gln | Glu | Ala | Pro | Tyr | Leu | Leu | Arg | Asn | Leu | Ser | Asp | His | |
| 655 | | | | 660 | | | | 665 | | | | 670 | | | | |
| aca | gtg | gcc | atc | agc | agt | tcc | acc | act | tta | gac | tgt | cat | gct | aat | ggt | 2307 |
| Thr | Val | Ala | Ile | Ser | Ser | Thr | Thr | Leu | Asp | Cys | His | Ala | Asn | Gly | |
| | | | | 675 | | | | 680 | | | | 685 | | | | |
| gtc | ccc | gag | cct | cag | atc | act | tgg | ttt | aaa | aac | aac | cac | aaa | ata | caa | 2355 |
| Val | Pro | Glu | Pro | Gln | Ile | Thr | Trp | Phe | Lys | Asn | Asn | His | Lys | Ile | Gln | |
| | | | 690 | | | | 695 | | | | 700 | | | | | |
| caa | gag | cct | gga | att | att | tta | gga | cca | gga | agc | agc | acg | ctg | ttt | att | 2403 |
| Gln | Glu | Pro | Gly | Ile | Ile | Leu | Gly | Pro | Gly | Ser | Ser | Thr | Leu | Phe | Ile | |
| | | | 705 | | | | 710 | | | | 715 | | | | | |
| gaa | aga | gtc | aca | gaa | gag | gat | gaa | ggt | gtc | tat | cac | tgc | aaa | gcc | acc | 2451 |
| Glu | Arg | Val | Thr | Glu | Glu | Asp | Glu | Gly | Val | Tyr | His | Cys | Lys | Ala | Thr | |
| | 720 | | | | 725 | | | | 730 | | | | | | | |
| aac | cag | aag | ggc | tct | gtg | gaa | agt | tca | gca | tac | ctc | act | gtt | caa | gga | 2499 |

```
Asn Gln Lys Gly Ser Val Glu Ser Ser Ala Tyr Leu Thr Val Gln Gly
735                 740                 745                 750 acc tcg gac aag tct aat ctg gag ctg atc act cta aca tgc acc tgt        2547
Thr Ser Asp Lys Ser Asn Leu Glu Leu Ile Thr Leu Thr Cys Thr Cys
                755                 760                 765 gtg gct gcg act ctc ttc tgg ctc cta tta acc ctc ctt atc cga aaa        2595
Val Ala Ala Thr Leu Phe Trp Leu Leu Leu Thr Leu Leu Ile Arg Lys
            770                 775                 780 atg aaa agg tct tct tct gaa ata aag act gac tac cta tca att ata        2643
Met Lys Arg Ser Ser Ser Glu Ile Lys Thr Asp Tyr Leu Ser Ile Ile
        785                 790                 795 atg gac cca gat gaa gtt cct ttg gat gag cag tgt gag cgg ctc cct        2691
Met Asp Pro Asp Glu Val Pro Leu Asp Glu Gln Cys Glu Arg Leu Pro
    800                 805                 810 tat gat gcc agc aag tgg gag ttt gcc cgg gag aga ctt aaa ctg ggc        2739
Tyr Asp Ala Ser Lys Trp Glu Phe Ala Arg Glu Arg Leu Lys Leu Gly
815                 820                 825                 830 aaa tca ctt gga aga ggg gct ttt gga aaa gtg gtt caa gca tca gca        2787
Lys Ser Leu Gly Arg Gly Ala Phe Gly Lys Val Val Gln Ala Ser Ala
                835                 840                 845 ttt ggc att aag aaa tca cct acg tgc cgg act gtg gct gtg aaa atg        2835
Phe Gly Ile Lys Lys Ser Pro Thr Cys Arg Thr Val Ala Val Lys Met
            850                 855                 860 ctg aaa gag ggg gcc acg gcc agc gag tac aaa gct ctg atg act gag        2883
Leu Lys Glu Gly Ala Thr Ala Ser Glu Tyr Lys Ala Leu Met Thr Glu
        865                 870                 875 cta aaa atc ttg acc cac att ggc cac cat ctg aac gtg gtt aac ctg        2931
Leu Lys Ile Leu Thr His Ile Gly His His Leu Asn Val Val Asn Leu
    880                 885                 890 ctg gga gcc tgc acc aag caa gga ggg cct ctg atg gtg att gtt gaa        2979
Leu Gly Ala Cys Thr Lys Gln Gly Gly Pro Leu Met Val Ile Val Glu
895                 900                 905                 910 tac tgc aaa tat gga aat ctc tcc aac tac ctc aag agc aaa cgt gac        3027
Tyr Cys Lys Tyr Gly Asn Leu Ser Asn Tyr Leu Lys Ser Lys Arg Asp
                915                 920                 925 tta ttt ttt ctc aac aag gat gca gca cta cac atg gag cct aag aaa        3075
Leu Phe Phe Leu Asn Lys Asp Ala Ala Leu His Met Glu Pro Lys Lys
            930                 935                 940 gaa aaa atg gag cca ggc ctg gaa caa ggc aag aaa cca aga cta gat        3123
Glu Lys Met Glu Pro Gly Leu Glu Gln Gly Lys Lys Pro Arg Leu Asp
        945                 950                 955 agc gtc acc agc agc gaa agc ttt gcg agc tcc ggc ttt cag gaa gat        3171
Ser Val Thr Ser Ser Glu Ser Phe Ala Ser Ser Gly Phe Gln Glu Asp
    960                 965                 970 aaa agt ctg agt gat gtt gag gaa gag gag gat tct gac ggt ttc tac        3219
Lys Ser Leu Ser Asp Val Glu Glu Glu Glu Asp Ser Asp Gly Phe Tyr
975                 980                 985                 990 aag gag ccc atc act atg gaa gat ctg att tct tac agt ttt caa gtg       3267
Lys Glu Pro Ile Thr Met Glu Asp Leu Ile Ser Tyr Ser Phe Gln Val
                995                 1000                1005 gcc aga ggc atg gag ttc ctg tct tcc aga aag tgc att cat cgg           3312
Ala Arg Gly Met Glu Phe Leu Ser Ser Arg Lys Cys Ile His Arg
            1010                1015                1020 gac ctg gca gcg aga aac att ctt tta tct gag aac aac gtg gtg           3357
Asp Leu Ala Ala Arg Asn Ile Leu Leu Ser Glu Asn Asn Val Val
        1025                1030                1035 aag att tgt gat ttt ggc ctt gcc cgg gat att tat aag aac ccc           3402
Lys Ile Cys Asp Phe Gly Leu Ala Arg Asp Ile Tyr Lys Asn Pro
    1040                1045                1050
```

```
gat tat gtg aga aaa gga gat act cga ctt cct ctg aaa tgg atg          3447
Asp Tyr Val Arg Lys Gly Asp Thr Arg Leu Pro Leu Lys Trp Met
            1055                1060                1065 gct ccc gaa tct atc ttt gac aaa atc tac agc acc aag agc gac          3492
Ala Pro Glu Ser Ile Phe Asp Lys Ile Tyr Ser Thr Lys Ser Asp
        1070                1075                1080 gtg tgg tct tac gga gta ttg ctg tgg gaa atc ttc tcc tta ggt          3537
Val Trp Ser Tyr Gly Val Leu Leu Trp Glu Ile Phe Ser Leu Gly
    1085                1090                1095 ggg tct cca tac cca gga gta caa atg gat gag gac ttt tgc agt          3582
Gly Ser Pro Tyr Pro Gly Val Gln Met Asp Glu Asp Phe Cys Ser
1100                1105                1110 cgc ctg agg gaa ggc atg agg atg aga gct cct gag tac tct act          3627
Arg Leu Arg Glu Gly Met Arg Met Arg Ala Pro Glu Tyr Ser Thr
                1115                1120                1125 cct gaa atc tat cag atc atg ctg gac tgc tgg cac aga gac cca          3672
Pro Glu Ile Tyr Gln Ile Met Leu Asp Cys Trp His Arg Asp Pro
            1130                1135                1140 aaa gaa agg cca aga ttt gca gaa ctt gtg gaa aaa cta ggt gat          3717
Lys Glu Arg Pro Arg Phe Ala Glu Leu Val Glu Lys Leu Gly Asp
        1145                1150                1155 ttg ctt caa gca aat gta caa cag gat ggt aaa gac tac atc cca          3762
Leu Leu Gln Ala Asn Val Gln Gln Asp Gly Lys Asp Tyr Ile Pro
    1160                1165                1170 atc aat gcc ata ctg aca gga aat agt ggg ttt aca tac tca act          3807
Ile Asn Ala Ile Leu Thr Gly Asn Ser Gly Phe Thr Tyr Ser Thr
1175                1180                1185 cct gcc ttc tct gag gac ttc ttc aag gaa agt att tca gct ccg          3852
Pro Ala Phe Ser Glu Asp Phe Phe Lys Glu Ser Ile Ser Ala Pro
                1190                1195                1200 aag ttt aat tca gga agc tct gat gat gtc aga tat gta aat gct          3897
Lys Phe Asn Ser Gly Ser Ser Asp Asp Val Arg Tyr Val Asn Ala
        1205                1210                1215 ttc aag ttc atg agc ctg gaa aga atc aaa acc ttt gaa gaa ctt          3942
Phe Lys Phe Met Ser Leu Glu Arg Ile Lys Thr Phe Glu Glu Leu
    1220                1225                1230 tta ccg aat gcc acc tcc atg ttt gat gac tac cag ggc gac agc          3987
Leu Pro Asn Ala Thr Ser Met Phe Asp Asp Tyr Gln Gly Asp Ser
1235                1240                1245 agc act ctg ttg gcc tct ccc atg ctg aag cgc ttc acc tgg act          4032
Ser Thr Leu Leu Ala Ser Pro Met Leu Lys Arg Phe Thr Trp Thr
                1250                1255                1260 gac agc aaa ccc aag gcc tcg ctc aag att gac ttg aga gta acc          4077
Asp Ser Lys Pro Lys Ala Ser Leu Lys Ile Asp Leu Arg Val Thr
        1265                1270                1275 agt aaa agt aag gag tcg ggg ctg tct gat gtc agc agg ccc agt          4122
Ser Lys Ser Lys Glu Ser Gly Leu Ser Asp Val Ser Arg Pro Ser
    1280                1285                1290 ttc tgc cat tcc agc tgt ggg cac gtc agc gaa ggc aag cgc agg          4167
Phe Cys His Ser Ser Cys Gly His Val Ser Glu Gly Lys Arg Arg
1295                1300                1305 ttc acc tac gac cac gct gag ctg gaa agg aaa atc gcg tgc tgc          4212
Phe Thr Tyr Asp His Ala Glu Leu Glu Arg Lys Ile Ala Cys Cys
                1310                1315                1320 tcc ccg ccc cca gac tac aac tcg gtg gtc ctg tac tcc acc cca          4257
Ser Pro Pro Pro Asp Tyr Asn Ser Val Val Leu Tyr Ser Thr Pro
        1325                1330                1335 ccc atc tag agtttgacac gaagccttat ttctagaagc acatgtgtat              4306
Pro Ile
```

```
ttatacccc  aggaaactag  cttttgccag  tattatgcat  atataagttt  acacctttat      4366 cttttccatgg  gagccagctg  cttttttgtga  ttttttttaat  agtgcttttt  ttttttgact    4426
aacaagaatg  taactccaga  tagagaaata  gtgacaagtg  aagaacacta  ctgctaaatc      4486
ctcatgttac  tcagtgttag  agaaatcctt  cctaaaccca  atgacttccc  tgctccaacc      4546
cccgccacct  cagggcacgc  aggaccagtt  tgattgagga  gctgcactga  tcacccaatg      4606
catcacgtac  cccactgggc  cagccctgca  gcccaaaacc  cagggcaaca  agcccgttag      4666
ccccagggga  tcactggctg  gcctgagcaa  catctcggga  gtcctctagc  aggcctaaga      4726
catgtgagga  ggaaaaggaa  aaaaagcaaa  agcaagggga  gaaaagagaa  accgggagaa      4786
ggcatgagaa  agaatttgag  acgcaccatg  tgggcacgga  ggggacgggg  gctcagcaat      4846
gccatttcag  tggcttccca  gctctgaccc  ttctacattt  gagggcccag  ccaggagcag      4906
atggacagcg  atgaggggac  attttctgga  ttctgggagg  caagaaaagg  acaaatatct      4966
tttttggaac  taaagcaaat  tttagacctt  tacctatgga  agtggttcta  tgtccattct      5026
cattcgtggc  atgttttgat  ttgtagcact  gagggtggca  ctcaactctg  agcccatact      5086
tttggctcct  ctagtaagat  gcactgaaaa  cttagccaga  gttaggttgt  ctccaggcca      5146
tgatggcctt  acactgaaaa  tgtcacattc  tattttgggt  attaatatat  agtccagaca      5206
cttaactcaa  tttcttggta  ttattctgtt  ttgcacagtt  agttgtgaaa  gaaagctgag      5266
aagaatgaaa  atgcagtcct  gaggagagtt  ttctccatat  caaaacgagg  gctgatggag      5326
gaaaaaggtc  aataaggtca  agggaagacc  ccgtctctat  accaaccaaa  ccaattcacc      5386
aacacagttg  ggacccaaaa  cacaggaagt  cagtcacgtt  tcctttttcat  ttaatgggga      5446 ttccactatc  tcacactaat  ctgaaaggat  gtggaagagc  attagctggc  gcatattaag      5506
cactttaagc  tccttgagta  aaaaggtggt  atgtaattta  tgcaaggtat  ttctccagtt      5566
gggactcagg  atattagtta  atgagccatc  actagaagaa  aagcccattt  tcaactgctt      5626
tgaaacttgc  ctggggtctg  agcatgatgg  gaatagggag  acagggtagg  aaagggcgcc      5686
tactcttcag  ggtctaaaga  tcaagtgggc  cttggatcgc  taagctggct  ctgtttgatg      5746
ctatttatgc  aagttagggt  ctatgtattt  a                                      5777
```

<210> SEQ ID NO 2
<211> LENGTH: 1338
<212> TYPE: PRT
<213> ORGANISM: Homo sapiens

<400> SEQUENCE: 2

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110
```

-continued

```
Pro Thr Ser Lys Lys Glu Thr Glu Ser Ala Ile Tyr Ile Phe Ile
    115                 120                 125

Ser Asp Thr Gly Arg Pro Phe Val Glu Met Tyr Ser Glu Ile Pro Glu
130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
```

-continued

```
            530                 535                 540
Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
                580                 585                 590

Arg Thr Val Asn Asn Arg Thr Met His Tyr Ser Ile Ser Lys Gln Lys
                595                 600                 605

Met Ala Ile Thr Lys Glu His Ser Ile Thr Leu Asn Leu Thr Ile Met
610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
                660                 665                 670

Ala Ile Ser Ser Ser Thr Thr Leu Asp Cys His Ala Asn Gly Val Pro
                675                 680                 685

Glu Pro Gln Ile Thr Trp Phe Lys Asn Asn His Lys Ile Gln Gln Glu
                690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
                740                 745                 750

Asp Lys Ser Asn Leu Glu Leu Ile Thr Leu Thr Cys Thr Cys Val Ala
                755                 760                 765

Ala Thr Leu Phe Trp Leu Leu Leu Thr Leu Leu Ile Arg Lys Met Lys
                770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
                820                 825                 830

Leu Gly Arg Gly Ala Phe Gly Lys Val Val Gln Ala Ser Ala Phe Gly
                835                 840                 845

Ile Lys Lys Ser Pro Thr Cys Arg Thr Val Ala Val Lys Met Leu Lys
850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
                900                 905                 910

Lys Tyr Gly Asn Leu Ser Asn Tyr Leu Lys Ser Lys Arg Asp Leu Phe
                915                 920                 925

Phe Leu Asn Lys Asp Ala Ala Leu His Met Glu Pro Lys Lys Glu Lys
                930                 935                 940

Met Glu Pro Gly Leu Glu Gln Gly Lys Lys Pro Arg Leu Asp Ser Val
945                 950                 955                 960
```

-continued

Thr Ser Ser Glu Ser Phe Ala Ser Ser Gly Phe Gln Glu Asp Lys Ser
            965                 970                 975

Leu Ser Asp Val Glu Glu Glu Asp Ser Asp Gly Phe Tyr Lys Glu
        980                 985                 990

Pro Ile Thr Met Glu Asp Leu Ile Ser Tyr Ser Phe Gln Val Ala Arg
            995                 1000                1005

Gly Met Glu Phe Leu Ser Ser Arg Lys Cys Ile His Arg Asp Leu
    1010                1015                1020

Ala Ala Arg Asn Ile Leu Leu Ser Glu Asn Asn Val Val Lys Ile
    1025                1030                1035

Cys Asp Phe Gly Leu Ala Arg Asp Ile Tyr Lys Asn Pro Asp Tyr
    1040                1045                1050

Val Arg Lys Gly Asp Thr Arg Leu Pro Leu Lys Trp Met Ala Pro
    1055                1060                1065

Glu Ser Ile Phe Asp Lys Ile Tyr Ser Thr Lys Ser Asp Val Trp
    1070                1075                1080

Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200

Asn Ser Gly Ser Ser Asp Asp Val Arg Tyr Val Asn Ala Phe Lys
    1205                1210                1215

Phe Met Ser Leu Glu Arg Ile Lys Thr Phe Glu Glu Leu Leu Pro
    1220                1225                1230

Asn Ala Thr Ser Met Phe Asp Asp Tyr Gln Gly Asp Ser Ser Thr
    1235                1240                1245

Leu Leu Ala Ser Pro Met Leu Lys Arg Phe Thr Trp Thr Asp Ser
    1250                1255                1260

Lys Pro Lys Ala Ser Leu Lys Ile Asp Leu Arg Val Thr Ser Lys
    1265                1270                1275

Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
    1295                1300                1305

Tyr Asp His Ala Glu Leu Glu Arg Lys Ile Ala Cys Cys Ser Pro
    1310                1315                1320

Pro Pro Asp Tyr Asn Ser Val Val Leu Tyr Ser Thr Pro Pro Ile
    1325                1330                1335

<210> SEQ ID NO 3
<211> LENGTH: 2292

```
<212> TYPE: DNA
<213> ORGANISM: Homo sapiens
<220> FEATURE:
<221> NAME/KEY: CDS
<222> LOCATION: (1)..(2292)

<400> SEQUENCE: 3 atg gag agc aag gtg ctg ctg gcc gtc gcc ctg tgg ctc tgc gtg gag        48
Met Glu Ser Lys Val Leu Leu Ala Val Ala Leu Trp Leu Cys Val Glu
1               5                   10                  15 acc cgg gcc gcc tct gtg ggt ttg cct agt gtt tct ctt gat ctg ccc        96
Thr Arg Ala Ala Ser Val Gly Leu Pro Ser Val Ser Leu Asp Leu Pro
            20                  25                  30 agg ctc agc ata caa aaa gac ata ctt aca att aag gct aat aca act       144
Arg Leu Ser Ile Gln Lys Asp Ile Leu Thr Ile Lys Ala Asn Thr Thr
        35                  40                  45 ctt caa att act tgc agg gga cag agg gac ttg gac tgg ctt tgg ccc       192
Leu Gln Ile Thr Cys Arg Gly Gln Arg Asp Leu Asp Trp Leu Trp Pro
    50                  55                  60 aat aat cag agt ggc agt gag caa agg gtg gag gtg act gag tgc agc       240
Asn Asn Gln Ser Gly Ser Glu Gln Arg Val Glu Val Thr Glu Cys Ser
65                  70                  75                  80 gat ggc ctc ttc tgt aag aca ctc aca att cca aaa gtg atc gga aat       288
Asp Gly Leu Phe Cys Lys Thr Leu Thr Ile Pro Lys Val Ile Gly Asn
                85                  90                  95 gac act gga gcc tac aag tgc ttc tac cgg gaa act gac ttg gcc tcg       336
Asp Thr Gly Ala Tyr Lys Cys Phe Tyr Arg Glu Thr Asp Leu Ala Ser
            100                 105                 110 gtc att tat gtc tat gtt caa gat tac aga tct cca ttt att gct tct       384
Val Ile Tyr Val Tyr Val Gln Asp Tyr Arg Ser Pro Phe Ile Ala Ser
        115                 120                 125 gtt agt gac caa cat gga gtc gtg tac att act gag aac aaa aac aaa       432
Val Ser Asp Gln His Gly Val Val Tyr Ile Thr Glu Asn Lys Asn Lys
    130                 135                 140 act gtg gtg att cca tgt ctc ggg tcc att tca aat ctc aac gtg tca       480
Thr Val Val Ile Pro Cys Leu Gly Ser Ile Ser Asn Leu Asn Val Ser
145                 150                 155                 160 ctt tgt gca aga tac cca gaa aag aga ttt gtt cct gat ggt aac aga       528
Leu Cys Ala Arg Tyr Pro Glu Lys Arg Phe Val Pro Asp Gly Asn Arg
                165                 170                 175 att tcc tgg gac agc aag aag ggc ttt act att ccc agc tac atg atc       576
Ile Ser Trp Asp Ser Lys Lys Gly Phe Thr Ile Pro Ser Tyr Met Ile
            180                 185                 190 agc tat gct ggc atg gtc ttc tgt gaa gca aaa att aat gat gaa agt       624
Ser Tyr Ala Gly Met Val Phe Cys Glu Ala Lys Ile Asn Asp Glu Ser
        195                 200                 205 tac cag tct att atg tac ata gtt gtc gtt gta ggg tat agg att tat       672
Tyr Gln Ser Ile Met Tyr Ile Val Val Val Gly Tyr Arg Ile Tyr
    210                 215                 220 gat gtg gtt ctg agt ccg tct cat gga att gaa cta tct gtt gga gaa       720
Asp Val Val Leu Ser Pro Ser His Gly Ile Glu Leu Ser Val Gly Glu
225                 230                 235                 240 aag ctt gtc tta aat tgt aca gca aga act gaa cta aat gtg ggg att       768
Lys Leu Val Leu Asn Cys Thr Ala Arg Thr Glu Leu Asn Val Gly Ile
                245                 250                 255 gac ttc aac tgg gaa tac cct tct tcg aag cat cag cat aag aaa ctt       816
Asp Phe Asn Trp Glu Tyr Pro Ser Ser Lys His Gln His Lys Lys Leu
            260                 265                 270 gta aac cga gac cta aaa acc cag tct ggg agt gag atg aag aaa ttt       864
Val Asn Arg Asp Leu Lys Thr Gln Ser Gly Ser Glu Met Lys Lys Phe
        275                 280                 285
```

```
ttg agc acc tta act ata gat ggt gta acc cgg agt gac caa gga ttg      912
Leu Ser Thr Leu Thr Ile Asp Gly Val Thr Arg Ser Asp Gln Gly Leu
    290                 295                 300 tac acc tgt gca gca tcc agt ggg ctg atg acc aag aag aac agc aca      960
Tyr Thr Cys Ala Ala Ser Ser Gly Leu Met Thr Lys Lys Asn Ser Thr
305                 310                 315                 320 ttt gtc agg gtc cat gaa aaa cct ttt gtt gct ttt gga agt ggc atg     1008
Phe Val Arg Val His Glu Lys Pro Phe Val Ala Phe Gly Ser Gly Met
                325                 330                 335 gaa tct ctg gtg gaa gcc acg gtg ggg gag cgt gtc aga atc cct gcg     1056
Glu Ser Leu Val Glu Ala Thr Val Gly Glu Arg Val Arg Ile Pro Ala
            340                 345                 350 aag tac ctt ggt tac cca ccc cca gaa ata aaa tgg tat aaa aat gga     1104
Lys Tyr Leu Gly Tyr Pro Pro Pro Glu Ile Lys Trp Tyr Lys Asn Gly
        355                 360                 365 ata ccc ctt gag tcc aat cac aca att aaa gcg ggg cat gta ctg acg     1152
Ile Pro Leu Glu Ser Asn His Thr Ile Lys Ala Gly His Val Leu Thr
    370                 375                 380 att atg gaa gtg agt gaa aga gac aca gga aat tac act gtc atc ctt     1200
Ile Met Glu Val Ser Glu Arg Asp Thr Gly Asn Tyr Thr Val Ile Leu
385                 390                 395                 400 acc aat ccc att tca aag gag aag cag agc cat gtg gtc tct ctg gtt     1248
Thr Asn Pro Ile Ser Lys Glu Lys Gln Ser His Val Val Ser Leu Val
                405                 410                 415 gtg tat gtc cca ccc cag att ggt gag aaa tct cta atc tct cct gtg     1296
Val Tyr Val Pro Pro Gln Ile Gly Glu Lys Ser Leu Ile Ser Pro Val
            420                 425                 430 gat tcc tac cag tac ggc acc act caa acg ctg aca tgt acg gtc tat     1344
Asp Ser Tyr Gln Tyr Gly Thr Thr Gln Thr Leu Thr Cys Thr Val Tyr
        435                 440                 445 gcc att cct ccc ccg cat cac atc cac tgg tat tgg cag ttg gag gaa     1392
Ala Ile Pro Pro Pro His His Ile His Trp Tyr Trp Gln Leu Glu Glu
    450                 455                 460 gag tgc gcc aac gag ccc agc caa gct gtc tca gtg aca aac cca tac     1440
Glu Cys Ala Asn Glu Pro Ser Gln Ala Val Ser Val Thr Asn Pro Tyr
465                 470                 475                 480 cct tgt gaa gaa tgg aga agt gtg gag gac ttc cag gga gga aat aaa     1488
Pro Cys Glu Glu Trp Arg Ser Val Glu Asp Phe Gln Gly Gly Asn Lys
                485                 490                 495 att gaa gtt aat aaa aat caa ttt gct cta att gaa gga aaa aac aaa     1536
Ile Glu Val Asn Lys Asn Gln Phe Ala Leu Ile Glu Gly Lys Asn Lys
            500                 505                 510 act gta agt acc ctt gtt atc caa gcg gca aat gtg tca gct ttg tac     1584
Thr Val Ser Thr Leu Val Ile Gln Ala Ala Asn Val Ser Ala Leu Tyr
        515                 520                 525 aaa tgt gaa gcg gtc aac aaa gtc ggg aga gga gag agg gtg atc tcc     1632
Lys Cys Glu Ala Val Asn Lys Val Gly Arg Gly Glu Arg Val Ile Ser
    530                 535                 540 ttc cac gtg acc agg ggt cct gaa att act ttg caa cct gac atg cag     1680
Phe His Val Thr Arg Gly Pro Glu Ile Thr Leu Gln Pro Asp Met Gln
545                 550                 555                 560 ccc act gag cag gag agc gtg tct ttg tgg tgc act gca gac aga tct     1728
Pro Thr Glu Gln Glu Ser Val Ser Leu Trp Cys Thr Ala Asp Arg Ser
                565                 570                 575 acg ttt gag aac ctc aca tgg tac aag ctt ggc cca cag cct ctg cca     1776
Thr Phe Glu Asn Leu Thr Trp Tyr Lys Leu Gly Pro Gln Pro Leu Pro
            580                 585                 590 atc cat gtg gga gag ttg ccc aca cct gtt tgc aag aac ttg gat act     1824
Ile His Val Gly Glu Leu Pro Thr Pro Val Cys Lys Asn Leu Asp Thr
```

```
                  595                 600                 605
ctt tgg aaa ttg aat gcc acc atg ttc tct aat agc aca aat gac att       1872
Leu Trp Lys Leu Asn Ala Thr Met Phe Ser Asn Ser Thr Asn Asp Ile
610                 615                 620 ttg atc atg gag ctt aag aat gca tcc ttg cag gac caa gga gac tat       1920
Leu Ile Met Glu Leu Lys Asn Ala Ser Leu Gln Asp Gln Gly Asp Tyr
625                 630                 635                 640 gtc tgc ctt gct caa gac agg aag acc aag aaa aga cat tgc gtg gtc       1968
Val Cys Leu Ala Gln Asp Arg Lys Thr Lys Lys Arg His Cys Val Val
                645                 650                 655 agg cag ctc aca gtc cta gag cgt gtg gca ccc acg atc aca gga aac       2016
Arg Gln Leu Thr Val Leu Glu Arg Val Ala Pro Thr Ile Thr Gly Asn
                660                 665                 670 ctg gag aat cag acg aca agt att ggg gaa agc atc gaa gtc tca tgc       2064
Leu Glu Asn Gln Thr Thr Ser Ile Gly Glu Ser Ile Glu Val Ser Cys
                675                 680                 685 acg gca tct ggg aat ccc cct cca cag atc atg tgg ttt aaa gat aat       2112
Thr Ala Ser Gly Asn Pro Pro Pro Gln Ile Met Trp Phe Lys Asp Asn
690                 695                 700 gag acc ctt gta gaa gac tca ggc att gta ttg aag gat ggg aac cgg       2160
Glu Thr Leu Val Glu Asp Ser Gly Ile Val Leu Lys Asp Gly Asn Arg
705                 710                 715                 720 aac ctc act atc cgc aga gtg agg aag gag gac gaa ggc ctc tac acc       2208
Asn Leu Thr Ile Arg Arg Val Arg Lys Glu Asp Glu Gly Leu Tyr Thr
                725                 730                 735 tgc cag gca tgc agt gtt ctt ggc tgt gca aaa gtg gag gca ttt ttc       2256
Cys Gln Ala Cys Ser Val Leu Gly Cys Ala Lys Val Glu Ala Phe Phe
                740                 745                 750 ata ata gaa ggt gcc cag gaa aag acg aac ttg gaa                       2292
Ile Ile Glu Gly Ala Gln Glu Lys Thr Asn Leu Glu
                755                 760

<210> SEQ ID NO 4
<211> LENGTH: 764
<212> TYPE: PRT
<213> ORGANISM: Homo sapiens

<400> SEQUENCE: 4

Met Glu Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160
```

```
Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575
```

```
Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
            595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
            675                 680                 685

Thr Ala Ser Gly Asn Pro Pro Pro Gln Ile Met Trp Phe Lys Asp Asn
            690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu
            755                 760

<210> SEQ ID NO 5
<211> LENGTH: 4195
<212> TYPE: DNA
<213> ORGANISM: Homo sapiens
<220> FEATURE:
<221> NAME/KEY: CDS
<222> LOCATION: (20)..(3913)

<400> SEQUENCE: 5
ccacgcgcag cggccggag atg cag cgg ggc gcc gcg ctg tgc ctg cga ctg         52
                    Met Gln Arg Gly Ala Ala Leu Cys Leu Arg Leu
                     1               5                  10 tgg ctc tgc ctg gga ctc ctg gac ggc ctg gtg agt ggc tac tcc atg        100
Trp Leu Cys Leu Gly Leu Leu Asp Gly Leu Val Ser Gly Tyr Ser Met
        15                  20                  25 acc ccc ccg acc ttg aac atc acg gag gag tca cac gtc atc gac acc        148
Thr Pro Pro Thr Leu Asn Ile Thr Glu Glu Ser His Val Ile Asp Thr
    30                  35                  40 ggt gac agc ctg tcc atc tcc tgc agg gga cag cac ccc ctc gag tgg        196
Gly Asp Ser Leu Ser Ile Ser Cys Arg Gly Gln His Pro Leu Glu Trp
45                  50                  55 gct tgg cca gga gct cag gag gcg cca gcc acc gga gac aag gac agc        244
Ala Trp Pro Gly Ala Gln Glu Ala Pro Ala Thr Gly Asp Lys Asp Ser
60                  65                  70                  75 gag gac acg ggg gtg gtg cga gac tgc gag ggc aca gac gcc agg ccc        292
Glu Asp Thr Gly Val Val Arg Asp Cys Glu Gly Thr Asp Ala Arg Pro
                80                  85                  90 tac tgc aag gtg ttg ctg ctg cac gag gta cat gcc aac gac aca ggc        340
Tyr Cys Lys Val Leu Leu Leu His Glu Val His Ala Asn Asp Thr Gly
            95                  100                 105 agc tac gtc tgc tac tac aag tac atc aag gca cgc atc gag ggc acc        388
Ser Tyr Val Cys Tyr Tyr Lys Tyr Ile Lys Ala Arg Ile Glu Gly Thr
            110                 115                 120
```

-continued

| | | |
|---|---|---|
| acg gcc gcc agc tcc tac gtg ttc gtg aga gac ttt gag cag cca ttc<br>Thr Ala Ala Ser Ser Tyr Val Phe Val Arg Asp Phe Glu Gln Pro Phe<br>125                           130                      135 | | 436 |
| atc aac aag cct gac acg ctc ttg gtc aac agg aag gac gcc atg tgg<br>Ile Asn Lys Pro Asp Thr Leu Leu Val Asn Arg Lys Asp Ala Met Trp<br>140                         145                         150                      155 | | 484 |
| gtg ccc tgt ctg gtg tcc atc ccc ggc ctc aat gtc acg ctg cgc tcg<br>Val Pro Cys Leu Val Ser Ile Pro Gly Leu Asn Val Thr Leu Arg Ser<br>                 160                         165                      170 | | 532 |
| caa agc tcg gtg ctg tgg cca gac ggg cag gag gtg gtg tgg gat gac<br>Gln Ser Ser Val Leu Trp Pro Asp Gly Gln Glu Val Val Trp Asp Asp<br>                      175                         180                      185 | | 580 |
| cgg cgg ggc atg ctc gtg tcc acg cca ctg ctg cac gat gcc ctg tac<br>Arg Arg Gly Met Leu Val Ser Thr Pro Leu Leu His Asp Ala Leu Tyr<br>               190                         195                      200 | | 628 |
| ctg cag tgc gag acc acc tgg gga gac cag gac ttc ctt tcc aac ccc<br>Leu Gln Cys Glu Thr Thr Trp Gly Asp Gln Asp Phe Leu Ser Asn Pro<br>205                         210                         215 | | 676 |
| ttc ctg gtg cac atc aca ggc aac gag ctc tat gac atc cag ctg ttg<br>Phe Leu Val His Ile Thr Gly Asn Glu Leu Tyr Asp Ile Gln Leu Leu<br>220                         225                        230                      235 | | 724 |
| ccc agg aag tcg ctg gag ctg ctg gta ggg gag aag ctg gtc ctg aac<br>Pro Arg Lys Ser Leu Glu Leu Leu Val Gly Glu Lys Leu Val Leu Asn<br>                         240                         245                      250 | | 772 |
| tgc acc gtg tgg gct gag ttt aac tca ggt gtc acc ttt gac tgg gac<br>Cys Thr Val Trp Ala Glu Phe Asn Ser Gly Val Thr Phe Asp Trp Asp<br>                 255                         260                      265 | | 820 |
| tac cca ggg aag cag gca gag cgg ggt aag tgg gtg ccc gag cga cgc<br>Tyr Pro Gly Lys Gln Ala Glu Arg Gly Lys Trp Val Pro Glu Arg Arg<br>             270                         275                      280 | | 868 |
| tcc cag cag acc cac aca gaa ctc tcc agc atc ctg acc atc cac aac<br>Ser Gln Gln Thr His Thr Glu Leu Ser Ser Ile Leu Thr Ile His Asn<br>285                         290                        295 | | 916 |
| gtc agc cag cac gac ctg ggc tcg tat gtg tgc aag gcc aac aac ggc<br>Val Ser Gln His Asp Leu Gly Ser Tyr Val Cys Lys Ala Asn Asn Gly<br>300                         305                        310                      315 | | 964 |
| atc cag cga ttt cgg gag agc acc gag gtc att gtg cat gaa aat ccc<br>Ile Gln Arg Phe Arg Glu Ser Thr Glu Val Ile Val His Glu Asn Pro<br>                      320                         325                      330 | | 1012 |
| ttc atc agc gtc gag tgg ctc aaa gga ccc atc ctg gag gcc acg gca<br>Phe Ile Ser Val Glu Trp Leu Lys Gly Pro Ile Leu Glu Ala Thr Ala<br>                 335                         340                      345 | | 1060 |
| gga gac gag ctg gtg aag ctg ccc gtg aag ctg gca gcg tac ccc ccg<br>Gly Asp Glu Leu Val Lys Leu Pro Val Lys Leu Ala Ala Tyr Pro Pro<br>             350                         355                      360 | | 1108 |
| ccc gag ttc cag tgg tac aag gat gga aag gca ctg tcc ggg cgc cac<br>Pro Glu Phe Gln Trp Tyr Lys Asp Gly Lys Ala Leu Ser Gly Arg His<br>365                         370                        375 | | 1156 |
| agt cca cat gcc ctg gtg ctc aag gag gtg aca gag gcc agc aca ggc<br>Ser Pro His Ala Leu Val Leu Lys Glu Val Thr Glu Ala Ser Thr Gly<br>380                         385                        390                      395 | | 1204 |
| acc tac acc ctc gcc ctg tgg aac tcc gct gct ggc ctg agg cgc aac<br>Thr Tyr Thr Leu Ala Leu Trp Asn Ser Ala Ala Gly Leu Arg Arg Asn<br>                      400                         405                      410 | | 1252 |
| atc agc ctg gag ctg gtg gtg aat gtg ccc ccc cag ata cat gag aag<br>Ile Ser Leu Glu Leu Val Val Asn Val Pro Pro Gln Ile His Glu Lys<br>               415                         420                      425 | | 1300 |
| gag gcc tcc tcc ccc agc atc tac tcg cgt cac agc cgc cag gcc ctc<br>Glu Ala Ser Ser Pro Ser Ile Tyr Ser Arg His Ser Arg Gln Ala Leu<br>             430                         435                      440 | | 1348 |

```
acc tgc acg gcc tac ggg gtg ccc ctg cct ctc agc atc cag tgg cac      1396
Thr Cys Thr Ala Tyr Gly Val Pro Leu Pro Leu Ser Ile Gln Trp His
    445                 450                 455 tgg cgg ccc tgg aca ccc tgc aag atg ttt gcc cag cgt agt ctc cgg      1444
Trp Arg Pro Trp Thr Pro Cys Lys Met Phe Ala Gln Arg Ser Leu Arg
460                 465                 470                 475 cgg cgg cag cag caa gac ctc atg cca cag tgc cgt gac tgg agg gcg      1492
Arg Arg Gln Gln Gln Asp Leu Met Pro Gln Cys Arg Asp Trp Arg Ala
                480                 485                 490 gtg acc acg cag gat gcc gtg aac ccc atc gag agc ctg gac acc tgg      1540
Val Thr Thr Gln Asp Ala Val Asn Pro Ile Glu Ser Leu Asp Thr Trp
    495                 500                 505 acc gag ttt gtg gag gga aag aat aag act gtg agc aag ctg gtg atc      1588
Thr Glu Phe Val Glu Gly Lys Asn Lys Thr Val Ser Lys Leu Val Ile
510                 515                 520 cag aat gcc aac gtg tct gcc atg tac aag tgt gtg gtc tcc aac aag      1636
Gln Asn Ala Asn Val Ser Ala Met Tyr Lys Cys Val Val Ser Asn Lys
                525                 530                 535 gtg ggc cag gat gag cgg ctc atc tac ttc tat gtg acc acc atc ccc      1684
Val Gly Gln Asp Glu Arg Leu Ile Tyr Phe Tyr Val Thr Thr Ile Pro
540                 545                 550                 555 gac ggc ttc acc atc gaa tcc aag cca tcc gag gag cta cta gag ggc      1732
Asp Gly Phe Thr Ile Glu Ser Lys Pro Ser Glu Glu Leu Leu Glu Gly
                560                 565                 570 cag ccg gtg ctc ctg agc tgc caa gcc gac agc tac aag tac gag cat      1780
Gln Pro Val Leu Leu Ser Cys Gln Ala Asp Ser Tyr Lys Tyr Glu His
    575                 580                 585 ctg cgc tgg tac cgc ctc aac ctg tcc acg ctg cac gat gcg cac ggg      1828
Leu Arg Trp Tyr Arg Leu Asn Leu Ser Thr Leu His Asp Ala His Gly
            590                 595                 600 aac ccg ctt ctg ctc gac tgc aag aac gtg cat ctg ttc gcc acc cct      1876
Asn Pro Leu Leu Leu Asp Cys Lys Asn Val His Leu Phe Ala Thr Pro
605                 610                 615 ctg gcc gcc agc ctg gag gag gtg gca cct ggg gcg cgc cac gcc acg      1924
Leu Ala Ala Ser Leu Glu Glu Val Ala Pro Gly Ala Arg His Ala Thr
620                 625                 630                 635 ctc agc ctg agt atc ccc cgc gtc gcg ccc gag cac gag ggc cac tat      1972
Leu Ser Leu Ser Ile Pro Arg Val Ala Pro Glu His Glu Gly His Tyr
                640                 645                 650 gtg tgc gaa gtg caa gac cgg cgc agc cat gac aag cac tgc cac aag      2020
Val Cys Glu Val Gln Asp Arg Arg Ser His Asp Lys His Cys His Lys
            655                 660                 665 aag tac ctg tcg gtg cag gcc ctg gaa gcc cct cgg ctc acg cag aac      2068
Lys Tyr Leu Ser Val Gln Ala Leu Glu Ala Pro Arg Leu Thr Gln Asn
            670                 675                 680 ttg acc gac ctc ctg gtg aac gtg agc gac tcg ctg gag atg cag tgc      2116
Leu Thr Asp Leu Leu Val Asn Val Ser Asp Ser Leu Glu Met Gln Cys
685                 690                 695 ttg gtg gcc gga gcg cac gcg ccc agc atc gtg tgg tac aaa gac gag      2164
Leu Val Ala Gly Ala His Ala Pro Ser Ile Val Trp Tyr Lys Asp Glu
700                 705                 710                 715 agg ctg ctg gag gaa aag tct gga gtc gac ttg gcg gac tcc aac cag      2212
Arg Leu Leu Glu Glu Lys Ser Gly Val Asp Leu Ala Asp Ser Asn Gln
                720                 725                 730 aag ctg agc atc cag cgc gtg cgc gag gag gat gcg gga cgc tat ctg      2260
Lys Leu Ser Ile Gln Arg Val Arg Glu Glu Asp Ala Gly Arg Tyr Leu
            735                 740                 745 tgc agc gtg tgc aac gcc aag ggc tgc gtc aac tcc tcc gcc agc gtg      2308
Cys Ser Val Cys Asn Ala Lys Gly Cys Val Asn Ser Ser Ala Ser Val
```

-continued

```
                750             755             760
gcc gtg gaa ggc tcc gag gat aag ggc agc atg gag atc gtg atc ctt    2356
Ala Val Glu Gly Ser Glu Asp Lys Gly Ser Met Glu Ile Val Ile Leu
765             770             775 gtc ggt acc ggc gtc atc gct gtc ttc ttc tgg gtc ctc ctc ctc ctc    2404
Val Gly Thr Gly Val Ile Ala Val Phe Phe Trp Val Leu Leu Leu Leu
780             785             790             795 atc ttc tgt aac atg agg agg ccg gcc cac gca gac atc aag acg ggc    2452
Ile Phe Cys Asn Met Arg Arg Pro Ala His Ala Asp Ile Lys Thr Gly
                800             805             810 tac ctg tcc atc atc atg gac ccc ggg gag gtg cct ctg gag gag caa    2500
Tyr Leu Ser Ile Ile Met Asp Pro Gly Glu Val Pro Leu Glu Glu Gln
            815             820             825 tgc gaa tac ctg tcc tac gat gcc agc cag tgg gaa ttc ccc cga gag    2548
Cys Glu Tyr Leu Ser Tyr Asp Ala Ser Gln Trp Glu Phe Pro Arg Glu
        830             835             840 cgg ctg cac ctg ggg aga gtg ctc ggc tac ggc gcc ttc ggg aag gtg    2596
Arg Leu His Leu Gly Arg Val Leu Gly Tyr Gly Ala Phe Gly Lys Val
845             850             855 gtg gaa gcc tcc gct ttc ggc atc cac aag ggc agc agc tgt gac acc    2644
Val Glu Ala Ser Ala Phe Gly Ile His Lys Gly Ser Ser Cys Asp Thr
860             865             870             875 gtg gcc gtg aaa atg ctg aaa gag ggc gcc acg gcc agc gag cac cgc    2692
Val Ala Val Lys Met Leu Lys Glu Gly Ala Thr Ala Ser Glu His Arg
                880             885             890 gcg ctg atg tcg gag ctc aag atc ctc att cac atc ggc aac cac ctc    2740
Ala Leu Met Ser Glu Leu Lys Ile Leu Ile His Ile Gly Asn His Leu
            895             900             905 aac gtg gtc aac ctc ctc ggg gcg tgc acc aag ccg cag ggc ccc ctc    2788
Asn Val Val Asn Leu Leu Gly Ala Cys Thr Lys Pro Gln Gly Pro Leu
        910             915             920 atg gtg atc gtg gag ttc tgc aag tac ggc aac ctc tcc aac ttc ctg    2836
Met Val Ile Val Glu Phe Cys Lys Tyr Gly Asn Leu Ser Asn Phe Leu
925             930             935 cgc gcc aag cgg gac gcc ttc agc ccc tgc gcg gag aag tct ccc gag    2884
Arg Ala Lys Arg Asp Ala Phe Ser Pro Cys Ala Glu Lys Ser Pro Glu
940             945             950             955 cag cgc gga cgc ttc cgc gcc atg gtg gag ctc gcc agg ctg gat cgg    2932
Gln Arg Gly Arg Phe Arg Ala Met Val Glu Leu Ala Arg Leu Asp Arg
                960             965             970 agg cgg ccg ggg agc agc gac agg gtc ctc ttc gcg cgg ttc tcg aag    2980
Arg Arg Pro Gly Ser Ser Asp Arg Val Leu Phe Ala Arg Phe Ser Lys
            975             980             985 acc gag ggc gga gcg agg cgg gct tct cca gac caa gaa gct gag gac    3028
Thr Glu Gly Gly Ala Arg Arg Ala Ser Pro Asp Gln Glu Ala Glu Asp
        990             995             1000 ctg tgg ctg agc ccg ctg acc atg gaa gat ctt gtc tgc tac agc ttc    3076
Leu Trp Leu Ser Pro Leu Thr Met Glu Asp Leu Val Cys Tyr Ser Phe
1005            1010            1015 cag gtg gcc aga ggg atg gag ttc ctg gct tcc cga aag tgc atc cac    3124
Gln Val Ala Arg Gly Met Glu Phe Leu Ala Ser Arg Lys Cys Ile His
1020            1025            1030            1035 aga gac ctg gct gct cgg aac att ctg ctg tcg gaa agc gac gtg gtg    3172
Arg Asp Leu Ala Ala Arg Asn Ile Leu Leu Ser Glu Ser Asp Val Val
                1040            1045            1050 aag atc tgt gac ttt ggc ctt gcc cgg gac atc tac aaa gac cct gac    3220
Lys Ile Cys Asp Phe Gly Leu Ala Arg Asp Ile Tyr Lys Asp Pro Asp
            1055            1060            1065 tac gtc cgc aag ggc agt gcc cgg ctg ccc ctg aag tgg atg gcc cct    3268
```

```
                Tyr Val Arg Lys Gly Ser Ala Arg Leu Pro Leu Lys Trp Met Ala Pro
                    1070                1075                1080 gaa agc atc ttc gac aag gtg tac acc acg cag agt gac gtg tgg tcc       3316
Glu Ser Ile Phe Asp Lys Val Tyr Thr Thr Gln Ser Asp Val Trp Ser
    1085                1090                1095 ttt ggg gtg ctt ctc tgg gag atc ttc tct ctg ggg gcc tcc ccg tac       3364
Phe Gly Val Leu Leu Trp Glu Ile Phe Ser Leu Gly Ala Ser Pro Tyr
1100                1105                1110                1115 cct ggg gtg cag atc aat gag gag ttc tgc cag cgg ctg aga gac ggc       3412
Pro Gly Val Gln Ile Asn Glu Glu Phe Cys Gln Arg Leu Arg Asp Gly
                1120                1125                1130 aca agg atg agg gcc ccg gag ctg gcc act ccc gcc ata cgc cgc atc       3460
Thr Arg Met Arg Ala Pro Glu Leu Ala Thr Pro Ala Ile Arg Arg Ile
            1135                1140                1145 atg ctg aac tgc tgg tcc gga gac ccc aag gcg aga cct gca ttc tcg       3508
Met Leu Asn Cys Trp Ser Gly Asp Pro Lys Ala Arg Pro Ala Phe Ser
        1150                1155                1160 gag ctg gtg gag atc ctg ggg gac ctg ctc cag ggc agg ggc ctg caa       3556
Glu Leu Val Glu Ile Leu Gly Asp Leu Leu Gln Gly Arg Gly Leu Gln
    1165                1170                1175 gag gaa gag gag gtc tgc atg gcc ccg cgc agc tct cag agc tca gaa       3604
Glu Glu Glu Glu Val Cys Met Ala Pro Arg Ser Ser Gln Ser Ser Glu
1180                1185                1190                1195 gag ggc agc ttc tcg cag gtg tcc acc atg gcc cta cac atc gcc cag       3652
Glu Gly Ser Phe Ser Gln Val Ser Thr Met Ala Leu His Ile Ala Gln
                1200                1205                1210 gct gac gct gag gac agc ccg cca agc ctg cag cgc cac agc ctg gcc       3700
Ala Asp Ala Glu Asp Ser Pro Pro Ser Leu Gln Arg His Ser Leu Ala
            1215                1220                1225 gcc agg tat tac aac tgg gtg tcc ttt ccc ggg tgc ctg gcc aga ggg       3748
Ala Arg Tyr Tyr Asn Trp Val Ser Phe Pro Gly Cys Leu Ala Arg Gly
        1230                1235                1240 gct gag acc cgt ggt tcc tcc agg atg aag aca ttt gag gaa ttc ccc       3796
Ala Glu Thr Arg Gly Ser Ser Arg Met Lys Thr Phe Glu Glu Phe Pro
    1245                1250                1255 atg acc cca acg acc tac aaa ggc tct gtg gac aac cag aca gac agt       3844
Met Thr Pro Thr Thr Tyr Lys Gly Ser Val Asp Asn Gln Thr Asp Ser
1260                1265                1270                1275 ggg atg gtg ctg gcc tcg gag gag ttt gag cag ata gag agc agg cat       3892
Gly Met Val Leu Ala Ser Glu Glu Phe Glu Gln Ile Glu Ser Arg His
                1280                1285                1290 aga caa gaa agc ggc ttc agg tagctgaagc agagagagag aaggcagcat          3943
Arg Gln Glu Ser Gly Phe Arg
            1295 acgtcagcat tttcttctct gcacttataa gaaagatcaa agactttaag actttcgcta     4003 tttcttctac tgctatctac tacaaacttc aaagaggaac caggaggaca agaggagcat     4063 gaaagtggac aaggagtgtg accactgaag caccacaggg aaggggttag gcctccggat     4123 gactgcgggc aggcctggat aatatccagc ctcccacaag aagctggtgg agcagagtgt     4183 tccctgactc ct                                                         4195

<210> SEQ ID NO 6
<211> LENGTH: 1298
<212> TYPE: PRT
<213> ORGANISM: Homo sapiens

<400> SEQUENCE: 6

Met Gln Arg Gly Ala Ala Leu Cys Leu Arg Leu Trp Leu Cys Leu Gly
1               5                   10                  15
```

-continued

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
    210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp
    290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
                325                 330                 335

Trp Leu Lys Gly Pro Ile Leu Glu Ala Thr Ala Gly Asp Glu Leu Val
            340                 345                 350

Lys Leu Pro Val Lys Leu Ala Ala Tyr Pro Pro Glu Phe Gln Trp
        355                 360                 365

Tyr Lys Asp Gly Lys Ala Leu Ser Gly Arg His Ser Pro His Ala Leu
    370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
                405                 410                 415

Val Val Asn Val Pro Pro Gln Ile His Glu Lys Glu Ala Ser Ser Pro
            420                 425                 430

-continued

```
Ser Ile Tyr Ser Arg His Ser Arg Gln Ala Leu Thr Cys Thr Ala Tyr
        435                 440                 445

Gly Val Pro Leu Pro Leu Ser Ile Gln Trp His Trp Arg Pro Trp Thr
    450                 455                 460

Pro Cys Lys Met Phe Ala Gln Arg Ser Leu Arg Arg Arg Gln Gln Gln
465                 470                 475                 480

Asp Leu Met Pro Gln Cys Arg Asp Trp Arg Ala Val Thr Thr Gln Asp
                485                 490                 495

Ala Val Asn Pro Ile Glu Ser Leu Asp Thr Trp Thr Glu Phe Val Glu
            500                 505                 510

Gly Lys Asn Lys Thr Val Ser Lys Leu Val Ile Gln Asn Ala Asn Val
        515                 520                 525

Ser Ala Met Tyr Lys Cys Val Val Ser Asn Lys Val Gly Gln Asp Glu
    530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
                565                 570                 575

Ser Cys Gln Ala Asp Ser Tyr Lys Tyr Glu His Leu Arg Trp Tyr Arg
            580                 585                 590

Leu Asn Leu Ser Thr Leu His Asp Ala His Gly Asn Pro Leu Leu Leu
        595                 600                 605

Asp Cys Lys Asn Val His Leu Phe Ala Thr Pro Leu Ala Ala Ser Leu
    610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
                645                 650                 655

Asp Arg Arg Ser His Asp Lys His Cys His Lys Lys Tyr Leu Ser Val
            660                 665                 670

Gln Ala Leu Glu Ala Pro Arg Leu Thr Gln Asn Leu Thr Asp Leu Leu
        675                 680                 685

Val Asn Val Ser Asp Ser Leu Glu Met Gln Cys Leu Val Ala Gly Ala
    690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
                725                 730                 735

Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
        755                 760                 765

Glu Asp Lys Gly Ser Met Glu Ile Val Ile Leu Val Gly Thr Gly Val
    770                 775                 780

Ile Ala Val Phe Phe Trp Val Leu Leu Leu Ile Phe Cys Asn Met
785                 790                 795                 800

Arg Arg Pro Ala His Ala Asp Ile Lys Thr Gly Tyr Leu Ser Ile Ile
                805                 810                 815

Met Asp Pro Gly Glu Val Pro Leu Glu Glu Gln Cys Glu Tyr Leu Ser
            820                 825                 830

Tyr Asp Ala Ser Gln Trp Glu Phe Pro Arg Glu Arg Leu His Leu Gly
        835                 840                 845

Arg Val Leu Gly Tyr Gly Ala Phe Gly Lys Val Val Glu Ala Ser Ala
```

```
                850                 855                 860
Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
                885                 890                 895

Leu Lys Ile Leu Ile His Ile Gly Asn His Leu Asn Val Val Asn Leu
                900                 905                 910

Leu Gly Ala Cys Thr Lys Pro Gln Gly Pro Leu Met Val Ile Val Glu
                915                 920                 925

Phe Cys Lys Tyr Gly Asn Leu Ser Asn Phe Leu Arg Ala Lys Arg Asp
930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Arg Pro Gly Ser
                965                 970                 975

Ser Asp Arg Val Leu Phe Ala Arg Phe Ser Lys Thr Glu Gly Gly Ala
                980                 985                 990

Arg Arg Ala Ser Pro Asp Gln Glu  Ala Glu Asp Leu Trp  Leu Ser Pro
                995                 1000                1005

Leu Thr  Met Glu Asp Leu Val  Cys Tyr Ser Phe Gln  Val Ala Arg Gly
     1010                1015                1020

Met  Glu Phe Leu Ala Ser  Arg Lys Cys Ile His  Arg Asp Leu Ala Ala
1025                1030                1035                1040

Arg Asn Ile Leu Leu  Ser Glu Ser Asp Val  Val Lys Ile Cys Asp  Phe
                1045                1050                1055

Gly Leu Ala Arg  Asp Ile Tyr Lys Asp  Pro Asp Tyr Val Arg  Lys Gly
                1060                1065                1070

Ser Ala Arg  Leu Pro Leu Lys Trp  Met Ala Pro Glu Ser  Ile Phe Asp
     1075                1080                1085

Lys Val  Tyr Thr Thr Gln Ser  Asp Val Trp Ser Phe  Gly Val Leu Leu
     1090                1095                1100

Trp  Glu Ile Phe Ser Leu  Gly Ala Ser Pro Tyr  Pro Gly Val Gln Ile
1105                1110                1115                1120

Asn Glu Glu Phe Cys  Gln Arg Leu Arg Asp  Gly Thr Arg Met Arg  Ala
                1125                1130                1135

Pro Glu Leu Ala  Thr Pro Ala Ile Arg  Arg Ile Met Leu Asn  Cys Trp
                1140                1145                1150

Ser Gly Asp Pro Lys Ala Arg Pro Ala Phe Ser Glu Leu Val Glu Ile
          1155                1160                1165

Leu Gly Asp Leu Leu Gln Gly  Arg Gly Leu Gln Glu  Glu Glu Glu Val
          1170                1175                1180

Cys  Met Ala Pro Arg Ser  Ser Gln Ser Ser Glu  Glu Gly Ser Phe Ser
1185                1190                1195                1200

Gln Val Ser Thr Met  Ala Leu His Ile Ala  Gln Ala Asp Ala Glu  Asp
                1205                1210                1215

Ser Pro Pro Ser  Leu Gln Arg His Ser  Leu Ala Ala Arg Tyr  Tyr Asn
                1220                1225                1230

Trp Val Ser  Phe Pro Gly Cys Leu  Ala Arg Gly Ala Glu  Thr Arg Gly
     1235                1240                1245

Ser Ser Arg Met Lys Thr  Phe Glu Glu Phe Pro Met  Thr Pro Thr Thr
     1250                1255                1260

Tyr  Lys Gly Ser Val Asp  Asn Gln Thr Asp Ser Gly Met Val Leu Ala
1265                1270                1275                1280
```

```
Ser Glu Glu Phe Glu  Gln Ile Glu Ser Arg   His Arg Gln Glu Ser   Gly
            1285                 1290                 1295

Phe Arg

<210> SEQ ID NO 7
<211> LENGTH: 1713
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-2 A
<220> FEATURE:
<221> NAME/KEY: CDS
<222> LOCATION: (1)..(1713)

<400> SEQUENCE: 7
```

| | | | | | | | | | | | | | | | | |
|---|---|---|---|---|---|---|---|---|---|---|---|---|---|---|---|---|
| atg | ccg | ctg | ctg | cta | ctg | ctg | ccc | ctg | ctg | tgg | gca | ggg | gcc | ctg | gct | 48 |
| Met | Pro | Leu | Leu | Leu | Leu | Leu | Pro | Leu | Leu | Trp | Ala | Gly | Ala | Leu | Ala | |
| 1 | | | | 5 | | | | | 10 | | | | | 15 | | |
| atg | gat | aag | ctt | gct | agc | gga | tcc | ttg | cct | agt | gtt | tct | ctt | gat | ctg | 96 |
| Met | Asp | Lys | Leu | Ala | Ser | Gly | Ser | Leu | Pro | Ser | Val | Ser | Leu | Asp | Leu | |
| | | | 20 | | | | | 25 | | | | | 30 | | | |
| ccc | agg | ctc | agc | ata | caa | aaa | gac | ata | ctt | aca | att | aag | gct | aat | aca | 144 |
| Pro | Arg | Leu | Ser | Ile | Gln | Lys | Asp | Ile | Leu | Thr | Ile | Lys | Ala | Asn | Thr | |
| | | | | 35 | | | | | 40 | | | | | 45 | | |
| act | ctt | caa | att | act | tgc | agg | gga | cag | agg | gac | ttg | gac | tgg | ctt | tgg | 192 |
| Thr | Leu | Gln | Ile | Thr | Cys | Arg | Gly | Gln | Arg | Asp | Leu | Asp | Trp | Leu | Trp | |
| 50 | | | | | 55 | | | | | 60 | | | | | | |
| ccc | aat | aat | cag | agt | ggc | agt | gag | caa | agg | gtg | gag | gtg | act | gag | tgc | 240 |
| Pro | Asn | Asn | Gln | Ser | Gly | Ser | Glu | Gln | Arg | Val | Glu | Val | Thr | Glu | Cys | |
| 65 | | | | | 70 | | | | | 75 | | | | | 80 | |
| agc | gat | ggc | ctc | ttc | tgt | aag | aca | ctc | aca | att | cca | aaa | gtg | atc | gga | 288 |
| Ser | Asp | Gly | Leu | Phe | Cys | Lys | Thr | Leu | Thr | Ile | Pro | Lys | Val | Ile | Gly | |
| | | | | 85 | | | | | 90 | | | | | 95 | | |
| aat | gac | act | gga | gcc | tac | aag | tgc | ttc | tac | cgg | gaa | act | gac | ttg | gcc | 336 |
| Asn | Asp | Thr | Gly | Ala | Tyr | Lys | Cys | Phe | Tyr | Arg | Glu | Thr | Asp | Leu | Ala | |
| | | | 100 | | | | | 105 | | | | | 110 | | | |
| tcg | gtc | att | tat | gtc | tat | gtt | caa | gat | tac | aga | tct | cca | ttt | att | gct | 384 |
| Ser | Val | Ile | Tyr | Val | Tyr | Val | Gln | Asp | Tyr | Arg | Ser | Pro | Phe | Ile | Ala | |
| | | | | 115 | | | | | 120 | | | | | 125 | | |
| tct | gtt | agt | gac | caa | cat | gga | gtc | gtg | tac | att | act | gag | aac | aaa | aac | 432 |
| Ser | Val | Ser | Asp | Gln | His | Gly | Val | Val | Tyr | Ile | Thr | Glu | Asn | Lys | Asn | |
| | 130 | | | | | 135 | | | | | 140 | | | | | |
| aaa | act | gtg | gtg | att | cca | tgt | ctc | ggg | tcc | att | tca | aat | ctc | aac | gtg | 480 |
| Lys | Thr | Val | Val | Ile | Pro | Cys | Leu | Gly | Ser | Ile | Ser | Asn | Leu | Asn | Val | |
| 145 | | | | | 150 | | | | | 155 | | | | | 160 | |
| tca | ctt | tgt | gca | aga | tac | cca | gaa | aag | aga | ttt | gtt | cct | gat | ggt | aac | 528 |
| Ser | Leu | Cys | Ala | Arg | Tyr | Pro | Glu | Lys | Arg | Phe | Val | Pro | Asp | Gly | Asn | |
| | | | | 165 | | | | | 170 | | | | | 175 | | |
| aga | att | tcc | tgg | gac | agc | aag | aag | ggc | ttt | act | att | ccc | agc | tac | atg | 576 |
| Arg | Ile | Ser | Trp | Asp | Ser | Lys | Lys | Gly | Phe | Thr | Ile | Pro | Ser | Tyr | Met | |
| | | | 180 | | | | | 185 | | | | | 190 | | | |
| atc | agc | tat | gct | ggc | atg | gtc | ttc | tgt | gaa | gca | aaa | att | aat | gat | gaa | 624 |
| Ile | Ser | Tyr | Ala | Gly | Met | Val | Phe | Cys | Glu | Ala | Lys | Ile | Asn | Asp | Glu | |
| | | | | 195 | | | | | 200 | | | | | 205 | | |
| agt | tac | cag | tct | att | atg | tac | ata | gtt | gtc | gtt | gta | ggg | tat | agg | att | 672 |
| Ser | Tyr | Gln | Ser | Ile | Met | Tyr | Ile | Val | Val | Val | Val | Gly | Tyr | Arg | Ile | |
| | 210 | | | | | 215 | | | | | 220 | | | | | |
| tat | gat | gtg | gtt | ctg | agt | ccg | tct | cat | gga | att | gaa | cta | tct | gtt | gga | 720 |

```
Tyr Asp Val Val Leu Ser Pro Ser His Gly Ile Glu Leu Ser Val Gly
225                 230                 235                 240 gaa aag ctt gtc tta aat tgt aca gca aga act gaa cta aat gtg ggg         768
Glu Lys Leu Val Leu Asn Cys Thr Ala Arg Thr Glu Leu Asn Val Gly
                245                 250                 255 att gac ttc aac tgg gaa tac cct tct tcg aag cat cag cat aag aaa         816
Ile Asp Phe Asn Trp Glu Tyr Pro Ser Ser Lys His Gln His Lys Lys
            260                 265                 270 ctt gta aac cga gac cta aaa acc cag tct ggg agt gag atg aag aaa         864
Leu Val Asn Arg Asp Leu Lys Thr Gln Ser Gly Ser Glu Met Lys Lys
        275                 280                 285 ttt ttg agc acc tta act ata gat ggt gta acc cgg agt gac caa gga         912
Phe Leu Ser Thr Leu Thr Ile Asp Gly Val Thr Arg Ser Asp Gln Gly
    290                 295                 300 ttg tac acc tgt gca gca tcc agt ggg ctg atg acc aag aag aac agc         960
Leu Tyr Thr Cys Ala Ala Ser Ser Gly Leu Met Thr Lys Lys Asn Ser
305                 310                 315                 320 aca ttt gtc agg gtc cat gaa gat ccc atc gaa ggt cgt ggt ggt ggt        1008
Thr Phe Val Arg Val His Glu Asp Pro Ile Glu Gly Arg Gly Gly Gly
                325                 330                 335 ggt ggt gat ccc aaa tct tgt gac aaa cct cac aca tgc cca ctg tgc        1056
Gly Gly Asp Pro Lys Ser Cys Asp Lys Pro His Thr Cys Pro Leu Cys
            340                 345                 350 cca gca cct gaa ctc ctg ggg gga ccg tca gtc ttc ctc ttc ccc cca        1104
Pro Ala Pro Glu Leu Leu Gly Gly Pro Ser Val Phe Leu Phe Pro Pro
        355                 360                 365 aaa ccc aag gac acc ctc atg atc tcc cgg acc cct gag gtc aca tgc        1152
Lys Pro Lys Asp Thr Leu Met Ile Ser Arg Thr Pro Glu Val Thr Cys
    370                 375                 380 gtg gtg gtg gac gtg agc cac gaa gac cct gag gtc aag ttc aac tgg        1200
Val Val Val Asp Val Ser His Glu Asp Pro Glu Val Lys Phe Asn Trp
385                 390                 395                 400 tac gtg gac ggc gtg gag gtg cat aat gcc aag aca aag ccg cgg gag        1248
Tyr Val Asp Gly Val Glu Val His Asn Ala Lys Thr Lys Pro Arg Glu
                405                 410                 415 gag cag tac aac agc acg tac cgt gtg gtc agc gtc ctc acc gtc ctg        1296
Glu Gln Tyr Asn Ser Thr Tyr Arg Val Val Ser Val Leu Thr Val Leu
            420                 425                 430 cac cag gac tgg ctg aat ggc aag gag tac aag tgc aag gtc tcc aac        1344
His Gln Asp Trp Leu Asn Gly Lys Glu Tyr Lys Cys Lys Val Ser Asn
        435                 440                 445 aaa gcc ctc cca gcc ccc atc gag aaa acc atc tcc aaa gcc aaa ggg        1392
Lys Ala Leu Pro Ala Pro Ile Glu Lys Thr Ile Ser Lys Ala Lys Gly
    450                 455                 460 cag ccc cga gaa cca cag gtg tac acc ctg ccc cca tcc cgg gat gag        1440
Gln Pro Arg Glu Pro Gln Val Tyr Thr Leu Pro Pro Ser Arg Asp Glu
465                 470                 475                 480 ctg acc aag aac cag gtc agc ctg acc tgc cta gtc aaa ggc ttc tat        1488
Leu Thr Lys Asn Gln Val Ser Leu Thr Cys Leu Val Lys Gly Phe Tyr
                485                 490                 495 ccc agc gac atc gcc gtg gag tgg gag agc aat ggg cag ccg gag aac        1536
Pro Ser Asp Ile Ala Val Glu Trp Glu Ser Asn Gly Gln Pro Glu Asn
            500                 505                 510 aac tac aag gcc acg cct ccc gtg ctg gac tcc gac ggc tcc ttc ttc        1584
Asn Tyr Lys Ala Thr Pro Pro Val Leu Asp Ser Asp Gly Ser Phe Phe
        515                 520                 525 ctc tac agc aag ctc acc gtg gac aag agc agg tgg cag cag ggg aac        1632
Leu Tyr Ser Lys Leu Thr Val Asp Lys Ser Arg Trp Gln Gln Gly Asn
    530                 535                 540
```

```
gtc ttc tca tgc tcc gtg atg cat gag gct ctg cac aac cac tac acg    1680
Val Phe Ser Cys Ser Val Met His Glu Ala Leu His Asn His Tyr Thr
545                 550                 555                 560 cag aag agc ctc tcc ctg tct ccg ggt aaa tga                        1713
Gln Lys Ser Leu Ser Leu Ser Pro Gly Lys
                565                 570
```

<210> SEQ ID NO 8
<211> LENGTH: 570
<212> TYPE: PRT
<213> ORGANISM: Artificial sequence
<220> FEATURE:
<223> OTHER INFORMATION: Synthetic polypeptide

<400> SEQUENCE: 8

```
Met Pro Leu Leu Leu Leu Pro Leu Leu Trp Ala Gly Ala Leu Ala
1               5                   10                  15

Met Asp Lys Leu Ala Ser Gly Ser Leu Pro Ser Val Ser Leu Asp Leu
                20                  25                  30

Pro Arg Leu Ser Ile Gln Lys Asp Ile Leu Thr Ile Lys Ala Asn Thr
            35                  40                  45

Thr Leu Gln Ile Thr Cys Arg Gly Gln Arg Asp Leu Asp Trp Leu Trp
    50                  55                  60

Pro Asn Asn Gln Ser Gly Ser Glu Gln Arg Val Glu Val Thr Glu Cys
65                  70                  75                  80

Ser Asp Gly Leu Phe Cys Lys Thr Leu Thr Ile Pro Lys Val Ile Gly
                85                  90                  95

Asn Asp Thr Gly Ala Tyr Lys Cys Phe Tyr Arg Glu Thr Asp Leu Ala
            100                 105                 110

Ser Val Ile Tyr Val Tyr Val Gln Asp Tyr Arg Ser Pro Phe Ile Ala
        115                 120                 125

Ser Val Ser Asp Gln His Gly Val Val Tyr Ile Thr Glu Asn Lys Asn
    130                 135                 140

Lys Thr Val Val Ile Pro Cys Leu Gly Ser Ile Ser Asn Leu Asn Val
145                 150                 155                 160

Ser Leu Cys Ala Arg Tyr Pro Glu Lys Arg Phe Val Pro Asp Gly Asn
                165                 170                 175

Arg Ile Ser Trp Asp Ser Lys Lys Gly Phe Thr Ile Pro Ser Tyr Met
            180                 185                 190

Ile Ser Tyr Ala Gly Met Val Phe Cys Glu Ala Lys Ile Asn Asp Glu
        195                 200                 205

Ser Tyr Gln Ser Ile Met Tyr Ile Val Val Val Gly Tyr Arg Ile
    210                 215                 220

Tyr Asp Val Val Leu Ser Pro Ser His Gly Ile Glu Leu Ser Val Gly
225                 230                 235                 240

Glu Lys Leu Val Leu Asn Cys Thr Ala Arg Thr Glu Leu Asn Val Gly
                245                 250                 255

Ile Asp Phe Asn Trp Glu Tyr Pro Ser Ser Lys His Gln His Lys Lys
            260                 265                 270

Leu Val Asn Arg Asp Leu Lys Thr Gln Ser Gly Ser Glu Met Lys Lys
        275                 280                 285

Phe Leu Ser Thr Leu Thr Ile Asp Gly Val Thr Arg Ser Asp Gln Gly
    290                 295                 300

Leu Tyr Thr Cys Ala Ala Ser Ser Gly Leu Met Thr Lys Lys Asn Ser
305                 310                 315                 320

Thr Phe Val Arg Val His Glu Asp Pro Ile Glu Gly Arg Gly Gly Gly
```

-continued

```
                    325                 330                 335
Gly Gly Asp Pro Lys Ser Cys Asp Lys Pro His Thr Cys Pro Leu Cys
            340                 345                 350

Pro Ala Pro Glu Leu Leu Gly Gly Pro Ser Val Phe Leu Phe Pro Pro
            355                 360                 365

Lys Pro Lys Asp Thr Leu Met Ile Ser Arg Thr Pro Glu Val Thr Cys
            370                 375                 380

Val Val Val Asp Val Ser His Glu Asp Pro Glu Val Lys Phe Asn Trp
385                 390                 395                 400

Tyr Val Asp Gly Val Glu Val His Asn Ala Lys Thr Lys Pro Arg Glu
                405                 410                 415

Glu Gln Tyr Asn Ser Thr Tyr Arg Val Val Ser Val Leu Thr Val Leu
            420                 425                 430

His Gln Asp Trp Leu Asn Gly Lys Glu Tyr Lys Cys Lys Val Ser Asn
            435                 440                 445

Lys Ala Leu Pro Ala Pro Ile Glu Lys Thr Ile Ser Lys Ala Lys Gly
            450                 455                 460

Gln Pro Arg Glu Pro Gln Val Tyr Thr Leu Pro Pro Ser Arg Asp Glu
465                 470                 475                 480

Leu Thr Lys Asn Gln Val Ser Leu Thr Cys Leu Val Lys Gly Phe Tyr
                485                 490                 495

Pro Ser Asp Ile Ala Val Glu Trp Glu Ser Asn Gly Gln Pro Glu Asn
            500                 505                 510

Asn Tyr Lys Ala Thr Pro Pro Val Leu Asp Ser Asp Gly Ser Phe Phe
            515                 520                 525

Leu Tyr Ser Lys Leu Thr Val Asp Lys Ser Arg Trp Gln Gln Gly Asn
530                 535                 540

Val Phe Ser Cys Ser Val Met His Glu Ala Leu His Asn His Tyr Thr
545                 550                 555                 560

Gln Lys Ser Leu Ser Leu Ser Pro Gly Lys
            565                 570

<210> SEQ ID NO 9
<211> LENGTH: 1416
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-2 B
<220> FEATURE:
<221> NAME/KEY: CDS
<222> LOCATION: (1)..(1416)

<400> SEQUENCE: 9 atg ccg ctg ctg cta ctg ctg ccc ctg ctg tgg gca ggg gcc ctg gct      48
Met Pro Leu Leu Leu Leu Leu Pro Leu Leu Trp Ala Gly Ala Leu Ala
1               5                   10                  15 atg gat aag ctt gct agc ggt acc ctc gag gat ggc cgc gga tcc ttg      96
Met Asp Lys Leu Ala Ser Gly Thr Leu Glu Asp Gly Arg Gly Ser Leu
            20                  25                  30 cct agt gtt tct ctt gat ctg ccc agg ctc agc ata caa aaa gac ata     144
Pro Ser Val Ser Leu Asp Leu Pro Arg Leu Ser Ile Gln Lys Asp Ile
        35                  40                  45 ctt aca att aag gct aat aca act ctt caa att act tgc agg gga cag     192
Leu Thr Ile Lys Ala Asn Thr Thr Leu Gln Ile Thr Cys Arg Gly Gln
    50                  55                  60
```

```
agg gac ttg gac tgg ctt tgg ccc aat aat cag agt ggc agt gag caa      240
Arg Asp Leu Asp Trp Leu Trp Pro Asn Asn Gln Ser Gly Ser Glu Gln
 65                  70                  75                  80 agg gtg gag gtg act gag tgc agc gat ggc ctc ttc tgt aag aca ctc      288
Arg Val Glu Val Thr Glu Cys Ser Asp Gly Leu Phe Cys Lys Thr Leu
                     85                  90                  95 aca att cca aaa gtg atc gga aat gac act gga gcc tac aag tgc ttc      336
Thr Ile Pro Lys Val Ile Gly Asn Asp Thr Gly Ala Tyr Lys Cys Phe
                100                 105                 110 tac cgg gaa act gac ttg gcc tcg gtc att tat gtc tat gtt caa gat      384
Tyr Arg Glu Thr Asp Leu Ala Ser Val Ile Tyr Val Tyr Val Gln Asp
            115                 120                 125 tac aga tct cca ttt att gct tct gtt agt gac caa cat gga gtc gtg      432
Tyr Arg Ser Pro Phe Ile Ala Ser Val Ser Asp Gln His Gly Val Val
130                 135                 140 tac att act gag aac aaa aac aaa act gtg gtg att cca tgt ctc ggg      480
Tyr Ile Thr Glu Asn Lys Asn Lys Thr Val Val Ile Pro Cys Leu Gly
145                 150                 155                 160 tcc att tca aat ctc aac gtg tca ctt tgt gca aga tac cca gaa aag      528
Ser Ile Ser Asn Leu Asn Val Ser Leu Cys Ala Arg Tyr Pro Glu Lys
                165                 170                 175 aga ttt gtt cct gat ggt aac aga att tcc tgg gac agc aag aag ggc      576
Arg Phe Val Pro Asp Gly Asn Arg Ile Ser Trp Asp Ser Lys Lys Gly
            180                 185                 190 ttt act att ccc agc tac atg atc agc tat gct ggc atg gtc ttc tgt      624
Phe Thr Ile Pro Ser Tyr Met Ile Ser Tyr Ala Gly Met Val Phe Cys
        195                 200                 205 gaa gca aaa att aat gat gaa agt tac cag tct att atg tac ata gtt      672
Glu Ala Lys Ile Asn Asp Glu Ser Tyr Gln Ser Ile Met Tyr Ile Val
210                 215                 220 gtc gtt gta ggg gat ccc atc gaa ggt cgt ggt ggt ggt ggt ggt gat      720
Val Val Val Gly Asp Pro Ile Glu Gly Arg Gly Gly Gly Gly Gly Asp
225                 230                 235                 240 ccc aaa tct tgt gac aaa cct cac aca tgc cca ctg tgc cca gca cct      768
Pro Lys Ser Cys Asp Lys Pro His Thr Cys Pro Leu Cys Pro Ala Pro
                245                 250                 255 gaa ctc ctg ggg gga ccg tca gtc ttc ctc ttc ccc cca aaa ccc aag      816
Glu Leu Leu Gly Gly Pro Ser Val Phe Leu Phe Pro Pro Lys Pro Lys
            260                 265                 270 gac acc ctc atg atc tcc cgg acc cct gag gtc aca tgc gtg gtg gtg      864
Asp Thr Leu Met Ile Ser Arg Thr Pro Glu Val Thr Cys Val Val Val
        275                 280                 285 gac gtg agc cac gaa gac cct gag gtc aag ttc aac tgg tac gtg gac      912
Asp Val Ser His Glu Asp Pro Glu Val Lys Phe Asn Trp Tyr Val Asp
    290                 295                 300 ggc gtg gag gtg cat aat gcc aag aca aag ccg cgg gag gag cag tac      960
Gly Val Glu Val His Asn Ala Lys Thr Lys Pro Arg Glu Glu Gln Tyr
305                 310                 315                 320 aac agc acg tac cgt gtg gtc agc gtc ctc acc gtc ctg cac cag gac     1008
Asn Ser Thr Tyr Arg Val Val Ser Val Leu Thr Val Leu His Gln Asp
                325                 330                 335 tgg ctg aat ggc aag gag tac aag tgc aag gtc tcc aac aaa gcc ctc     1056
Trp Leu Asn Gly Lys Glu Tyr Lys Cys Lys Val Ser Asn Lys Ala Leu
            340                 345                 350 cca gcc ccc atc gag aaa acc atc tcc aaa gcc aaa ggg cag ccc cga     1104
Pro Ala Pro Ile Glu Lys Thr Ile Ser Lys Ala Lys Gly Gln Pro Arg
        355                 360                 365 gaa cca cag gtg tac acc ctg ccc cca tcc cgg gat gag ctg acc aag     1152
Glu Pro Gln Val Tyr Thr Leu Pro Pro Ser Arg Asp Glu Leu Thr Lys
    370                 375                 380
```

-continued

```
aac cag gtc agc ctg acc tgc cta gtc aaa ggc ttc tat ccc agc gac         1200
Asn Gln Val Ser Leu Thr Cys Leu Val Lys Gly Phe Tyr Pro Ser Asp
385                 390                 395                 400 atc gcc gtg gag tgg gag agc aat ggg cag ccg gag aac aac tac aag         1248
Ile Ala Val Glu Trp Glu Ser Asn Gly Gln Pro Glu Asn Asn Tyr Lys
                405                 410                 415 gcc acg cct ccc gtg ctg gac tcc gac ggc tcc ttc ttc ctc tac agc         1296
Ala Thr Pro Pro Val Leu Asp Ser Asp Gly Ser Phe Phe Leu Tyr Ser
            420                 425                 430 aag ctc acc gtg gac aag agc agg tgg cag cag ggg aac gtc ttc tca         1344
Lys Leu Thr Val Asp Lys Ser Arg Trp Gln Gln Gly Asn Val Phe Ser
        435                 440                 445 tgc tcc gtg atg cat gag gct ctg cac aac cac tac acg cag aag agc         1392
Cys Ser Val Met His Glu Ala Leu His Asn His Tyr Thr Gln Lys Ser
    450                 455                 460 ctc tcc ctg tct ccg ggt aaa tga                                         1416
Leu Ser Leu Ser Pro Gly Lys
465                 470
```

<210> SEQ ID NO 10
<211> LENGTH: 471
<212> TYPE: PRT
<213> ORGANISM: Artificial sequence
<220> FEATURE:
<223> OTHER INFORMATION: Synthetic polypeptide

<400> SEQUENCE: 10

```
Met Pro Leu Leu Leu Leu Pro Leu Leu Trp Ala Gly Ala Leu Ala
1               5                   10                  15

Met Asp Lys Leu Ala Ser Gly Thr Leu Glu Asp Gly Arg Gly Ser Leu
            20                  25                  30

Pro Ser Val Ser Leu Asp Leu Pro Arg Leu Ser Ile Gln Lys Asp Ile
        35                  40                  45

Leu Thr Ile Lys Ala Asn Thr Thr Leu Gln Ile Thr Cys Arg Gly Gln
    50                  55                  60

Arg Asp Leu Asp Trp Leu Trp Pro Asn Asn Gln Ser Gly Ser Glu Gln
65                  70                  75                  80

Arg Val Glu Val Thr Glu Cys Ser Asp Gly Leu Phe Cys Lys Thr Leu
                85                  90                  95

Thr Ile Pro Lys Val Ile Gly Asn Asp Thr Gly Ala Tyr Lys Cys Phe
            100                 105                 110

Tyr Arg Glu Thr Asp Leu Ala Ser Val Ile Tyr Val Tyr Val Gln Asp
        115                 120                 125

Tyr Arg Ser Pro Phe Ile Ala Ser Val Ser Asp Gln His Gly Val Val
    130                 135                 140

Tyr Ile Thr Glu Asn Lys Asn Lys Thr Val Val Ile Pro Cys Leu Gly
145                 150                 155                 160

Ser Ile Ser Asn Leu Asn Val Ser Leu Cys Ala Arg Tyr Pro Glu Lys
                165                 170                 175

Arg Phe Val Pro Asp Gly Asn Arg Ile Ser Trp Asp Ser Lys Lys Gly
            180                 185                 190

Phe Thr Ile Pro Ser Tyr Met Ile Ser Tyr Ala Gly Met Val Phe Cys
        195                 200                 205

Glu Ala Lys Ile Asn Asp Glu Ser Tyr Gln Ser Ile Met Tyr Ile Val
    210                 215                 220

Val Val Val Gly Asp Pro Ile Glu Gly Arg Gly Gly Gly Gly Gly Asp
225                 230                 235                 240
```

```
Pro Lys Ser Cys Asp Lys Pro His Thr Cys Pro Leu Cys Pro Ala Pro
            245                 250                 255

Glu Leu Leu Gly Gly Pro Ser Val Phe Leu Phe Pro Pro Lys Pro Lys
        260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Ala Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 11
<211> LENGTH: 1434
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-2 C
<220> FEATURE:
<221> NAME/KEY: CDS
<222> LOCATION: (1)..(1434)

<400> SEQUENCE: 11 atg ccg ctg ctg cta ctg ctg ccc ctg ctg tgg gca ggg gcc ctg gct    48
Met Pro Leu Leu Leu Leu Leu Pro Leu Leu Trp Ala Gly Ala Leu Ala
1               5                   10                  15 atg gat aag ctt gct agc ggt acc ctc gag gat ggc cgc gga tcc ttg    96
Met Asp Lys Leu Ala Ser Gly Thr Leu Glu Asp Gly Arg Gly Ser Leu
            20                  25                  30 cct agt gtt tct ctt gat ctg ccc agg ctc agc ata caa aaa gac ata   144
Pro Ser Val Ser Leu Asp Leu Pro Arg Leu Ser Ile Gln Lys Asp Ile
        35                  40                  45 ctt aca att aag gct aat aca act ctt caa att act tgc agg gga cag   192
Leu Thr Ile Lys Ala Asn Thr Thr Leu Gln Ile Thr Cys Arg Gly Gln
    50                  55                  60 agg gac ttg gac tgg ctt tgg ccc aat aat cag agt ggc agt gag caa   240
```

-continued

```
Arg Asp Leu Asp Trp Leu Trp Pro Asn Asn Gln Ser Gly Ser Glu Gln
 65              70                  75                  80 agg gtg gag gtg act gag tgc agc gat ggc ctc ttc tgt aag aca ctc    288
Arg Val Glu Val Thr Glu Cys Ser Asp Gly Leu Phe Cys Lys Thr Leu
                 85                  90                  95 aca att cca aaa gtg atc gga aat gac act gga gcc tac aag tgc ttc    336
Thr Ile Pro Lys Val Ile Gly Asn Asp Thr Gly Ala Tyr Lys Cys Phe
            100                 105                 110 tac cgg gaa act gac ttg gcc tcg gtc att tat gtc tat gtt caa gat    384
Tyr Arg Glu Thr Asp Leu Ala Ser Val Ile Tyr Val Tyr Val Gln Asp
        115                 120                 125 tac aga tct cca ttt att gct tct gtt agt gac caa cat gga gtc gtg    432
Tyr Arg Ser Pro Phe Ile Ala Ser Val Ser Asp Gln His Gly Val Val
    130                 135                 140 tac att act gag aac aaa aac aaa act gtg gtg att cca tgt ctc ggg    480
Tyr Ile Thr Glu Asn Lys Asn Lys Thr Val Val Ile Pro Cys Leu Gly
145                 150                 155                 160 tcc att tca aat ctc aac gtg tca ctt tgt gca aga tac cca gaa aag    528
Ser Ile Ser Asn Leu Asn Val Ser Leu Cys Ala Arg Tyr Pro Glu Lys
                165                 170                 175 aga ttt gtt cct gat ggt aac aga att tcc tgg gac agc aag aag ggc    576
Arg Phe Val Pro Asp Gly Asn Arg Ile Ser Trp Asp Ser Lys Lys Gly
            180                 185                 190 ttt act att ccc agc tac atg atc agc tat gct ggc atg gtc ttc tgt    624
Phe Thr Ile Pro Ser Tyr Met Ile Ser Tyr Ala Gly Met Val Phe Cys
        195                 200                 205 gaa gca aaa att aat gat gaa agt tac cag tct att atg tac ata gtt    672
Glu Ala Lys Ile Asn Asp Glu Ser Tyr Gln Ser Ile Met Tyr Ile Val
    210                 215                 220 gtc gtt gta ggg tat agg att tat gat gtg gat ccc atc gaa ggt cgt    720
Val Val Val Gly Tyr Arg Ile Tyr Asp Val Asp Pro Ile Glu Gly Arg
225                 230                 235                 240 ggt ggt ggt ggt gat ccc aaa tct tgt gac aaa cct cac aca tgc        768
Gly Gly Gly Gly Gly Asp Pro Lys Ser Cys Asp Lys Pro His Thr Cys
                245                 250                 255 cca ctg tgc cca gca cct gaa ctc ctg ggg gga ccg tca gtc ttc ctc    816
Pro Leu Cys Pro Ala Pro Glu Leu Leu Gly Gly Pro Ser Val Phe Leu
            260                 265                 270 ttc ccc cca aaa ccc aag gac acc ctc atg atc tcc cgg acc cct gag    864
Phe Pro Pro Lys Pro Lys Asp Thr Leu Met Ile Ser Arg Thr Pro Glu
        275                 280                 285 gtc aca tgc gtg gtg gtg gac gtg agc cac gaa gac cct gag gtc aag    912
Val Thr Cys Val Val Val Asp Val Ser His Glu Asp Pro Glu Val Lys
    290                 295                 300 ttc aac tgg tac gtg gac ggc gtg gag gtg cat aat gcc aag aca aag    960
Phe Asn Trp Tyr Val Asp Gly Val Glu Val His Asn Ala Lys Thr Lys
305                 310                 315                 320 ccg cgg gag gag cag tac aac agc acg tac cgt gtg gtc agc gtc ctc   1008
Pro Arg Glu Glu Gln Tyr Asn Ser Thr Tyr Arg Val Val Ser Val Leu
                325                 330                 335 acc gtc ctg cac cag gac tgg ctg aat ggc aag gag tac aag tgc aag   1056
Thr Val Leu His Gln Asp Trp Leu Asn Gly Lys Glu Tyr Lys Cys Lys
            340                 345                 350 gtc tcc aac aaa gcc ctc cca gcc ccc atc gag aaa acc atc tcc aaa   1104
Val Ser Asn Lys Ala Leu Pro Ala Pro Ile Glu Lys Thr Ile Ser Lys
        355                 360                 365 gcc aaa ggg cag ccc cga gaa cca cag gtg tac acc ctg ccc cca tcc   1152
Ala Lys Gly Gln Pro Arg Glu Pro Gln Val Tyr Thr Leu Pro Pro Ser
    370                 375                 380
```

```
cgg gat gag ctg acc aag aac cag gtc agc ctg acc tgc cta gtc aaa    1200
Arg Asp Glu Leu Thr Lys Asn Gln Val Ser Leu Thr Cys Leu Val Lys
385                 390                 395                 400 ggc ttc tat ccc agc gac atc gcc gtg gag tgg gag agc aat ggg cag    1248
Gly Phe Tyr Pro Ser Asp Ile Ala Val Glu Trp Glu Ser Asn Gly Gln
            405                 410                 415 ccg gag aac aac tac aag gcc acg cct ccc gtg ctg gac tcc gac ggc    1296
Pro Glu Asn Asn Tyr Lys Ala Thr Pro Pro Val Leu Asp Ser Asp Gly
        420                 425                 430 tcc ttc ttc ctc tac agc aag ctc acc gtg gac aag agc agg tgg cag    1344
Ser Phe Phe Leu Tyr Ser Lys Leu Thr Val Asp Lys Ser Arg Trp Gln
    435                 440                 445 cag ggg aac gtc ttc tca tgc tcc gtg atg cat gag gct ctg cac aac    1392
Gln Gly Asn Val Phe Ser Cys Ser Val Met His Glu Ala Leu His Asn
450                 455                 460 cac tac acg cag aag agc ctc tcc ctg tct ccg ggt aaa tga            1434
His Tyr Thr Gln Lys Ser Leu Ser Leu Ser Pro Gly Lys
465                 470                 475

<210> SEQ ID NO 12
<211> LENGTH: 477
<212> TYPE: PRT
<213> ORGANISM: Artificial sequence
<220> FEATURE:
<223> OTHER INFORMATION: Synthetic polypeptide

<400> SEQUENCE: 12

Met Pro Leu Leu Leu Leu Pro Leu Leu Trp Ala Gly Ala Leu Ala
1               5                   10                  15

Met Asp Lys Leu Ala Ser Gly Thr Leu Glu Asp Gly Arg Gly Ser Leu
            20                  25                  30

Pro Ser Val Ser Leu Asp Leu Pro Arg Leu Ser Ile Gln Lys Asp Ile
        35                  40                  45

Leu Thr Ile Lys Ala Asn Thr Thr Leu Gln Ile Thr Cys Arg Gly Gln
    50                  55                  60

Arg Asp Leu Asp Trp Leu Trp Pro Asn Asn Gln Ser Gly Ser Glu Gln
65                  70                  75                  80

Arg Val Glu Val Thr Glu Cys Ser Asp Gly Leu Phe Cys Lys Thr Leu
                85                  90                  95

Thr Ile Pro Lys Val Ile Gly Asn Asp Thr Gly Ala Tyr Lys Cys Phe
            100                 105                 110

Tyr Arg Glu Thr Asp Leu Ala Ser Val Ile Tyr Val Tyr Val Gln Asp
        115                 120                 125

Tyr Arg Ser Pro Phe Ile Ala Ser Val Ser Asp Gln His Gly Val Val
    130                 135                 140

Tyr Ile Thr Glu Asn Lys Asn Lys Thr Val Val Ile Pro Cys Leu Gly
145                 150                 155                 160

Ser Ile Ser Asn Leu Asn Val Ser Leu Cys Ala Arg Tyr Pro Glu Lys
                165                 170                 175

Arg Phe Val Pro Asp Gly Asn Arg Ile Ser Trp Asp Ser Lys Lys Gly
            180                 185                 190

Phe Thr Ile Pro Ser Tyr Met Ile Ser Tyr Ala Gly Met Val Phe Cys
        195                 200                 205

Glu Ala Lys Ile Asn Asp Glu Ser Tyr Gln Ser Ile Met Tyr Ile Val
    210                 215                 220

Val Val Val Gly Tyr Arg Ile Tyr Asp Val Asp Pro Ile Glu Gly Arg
225                 230                 235                 240
```

```
Gly Gly Gly Gly Gly Asp Pro Lys Ser Cys Asp Lys Pro His Thr Cys
            245                 250                 255

Pro Leu Cys Pro Ala Pro Glu Leu Leu Gly Gly Pro Ser Val Phe Leu
        260                 265                 270

Phe Pro Pro Lys Pro Lys Asp Thr Leu Met Ile Ser Arg Thr Pro Glu
            275                 280                 285

Val Thr Cys Val Val Val Asp Val Ser His Glu Asp Pro Glu Val Lys
        290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Ala Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475

<210> SEQ ID NO 13
<211> LENGTH: 1452
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-2 D
<220> FEATURE:
<221> NAME/KEY: CDS
<222> LOCATION: (1)..(1452)

<400> SEQUENCE: 13 atg ccg ctg ctg cta ctg ctg ccc ctg ctg tgg gca ggg gcc ctg gct     48
Met Pro Leu Leu Leu Leu Leu Pro Leu Leu Trp Ala Gly Ala Leu Ala
1               5                   10                  15 atg gat aag ctt gct agc ggt acc ctc gag gat ggc cgc gga tcc ttg     96
Met Asp Lys Leu Ala Ser Gly Thr Leu Glu Asp Gly Arg Gly Ser Leu
                20                  25                  30 cct agt gtt tct ctt gat ctg ccc agg ctc agc ata caa aaa gac ata    144
Pro Ser Val Ser Leu Asp Leu Pro Arg Leu Ser Ile Gln Lys Asp Ile
            35                  40                  45 ctt aca att aag gct aat aca act ctt caa att act tgc agg gga cag    192
Leu Thr Ile Lys Ala Asn Thr Thr Leu Gln Ile Thr Cys Arg Gly Gln
        50                  55                  60 agg gac ttg gac tgg ctt tgg ccc aat aat cag agt ggc agt gag caa    240
Arg Asp Leu Asp Trp Leu Trp Pro Asn Asn Gln Ser Gly Ser Glu Gln
```

```
                65                  70                  75                  80
agg gtg gag gtg act gag tgc agc gat ggc ctc ttc tgt aag aca ctc     288
Arg Val Glu Val Thr Glu Cys Ser Asp Gly Leu Phe Cys Lys Thr Leu
                        85                  90                  95 aca att cca aaa gtg atc gga aat gac act gga gcc tac aag tgc ttc     336
Thr Ile Pro Lys Val Ile Gly Asn Asp Thr Gly Ala Tyr Lys Cys Phe
                100                 105                 110 tac cgg gaa act gac ttg gcc tcg gtc att tat gtc tat gtt caa gat     384
Tyr Arg Glu Thr Asp Leu Ala Ser Val Ile Tyr Val Tyr Val Gln Asp
            115                 120                 125 tac aga tct cca ttt att gct tct gtt agt gac caa cat gga gtc gtg     432
Tyr Arg Ser Pro Phe Ile Ala Ser Val Ser Asp Gln His Gly Val Val
        130                 135                 140 tac att act gag aac aaa aac aaa act gtg gtg att cca tgt ctc ggg     480
Tyr Ile Thr Glu Asn Lys Asn Lys Thr Val Val Ile Pro Cys Leu Gly
145                 150                 155                 160 tcc att tca aat ctc aac gtg tca ctt tgt gca aga tac cca gaa aag     528
Ser Ile Ser Asn Leu Asn Val Ser Leu Cys Ala Arg Tyr Pro Glu Lys
                165                 170                 175 aga ttt gtt cct gat ggt aac aga att tcc tgg gac agc aag aag ggc     576
Arg Phe Val Pro Asp Gly Asn Arg Ile Ser Trp Asp Ser Lys Lys Gly
                180                 185                 190 ttt act att ccc agc tac atg atc agc tat gct ggc atg gtc ttc tgt     624
Phe Thr Ile Pro Ser Tyr Met Ile Ser Tyr Ala Gly Met Val Phe Cys
            195                 200                 205 gaa gca aaa att aat gat gaa agt tac cag tct att atg tac ata gtt     672
Glu Ala Lys Ile Asn Asp Glu Ser Tyr Gln Ser Ile Met Tyr Ile Val
        210                 215                 220 gtc gtt gta ggg tat agg att tat gat gtg gtt ctg agt ccg tct cat     720
Val Val Val Gly Tyr Arg Ile Tyr Asp Val Val Leu Ser Pro Ser His
225                 230                 235                 240 gat ccc atc gaa ggt cgt ggt ggt ggt ggt gat ccc aaa tct tgt         768
Asp Pro Ile Glu Gly Arg Gly Gly Gly Gly Asp Pro Lys Ser Cys
                245                 250                 255 gac aaa cct cac aca tgc cca ctg tgc cca gca cct gaa ctc ctg ggg     816
Asp Lys Pro His Thr Cys Pro Leu Cys Pro Ala Pro Glu Leu Leu Gly
                260                 265                 270 gga ccg tca gtc ttc ctc ttc ccc cca aaa ccc aag gac acc ctc atg     864
Gly Pro Ser Val Phe Leu Phe Pro Pro Lys Pro Lys Asp Thr Leu Met
            275                 280                 285 atc tcc cgg acc cct gag gtc aca tgc gtg gtg gtg gac gtg agc cac     912
Ile Ser Arg Thr Pro Glu Val Thr Cys Val Val Val Asp Val Ser His
        290                 295                 300 gaa gac cct gag gtc aag ttc aac tgg tac gtg gac ggc gtg gag gtg     960
Glu Asp Pro Glu Val Lys Phe Asn Trp Tyr Val Asp Gly Val Glu Val
305                 310                 315                 320 cat aat gcc aag aca aag ccg cgg gag gag cag tac aac agc acg tac    1008
His Asn Ala Lys Thr Lys Pro Arg Glu Glu Gln Tyr Asn Ser Thr Tyr
                325                 330                 335 cgt gtg gtc agc gtc ctc acc gtc ctg cac cag gac tgg ctg aat ggc    1056
Arg Val Val Ser Val Leu Thr Val Leu His Gln Asp Trp Leu Asn Gly
                340                 345                 350 aag gag tac aag tgc aag gtc tcc aac aaa gcc ctc cca gcc ccc atc    1104
Lys Glu Tyr Lys Cys Lys Val Ser Asn Lys Ala Leu Pro Ala Pro Ile
            355                 360                 365 gag aaa acc atc tcc aaa gcc aaa ggg cag ccc cga gaa cca cag gtg    1152
Glu Lys Thr Ile Ser Lys Ala Lys Gly Gln Pro Arg Glu Pro Gln Val
        370                 375                 380 tac acc ctg ccc cca tcc cgg gat gag ctg acc aag aac cag gtc agc    1200
```

```
Tyr Thr Leu Pro Pro Ser Arg Asp Glu Leu Thr Lys Asn Gln Val Ser
385                 390                 395                 400 ctg acc tgc cta gtc aaa ggc ttc tat ccc agc gac atc gcc gtg gag      1248
Leu Thr Cys Leu Val Lys Gly Phe Tyr Pro Ser Asp Ile Ala Val Glu
                405                 410                 415 tgg gag agc aat ggg cag ccg gag aac aac tac aag gcc acg cct ccc      1296
Trp Glu Ser Asn Gly Gln Pro Glu Asn Asn Tyr Lys Ala Thr Pro Pro
            420                 425                 430 gtg ctg gac tcc gac ggc tcc ttc ttc ctc tac agc aag ctc acc gtg      1344
Val Leu Asp Ser Asp Gly Ser Phe Phe Leu Tyr Ser Lys Leu Thr Val
        435                 440                 445 gac aag agc agg tgg cag cag ggg aac gtc ttc tca tgc tcc gtg atg      1392
Asp Lys Ser Arg Trp Gln Gln Gly Asn Val Phe Ser Cys Ser Val Met
    450                 455                 460 cat gag gct ctg cac aac cac tac acg cag aag agc ctc tcc ctg tct      1440
His Glu Ala Leu His Asn His Tyr Thr Gln Lys Ser Leu Ser Leu Ser
465                 470                 475                 480 ccg ggt aaa tga                                                      1452
Pro Gly Lys <210> SEQ ID NO 14
<211> LENGTH: 483
<212> TYPE: PRT
<213> ORGANISM: Artificial sequence
<220> FEATURE:
<223> OTHER INFORMATION: Synthetic polypeptide

<400> SEQUENCE: 14

Met Pro Leu Leu Leu Leu Leu Pro Leu Leu Trp Ala Gly Ala Leu Ala
1               5                   10                  15

Met Asp Lys Leu Ala Ser Gly Thr Leu Glu Asp Gly Arg Gly Ser Leu
            20                  25                  30

Pro Ser Val Ser Leu Asp Leu Pro Arg Leu Ser Ile Gln Lys Asp Ile
        35                  40                  45

Leu Thr Ile Lys Ala Asn Thr Thr Leu Gln Ile Thr Cys Arg Gly Gln
    50                  55                  60

Arg Asp Leu Asp Trp Leu Trp Pro Asn Asn Gln Ser Gly Ser Glu Gln
65                  70                  75                  80

Arg Val Glu Val Thr Glu Cys Ser Asp Gly Leu Phe Cys Lys Thr Leu
                85                  90                  95

Thr Ile Pro Lys Val Ile Gly Asn Asp Thr Gly Ala Tyr Lys Cys Phe
            100                 105                 110

Tyr Arg Glu Thr Asp Leu Ala Ser Val Ile Tyr Val Tyr Val Gln Asp
        115                 120                 125

Tyr Arg Ser Pro Phe Ile Ala Ser Val Ser Asp Gln His Gly Val Val
    130                 135                 140

Tyr Ile Thr Glu Asn Lys Asn Lys Thr Val Val Ile Pro Cys Leu Gly
145                 150                 155                 160

Ser Ile Ser Asn Leu Asn Val Ser Leu Cys Ala Arg Tyr Pro Glu Lys
                165                 170                 175

Arg Phe Val Pro Asp Gly Asn Arg Ile Ser Trp Asp Ser Lys Lys Gly
            180                 185                 190

Phe Thr Ile Pro Ser Tyr Met Ile Ser Tyr Ala Gly Met Val Phe Cys
        195                 200                 205

Glu Ala Lys Ile Asn Asp Glu Ser Tyr Gln Ser Ile Met Tyr Ile Val
    210                 215                 220

Val Val Val Gly Tyr Arg Ile Tyr Asp Val Val Leu Ser Pro Ser His
```

```
                225                 230                 235                 240
Asp Pro Ile Glu Gly Arg Gly Gly Gly Asp Pro Lys Ser Cys
                    245                 250                 255

Asp Lys Pro His Thr Cys Pro Leu Cys Pro Ala Pro Glu Leu Leu Gly
                260                 265                 270

Gly Pro Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
        290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Ala Thr Pro Pro
            420                 425                 430

Val Leu Asp Ser Asp Gly Ser Phe Phe Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys

<210> SEQ ID NO 15
<211> LENGTH: 1479
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-2 E
<220> FEATURE:
<221> NAME/KEY: CDS
<222> LOCATION: (1)..(1479)

<400> SEQUENCE: 15 atg ccg ctg ctg cta ctg ctg ccc ctg ctg tgg gca ggg gcc ctg gct     48
Met Pro Leu Leu Leu Leu Leu Pro Leu Leu Trp Ala Gly Ala Leu Ala
1               5                   10                  15 atg gat aag ctt gct agc ggt acc ctc gag gat ggc cgc gga tcc ttg     96
Met Asp Lys Leu Ala Ser Gly Thr Leu Glu Asp Gly Arg Gly Ser Leu
                20                  25                  30 cct agt gtt tct ctt gat ctg ccc agg ctc agc ata caa aaa gac ata    144
Pro Ser Val Ser Leu Asp Leu Pro Arg Leu Ser Ile Gln Lys Asp Ile
            35                  40                  45 ctt aca att aag gct aat aca act ctt caa att act tgc agg gga cag    192
Leu Thr Ile Lys Ala Asn Thr Thr Leu Gln Ile Thr Cys Arg Gly Gln
```

```
                50                     55                     60
agg gac ttg gac tgg ctt tgg ccc aat aat cag agt ggc agt gag caa      240
Arg Asp Leu Asp Trp Leu Trp Pro Asn Asn Gln Ser Gly Ser Glu Gln
 65                  70                  75                  80 agg gtg gag gtg act gag tgc agc gat ggc ctc ttc tgt aag aca ctc      288
Arg Val Glu Val Thr Glu Cys Ser Asp Gly Leu Phe Cys Lys Thr Leu
                 85                  90                  95 aca att cca aaa gtg atc gga aat gac act gga gcc tac aag tgc ttc      336
Thr Ile Pro Lys Val Ile Gly Asn Asp Thr Gly Ala Tyr Lys Cys Phe
            100                 105                 110 tac cgg gaa act gac ttg gcc tcg gtc att tat gtc tat gtt caa gat      384
Tyr Arg Glu Thr Asp Leu Ala Ser Val Ile Tyr Val Tyr Val Gln Asp
        115                 120                 125 tac aga tct cca ttt att gct tct gtt agt gac caa cat gga gtc gtg      432
Tyr Arg Ser Pro Phe Ile Ala Ser Val Ser Asp Gln His Gly Val Val
    130                 135                 140 tac att act gag aac aaa aac aaa act gtg gtg att cca tgt ctc ggg      480
Tyr Ile Thr Glu Asn Lys Asn Lys Thr Val Val Ile Pro Cys Leu Gly
145                 150                 155                 160 tcc att tca aat ctc aac gtg tca ctt tgt gca aga tac cca gaa aag      528
Ser Ile Ser Asn Leu Asn Val Ser Leu Cys Ala Arg Tyr Pro Glu Lys
                165                 170                 175 aga ttt gtt cct gat ggt aac aga att tcc tgg gac agc aag aag ggc      576
Arg Phe Val Pro Asp Gly Asn Arg Ile Ser Trp Asp Ser Lys Lys Gly
            180                 185                 190 ttt act att ccc agc tac atg atc agc tat gct ggc atg gtc ttc tgt      624
Phe Thr Ile Pro Ser Tyr Met Ile Ser Tyr Ala Gly Met Val Phe Cys
        195                 200                 205 gaa gca aaa att aat gat gaa agt tac cag tct att atg tac ata gtt      672
Glu Ala Lys Ile Asn Asp Glu Ser Tyr Gln Ser Ile Met Tyr Ile Val
    210                 215                 220 gtc gtt gta ggg tat agg att tat gat gtg gtt ctg agt ccg tct cat      720
Val Val Val Gly Tyr Arg Ile Tyr Asp Val Val Leu Ser Pro Ser His
225                 230                 235                 240 gga att gaa cta tct gtt gga gaa aag gat ccc atc gaa ggt cgt ggt      768
Gly Ile Glu Leu Ser Val Gly Glu Lys Asp Pro Ile Glu Gly Arg Gly
                245                 250                 255 ggt ggt ggt ggt gat ccc aaa tct tgt gac aaa cct cac aca tgc cca      816
Gly Gly Gly Gly Asp Pro Lys Ser Cys Asp Lys Pro His Thr Cys Pro
            260                 265                 270 ctg tgc cca gca cct gaa ctc ctg ggg gga ccg tca gtc ttc ctc ttc      864
Leu Cys Pro Ala Pro Glu Leu Leu Gly Gly Pro Ser Val Phe Leu Phe
        275                 280                 285 ccc cca aaa ccc aag gac acc ctc atg atc tcc cgg acc cct gag gtc      912
Pro Pro Lys Pro Lys Asp Thr Leu Met Ile Ser Arg Thr Pro Glu Val
    290                 295                 300 aca tgc gtg gtg gtg gac gtg agc cac gaa gac cct gag gtc aag ttc      960
Thr Cys Val Val Val Asp Val Ser His Glu Asp Pro Glu Val Lys Phe
305                 310                 315                 320 aac tgg tac gtg gac ggc gtg gag gtg cat aat gcc aag aca aag ccg     1008
Asn Trp Tyr Val Asp Gly Val Glu Val His Asn Ala Lys Thr Lys Pro
                325                 330                 335 cgg gag gag cag tac aac agc acg tac cgt gtg gtc agc gtc ctc acc     1056
Arg Glu Glu Gln Tyr Asn Ser Thr Tyr Arg Val Val Ser Val Leu Thr
            340                 345                 350 gtc ctg cac cag gac tgg ctg aat ggc aag gag tac aag tgc aag gtc     1104
Val Leu His Gln Asp Trp Leu Asn Gly Lys Glu Tyr Lys Cys Lys Val
        355                 360                 365 tcc aac aaa gcc ctc cca gcc ccc atc gag aaa acc atc tcc aaa gcc     1152
```

```
Ser Asn Lys Ala Leu Pro Ala Pro Ile Glu Lys Thr Ile Ser Lys Ala
        370                 375                 380 aaa ggg cag ccc cga gaa cca cag gtg tac acc ctg ccc cca tcc cgg      1200
Lys Gly Gln Pro Arg Glu Pro Gln Val Tyr Thr Leu Pro Pro Ser Arg
385                 390                 395                 400 gat gag ctg acc aag aac cag gtc agc ctg acc tgc cta gtc aaa ggc      1248
Asp Glu Leu Thr Lys Asn Gln Val Ser Leu Thr Cys Leu Val Lys Gly
                405                 410                 415 ttc tat ccc agc gac atc gcc gtg gag tgg gag agc aat ggg cag ccg      1296
Phe Tyr Pro Ser Asp Ile Ala Val Glu Trp Glu Ser Asn Gly Gln Pro
            420                 425                 430 gag aac aac tac aag gcc acg cct ccc gtg ctg gac tcc gac ggc tcc      1344
Glu Asn Asn Tyr Lys Ala Thr Pro Pro Val Leu Asp Ser Asp Gly Ser
        435                 440                 445 ttc ttc ctc tac agc aag ctc acc gtg gac aag agc agg tgg cag cag      1392
Phe Phe Leu Tyr Ser Lys Leu Thr Val Asp Lys Ser Arg Trp Gln Gln
    450                 455                 460 ggg aac gtc ttc tca tgc tcc gtg atg cat gag gct ctg cac aac cac      1440
Gly Asn Val Phe Ser Cys Ser Val Met His Glu Ala Leu His Asn His
465                 470                 475                 480 tac acg cag aag agc ctc tcc ctg tct ccg ggt aaa tga                  1479
Tyr Thr Gln Lys Ser Leu Ser Leu Ser Pro Gly Lys
                485                 490

<210> SEQ ID NO 16
<211> LENGTH: 492
<212> TYPE: PRT
<213> ORGANISM: Artificial sequence
<220> FEATURE:
<223> OTHER INFORMATION: Synthetic polypeptide

<400> SEQUENCE: 16

Met Pro Leu Leu Leu Leu Pro Leu Leu Trp Ala Gly Ala Leu Ala
1               5                   10                  15

Met Asp Lys Leu Ala Ser Gly Thr Leu Glu Asp Gly Arg Gly Ser Leu
            20                  25                  30

Pro Ser Val Ser Leu Asp Leu Pro Arg Leu Ser Ile Gln Lys Asp Ile
        35                  40                  45

Leu Thr Ile Lys Ala Asn Thr Thr Leu Gln Ile Thr Cys Arg Gly Gln
    50                  55                  60

Arg Asp Leu Asp Trp Leu Trp Pro Asn Asn Gln Ser Gly Ser Glu Gln
65                  70                  75                  80

Arg Val Glu Val Thr Glu Cys Ser Asp Gly Leu Phe Cys Lys Thr Leu
                85                  90                  95

Thr Ile Pro Lys Val Ile Gly Asn Asp Thr Gly Ala Tyr Lys Cys Phe
            100                 105                 110

Tyr Arg Glu Thr Asp Leu Ala Ser Val Ile Tyr Val Tyr Val Gln Asp
        115                 120                 125

Tyr Arg Ser Pro Phe Ile Ala Ser Val Ser Asp Gln His Gly Val Val
    130                 135                 140

Tyr Ile Thr Glu Asn Lys Asn Lys Thr Val Val Ile Pro Cys Leu Gly
145                 150                 155                 160

Ser Ile Ser Asn Leu Asn Val Ser Leu Cys Ala Arg Tyr Pro Glu Lys
                165                 170                 175

Arg Phe Val Pro Asp Gly Asn Arg Ile Ser Trp Asp Ser Lys Lys Gly
            180                 185                 190

Phe Thr Ile Pro Ser Tyr Met Ile Ser Tyr Ala Gly Met Val Phe Cys
        195                 200                 205
```

```
Glu Ala Lys Ile Asn Asp Glu Ser Tyr Gln Ser Ile Met Tyr Ile Val
    210                 215                 220

Val Val Val Gly Tyr Arg Ile Tyr Asp Val Val Leu Ser Pro Ser His
225                 230                 235                 240

Gly Ile Glu Leu Ser Val Gly Glu Lys Asp Pro Ile Glu Gly Arg Gly
                245                 250                 255

Gly Gly Gly Gly Asp Pro Lys Ser Cys Asp Lys Pro His Thr Cys Pro
            260                 265                 270

Leu Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Ala Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490

<210> SEQ ID NO 17
<211> LENGTH: 1113
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-2 F
<220> FEATURE:
<221> NAME/KEY: CDS
<222> LOCATION: (1)..(1113)

<400> SEQUENCE: 17 atg ccg ctg ctg cta ctg ctg ccc ctg ctg tgg gca ggg gcc ctg gct      48
Met Pro Leu Leu Leu Leu Leu Pro Leu Leu Trp Ala Gly Ala Leu Ala
1               5                   10                  15 atg gat aag ctt gct agc ggt acc ctc gag gat ggc cgc gga tcc ttg      96
Met Asp Lys Leu Ala Ser Gly Thr Leu Glu Asp Gly Arg Gly Ser Leu
                20                  25                  30
```

| | | |
|---|---|---|
| cct agt gtt tct ctt gat ctg ccc agg ctc agc ata caa aaa gac ata<br>Pro Ser Val Ser Leu Asp Leu Pro Arg Leu Ser Ile Gln Lys Asp Ile<br>35 40 45 | | 144 |
| ctt aca att aag gct aat aca act ctt caa att act tgc agg gga cag<br>Leu Thr Ile Lys Ala Asn Thr Thr Leu Gln Ile Thr Cys Arg Gly Gln<br>50 55 60 | | 192 |
| agg gac ttg gac tgg ctt tgg ccc aat aat cag agt ggc agt gag caa<br>Arg Asp Leu Asp Trp Leu Trp Pro Asn Asn Gln Ser Gly Ser Glu Gln<br>65 70 75 80 | | 240 |
| agg gtg gag gtg act gag tgc agc gat ggc ctc ttc tgt aag aca ctc<br>Arg Val Glu Val Thr Glu Cys Ser Asp Gly Leu Phe Cys Lys Thr Leu<br>85 90 95 | | 288 |
| aca att cca aaa gtg atc gga aat gac act gga gcc tac aag tgc ttc<br>Thr Ile Pro Lys Val Ile Gly Asn Asp Thr Gly Ala Tyr Lys Cys Phe<br>100 105 110 | | 336 |
| tac cgg gaa act gac ttg gcc tcg gtc att tat gtc tat gtt caa gat<br>Tyr Arg Glu Thr Asp Leu Ala Ser Val Ile Tyr Val Tyr Val Gln Asp<br>115 120 125 | | 384 |
| ccc atc gaa ggt cgt ggt ggt ggt ggt gat ccc aaa tct tgt gac<br>Pro Ile Glu Gly Arg Gly Gly Gly Gly Gly Asp Pro Lys Ser Cys Asp<br>130 135 140 | | 432 |
| aaa cct cac aca tgc cca ctg tgc cca gca cct gaa ctc ctg ggg gga<br>Lys Pro His Thr Cys Pro Leu Cys Pro Ala Pro Glu Leu Leu Gly Gly<br>145 150 155 160 | | 480 |
| ccg tca gtc ttc ctc ttc ccc cca aaa ccc aag gac acc ctc atg atc<br>Pro Ser Val Phe Leu Phe Pro Pro Lys Pro Lys Asp Thr Leu Met Ile<br>165 170 175 | | 528 |
| tcc cgg acc cct gag gtc aca tgc gtg gtg gtg gac gtg agc cac gaa<br>Ser Arg Thr Pro Glu Val Thr Cys Val Val Val Asp Val Ser His Glu<br>180 185 190 | | 576 |
| gac cct gag gtc aag ttc aac tgg tac gtg gac ggc gtg gag gtg cat<br>Asp Pro Glu Val Lys Phe Asn Trp Tyr Val Asp Gly Val Glu Val His<br>195 200 205 | | 624 |
| aat gcc aag aca aag ccg cgg gag gag cag tac aac agc acg tac cgt<br>Asn Ala Lys Thr Lys Pro Arg Glu Glu Gln Tyr Asn Ser Thr Tyr Arg<br>210 215 220 | | 672 |
| gtg gtc agc gtc ctc acc gtc ctg cac cag gac tgg ctg aat ggc aag<br>Val Val Ser Val Leu Thr Val Leu His Gln Asp Trp Leu Asn Gly Lys<br>225 230 235 240 | | 720 |
| gag tac aag tgc aag gtc tcc aac aaa gcc ctc cca gcc ccc atc gag<br>Glu Tyr Lys Cys Lys Val Ser Asn Lys Ala Leu Pro Ala Pro Ile Glu<br>245 250 255 | | 768 |
| aaa acc atc tcc aaa gcc aaa ggg cag ccc cga gaa cca cag gtg tac<br>Lys Thr Ile Ser Lys Ala Lys Gly Gln Pro Arg Glu Pro Gln Val Tyr<br>260 265 270 | | 816 |
| acc ctg ccc cca tcc cgg gat gag ctg acc aag aac cag gtc agc ctg<br>Thr Leu Pro Pro Ser Arg Asp Glu Leu Thr Lys Asn Gln Val Ser Leu<br>275 280 285 | | 864 |
| acc tgc cta gtc aaa ggc ttc tat ccc agc gac atc gcc gtg gag tgg<br>Thr Cys Leu Val Lys Gly Phe Tyr Pro Ser Asp Ile Ala Val Glu Trp<br>290 295 300 | | 912 |
| gag agc aat ggg cag ccg gag aac aac tac aag gcc acg cct ccc gtg<br>Glu Ser Asn Gly Gln Pro Glu Asn Asn Tyr Lys Ala Thr Pro Pro Val<br>305 310 315 320 | | 960 |
| ctg gac tcc gac ggc tcc ttc ttc ctc tac agc aag ctc acc gtg gac<br>Leu Asp Ser Asp Gly Ser Phe Phe Leu Tyr Ser Lys Leu Thr Val Asp<br>325 330 335 | | 1008 |
| aag agc agg tgg cag cag ggg aac gtc ttc tca tgc tcc gtg atg cat<br>Lys Ser Arg Trp Gln Gln Gly Asn Val Phe Ser Cys Ser Val Met His<br>340 345 350 | | 1056 |

```
gag gct ctg cac aac cac tac acg cag aag agc ctc tcc ctg tct ccg    1104
Glu Ala Leu His Asn His Tyr Thr Gln Lys Ser Leu Ser Leu Ser Pro
        355                 360                 365 ggt aaa tga                                                         1113
Gly Lys
    370
```

<210> SEQ ID NO 18
<211> LENGTH: 370
<212> TYPE: PRT
<213> ORGANISM: Artificial sequence
<220> FEATURE:
<223> OTHER INFORMATION: Synthetic polypeptide

<400> SEQUENCE: 18

```
Met Pro Leu Leu Leu Leu Pro Leu Leu Trp Ala Gly Ala Leu Ala
1               5                   10                  15

Met Asp Lys Leu Ala Ser Gly Thr Leu Glu Asp Gly Arg Gly Ser Leu
                20                  25                  30

Pro Ser Val Ser Leu Asp Leu Pro Arg Leu Ser Ile Gln Lys Asp Ile
            35                  40                  45

Leu Thr Ile Lys Ala Asn Thr Thr Leu Gln Ile Thr Cys Arg Gly Gln
    50                  55                  60

Arg Asp Leu Asp Trp Leu Trp Pro Asn Asn Gln Ser Gly Ser Glu Gln
65                  70                  75                  80

Arg Val Glu Val Thr Glu Cys Ser Asp Gly Leu Phe Cys Lys Thr Leu
                85                  90                  95

Thr Ile Pro Lys Val Ile Gly Asn Asp Thr Gly Ala Tyr Lys Cys Phe
            100                 105                 110

Tyr Arg Glu Thr Asp Leu Ala Ser Val Ile Tyr Val Tyr Val Gln Asp
        115                 120                 125

Pro Ile Glu Gly Arg Gly Gly Gly Gly Asp Pro Lys Ser Cys Asp
    130                 135                 140

Lys Pro His Thr Cys Pro Leu Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Asp Glu Leu Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Ala Thr Pro Pro Val
305                 310                 315                 320
```

-continued

```
Leu Asp Ser Asp Gly Ser Phe Leu Tyr Ser Lys Leu Thr Val Asp
            325                 330                 335

Lys Ser Arg Trp Gln Gln Gly Asn Val Phe Ser Cys Ser Val Met His
        340                 345                 350

Glu Ala Leu His Asn His Tyr Thr Gln Lys Ser Leu Ser Leu Ser Pro
            355                 360                 365

Gly Lys
    370

<210> SEQ ID NO 19
<211> LENGTH: 1425
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-2 G
<220> FEATURE:
<221> NAME/KEY: CDS
<222> LOCATION: (1)..(1425)

<400> SEQUENCE: 19 atg ccg ctg ctg cta ctg ctg ccc ctg ctg tgg gca ggg gcc ctg gct      48
Met Pro Leu Leu Leu Leu Leu Pro Leu Leu Trp Ala Gly Ala Leu Ala
1               5                   10                  15 atg gat aag ctt gct agc gtt caa gat tac aga tct cca ttt att gct      96
Met Asp Lys Leu Ala Ser Val Gln Asp Tyr Arg Ser Pro Phe Ile Ala
                20                  25                  30 tct gtt agt gac caa cat gga gtc gtg tac att act gag aac aaa aac    144
Ser Val Ser Asp Gln His Gly Val Val Tyr Ile Thr Glu Asn Lys Asn
            35                  40                  45 aaa act gtg gtg att cca tgt ctc ggg tcc att tca aat ctc aac gtg    192
Lys Thr Val Val Ile Pro Cys Leu Gly Ser Ile Ser Asn Leu Asn Val
        50                  55                  60 tca ctt tgt gca aga tac cca gaa aag aga ttt gtt cct gat ggt aac    240
Ser Leu Cys Ala Arg Tyr Pro Glu Lys Arg Phe Val Pro Asp Gly Asn
65                  70                  75                  80 aga att tcc tgg gac agc aag aag ggc ttt act att ccc agc tac atg    288
Arg Ile Ser Trp Asp Ser Lys Lys Gly Phe Thr Ile Pro Ser Tyr Met
                85                  90                  95 atc agc tat gct ggc atg gtc ttc tgt gaa gca aaa att aat gat gaa    336
Ile Ser Tyr Ala Gly Met Val Phe Cys Glu Ala Lys Ile Asn Asp Glu
            100                 105                 110 agt tac cag tct att atg tac ata gtt gtc gtt gta ggg tat agg att    384
Ser Tyr Gln Ser Ile Met Tyr Ile Val Val Val Val Gly Tyr Arg Ile
        115                 120                 125 tat gat gtg gtt ctg agt ccg tct cat gga att gaa cta tct gtt gga    432
Tyr Asp Val Val Leu Ser Pro Ser His Gly Ile Glu Leu Ser Val Gly
    130                 135                 140 gaa aag ctt gtc tta aat tgt aca gca aga act gaa cta aat gtg ggg    480
Glu Lys Leu Val Leu Asn Cys Thr Ala Arg Thr Glu Leu Asn Val Gly
145                 150                 155                 160 att gac ttc aac tgg gaa tac cct tct tcg aag cat cag cat aag aaa    528
Ile Asp Phe Asn Trp Glu Tyr Pro Ser Ser Lys His Gln His Lys Lys
                165                 170                 175 ctt gta aac cga gac cta aaa acc cag tct ggg agt gag atg aag aaa    576
Leu Val Asn Arg Asp Leu Lys Thr Gln Ser Gly Ser Glu Met Lys Lys
            180                 185                 190 ttt ttg agc acc tta act ata gat ggt gta acc cgg agt gac caa gga    624
Phe Leu Ser Thr Leu Thr Ile Asp Gly Val Thr Arg Ser Asp Gln Gly
        195                 200                 205
```

```
ttg tac acc tgt gca gca tcc agt ggg ctg atg acc aag aag aac agc      672
Leu Tyr Thr Cys Ala Ala Ser Ser Gly Leu Met Thr Lys Lys Asn Ser
    210                 215                 220 aca ttt gtc agg gtc cat gaa gat ccc atc gaa ggt cgt ggt ggt ggt      720
Thr Phe Val Arg Val His Glu Asp Pro Ile Glu Gly Arg Gly Gly Gly
225                 230                 235                 240 ggt ggt gat ccc aaa tct tgt gac aaa cct cac aca tgc cca ctg tgc      768
Gly Gly Asp Pro Lys Ser Cys Asp Lys Pro His Thr Cys Pro Leu Cys
                245                 250                 255 cca gca cct gaa ctc ctg ggg gga ccg tca gtc ttc ctc ttc ccc cca      816
Pro Ala Pro Glu Leu Leu Gly Gly Pro Ser Val Phe Leu Phe Pro Pro
            260                 265                 270 aaa ccc aag gac acc ctc atg atc tcc cgg acc cct gag gtc aca tgc      864
Lys Pro Lys Asp Thr Leu Met Ile Ser Arg Thr Pro Glu Val Thr Cys
        275                 280                 285 gtg gtg gtg gac gtg agc cac gaa gac cct gag gtc aag ttc aac tgg      912
Val Val Val Asp Val Ser His Glu Asp Pro Glu Val Lys Phe Asn Trp
    290                 295                 300 tac gtg gac ggc gtg gag gtg cat aat gcc aag aca aag ccg cgg gag      960
Tyr Val Asp Gly Val Glu Val His Asn Ala Lys Thr Lys Pro Arg Glu
305                 310                 315                 320 gag cag tac aac agc acg tac cgt gtg gtc agc gtc ctc acc gtc ctg     1008
Glu Gln Tyr Asn Ser Thr Tyr Arg Val Val Ser Val Leu Thr Val Leu
                325                 330                 335 cac cag gac tgg ctg aat ggc aag gag tac aag tgc aag gtc tcc aac     1056
His Gln Asp Trp Leu Asn Gly Lys Glu Tyr Lys Cys Lys Val Ser Asn
            340                 345                 350 aaa gcc ctc cca gcc ccc atc gag aaa acc atc tcc aaa gcc aaa ggg     1104
Lys Ala Leu Pro Ala Pro Ile Glu Lys Thr Ile Ser Lys Ala Lys Gly
        355                 360                 365 cag ccc cga gaa cca cag gtg tac acc ctg ccc cca tcc cgg gat gag     1152
Gln Pro Arg Glu Pro Gln Val Tyr Thr Leu Pro Pro Ser Arg Asp Glu
    370                 375                 380 ctg acc aag aac cag gtc agc ctg acc tgc cta gtc aaa ggc ttc tat     1200
Leu Thr Lys Asn Gln Val Ser Leu Thr Cys Leu Val Lys Gly Phe Tyr
385                 390                 395                 400 ccc agc gac atc gcc gtg gag tgg gag agc aat ggg cag ccg gag aac     1248
Pro Ser Asp Ile Ala Val Glu Trp Glu Ser Asn Gly Gln Pro Glu Asn
                405                 410                 415 aac tac aag gcc acg cct ccc gtg ctg gac tcc gac ggc tcc ttc ttc     1296
Asn Tyr Lys Ala Thr Pro Pro Val Leu Asp Ser Asp Gly Ser Phe Phe
            420                 425                 430 ctc tac agc aag ctc acc gtg gac aag agc agg tgg cag cag ggg aac     1344
Leu Tyr Ser Lys Leu Thr Val Asp Lys Ser Arg Trp Gln Gln Gly Asn
        435                 440                 445 gtc ttc tca tgc tcc gtg atg cat gag gct ctg cac aac cac tac acg     1392
Val Phe Ser Cys Ser Val Met His Glu Ala Leu His Asn His Tyr Thr
    450                 455                 460 cag aag agc ctc tcc ctg tct ccg ggt aaa tga                         1425
Gln Lys Ser Leu Ser Leu Ser Pro Gly Lys
465                 470
```

<210> SEQ ID NO 20
<211> LENGTH: 474
<212> TYPE: PRT
<213> ORGANISM: Artificial sequence
<220> FEATURE:
<223> OTHER INFORMATION: Synthetic polypeptide

<400> SEQUENCE: 20

```
Met Pro Leu Leu Leu Leu Pro Leu Leu Trp Ala Gly Ala Leu Ala
1               5                   10                  15

Met Asp Lys Leu Ala Ser Val Gln Asp Tyr Arg Ser Pro Phe Ile Ala
            20                  25                  30

Ser Val Ser Asp Gln His Gly Val Val Tyr Ile Thr Glu Asn Lys Asn
        35                  40                  45

Lys Thr Val Val Ile Pro Cys Leu Gly Ser Ile Ser Asn Leu Asn Val
    50                  55                  60

Ser Leu Cys Ala Arg Tyr Pro Glu Lys Arg Phe Val Pro Asp Gly Asn
65                  70                  75                  80

Arg Ile Ser Trp Asp Ser Lys Lys Gly Phe Thr Ile Pro Ser Tyr Met
                85                  90                  95

Ile Ser Tyr Ala Gly Met Val Phe Cys Glu Ala Lys Ile Asn Asp Glu
                100                 105                 110

Ser Tyr Gln Ser Ile Met Tyr Ile Val Val Val Gly Tyr Arg Ile
            115                 120                 125

Tyr Asp Val Val Leu Ser Pro Ser His Gly Ile Glu Leu Ser Val Gly
    130                 135                 140

Glu Lys Leu Val Leu Asn Cys Thr Ala Arg Thr Glu Leu Asn Val Gly
145                 150                 155                 160

Ile Asp Phe Asn Trp Glu Tyr Pro Ser Ser Lys His Gln His Lys Lys
                165                 170                 175

Leu Val Asn Arg Asp Leu Lys Thr Gln Ser Gly Ser Glu Met Lys Lys
            180                 185                 190

Phe Leu Ser Thr Leu Thr Ile Asp Gly Val Thr Arg Ser Asp Gln Gly
        195                 200                 205

Leu Tyr Thr Cys Ala Ala Ser Ser Gly Leu Met Thr Lys Lys Asn Ser
    210                 215                 220

Thr Phe Val Arg Val His Glu Asp Pro Ile Glu Gly Arg Gly Gly Gly
225                 230                 235                 240

Gly Gly Asp Pro Lys Ser Cys Asp Lys Pro His Thr Cys Pro Leu Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
    275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Ala Thr Pro Pro Val Leu Asp Ser Asp Gly Ser Phe Phe
```

```
                    420             425             430
Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
        450                 455                 460

Gln Lys Ser Leu Ser Leu Ser Pro Gly Lys
465                 470

<210> SEQ ID NO 21
<211> LENGTH: 1107
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-2 H
<220> FEATURE:
<221> NAME/KEY: CDS
<222> LOCATION: (1)..(1107)

<400> SEQUENCE: 21 atg ccg ctg ctg cta ctg ctg ccc ctg ctg tgg gca ggg gcc ctg gct       48
Met Pro Leu Leu Leu Leu Leu Pro Leu Leu Trp Ala Gly Ala Leu Ala
1               5                   10                  15 atg gat aag ctt gct agc gtt caa gat tac aga tct cca ttt att gct       96
Met Asp Lys Leu Ala Ser Val Gln Asp Tyr Arg Ser Pro Phe Ile Ala
                20                  25                  30 tct gtt agt gac caa cat gga gtc gtg tac att act gag aac aaa aac      144
Ser Val Ser Asp Gln His Gly Val Val Tyr Ile Thr Glu Asn Lys Asn
            35                  40                  45 aaa act gtg gtt att cca tgt ctc ggg tcc att tca aat ctc aac gtg      192
Lys Thr Val Val Ile Pro Cys Leu Gly Ser Ile Ser Asn Leu Asn Val
        50                  55                  60 tca ctt tgt gca aga tac cca gaa aag aga ttt gtt cct gat ggt aac      240
Ser Leu Cys Ala Arg Tyr Pro Glu Lys Arg Phe Val Pro Asp Gly Asn
65                  70                  75                  80 aga att tcc tgg gac agc aag aag ggc ttt act att ccc agc tac atg      288
Arg Ile Ser Trp Asp Ser Lys Lys Gly Phe Thr Ile Pro Ser Tyr Met
                85                  90                  95 atc agc tat gct ggc atg gtc ttc tgt gaa gca aaa att aat gat gaa      336
Ile Ser Tyr Ala Gly Met Val Phe Cys Glu Ala Lys Ile Asn Asp Glu
                100                 105                 110 agt tac cag tct att atg tac ata gtt gtc gtt gta ggg gat ccc atc      384
Ser Tyr Gln Ser Ile Met Tyr Ile Val Val Val Val Gly Asp Pro Ile
            115                 120                 125 gaa ggt cgt ggt ggt ggt ggt gat ccc aaa tct tgt gac aaa cct           432
Glu Gly Arg Gly Gly Gly Gly Asp Pro Lys Ser Cys Asp Lys Pro
        130                 135                 140 cac aca tgc cca ctg tgc cca gca cct gaa ctc ctg ggg gga ccg tca      480
His Thr Cys Pro Leu Cys Pro Ala Pro Glu Leu Leu Gly Gly Pro Ser
145                 150                 155                 160 gtc ttc ctc ttc ccc cca aaa ccc aag gac acc ctc atg atc tcc cgg      528
Val Phe Leu Phe Pro Pro Lys Pro Lys Asp Thr Leu Met Ile Ser Arg
                165                 170                 175 acc cct gag gtc aca tgc gtg gtg gtg gac gtg agc cac gaa gac cct      576
Thr Pro Glu Val Thr Cys Val Val Val Asp Val Ser His Glu Asp Pro
                180                 185                 190 gag gtc aag ttc aac tgg tac gtg gac ggc gtg gag gtg cat aat gcc      624
Glu Val Lys Phe Asn Trp Tyr Val Asp Gly Val Glu Val His Asn Ala
            195                 200                 205
```

-continued

```
aag aca aag ccg cgg gag gag cag tac aac agc acg tac cgt gtg gtc    672
Lys Thr Lys Pro Arg Glu Glu Gln Tyr Asn Ser Thr Tyr Arg Val Val
210                 215                 220 agc gtc ctc acc gtc ctg cac cag gac tgg ctg aat ggc aag gag tac    720
Ser Val Leu Thr Val Leu His Gln Asp Trp Leu Asn Gly Lys Glu Tyr
225                 230                 235                 240 aag tgc aag gtc tcc aac aaa gcc ctc cca gcc ccc atc gag aaa acc    768
Lys Cys Lys Val Ser Asn Lys Ala Leu Pro Ala Pro Ile Glu Lys Thr
                245                 250                 255 atc tcc aaa gcc aaa ggg cag ccc cga gaa cca cag gtg tac acc ctg    816
Ile Ser Lys Ala Lys Gly Gln Pro Arg Glu Pro Gln Val Tyr Thr Leu
            260                 265                 270 ccc cca tcc cgg gat gag ctg acc aag aac cag gtc agc ctg acc tgc    864
Pro Pro Ser Arg Asp Glu Leu Thr Lys Asn Gln Val Ser Leu Thr Cys
        275                 280                 285 cta gtc aaa ggc ttc tat ccc agc gac atc gcc gtg gag tgg gag agc    912
Leu Val Lys Gly Phe Tyr Pro Ser Asp Ile Ala Val Glu Trp Glu Ser
    290                 295                 300 aat ggg cag ccg gag aac aac tac aag gcc acg cct ccc gtg ctg gac    960
Asn Gly Gln Pro Glu Asn Asn Tyr Lys Ala Thr Pro Pro Val Leu Asp
305                 310                 315                 320 tcc gac ggc tcc ttc ttc ctc tac agc aag ctc acc gtg gac aag agc    1008
Ser Asp Gly Ser Phe Phe Leu Tyr Ser Lys Leu Thr Val Asp Lys Ser
                325                 330                 335 agg tgg cag cag ggg aac gtc ttc tca tgc tcc gtg atg cat gag gct    1056
Arg Trp Gln Gln Gly Asn Val Phe Ser Cys Ser Val Met His Glu Ala
            340                 345                 350 ctg cac aac cac tac acg cag aag agc ctc tcc ctg tct ccg ggt aaa    1104
Leu His Asn His Tyr Thr Gln Lys Ser Leu Ser Leu Ser Pro Gly Lys
        355                 360                 365 tga                                                                 1107
```

<210> SEQ ID NO 22
<211> LENGTH: 368
<212> TYPE: PRT
<213> ORGANISM: Artificial sequence
<220> FEATURE:
<223> OTHER INFORMATION: Synthetic polypeptide

<400> SEQUENCE: 22

```
Met Pro Leu Leu Leu Leu Pro Leu Leu Trp Ala Gly Ala Leu Ala
1               5                   10                  15

Met Asp Lys Leu Ala Ser Val Gln Asp Tyr Arg Ser Pro Phe Ile Ala
            20                  25                  30

Ser Val Ser Asp Gln His Gly Val Val Tyr Ile Thr Glu Asn Lys Asn
        35                  40                  45

Lys Thr Val Val Ile Pro Cys Leu Gly Ser Ile Ser Asn Leu Asn Val
    50                  55                  60

Ser Leu Cys Ala Arg Tyr Pro Glu Lys Arg Phe Val Pro Asp Gly Asn
65                  70                  75                  80

Arg Ile Ser Trp Asp Ser Lys Lys Gly Phe Thr Ile Pro Ser Tyr Met
                85                  90                  95

Ile Ser Tyr Ala Gly Met Val Phe Cys Glu Ala Lys Ile Asn Asp Glu
            100                 105                 110

Ser Tyr Gln Ser Ile Met Tyr Ile Val Val Val Gly Asp Pro Ile
        115                 120                 125

Glu Gly Arg Gly Gly Gly Gly Asp Pro Lys Ser Cys Asp Lys Pro
    130                 135                 140
```

-continued

```
His Thr Cys Pro Leu Cys Pro Ala Pro Glu Leu Leu Gly Gly Pro Ser
145                 150                 155                 160

Val Phe Leu Phe Pro Lys Pro Lys Asp Thr Leu Met Ile Ser Arg
            165                 170                 175

Thr Pro Glu Val Thr Cys Val Val Val Asp Val Ser His Glu Asp Pro
        180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Asp Glu Leu Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Ala Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365
```

<210> SEQ ID NO 23
<211> LENGTH: 1125
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-2 I
<220> FEATURE:
<221> NAME/KEY: CDS
<222> LOCATION: (1)..(1125)

<400> SEQUENCE: 23

```
atg ccg ctg ctg cta ctg ctg ccc ctg ctg tgg gca ggg gcc ctg gct      48
Met Pro Leu Leu Leu Leu Leu Pro Leu Leu Trp Ala Gly Ala Leu Ala
1               5                   10                  15 atg gat aag ctt gct agc gtt caa gat tac aga tct cca ttt att gct      96
Met Asp Lys Leu Ala Ser Val Gln Asp Tyr Arg Ser Pro Phe Ile Ala
            20                  25                  30 tct gtt agt gac caa cat gga gtc gtg tac att act gag aac aaa aac    144
Ser Val Ser Asp Gln His Gly Val Val Tyr Ile Thr Glu Asn Lys Asn
        35                  40                  45 aaa act gtg gtg att cca tgt ctc ggg tcc att tca aat ctc aac gtg    192
Lys Thr Val Val Ile Pro Cys Leu Gly Ser Ile Ser Asn Leu Asn Val
    50                  55                  60 tca ctt tgt gca aga tac cca gaa aag aga ttt gtt cct gat ggt aac    240
Ser Leu Cys Ala Arg Tyr Pro Glu Lys Arg Phe Val Pro Asp Gly Asn
65                  70                  75                  80 aga att tcc tgg gac agc aag aag ggc ttt act att ccc agc tac atg    288
```

```
Arg Ile Ser Trp Asp Ser Lys Lys Gly Phe Thr Ile Pro Ser Tyr Met
                85                  90                  95 atc agc tat gct ggc atg gtc ttc tgt gaa gca aaa att aat gat gaa      336
Ile Ser Tyr Ala Gly Met Val Phe Cys Glu Ala Lys Ile Asn Asp Glu
            100                 105                 110 agt tac cag tct att atg tac ata gtt gtc gtt gta ggg tat agg att      384
Ser Tyr Gln Ser Ile Met Tyr Ile Val Val Val Val Gly Tyr Arg Ile
        115                 120                 125 tat gat gtg gat ccc atc gaa ggt cgt ggt ggt ggt ggt gat ccc          432
Tyr Asp Val Asp Pro Ile Glu Gly Arg Gly Gly Gly Gly Asp Pro
130                 135                 140 aaa tct tgt gac aaa cct cac aca tgc cca ctg tgc cca gca cct gaa      480
Lys Ser Cys Asp Lys Pro His Thr Cys Pro Leu Cys Pro Ala Pro Glu
145                 150                 155                 160 ctc ctg ggg gga ccg tca gtc ttc ctc ttc ccc cca aaa ccc aag gac      528
Leu Leu Gly Gly Pro Ser Val Phe Leu Phe Pro Pro Lys Pro Lys Asp
                165                 170                 175 acc ctc atg atc tcc cgg acc cct gag gtc aca tgc gtg gtg gtg gac      576
Thr Leu Met Ile Ser Arg Thr Pro Glu Val Thr Cys Val Val Val Asp
            180                 185                 190 gtg agc cac gaa gac cct gag gtc aag ttc aac tgg tac gtg gac ggc      624
Val Ser His Glu Asp Pro Glu Val Lys Phe Asn Trp Tyr Val Asp Gly
        195                 200                 205 gtg gag gtg cat aat gcc aag aca aag ccg cgg gag gag cag tac aac      672
Val Glu Val His Asn Ala Lys Thr Lys Pro Arg Glu Glu Gln Tyr Asn
    210                 215                 220 agc acg tac cgt gtg gtc agc gtc ctc acc gtc ctg cac cag gac tgg      720
Ser Thr Tyr Arg Val Val Ser Val Leu Thr Val Leu His Gln Asp Trp
225                 230                 235                 240 ctg aat ggc aag gag tac aag tgc aag gtc tcc aac aaa gcc ctc cca      768
Leu Asn Gly Lys Glu Tyr Lys Cys Lys Val Ser Asn Lys Ala Leu Pro
                245                 250                 255 gcc ccc atc gag aaa acc atc tcc aaa gcc aaa ggg cag ccc cga gaa      816
Ala Pro Ile Glu Lys Thr Ile Ser Lys Ala Lys Gly Gln Pro Arg Glu
            260                 265                 270 cca cag gtg tac acc ctg ccc cca tcc cgg gat gag ctg acc aag aac      864
Pro Gln Val Tyr Thr Leu Pro Pro Ser Arg Asp Glu Leu Thr Lys Asn
        275                 280                 285 cag gtc agc ctg acc tgc cta gtc aaa ggc ttc tat ccc agc gac atc      912
Gln Val Ser Leu Thr Cys Leu Val Lys Gly Phe Tyr Pro Ser Asp Ile
    290                 295                 300 gcc gtg gag tgg gag agc aat ggg cag ccg gag aac aac tac aag gcc      960
Ala Val Glu Trp Glu Ser Asn Gly Gln Pro Glu Asn Asn Tyr Lys Ala
305                 310                 315                 320 acg cct ccc gtg ctg gac tcc gac ggc tcc ttc ttc ctc tac agc aag     1008
Thr Pro Pro Val Leu Asp Ser Asp Gly Ser Phe Phe Leu Tyr Ser Lys
                325                 330                 335 ctc acc gtg gac aag agc agg tgg cag cag ggg aac gtc ttc tca tgc     1056
Leu Thr Val Asp Lys Ser Arg Trp Gln Gln Gly Asn Val Phe Ser Cys
            340                 345                 350 tcc gtg atg cat gag gct ctg cac aac cac tac acg cag aag agc ctc     1104
Ser Val Met His Glu Ala Leu His Asn His Tyr Thr Gln Lys Ser Leu
        355                 360                 365 tcc ctg tct ccg ggt aaa tga                                          1125
Ser Leu Ser Pro Gly Lys
    370

<210> SEQ ID NO 24
<211> LENGTH: 374
<212> TYPE: PRT
```

<213> ORGANISM: Artificial sequence
<220> FEATURE:
<223> OTHER INFORMATION: Synthetic polypeptide

<400> SEQUENCE: 24

```
Met Pro Leu Leu Leu Leu Pro Leu Leu Trp Ala Gly Ala Leu Ala
1               5                   10                  15

Met Asp Lys Leu Ala Ser Val Gln Asp Tyr Arg Ser Pro Phe Ile Ala
                20                  25                  30

Ser Val Ser Asp Gln His Gly Val Val Tyr Ile Thr Glu Asn Lys Asn
            35                  40                  45

Lys Thr Val Val Ile Pro Cys Leu Gly Ser Ile Ser Asn Leu Asn Val
        50                  55                  60

Ser Leu Cys Ala Arg Tyr Pro Glu Lys Arg Phe Val Pro Asp Gly Asn
65                  70                  75                  80

Arg Ile Ser Trp Asp Ser Lys Lys Gly Phe Thr Ile Pro Ser Tyr Met
                85                  90                  95

Ile Ser Tyr Ala Gly Met Val Phe Cys Glu Ala Lys Ile Asn Asp Glu
            100                 105                 110

Ser Tyr Gln Ser Ile Met Tyr Ile Val Val Val Gly Tyr Arg Ile
        115                 120                 125

Tyr Asp Val Asp Pro Ile Glu Gly Arg Gly Gly Gly Gly Asp Pro
    130                 135                 140

Lys Ser Cys Asp Lys Pro His Thr Cys Pro Leu Cys Pro Ala Pro Glu
145                 150                 155                 160

Leu Leu Gly Gly Pro Ser Val Phe Leu Phe Pro Pro Lys Pro Lys Asp
                165                 170                 175

Thr Leu Met Ile Ser Arg Thr Pro Glu Val Thr Cys Val Val Val Asp
            180                 185                 190

Val Ser His Glu Asp Pro Glu Val Lys Phe Asn Trp Tyr Val Asp Gly
        195                 200                 205

Val Glu Val His Asn Ala Lys Thr Lys Pro Arg Glu Glu Gln Tyr Asn
    210                 215                 220

Ser Thr Tyr Arg Val Val Ser Val Leu Thr Val Leu His Gln Asp Trp
225                 230                 235                 240

Leu Asn Gly Lys Glu Tyr Lys Cys Lys Val Ser Asn Lys Ala Leu Pro
                245                 250                 255

Ala Pro Ile Glu Lys Thr Ile Ser Lys Ala Lys Gly Gln Pro Arg Glu
            260                 265                 270

Pro Gln Val Tyr Thr Leu Pro Pro Ser Arg Asp Glu Leu Thr Lys Asn
        275                 280                 285

Gln Val Ser Leu Thr Cys Leu Val Lys Gly Phe Tyr Pro Ser Asp Ile
    290                 295                 300

Ala Val Glu Trp Glu Ser Asn Gly Gln Pro Glu Asn Asn Tyr Lys Ala
305                 310                 315                 320

Thr Pro Pro Val Leu Asp Ser Asp Gly Ser Phe Phe Leu Tyr Ser Lys
                325                 330                 335

Leu Thr Val Asp Lys Ser Arg Trp Gln Gln Gly Asn Val Phe Ser Cys
            340                 345                 350

Ser Val Met His Glu Ala Leu His Asn His Tyr Thr Gln Lys Ser Leu
        355                 360                 365

Ser Leu Ser Pro Gly Lys
    370
```

<210> SEQ ID NO 25
<211> LENGTH: 1143
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-2 J
<220> FEATURE:
<221> NAME/KEY: CDS
<222> LOCATION: (1)..(1143)

<400> SEQUENCE: 25

```
atg ccg ctg ctg cta ctg ctg ccc ctg ctg tgg gca ggg gcc ctg gct      48
Met Pro Leu Leu Leu Leu Leu Pro Leu Leu Trp Ala Gly Ala Leu Ala
1               5                   10                  15 atg gat aag ctt gct agc gtt caa gat tac aga tct cca ttt att gct      96
Met Asp Lys Leu Ala Ser Val Gln Asp Tyr Arg Ser Pro Phe Ile Ala
            20                  25                  30 tct gtt agt gac caa cat gga gtc gtg tac att act gag aac aaa aac     144
Ser Val Ser Asp Gln His Gly Val Val Tyr Ile Thr Glu Asn Lys Asn
        35                  40                  45 aaa act gtg gtg att cca tgt ctc ggg tcc att tca aat ctc aac gtg     192
Lys Thr Val Val Ile Pro Cys Leu Gly Ser Ile Ser Asn Leu Asn Val
    50                  55                  60 tca ctt tgt gca aga tac cca gaa aag aga ttt gtt cct gat ggt aac     240
Ser Leu Cys Ala Arg Tyr Pro Glu Lys Arg Phe Val Pro Asp Gly Asn
65                  70                  75                  80 aga att tcc tgg gac agc aag aag ggc ttt act att ccc agc tac atg     288
Arg Ile Ser Trp Asp Ser Lys Lys Gly Phe Thr Ile Pro Ser Tyr Met
                85                  90                  95 atc agc tat gct ggc atg gtc ttc tgt gaa gca aaa att aat gat gaa     336
Ile Ser Tyr Ala Gly Met Val Phe Cys Glu Ala Lys Ile Asn Asp Glu
            100                 105                 110 agt tac cag tct att atg tac ata gtt gtc gtt gta ggg tat agg att     384
Ser Tyr Gln Ser Ile Met Tyr Ile Val Val Val Gly Tyr Arg Ile
        115                 120                 125 tat gat gtg gtt ctg agt ccg tct cat gat ccc atc gaa ggt cgt ggt     432
Tyr Asp Val Val Leu Ser Pro Ser His Asp Pro Ile Glu Gly Arg Gly
    130                 135                 140 ggt ggt ggt ggt gat ccc aaa tct tgt gac aaa cct cac aca tgc cca     480
Gly Gly Gly Gly Asp Pro Lys Ser Cys Asp Lys Pro His Thr Cys Pro
145                 150                 155                 160 ctg tgc cca gca cct gaa ctc ctg ggg gga ccg tca gtc ttc ctc ttc     528
Leu Cys Pro Ala Pro Glu Leu Leu Gly Gly Pro Ser Val Phe Leu Phe
                165                 170                 175 ccc cca aaa ccc aag gac acc ctc atg atc tcc cgg acc cct gag gtc     576
Pro Pro Lys Pro Lys Asp Thr Leu Met Ile Ser Arg Thr Pro Glu Val
            180                 185                 190 aca tgc gtg gtg gtg gac gtg agc cac gaa gac cct gag gtc aag ttc     624
Thr Cys Val Val Val Asp Val Ser His Glu Asp Pro Glu Val Lys Phe
        195                 200                 205 aac tgg tac gtg gac ggc gtg gag gtg cat aat gcc aag aca aag ccg     672
Asn Trp Tyr Val Asp Gly Val Glu Val His Asn Ala Lys Thr Lys Pro
    210                 215                 220 cgg gag gag cag tac aac agc acg tac cgt gtg gtc agc gtc ctc acc     720
Arg Glu Glu Gln Tyr Asn Ser Thr Tyr Arg Val Val Ser Val Leu Thr
225                 230                 235                 240 gtc ctg cac cag gac tgg ctg aat ggc aag gag tac aag tgc aag gtc     768
Val Leu His Gln Asp Trp Leu Asn Gly Lys Glu Tyr Lys Cys Lys Val
                245                 250                 255
```

-continued

```
tcc aac aaa gcc ctc cca gcc ccc atc gag aaa acc atc tcc aaa gcc    816
Ser Asn Lys Ala Leu Pro Ala Pro Ile Glu Lys Thr Ile Ser Lys Ala
        260                 265                 270 aaa ggg cag ccc cga gaa cca cag gtg tac acc ctg ccc cca tcc cgg    864
Lys Gly Gln Pro Arg Glu Pro Gln Val Tyr Thr Leu Pro Pro Ser Arg
    275                 280                 285 gat gag ctg acc aag aac cag gtc agc ctg acc tgc cta gtc aaa ggc    912
Asp Glu Leu Thr Lys Asn Gln Val Ser Leu Thr Cys Leu Val Lys Gly
290                 295                 300 ttc tat ccc agc gac atc gcc gtg gag tgg gag agc aat ggg cag ccg    960
Phe Tyr Pro Ser Asp Ile Ala Val Glu Trp Glu Ser Asn Gly Gln Pro
305                 310                 315                 320 gag aac aac tac aag gcc acg cct ccc gtg ctg gac tcc gac ggc tcc    1008
Glu Asn Asn Tyr Lys Ala Thr Pro Pro Val Leu Asp Ser Asp Gly Ser
                325                 330                 335 ttc ttc ctc tac agc aag ctc acc gtg gac aag agc agg tgg cag cag    1056
Phe Phe Leu Tyr Ser Lys Leu Thr Val Asp Lys Ser Arg Trp Gln Gln
            340                 345                 350 ggg aac gtc ttc tca tgc tcc gtg atg cat gag gct ctg cac aac cac    1104
Gly Asn Val Phe Ser Cys Ser Val Met His Glu Ala Leu His Asn His
        355                 360                 365 tac acg cag aag agc ctc tcc ctg tct ccg ggt aaa tga                1143
Tyr Thr Gln Lys Ser Leu Ser Leu Ser Pro Gly Lys
    370                 375                 380
```

<210> SEQ ID NO 26
<211> LENGTH: 380
<212> TYPE: PRT
<213> ORGANISM: Artificial sequence
<220> FEATURE:
<223> OTHER INFORMATION: Synthetic polypeptide

<400> SEQUENCE: 26

```
Met Pro Leu Leu Leu Leu Leu Pro Leu Leu Trp Ala Gly Ala Leu Ala
1               5                   10                  15

Met Asp Lys Leu Ala Ser Val Gln Asp Tyr Arg Ser Pro Phe Ile Ala
            20                  25                  30

Ser Val Ser Asp Gln His Gly Val Tyr Ile Thr Glu Asn Lys Asn
        35                  40                  45

Lys Thr Val Val Ile Pro Cys Leu Gly Ser Ile Ser Asn Leu Asn Val
    50                  55                  60

Ser Leu Cys Ala Arg Tyr Pro Glu Lys Arg Phe Val Pro Asp Gly Asn
65                  70                  75                  80

Arg Ile Ser Trp Asp Ser Lys Lys Gly Phe Thr Ile Pro Ser Tyr Met
                85                  90                  95

Ile Ser Tyr Ala Gly Met Val Phe Cys Glu Ala Lys Ile Asn Asp Glu
            100                 105                 110

Ser Tyr Gln Ser Ile Met Tyr Ile Val Val Val Gly Tyr Arg Ile
        115                 120                 125

Tyr Asp Val Val Leu Ser Pro Ser His Asp Pro Ile Glu Gly Arg Gly
    130                 135                 140

Gly Gly Gly Gly Asp Pro Lys Ser Cys Asp Lys Pro His Thr Cys Pro
145                 150                 155                 160

Leu Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
```

```
                 195                 200                 205
Asn Trp Tyr Val Asp Gly Val Glu Val His Asn Ala Lys Thr Lys Pro
    210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
                260                 265                 270

Lys Gly Gln Pro Arg Glu Pro Gln Val Tyr Thr Leu Pro Pro Ser Arg
            275                 280                 285

Asp Glu Leu Thr Lys Asn Gln Val Ser Leu Thr Cys Leu Val Lys Gly
        290                 295                 300

Phe Tyr Pro Ser Asp Ile Ala Val Glu Trp Glu Ser Asn Gly Gln Pro
305                 310                 315                 320

Glu Asn Asn Tyr Lys Ala Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
    370                 375                 380

<210> SEQ ID NO 27
<211> LENGTH: 1170
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-2 K
<220> FEATURE:
<221> NAME/KEY: CDS
<222> LOCATION: (1)..(1170)

<400> SEQUENCE: 27 atg ccg ctg ctg cta ctg ctg ccc ctg ctg tgg gca ggg gcc ctg gct    48
Met Pro Leu Leu Leu Leu Leu Pro Leu Leu Trp Ala Gly Ala Leu Ala
1               5                   10                  15 atg gat aag ctt gct agc gtt caa gat tac aga tct cca ttt att gct    96
Met Asp Lys Leu Ala Ser Val Gln Asp Tyr Arg Ser Pro Phe Ile Ala
            20                  25                  30 tct gtt agt gac caa cat gga gtc gtg tac att act gag aac aaa aac   144
Ser Val Ser Asp Gln His Gly Val Val Tyr Ile Thr Glu Asn Lys Asn
        35                  40                  45 aaa act gtg gtg att cca tgt ctc ggg tcc att tca aat ctc aac gtg   192
Lys Thr Val Val Ile Pro Cys Leu Gly Ser Ile Ser Asn Leu Asn Val
    50                  55                  60 tca ctt tgt gca aga tac cca gaa aag aga ttt gtt cct gat ggt aac   240
Ser Leu Cys Ala Arg Tyr Pro Glu Lys Arg Phe Val Pro Asp Gly Asn
65                  70                  75                  80 aga att tcc tgg gac agc aag aag ggc ttt act att ccc agc tac atg   288
Arg Ile Ser Trp Asp Ser Lys Lys Gly Phe Thr Ile Pro Ser Tyr Met
                85                  90                  95 atc agc tat gct ggc atg gtc ttc tgt gaa gca aaa att aat gat gaa   336
Ile Ser Tyr Ala Gly Met Val Phe Cys Glu Ala Lys Ile Asn Asp Glu
            100                 105                 110
```

```
agt tac cag tct att atg tac ata gtt gtc gtt gta ggg tat agg att      384
Ser Tyr Gln Ser Ile Met Tyr Ile Val Val Val Val Gly Tyr Arg Ile
        115                 120                 125 tat gat gtg gtt ctg agt ccg tct cat gga att gaa cta tct gtt gga      432
Tyr Asp Val Val Leu Ser Pro Ser His Gly Ile Glu Leu Ser Val Gly
    130                 135                 140 gaa aag gat ccc atc gaa ggt cgt ggt ggt ggt ggt gat ccc aaa          480
Glu Lys Asp Pro Ile Glu Gly Arg Gly Gly Gly Gly Asp Pro Lys
145                 150                 155                 160 tct tgt gac aaa cct cac aca tgc cca ctg tgc cca gca cct gaa ctc      528
Ser Cys Asp Lys Pro His Thr Cys Pro Leu Cys Pro Ala Pro Glu Leu
                165                 170                 175 ctg ggg gga ccg tca gtc ttc ctc ttc ccc cca aaa ccc aag gac acc      576
Leu Gly Gly Pro Ser Val Phe Leu Phe Pro Pro Lys Pro Lys Asp Thr
            180                 185                 190 ctc atg atc tcc cgg acc cct gag gtc aca tgc gtg gtg gtg gac gtg      624
Leu Met Ile Ser Arg Thr Pro Glu Val Thr Cys Val Val Val Asp Val
        195                 200                 205 agc cac gaa gac cct gag gtc aag ttc aac tgg tac gtg gac ggc gtg      672
Ser His Glu Asp Pro Glu Val Lys Phe Asn Trp Tyr Val Asp Gly Val
    210                 215                 220 gag gtg cat aat gcc aag aca aag ccg cgg gag gag cag tac aac agc      720
Glu Val His Asn Ala Lys Thr Lys Pro Arg Glu Glu Gln Tyr Asn Ser
225                 230                 235                 240 acg tac cgt gtg gtc agc gtc ctc acc gtc ctg cac cag gac tgg ctg      768
Thr Tyr Arg Val Val Ser Val Leu Thr Val Leu His Gln Asp Trp Leu
                245                 250                 255 aat ggc aag gag tac aag tgc aag gtc tcc aac aaa gcc ctc cca gcc      816
Asn Gly Lys Glu Tyr Lys Cys Lys Val Ser Asn Lys Ala Leu Pro Ala
            260                 265                 270 ccc atc gag aaa acc atc tcc aaa gcc aaa ggg cag ccc cga gaa cca      864
Pro Ile Glu Lys Thr Ile Ser Lys Ala Lys Gly Gln Pro Arg Glu Pro
        275                 280                 285 cag gtg tac acc ctg ccc cca tcc cgg gat gag ctg acc aag aac cag      912
Gln Val Tyr Thr Leu Pro Pro Ser Arg Asp Glu Leu Thr Lys Asn Gln
    290                 295                 300 gtc agc ctg acc tgc cta gtc aaa ggc ttc tat ccc agc gac atc gcc      960
Val Ser Leu Thr Cys Leu Val Lys Gly Phe Tyr Pro Ser Asp Ile Ala
305                 310                 315                 320 gtg gag tgg gag agc aat ggg cag ccg gag aac aac tac aag gcc acg     1008
Val Glu Trp Glu Ser Asn Gly Gln Pro Glu Asn Asn Tyr Lys Ala Thr
                325                 330                 335 cct ccc gtg ctg gac tcc gac ggc tcc ttc ttc ctc tac agc aag ctc     1056
Pro Pro Val Leu Asp Ser Asp Gly Ser Phe Phe Leu Tyr Ser Lys Leu
            340                 345                 350 acc gtg gac aag agc agg tgg cag cag ggg aac gtc ttc tca tgc tcc     1104
Thr Val Asp Lys Ser Arg Trp Gln Gln Gly Asn Val Phe Ser Cys Ser
        355                 360                 365 gtg atg cat gag gct ctg cac aac cac tac acg cag aag agc ctc tcc     1152
Val Met His Glu Ala Leu His Asn His Tyr Thr Gln Lys Ser Leu Ser
    370                 375                 380 ctg tct ccg ggt aaa tga                                             1170
Leu Ser Pro Gly Lys
385

<210> SEQ ID NO 28
<211> LENGTH: 389
<212> TYPE: PRT
<213> ORGANISM: Artificial sequence
<220> FEATURE:
<223> OTHER INFORMATION: Synthetic polypeptide
```

<400> SEQUENCE: 28

```
Met Pro Leu Leu Leu Leu Pro Leu Leu Trp Ala Gly Ala Leu Ala
1               5                   10                  15

Met Asp Lys Leu Ala Ser Val Gln Asp Tyr Arg Ser Pro Phe Ile Ala
            20                  25                  30

Ser Val Ser Asp Gln His Gly Val Val Tyr Ile Thr Glu Asn Lys Asn
        35                  40                  45

Lys Thr Val Val Ile Pro Cys Leu Gly Ser Ile Ser Asn Leu Asn Val
    50                  55                  60

Ser Leu Cys Ala Arg Tyr Pro Glu Lys Arg Phe Val Pro Asp Gly Asn
65                  70                  75                  80

Arg Ile Ser Trp Asp Ser Lys Lys Gly Phe Thr Ile Pro Ser Tyr Met
                85                  90                  95

Ile Ser Tyr Ala Gly Met Val Phe Cys Glu Ala Lys Ile Asn Asp Glu
            100                 105                 110

Ser Tyr Gln Ser Ile Met Tyr Ile Val Val Val Gly Tyr Arg Ile
        115                 120                 125

Tyr Asp Val Val Leu Ser Pro Ser His Gly Ile Glu Leu Ser Val Gly
130                 135                 140

Glu Lys Asp Pro Ile Glu Gly Arg Gly Gly Gly Gly Asp Pro Lys
145                 150                 155                 160

Ser Cys Asp Lys Pro His Thr Cys Pro Leu Cys Pro Ala Pro Glu Leu
                165                 170                 175

Leu Gly Gly Pro Ser Val Phe Leu Phe Pro Pro Lys Pro Lys Asp Thr
            180                 185                 190

Leu Met Ile Ser Arg Thr Pro Glu Val Thr Cys Val Val Val Asp Val
        195                 200                 205

Ser His Glu Asp Pro Glu Val Lys Phe Asn Trp Tyr Val Asp Gly Val
210                 215                 220

Glu Val His Asn Ala Lys Thr Lys Pro Arg Glu Glu Gln Tyr Asn Ser
225                 230                 235                 240

Thr Tyr Arg Val Val Ser Val Leu Thr Val Leu His Gln Asp Trp Leu
                245                 250                 255

Asn Gly Lys Glu Tyr Lys Cys Lys Val Ser Asn Lys Ala Leu Pro Ala
            260                 265                 270

Pro Ile Glu Lys Thr Ile Ser Lys Ala Lys Gly Gln Pro Arg Glu Pro
        275                 280                 285

Gln Val Tyr Thr Leu Pro Pro Ser Arg Asp Glu Leu Thr Lys Asn Gln
    290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Ala Thr
                325                 330                 335

Pro Pro Val Leu Asp Ser Asp Gly Ser Phe Phe Leu Tyr Ser Lys Leu
            340                 345                 350

Thr Val Asp Lys Ser Arg Trp Gln Gln Gly Asn Val Phe Ser Cys Ser
        355                 360                 365

Val Met His Glu Ala Leu His Asn His Tyr Thr Gln Lys Ser Leu Ser
    370                 375                 380

Leu Ser Pro Gly Lys
385
```

```
<210> SEQ ID NO 29
<211> LENGTH: 1116
<212> TYPE: DNA
<213> ORGANISM: Artificial sequence
<220> FEATURE:
<223> OTHER INFORMATION: Synthetic nucleotide
<220> FEATURE:
<221> NAME/KEY: misc_feature
<223> OTHER INFORMATION: R-2 L
<220> FEATURE:
<221> NAME/KEY: CDS
<222> LOCATION: (1)..(1116)

<400> SEQUENCE: 29
```

| atg ccg ctg ctg cta ctg ctg ccc ctg ctg tgg gca ggg gcc ctg gct | 48 |
|---|---|
| Met Pro Leu Leu Leu Leu Leu Pro Leu Leu Trp Ala Gly Ala Leu Ala | |
| 1               5                   10                  15 | |

| atg gat aag ctt gct agc tat agg att tat gat gtg gtt ctg agt ccg | 96 |
|---|---|
| Met Asp Lys Leu Ala Ser Tyr Arg Ile Tyr Asp Val Val Leu Ser Pro | |
|             20                  25                  30 | |

| tct cat gga att gaa cta tct gtt gga gaa aag ctt gtc tta aat tgt | 144 |
|---|---|
| Ser His Gly Ile Glu Leu Ser Val Gly Glu Lys Leu Val Leu Asn Cys | |
|         35                  40                  45 | |

| aca gca aga act gaa cta aat gtg ggg att gac ttc aac tgg gaa tac | 192 |
|---|---|
| Thr Ala Arg Thr Glu Leu Asn Val Gly Ile Asp Phe Asn Trp Glu Tyr | |
|     50                  55                  60 | |

| cct tct tcg aag cat cag cat aag aaa ctt gta aac cga gac cta aaa | 240 |
|---|---|
| Pro Ser Ser Lys His Gln His Lys Lys Leu Val Asn Arg Asp Leu Lys | |
| 65                  70                  75                  80 | |

| acc cag tct ggg agt gag atg aag aaa ttt ttg agc acc tta act ata | 288 |
|---|---|
| Thr Gln Ser Gly Ser Glu Met Lys Lys Phe Leu Ser Thr Leu Thr Ile | |
|             85                  90                  95 | |

| gat ggt gta acc cgg agt gac caa gga ttg tac acc tgt gca gca tcc | 336 |
|---|---|
| Asp Gly Val Thr Arg Ser Asp Gln Gly Leu Tyr Thr Cys Ala Ala Ser | |
|         100                 105                 110 | |

| agt ggg ctg atg acc aag aag aac agc aca ttt gtc agg gtc cat gaa | 384 |
|---|---|
| Ser Gly Leu Met Thr Lys Lys Asn Ser Thr Phe Val Arg Val His Glu | |
|     115                 120                 125 | |

| gat ccc atc gaa ggt cgt ggt ggt ggt ggt ggt gat ccc aaa tct tgt | 432 |
|---|---|
| Asp Pro Ile Glu Gly Arg Gly Gly Gly Gly Gly Asp Pro Lys Ser Cys | |
| 130                 135                 140 | |

| gac aaa cct cac aca tgc cca ctg tgc cca gca cct gaa ctc ctg ggg | 480 |
|---|---|
| Asp Lys Pro His Thr Cys Pro Leu Cys Pro Ala Pro Glu Leu Leu Gly | |
| 145                 150                 155                 160 | |

| gga ccg tca gtc ttc ctc ttc ccc cca aaa ccc aag gac acc ctc atg | 528 |
|---|---|
| Gly Pro Ser Val Phe Leu Phe Pro Pro Lys Pro Lys Asp Thr Leu Met | |
|             165                 170                 175 | |

| atc tcc cgg acc cct gag gtc aca tgc gtg gtg gtg gac gtg agc cac | 576 |
|---|---|
| Ile Ser Arg Thr Pro Glu Val Thr Cys Val Val Val Asp Val Ser His | |
|         180                 185                 190 | |

| gaa gac cct gag gtc aag ttc aac tgg tac gtg gac ggc gtg gag gtg | 624 |
|---|---|
| Glu Asp Pro Glu Val Lys Phe Asn Trp Tyr Val Asp Gly Val Glu Val | |
|     195                 200                 205 | |

| cat aat gcc aag aca aag ccg cgg gag gag cag tac aac agc acg tac | 672 |
|---|---|
| His Asn Ala Lys Thr Lys Pro Arg Glu Glu Gln Tyr Asn Ser Thr Tyr | |
| 210                 215                 220 | |

| cgt gtg gtc agc gtc ctc acc gtc ctg cac cag gac tgg ctg aat ggc | 720 |
|---|---|
| Arg Val Val Ser Val Leu Thr Val Leu His Gln Asp Trp Leu Asn Gly | |
| 225                 230                 235                 240 | |

| aag gag tac aag tgc aag gtc tcc aac aaa gcc ctc cca gcc ccc atc | 768 |
|---|---|
| Lys Glu Tyr Lys Cys Lys Val Ser Asn Lys Ala Leu Pro Ala Pro Ile | |
|             245                 250                 255 | |

```
gag aaa acc atc tcc aaa gcc aaa ggg cag ccc cga gaa cca cag gtg     816
Glu Lys Thr Ile Ser Lys Ala Lys Gly Gln Pro Arg Glu Pro Gln Val
        260                 265                 270 tac acc ctg ccc cca tcc cgg gat gag ctg acc aag aac cag gtc agc     864
Tyr Thr Leu Pro Pro Ser Arg Asp Glu Leu Thr Lys Asn Gln Val Ser
275                 280                 285 ctg acc tgc cta gtc aaa ggc ttc tat ccc agc gac atc gcc gtg gag     912
Leu Thr Cys Leu Val Lys Gly Phe Tyr Pro Ser Asp Ile Ala Val Glu
        290                 295                 300 tgg gag agc aat ggg cag ccg gag aac aac tac aag gcc acg cct ccc     960
Trp Glu Ser Asn Gly Gln Pro Glu Asn Asn Tyr Lys Ala Thr Pro Pro
305                 310                 315                 320 gtg ctg gac tcc gac ggc tcc ttc ttc ctc tac agc aag ctc acc gtg    1008
Val Leu Asp Ser Asp Gly Ser Phe Phe Leu Tyr Ser Lys Leu Thr Val
            325                 330                 335 gac aag agc agg tgg cag cag ggg aac gtc ttc tca tgc tcc gtg atg    1056
Asp Lys Ser Arg Trp Gln Gln Gly Asn Val Phe Ser Cys Ser Val Met
        340                 345                 350 cat gag gct ctg cac aac cac tac acg cag aag agc ctc tcc ctg tct    1104
His Glu Ala Leu His Asn His Tyr Thr Gln Lys Ser Leu Ser Leu Ser
    355                 360                 365 ccg ggt aaa tga                                                     1116
Pro Gly Lys
    370

<210> SEQ ID NO 30
<211> LENGTH: 371
<212> TYPE: PRT
<213> ORGANISM: Artificial sequence
<220> FEATURE:
<223> OTHER INFORMATION: Synthetic polypeptide

<400> SEQUENCE: 30

Met Pro Leu Leu Leu Leu Pro Leu Leu Trp Ala Gly Ala Leu Ala
1               5                   10                  15

Met Asp Lys Leu Ala Ser Tyr Arg Ile Tyr Asp Val Val Leu Ser Pro
                20                  25                  30

Ser His Gly Ile Glu Leu Ser Val Gly Glu Lys Leu Val Leu Asn Cys
            35                  40                  45

Thr Ala Arg Thr Glu Leu Asn Val Gly Ile Asp Phe Asn Trp Glu Tyr
        50                  55                  60

Pro Ser Ser Lys His Gln His Lys Lys Leu Val Asn Arg Asp Leu Lys
65                  70                  75                  80

Thr Gln Ser Gly Ser Glu Met Lys Lys Phe Leu Ser Thr Leu Thr Ile
                85                  90                  95

Asp Gly Val Thr Arg Ser Asp Gln Gly Leu Tyr Thr Cys Ala Ala Ser
            100                 105                 110

Ser Gly Leu Met Thr Lys Lys Asn Ser Thr Phe Val Arg Val His Glu
        115                 120                 125

Asp Pro Ile Glu Gly Arg Gly Gly Gly Gly Asp Pro Lys Ser Cys
    130                 135                 140

Asp Lys Pro His Thr Cys Pro Leu Cys Pro Ala Pro Glu Leu Leu Gly
145                 150                 155                 160

Gly Pro Ser Val Phe Leu Phe Pro Pro Lys Pro Lys Asp Thr Leu Met
                165                 170                 175

Ile Ser Arg Thr Pro Glu Val Thr Cys Val Val Val Asp Val Ser His
            180                 185                 190

Glu Asp Pro Glu Val Lys Phe Asn Trp Tyr Val Asp Gly Val Glu Val
```

```
                195                 200                 205
His Asn Ala Lys Thr Lys Pro Arg Glu Glu Gln Tyr Asn Ser Thr Tyr
    210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Ala Leu Pro Ala Pro Ile
                245                 250                 255

Glu Lys Thr Ile Ser Lys Ala Lys Gly Gln Pro Arg Glu Pro Gln Val
                260                 265                 270

Tyr Thr Leu Pro Pro Ser Arg Asp Glu Leu Thr Lys Asn Gln Val Ser
            275                 280                 285

Leu Thr Cys Leu Val Lys Gly Phe Tyr Pro Ser Asp Ile Ala Val Glu
        290                 295                 300

Trp Glu Ser Asn Gly Gln Pro Glu Asn Asn Tyr Lys Ala Thr Pro Pro
305                 310                 315                 320

Val Leu Asp Ser Asp Gly Ser Phe Phe Leu Tyr Ser Lys Leu Thr Val
                325                 330                 335

Asp Lys Ser Arg Trp Gln Gln Gly Asn Val Phe Ser Cys Ser Val Met
                340                 345                 350

His Glu Ala Leu His Asn His Tyr Thr Gln Lys Ser Leu Ser Leu Ser
            355                 360                 365

Pro Gly Lys
    370

<210> SEQ ID NO 31
<211> LENGTH: 1368
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-3 A
<220> FEATURE:
<221> NAME/KEY: CDS
<222> LOCATION: (1)..(1368)

<400> SEQUENCE: 31 atg ccg ctg ctg cta ctg ctg ccc ctg ctg tgg gca ggg gcc ctg gct     48
Met Pro Leu Leu Leu Leu Leu Pro Leu Leu Trp Ala Gly Ala Leu Ala
1               5                   10                  15 atg gat aag ctt cca ttc atc aac aag cct gac acg ctc ttg gtc aac     96
Met Asp Lys Leu Pro Phe Ile Asn Lys Pro Asp Thr Leu Leu Val Asn
            20                  25                  30 agg aag gac gcc atg tgg gtg ccc tgt ctg gtg tcc atc ccc ggc ctc    144
Arg Lys Asp Ala Met Trp Val Pro Cys Leu Val Ser Ile Pro Gly Leu
        35                  40                  45 aat gtc acg ctg cgc tcg caa agc tcg gtg ctg tgg cca gac ggg cag    192
Asn Val Thr Leu Arg Ser Gln Ser Ser Val Leu Trp Pro Asp Gly Gln
    50                  55                  60 gag gtg gtg tgg gat gac cgg cgg ggc atg ctc gtg tcc acg cca ctg    240
Glu Val Val Trp Asp Asp Arg Arg Gly Met Leu Val Ser Thr Pro Leu
65                  70                  75                  80 ctg cac gat gcc ctg tac ctg cag tgc gag acc acc tgg gga gac cag    288
Leu His Asp Ala Leu Tyr Leu Gln Cys Glu Thr Thr Trp Gly Asp Gln
                85                  90                  95 gac ttc ctt tcc aac ccc ttc ctg gtg cac atc aca ggc aac gag ctc    336
Asp Phe Leu Ser Asn Pro Phe Leu Val His Ile Thr Gly Asn Glu Leu
            100                 105                 110
```

```
tat gac atc cag ctg ttg ccc agg aag tcg ctg gag ctg ctg gta ggg     384
Tyr Asp Ile Gln Leu Leu Pro Arg Lys Ser Leu Glu Leu Leu Val Gly
        115                 120                 125 gag aag ctg gtc ctg aac tgc acc gtg tgg gct gag ttt aac tca ggt     432
Glu Lys Leu Val Leu Asn Cys Thr Val Trp Ala Glu Phe Asn Ser Gly
    130                 135                 140 gtc acc ttt gac tgg gac tac cca ggg aag cag gca gag cgg ggt aag     480
Val Thr Phe Asp Trp Asp Tyr Pro Gly Lys Gln Ala Glu Arg Gly Lys
145                 150                 155                 160 tgg gtg ccc gag cga cgc tcc cag cag acc cac aca gaa ctc tcc agc     528
Trp Val Pro Glu Arg Arg Ser Gln Gln Thr His Thr Glu Leu Ser Ser
                165                 170                 175 atc ctg acc atc cac aac gtg agc cag cac gac ctg ggc tcg tat gtg     576
Ile Leu Thr Ile His Asn Val Ser Gln His Asp Leu Gly Ser Tyr Val
            180                 185                 190 tgc aag gcc aac aac ggc atc cag cga ttt cgg gag agc acc gag gtc     624
Cys Lys Ala Asn Asn Gly Ile Gln Arg Phe Arg Glu Ser Thr Glu Val
        195                 200                 205 att gtg cat gag gat ccc atc gaa ggt cgt ggt ggt ggt ggt ggt gat     672
Ile Val His Glu Asp Pro Ile Glu Gly Arg Gly Gly Gly Gly Gly Asp
    210                 215                 220 ccc aaa tct tgt gac aaa cct cac aca tgc cca ctg tgc cca gca cct     720
Pro Lys Ser Cys Asp Lys Pro His Thr Cys Pro Leu Cys Pro Ala Pro
225                 230                 235                 240 gaa ctc ctg ggg gga ccg tca gtc ttc ctc ttc ccc cca aaa ccc aag     768
Glu Leu Leu Gly Gly Pro Ser Val Phe Leu Phe Pro Pro Lys Pro Lys
                245                 250                 255 gac acc ctc atg atc tcc cgg acc cct gag gtc aca tgc gtg gtg gtg     816
Asp Thr Leu Met Ile Ser Arg Thr Pro Glu Val Thr Cys Val Val Val
            260                 265                 270 gac gtg agc cac gaa gac cct gag gtc aag ttc aac tgg tac gtg gac     864
Asp Val Ser His Glu Asp Pro Glu Val Lys Phe Asn Trp Tyr Val Asp
        275                 280                 285 ggc gtg gag gtg cat aat gcc aag aca aag ccg cgg gag gag cag tac     912
Gly Val Glu Val His Asn Ala Lys Thr Lys Pro Arg Glu Glu Gln Tyr
    290                 295                 300 aac agc acg tac cgt gtg gtc agc gtc ctc acc gtc ctg cac cag gac     960
Asn Ser Thr Tyr Arg Val Val Ser Val Leu Thr Val Leu His Gln Asp
305                 310                 315                 320 tgg ctg aat ggc aag gag tac aag tgc aag gtc tcc aac aaa gcc ctc    1008
Trp Leu Asn Gly Lys Glu Tyr Lys Cys Lys Val Ser Asn Lys Ala Leu
                325                 330                 335 cca gcc ccc atc gag aaa acc atc tcc aaa gcc aaa ggg cag ccc cga    1056
Pro Ala Pro Ile Glu Lys Thr Ile Ser Lys Ala Lys Gly Gln Pro Arg
            340                 345                 350 gaa cca cag gtg tac acc ctg ccc cca tcc cgg gat gag ctg acc aag    1104
Glu Pro Gln Val Tyr Thr Leu Pro Pro Ser Arg Asp Glu Leu Thr Lys
        355                 360                 365 aac cag gtc agc ctg acc tgc cta gtc aaa ggc ttc tat ccc agc gac    1152
Asn Gln Val Ser Leu Thr Cys Leu Val Lys Gly Phe Tyr Pro Ser Asp
    370                 375                 380 atc gcc gtg gag tgg gag agc aat ggg cag ccg gag aac aac tac aag    1200
Ile Ala Val Glu Trp Glu Ser Asn Gly Gln Pro Glu Asn Asn Tyr Lys
385                 390                 395                 400 gcc acg cct ccc gtg ctg gac tcc gac ggc tcc ttc ttc ctc tac agc    1248
Ala Thr Pro Pro Val Leu Asp Ser Asp Gly Ser Phe Phe Leu Tyr Ser
                405                 410                 415 aag ctc acc gtg gac aag agc agg tgg cag cag ggg aac gtc ttc tca    1296
Lys Leu Thr Val Asp Lys Ser Arg Trp Gln Gln Gly Asn Val Phe Ser
            420                 425                 430
```

```
tgc tcc gtg atg cat gag gct ctg cac aac cac tac acg cag aag agc      1344
Cys Ser Val Met His Glu Ala Leu His Asn His Tyr Thr Gln Lys Ser
        435                 440                 445 ctc tcc ctg tct ccg ggt aaa tga                                      1368
Leu Ser Leu Ser Pro Gly Lys
        450                 455

<210> SEQ ID NO 32
<211> LENGTH: 455
<212> TYPE: PRT
<213> ORGANISM: Artificial sequence
<220> FEATURE:
<223> OTHER INFORMATION: Synthetic polypeptide

<400> SEQUENCE: 32

Met Pro Leu Leu Leu Leu Pro Leu Leu Trp Ala Gly Ala Leu Ala
1               5                   10                  15

Met Asp Lys Leu Pro Phe Ile Asn Lys Pro Asp Thr Leu Leu Val Asn
                20                  25                  30

Arg Lys Asp Ala Met Trp Val Pro Cys Leu Val Ser Ile Pro Gly Leu
        35                  40                  45

Asn Val Thr Leu Arg Ser Gln Ser Ser Val Leu Trp Pro Asp Gly Gln
    50                  55                  60

Glu Val Val Trp Asp Asp Arg Arg Gly Met Leu Val Ser Thr Pro Leu
65                  70                  75                  80

Leu His Asp Ala Leu Tyr Leu Gln Cys Glu Thr Thr Trp Gly Asp Gln
                85                  90                  95

Asp Phe Leu Ser Asn Pro Phe Leu Val His Ile Thr Gly Asn Glu Leu
            100                 105                 110

Tyr Asp Ile Gln Leu Leu Pro Arg Lys Ser Leu Glu Leu Leu Val Gly
        115                 120                 125

Glu Lys Leu Val Leu Asn Cys Thr Val Trp Ala Glu Phe Asn Ser Gly
    130                 135                 140

Val Thr Phe Asp Trp Asp Tyr Pro Gly Lys Gln Ala Glu Arg Gly Lys
145                 150                 155                 160

Trp Val Pro Glu Arg Arg Ser Gln Gln Thr His Thr Glu Leu Ser Ser
                165                 170                 175

Ile Leu Thr Ile His Asn Val Ser Gln His Asp Leu Gly Ser Tyr Val
            180                 185                 190

Cys Lys Ala Asn Asn Gly Ile Gln Arg Phe Arg Glu Ser Thr Glu Val
        195                 200                 205

Ile Val His Glu Asp Pro Ile Glu Gly Arg Gly Gly Gly Gly Asp
    210                 215                 220

Pro Lys Ser Cys Asp Lys Pro His Thr Cys Pro Leu Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320
```

```
Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Ala Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
            450                 455

<210> SEQ ID NO 33
<211> LENGTH: 1059
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-3 B
<220> FEATURE:
<221> NAME/KEY: CDS
<222> LOCATION: (1)..(1059)

<400> SEQUENCE: 33 atg ccg ctg ctg cta ctg ctg ccc ctg ctg tgg gca ggg gcc ctg gct    48
Met Pro Leu Leu Leu Leu Leu Pro Leu Leu Trp Ala Gly Ala Leu Ala
1               5                   10                  15 atg gat aag ctt cca ttc atc aac aag cct gac acg ctc ttg gtc aac    96
Met Asp Lys Leu Pro Phe Ile Asn Lys Pro Asp Thr Leu Leu Val Asn
                20                  25                  30 agg aag gac gcc atg tgg gtg ccc tgt ctg gtg tcc atc ccc ggc ctc   144
Arg Lys Asp Ala Met Trp Val Pro Cys Leu Val Ser Ile Pro Gly Leu
            35                  40                  45 aat gtc acg ctg cgc tcg caa agc tcg gtg ctg tgg cca gac ggg cag   192
Asn Val Thr Leu Arg Ser Gln Ser Ser Val Leu Trp Pro Asp Gly Gln
        50                  55                  60 gag gtg gtg tgg gat gac cgg cgg ggc atg ctc gtg tcc acg cca ctg   240
Glu Val Val Trp Asp Asp Arg Arg Gly Met Leu Val Ser Thr Pro Leu
65                  70                  75                  80 ctg cac gat gcc ctg tac ctg cag tgc gag acc acc tgg gga gac cag   288
Leu His Asp Ala Leu Tyr Leu Gln Cys Glu Thr Thr Trp Gly Asp Gln
                85                  90                  95 gac ttc ctt tcc aac ccc ttc ctg gtg cac atc aca ggg gat ccc atc   336
Asp Phe Leu Ser Asn Pro Phe Leu Val His Ile Thr Gly Asp Pro Ile
            100                 105                 110 gaa ggt cgt ggt ggt ggt ggt ggt gat ccc aaa tct tgt gac aaa cct   384
Glu Gly Arg Gly Gly Gly Gly Gly Asp Pro Lys Ser Cys Asp Lys Pro
        115                 120                 125 cac aca tgc cca ctg tgc cca gca cct gaa ctc ctg ggg gga ccg tca   432
His Thr Cys Pro Leu Cys Pro Ala Pro Glu Leu Leu Gly Gly Pro Ser
    130                 135                 140
```

```
gtc ttc ctc ttc ccc cca aaa ccc aag gac acc ctc atg atc tcc cgg      480
Val Phe Leu Phe Pro Pro Lys Pro Lys Asp Thr Leu Met Ile Ser Arg
145                 150                 155                 160 acc cct gag gtc aca tgc gtg gtg gtg gac gtg agc cac gaa gac cct      528
Thr Pro Glu Val Thr Cys Val Val Val Asp Val Ser His Glu Asp Pro
                165                 170                 175 gag gtc aag ttc aac tgg tac gtg gac ggc gtg gag gtg cat aat gcc      576
Glu Val Lys Phe Asn Trp Tyr Val Asp Gly Val Glu Val His Asn Ala
            180                 185                 190 aag aca aag ccg cgg gag gag cag tac aac agc acg tac cgt gtg gtc      624
Lys Thr Lys Pro Arg Glu Glu Gln Tyr Asn Ser Thr Tyr Arg Val Val
        195                 200                 205 agc gtc ctc acc gtc ctg cac cag gac tgg ctg aat ggc aag gag tac      672
Ser Val Leu Thr Val Leu His Gln Asp Trp Leu Asn Gly Lys Glu Tyr
    210                 215                 220 aag tgc aag gtc tcc aac aaa gcc ctc cca gcc ccc atc gag aaa acc      720
Lys Cys Lys Val Ser Asn Lys Ala Leu Pro Ala Pro Ile Glu Lys Thr
225                 230                 235                 240 atc tcc aaa gcc aaa ggg cag ccc cga gaa cca cag gtg tac acc ctg      768
Ile Ser Lys Ala Lys Gly Gln Pro Arg Glu Pro Gln Val Tyr Thr Leu
                245                 250                 255 ccc cca tcc cgg gat gag ctg acc aag aac cag gtc agc ctg acc tgc      816
Pro Pro Ser Arg Asp Glu Leu Thr Lys Asn Gln Val Ser Leu Thr Cys
            260                 265                 270 cta gtc aaa ggc ttc tat ccc agc gac atc gcc gtg gag tgg gag agc      864
Leu Val Lys Gly Phe Tyr Pro Ser Asp Ile Ala Val Glu Trp Glu Ser
        275                 280                 285 aat ggg cag ccg gag aac aac tac aag gcc acg cct ccc gtg ctg gac      912
Asn Gly Gln Pro Glu Asn Asn Tyr Lys Ala Thr Pro Pro Val Leu Asp
    290                 295                 300 tcc gac ggc tcc ttc ttc ctc tac agc aag ctc acc gtg gac aag agc      960
Ser Asp Gly Ser Phe Phe Leu Tyr Ser Lys Leu Thr Val Asp Lys Ser
305                 310                 315                 320 agg tgg cag cag ggg aac gtc ttc tca tgc tcc gtg atg cat gag gct     1008
Arg Trp Gln Gln Gly Asn Val Phe Ser Cys Ser Val Met His Glu Ala
                325                 330                 335 ctg cac aac cac tac acg cag aag agc ctc tcc ctg tct ccg ggt aaa     1056
Leu His Asn His Tyr Thr Gln Lys Ser Leu Ser Leu Ser Pro Gly Lys
            340                 345                 350 tga                                                                  1059
```

<210> SEQ ID NO 34
<211> LENGTH: 352
<212> TYPE: PRT
<213> ORGANISM: Artificial sequence
<220> FEATURE:
<223> OTHER INFORMATION: Synthetic polypeptide

<400> SEQUENCE: 34

Met Pro Leu Leu Leu Leu Leu Pro Leu Leu Trp Ala Gly Ala Leu Ala
1               5                   10                  15

Met Asp Lys Leu Pro Phe Ile Asn Lys Pro Asp Thr Leu Leu Val Asn
            20                  25                  30

Arg Lys Asp Ala Met Trp Val Pro Cys Leu Val Ser Ile Pro Gly Leu
        35                  40                  45

Asn Val Thr Leu Arg Ser Gln Ser Ser Val Leu Trp Pro Asp Gly Gln
    50                  55                  60

Glu Val Val Trp Asp Asp Arg Arg Gly Met Leu Val Ser Thr Pro Leu
65                  70                  75                  80

```
Leu His Asp Ala Leu Tyr Leu Gln Cys Glu Thr Thr Trp Gly Asp Gln
            85                  90                  95

Asp Phe Leu Ser Asn Pro Phe Leu Val His Ile Thr Gly Asp Pro Ile
            100                 105                 110

Glu Gly Arg Gly Gly Gly Gly Asp Pro Lys Ser Cys Asp Lys Pro
            115                 120                 125

His Thr Cys Pro Leu Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
    195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Asp Glu Leu Thr Lys Asn Gln Val Ser Leu Thr Cys
            260                 265                 270

Leu Val Lys Gly Phe Tyr Pro Ser Asp Ile Ala Val Glu Trp Ser
    275                 280                 285

Asn Gly Gln Pro Glu Asn Asn Tyr Lys Ala Thr Pro Pro Val Leu Asp
290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350
```

<210> SEQ ID NO 35
<211> LENGTH: 1422
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-3 C
<220> FEATURE:
<221> NAME/KEY: CDS
<222> LOCATION: (1)..(1422)

<400> SEQUENCE: 35

```
atg cag cgg ggc gcc gcg ctg tgc ctg cga ctg tgg ctc tgc ctg gga      48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg      96
Leu Leu Asp Gly Leu Val Ser Gly Tyr Ser Met Thr Pro Pro Thr Leu
            20                  25                  30 aac atc acg gag gag tca cac gtc atc gac acc ggt gac agc ctg tcc     144
Asn Ile Thr Glu Glu Ser His Val Ile Asp Thr Gly Asp Ser Leu Ser
        35                  40                  45
```

-continued

| | | |
|---|---|---|
| atc tcc tgc agg gga cag cac ccc ctc gag tgg gct tgg cca gga gct<br>Ile Ser Cys Arg Gly Gln His Pro Leu Glu Trp Ala Trp Pro Gly Ala<br>50              55                  60 | 192 | |
| cag gag gcg cca gcc acc gga gac aag gac agc gag gac acg ggg gtg<br>Gln Glu Ala Pro Ala Thr Gly Asp Lys Asp Ser Glu Asp Thr Gly Val<br>65              70                  75                  80 | 240 | |
| gtg cga gac tgc gag ggc aca gac gcc agg ccc tac tgc aag gtg ttg<br>Val Arg Asp Cys Glu Gly Thr Asp Ala Arg Pro Tyr Cys Lys Val Leu<br>                    85                  90                  95 | 288 | |
| ctg ctg cac gag gta cat gcc aac gac aca ggc agc tac gtc tgc tac<br>Leu Leu His Glu Val His Ala Asn Asp Thr Gly Ser Tyr Val Cys Tyr<br>                    100                 105                 110 | 336 | |
| tac aag tac atc aag gca cgc atc gag ggc acc acg gcc gcc agc tcc<br>Tyr Lys Tyr Ile Lys Ala Arg Ile Glu Gly Thr Thr Ala Ala Ser Ser<br>            115                 120                 125 | 384 | |
| tac gtg ttc gtg aga gac ttt gag cag cca ttc atc aac aag cct gac<br>Tyr Val Phe Val Arg Asp Phe Glu Gln Pro Phe Ile Asn Lys Pro Asp<br>130                 135                 140 | 432 | |
| acg ctc ttg gtc aac agg aag gac gcc atg tgg gtg ccc tgt ctg gtg<br>Thr Leu Leu Val Asn Arg Lys Asp Ala Met Trp Val Pro Cys Leu Val<br>145                 150                 155                 160 | 480 | |
| tcc atc ccc ggc ctc aat gtc acg ctg cgc tcg caa agc tcg gtg ctg<br>Ser Ile Pro Gly Leu Asn Val Thr Leu Arg Ser Gln Ser Ser Val Leu<br>                    165                 170                 175 | 528 | |
| tgg cca gac ggg cag gag gtg gtg tgg gat gac cgg cgg ggc atg ctc<br>Trp Pro Asp Gly Gln Glu Val Val Trp Asp Asp Arg Arg Gly Met Leu<br>                    180                 185                 190 | 576 | |
| gtg tcc acg cca ctg ctg cac gat gcc ctg tac ctg cag tgc gag acc<br>Val Ser Thr Pro Leu Leu His Asp Ala Leu Tyr Leu Gln Cys Glu Thr<br>            195                 200                 205 | 624 | |
| acc tgg gga gac cag gac ttc ctt tcc aac ccc ttc ctg gtg cac atc<br>Thr Trp Gly Asp Gln Asp Phe Leu Ser Asn Pro Phe Leu Val His Ile<br>210                 215                 220 | 672 | |
| aca ggc aac gag ctc gcg gat ccc atc gaa ggt cgt ggt ggt ggt ggt<br>Thr Gly Asn Glu Leu Ala Asp Pro Ile Glu Gly Arg Gly Gly Gly Gly<br>225                 230                 235                 240 | 720 | |
| ggt gat ccc aaa tct tgt gac aaa cct cac aca tgc cca ctg tgc cca<br>Gly Asp Pro Lys Ser Cys Asp Lys Pro His Thr Cys Pro Leu Cys Pro<br>                    245                 250                 255 | 768 | |
| gca cct gaa ctc ctg ggg gga ccg tca gtc ttc ctc ttc ccc cca aaa<br>Ala Pro Glu Leu Leu Gly Gly Pro Ser Val Phe Leu Phe Pro Pro Lys<br>                    260                 265                 270 | 816 | |
| ccc aag gac acc ctc atg atc tcc cgg acc cct gag gtc aca tgc gtg<br>Pro Lys Asp Thr Leu Met Ile Ser Arg Thr Pro Glu Val Thr Cys Val<br>            275                 280                 285 | 864 | |
| gtg gtg gac gtg agc cac gaa gac cct gag gtc aag ttc aac tgg tac<br>Val Val Asp Val Ser His Glu Asp Pro Glu Val Lys Phe Asn Trp Tyr<br>290                 295                 300 | 912 | |
| gtg gac ggc gtg gag gtg cat aat gcc aag aca aag ccg cgg gag gag<br>Val Asp Gly Val Glu Val His Asn Ala Lys Thr Lys Pro Arg Glu Glu<br>305                 310                 315                 320 | 960 | |
| cag tac aac agc acg tac cgt gtg gtc agc gtc ctc acc gtc ctg cac<br>Gln Tyr Asn Ser Thr Tyr Arg Val Val Ser Val Leu Thr Val Leu His<br>                    325                 330                 335 | 1008 | |
| cag gac tgg ctg aat ggc aag gag tac aag tgc aag gtc tcc aac aaa<br>Gln Asp Trp Leu Asn Gly Lys Glu Tyr Lys Cys Lys Val Ser Asn Lys<br>                    340                 345                 350 | 1056 | |
| gcc ctc cca gcc ccc atc gag aaa acc atc tcc aaa gcc aaa ggg cag<br>Ala Leu Pro Ala Pro Ile Glu Lys Thr Ile Ser Lys Ala Lys Gly Gln<br>            355                 360                 365 | 1104 | |

-continued

```
ccc cga gaa cca cag gtg tac acc ctg ccc cca tcc cgg gat gag ctg    1152
Pro Arg Glu Pro Gln Val Tyr Thr Leu Pro Pro Ser Arg Asp Glu Leu
    370                 375                 380 acc aag aac cag gtc agc ctg acc tgc cta gtc aaa ggc ttc tat ccc    1200
Thr Lys Asn Gln Val Ser Leu Thr Cys Leu Val Lys Gly Phe Tyr Pro
385                 390                 395                 400 agc gac atc gcc gtg gag tgg gag agc aat ggg cag ccg gag aac aac    1248
Ser Asp Ile Ala Val Glu Trp Glu Ser Asn Gly Gln Pro Glu Asn Asn
                405                 410                 415 tac aag gcc acg cct ccc gtg ctg gac tcc gac ggc tcc ttc ttc ctc    1296
Tyr Lys Ala Thr Pro Pro Val Leu Asp Ser Asp Gly Ser Phe Phe Leu
            420                 425                 430 tac agc aag ctc acc gtg gac aag agc agg tgg cag cag ggg aac gtc    1344
Tyr Ser Lys Leu Thr Val Asp Lys Ser Arg Trp Gln Gln Gly Asn Val
        435                 440                 445 ttc tca tgc tcc gtg atg cat gag gct ctg cac aac cac tac acg cag    1392
Phe Ser Cys Ser Val Met His Glu Ala Leu His Asn His Tyr Thr Gln
    450                 455                 460 aag agc ctc tcc ctg tct ccg ggt aaa tga                            1422
Lys Ser Leu Ser Leu Ser Pro Gly Lys
465                 470
```

<210> SEQ ID NO 36
<211> LENGTH: 473
<212> TYPE: PRT
<213> ORGANISM: Artificial sequence
<220> FEATURE:
<223> OTHER INFORMATION: Synthetic polypeptide

<400> SEQUENCE: 36

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
```

```
            210                 215                 220
Thr Gly Asn Glu Leu Ala Asp Pro Ile Glu Gly Arg Gly Gly Gly
225                 230                 235                 240

Gly Asp Pro Lys Ser Cys Asp Lys Pro His Thr Cys Pro Leu Cys Pro
                245                 250                 255

Ala Pro Glu Leu Leu Gly Gly Pro Ser Val Phe Leu Phe Pro Pro Lys
                260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
                340                 345                 350

Ala Leu Pro Ala Pro Ile Glu Lys Thr Ile Ser Lys Ala Lys Gly Gln
                355                 360                 365

Pro Arg Glu Pro Gln Val Tyr Thr Leu Pro Pro Ser Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Ala Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
            450                 455                 460

Lys Ser Leu Ser Leu Ser Pro Gly Lys
465                 470

<210> SEQ ID NO 37
<211> LENGTH: 1410
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-3 D
<220> FEATURE:
<221> NAME/KEY: CDS
<222> LOCATION: (1)..(1410)

<400> SEQUENCE: 37 atg cag cgg ggc gcc gcg ctg tgc ctg cga ctg tgg ctc tgc ctg gga      48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccg acc ttg          96
Leu Leu Asp Gly Leu Val Ser Gly Tyr Ser Met Thr Pro Thr Leu
            20                  25                  30 aac atc acg gag gag tca cac gtc atc gac acc ggt gac agc ctg tcc     144
Asn Ile Thr Glu Glu Ser His Val Ile Asp Thr Gly Asp Ser Leu Ser
        35                  40                  45 atc tcc tgc agg gga cag cac ccc ctc gag tgg gct tgg cca gga gct     192
```

-continued

```
Ile Ser Cys Arg Gly Gln His Pro Leu Glu Trp Ala Trp Pro Gly Ala
 50                  55                  60 cag gag gcg cca gcc acc gga gac aag gac agc gag gac acg ggg gtg      240
Gln Glu Ala Pro Ala Thr Gly Asp Lys Asp Ser Glu Asp Thr Gly Val
 65                  70                  75                  80 gtg cga gac tgc gag ggc aca gac gcc agg ccc tac tgc aag gtg ttg      288
Val Arg Asp Cys Glu Gly Thr Asp Ala Arg Pro Tyr Cys Lys Val Leu
                     85                  90                  95 ctg ctg cac gag gta cat gcc aac gac aca ggc agc tac gtc tgc tac      336
Leu Leu His Glu Val His Ala Asn Asp Thr Gly Ser Tyr Val Cys Tyr
                100                 105                 110 tac aag tac atc aag gca cgc atc gag ggc acc acg gcc gcc agc tcc      384
Tyr Lys Tyr Ile Lys Ala Arg Ile Glu Gly Thr Thr Ala Ala Ser Ser
            115                 120                 125 tac gtg ttc gtg aga gac ttt gag cag cca ttc atc aac aag cct gac      432
Tyr Val Phe Val Arg Asp Phe Glu Gln Pro Phe Ile Asn Lys Pro Asp
130                 135                 140 acg ctc ttg gtc aac agg aag gac gcc atg tgg gtg ccc tgt ctg gtg      480
Thr Leu Leu Val Asn Arg Lys Asp Ala Met Trp Val Pro Cys Leu Val
145                 150                 155                 160 tcc atc ccc ggc ctc aat gtc acg ctg cgc tcg caa agc tcg gtg ctg      528
Ser Ile Pro Gly Leu Asn Val Thr Leu Arg Ser Gln Ser Ser Val Leu
                    165                 170                 175 tgg cca gac ggg cag gag gtg gtg tgg gat gac cgg cgg ggc atg ctc      576
Trp Pro Asp Gly Gln Glu Val Val Trp Asp Asp Arg Arg Gly Met Leu
                180                 185                 190 gtg tcc acg cca ctg ctg cac gat gcc ctg tac ctg cag tgc gag acc      624
Val Ser Thr Pro Leu Leu His Asp Ala Leu Tyr Leu Gln Cys Glu Thr
            195                 200                 205 acc tgg gga gac cag gac ttc ctt tcc aac ccc ttc ctg gtg cac atc      672
Thr Trp Gly Asp Gln Asp Phe Leu Ser Asn Pro Phe Leu Val His Ile
210                 215                 220 aca ggg gat ccc atc gaa ggt cgt ggt ggt ggt ggt gat ccc aaa          720
Thr Gly Asp Pro Ile Glu Gly Arg Gly Gly Gly Gly Asp Pro Lys
225                 230                 235                 240 tct tgt gac aaa cct cac aca tgc cca ctg tgc cca gca cct gaa ctc      768
Ser Cys Asp Lys Pro His Thr Cys Pro Leu Cys Pro Ala Pro Glu Leu
                    245                 250                 255 ctg ggg gga ccg tca gtc ttc ctc ttc ccc cca aaa ccc aag gac acc      816
Leu Gly Gly Pro Ser Val Phe Leu Phe Pro Pro Lys Pro Lys Asp Thr
                260                 265                 270 ctc atg atc tcc cgg acc cct gag gtc aca tgc gtg gtg gtg gac gtg      864
Leu Met Ile Ser Arg Thr Pro Glu Val Thr Cys Val Val Val Asp Val
            275                 280                 285 agc cac gaa gac cct gag gtc aag ttc aac tgg tac gtg gac ggc gtg      912
Ser His Glu Asp Pro Glu Val Lys Phe Asn Trp Tyr Val Asp Gly Val
290                 295                 300 gag gtg cat aat gcc aag aca aag ccg cgg gag gag cag tac aac agc      960
Glu Val His Asn Ala Lys Thr Lys Pro Arg Glu Glu Gln Tyr Asn Ser
305                 310                 315                 320 acg tac cgt gtg gtc agc gtc ctc acc gtc ctg cac cag gac tgg ctg     1008
Thr Tyr Arg Val Val Ser Val Leu Thr Val Leu His Gln Asp Trp Leu
                    325                 330                 335 aat ggc aag gag tac aag tgc aag gtc tcc aac aaa gcc ctc cca gcc     1056
Asn Gly Lys Glu Tyr Lys Cys Lys Val Ser Asn Lys Ala Leu Pro Ala
                340                 345                 350 ccc atc gag aaa acc atc tcc aaa gcc aaa ggg cag ccc cga gaa cca     1104
Pro Ile Glu Lys Thr Ile Ser Lys Ala Lys Gly Gln Pro Arg Glu Pro
            355                 360                 365
```

```
cag gtg tac acc ctg ccc cca tcc cgg gat gag ctg acc aag aac cag      1152
Gln Val Tyr Thr Leu Pro Pro Ser Arg Asp Glu Leu Thr Lys Asn Gln
    370                 375                 380 gtc agc ctg acc tgc cta gtc aaa ggc ttc tat ccc agc gac atc gcc      1200
Val Ser Leu Thr Cys Leu Val Lys Gly Phe Tyr Pro Ser Asp Ile Ala
385                 390                 395                 400 gtg gag tgg gag agc aat ggg cag ccg gag aac aac tac aag gcc acg      1248
Val Glu Trp Glu Ser Asn Gly Gln Pro Glu Asn Asn Tyr Lys Ala Thr
                405                 410                 415 cct ccc gtg ctg gac tcc gac ggc tcc ttc ttc ctc tac agc aag ctc      1296
Pro Pro Val Leu Asp Ser Asp Gly Ser Phe Phe Leu Tyr Ser Lys Leu
            420                 425                 430 acc gtg gac aag agc agg tgg cag cag ggg aac gtc ttc tca tgc tcc      1344
Thr Val Asp Lys Ser Arg Trp Gln Gln Gly Asn Val Phe Ser Cys Ser
        435                 440                 445 gtg atg cat gag gct ctg cac aac cac tac acg cag aag agc ctc tcc      1392
Val Met His Glu Ala Leu His Asn His Tyr Thr Gln Lys Ser Leu Ser
450                 455                 460 ctg tct ccg ggt aaa tga                                              1410
Leu Ser Pro Gly Lys
465

<210> SEQ ID NO 38
<211> LENGTH: 469
<212> TYPE: PRT
<213> ORGANISM: Artificial sequence
<220> FEATURE:
<223> OTHER INFORMATION: Synthetic polypeptide

<400> SEQUENCE: 38

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
    210                 215                 220
```

```
Thr Gly Asp Pro Ile Glu Gly Arg Gly Gly Gly Asp Pro Lys
225                 230                 235                 240

Ser Cys Asp Lys Pro His Thr Cys Pro Leu Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Ala Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
    450                 455                 460

Leu Ser Pro Gly Lys
465

<210> SEQ ID NO 39
<211> LENGTH: 1404
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-3 E
<220> FEATURE:
<221> NAME/KEY: CDS
<222> LOCATION: (1)..(1404)

<400> SEQUENCE: 39 atg cag cgg ggc gcc gcg ctg tgc ctg cga ctg tgg ctc tgc ctg gga       48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg       96
Leu Leu Asp Gly Leu Val Ser Gly Tyr Ser Met Thr Pro Pro Thr Leu
            20                  25                  30 aac atc acg gag gag tca cac gtc atc gac acc ggt gac agc ctg tcc      144
Asn Ile Thr Glu Glu Ser His Val Ile Asp Thr Gly Asp Ser Leu Ser
        35                  40                  45 atc tcc tgc agg gga cag cac ccc ctc gag tgg gct tgg cca gga gct      192
Ile Ser Cys Arg Gly Gln His Pro Leu Glu Trp Ala Trp Pro Gly Ala
```

-continued

```
       50                  55                  60
cag gag gcg cca gcc acc gga gac aag gac agc gag gac acg ggg gtg        240
Gln Glu Ala Pro Ala Thr Gly Asp Lys Asp Ser Glu Asp Thr Gly Val
 65              70                  75                  80 gtg cga gac tgc gag ggc aca gac gcc agg ccc tac tgc aag gtg ttg        288
Val Arg Asp Cys Glu Gly Thr Asp Ala Arg Pro Tyr Cys Lys Val Leu
                 85                  90                  95 ctg ctg cac gag gta cat gcc aac gac aca ggc agc tac gtc tgc tac        336
Leu Leu His Glu Val His Ala Asn Asp Thr Gly Ser Tyr Val Cys Tyr
            100                 105                 110 tac aag tac atc aag gca cgc atc gag ggc acc acg gcc gcc agc tcc        384
Tyr Lys Tyr Ile Lys Ala Arg Ile Glu Gly Thr Thr Ala Ala Ser Ser
        115                 120                 125 tac gtg ttc gtg aga gac ttt gag cag cca ttc atc aac aag cct gac        432
Tyr Val Phe Val Arg Asp Phe Glu Gln Pro Phe Ile Asn Lys Pro Asp
    130                 135                 140 acg ctc ttg gtc aac agg aag gac gcc atg tgg gtg ccc tgt ctg gtg        480
Thr Leu Leu Val Asn Arg Lys Asp Ala Met Trp Val Pro Cys Leu Val
145                 150                 155                 160 tcc atc ccc ggc ctc aat gtc acg ctg cgc tcg caa agc tcg gtg ctg        528
Ser Ile Pro Gly Leu Asn Val Thr Leu Arg Ser Gln Ser Ser Val Leu
                165                 170                 175 tgg cca gac ggg cag gag gtg gtg tgg gat gac cgg cgg ggc atg ctc        576
Trp Pro Asp Gly Gln Glu Val Val Trp Asp Asp Arg Arg Gly Met Leu
            180                 185                 190 gtg tcc acg cca ctg ctg cac gat gcc ctg tac ctg cag tgc gag acc        624
Val Ser Thr Pro Leu Leu His Asp Ala Leu Tyr Leu Gln Cys Glu Thr
        195                 200                 205 acc tgg gga gac cag gac ttc ctt tcc aac ccc ttc ctg gtg cac gcg        672
Thr Trp Gly Asp Gln Asp Phe Leu Ser Asn Pro Phe Leu Val His Ala
    210                 215                 220 gat ccc atc gaa ggt cgt ggt ggt ggt ggt gat ccc aaa tct tgt             720
Asp Pro Ile Glu Gly Arg Gly Gly Gly Gly Asp Pro Lys Ser Cys
225                 230                 235                 240 gac aaa cct cac aca tgc cca ctg tgc cca gca cct gaa ctc ctg ggg        768
Asp Lys Pro His Thr Cys Pro Leu Cys Pro Ala Pro Glu Leu Leu Gly
                245                 250                 255 gga ccg tca gtc ttc ctc ttc ccc cca aaa ccc aag gac acc ctc atg        816
Gly Pro Ser Val Phe Leu Phe Pro Pro Lys Pro Lys Asp Thr Leu Met
            260                 265                 270 atc tcc cgg acc cct gag gtc aca tgc gtg gtg gtg gac gtg agc cac        864
Ile Ser Arg Thr Pro Glu Val Thr Cys Val Val Val Asp Val Ser His
        275                 280                 285 gaa gac cct gag gtc aag ttc aac tgg tac gtg gac ggc gtg gag gtg        912
Glu Asp Pro Glu Val Lys Phe Asn Trp Tyr Val Asp Gly Val Glu Val
    290                 295                 300 cat aat gcc aag aca aag ccg cgg gag gag cag tac aac agc acg tac        960
His Asn Ala Lys Thr Lys Pro Arg Glu Glu Gln Tyr Asn Ser Thr Tyr
305                 310                 315                 320 cgt gtg gtc agc gtc ctc acc gtc ctg cac cag gac tgg ctg aat ggc       1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc       1056
Lys Glu Tyr Lys Cys Lys Val Ser Asn Lys Ala Leu Pro Ala Pro Ile
            340                 345                 350 gag aaa acc atc tcc aaa gcc aaa ggg cag ccc cga gaa cca cag gtg       1104
Glu Lys Thr Ile Ser Lys Ala Lys Gly Gln Pro Arg Glu Pro Gln Val
        355                 360                 365 tac acc ctg ccc cca tcc cgg gat gag ctg acc aag aac cag gtc agc       1152
```

```
                Tyr Thr Leu Pro Pro Ser Arg Asp Glu Leu Thr Lys Asn Gln Val Ser
                    370                 375                 380 ctg acc tgc cta gtc aaa ggc ttc tat ccc agc gac atc gcc gtg gag      1200
Leu Thr Cys Leu Val Lys Gly Phe Tyr Pro Ser Asp Ile Ala Val Glu
385                 390                 395                 400 tgg gag agc aat ggg cag ccg gag aac aac tac aag gcc acg cct ccc      1248
Trp Glu Ser Asn Gly Gln Pro Glu Asn Asn Tyr Lys Ala Thr Pro Pro
                405                 410                 415 gtg ctg gac tcc gac ggc tcc ttc ttc ctc tac agc aag ctc acc gtg      1296
Val Leu Asp Ser Asp Gly Ser Phe Phe Leu Tyr Ser Lys Leu Thr Val
            420                 425                 430 gac aag agc agg tgg cag cag ggg aac gtc ttc tca tgc tcc gtg atg      1344
Asp Lys Ser Arg Trp Gln Gln Gly Asn Val Phe Ser Cys Ser Val Met
        435                 440                 445 cat gag gct ctg cac aac cac tac acg cag aag agc ctc tcc ctg tct      1392
His Glu Ala Leu His Asn His Tyr Thr Gln Lys Ser Leu Ser Leu Ser
    450                 455                 460 ccg ggt aaa tga                                                      1404
Pro Gly Lys
465
```

<210> SEQ ID NO 40
<211> LENGTH: 467
<212> TYPE: PRT
<213> ORGANISM: Artificial sequence
<220> FEATURE:
<223> OTHER INFORMATION: Synthetic polypeptide

<400> SEQUENCE: 40

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
                20                  25                  30

Asn Ile Thr Glu Glu Ser His Val Ile Asp Thr Gly Asp Ser Leu Ser
            35                  40                  45

Ile Ser Cys Arg Gly Gln His Pro Leu Glu Trp Ala Trp Pro Gly Ala
        50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
                100                 105                 110

Tyr Lys Tyr Ile Lys Ala Arg Ile Glu Gly Thr Thr Ala Ala Ser Ser
            115                 120                 125

Tyr Val Phe Val Arg Asp Phe Glu Gln Pro Phe Ile Asn Lys Pro Asp
        130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ala
    210                 215                 220
```

-continued

```
Asp Pro Ile Glu Gly Arg Gly Gly Gly Asp Pro Lys Ser Cys
225                 230                 235                 240

Asp Lys Pro His Thr Cys Pro Leu Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Ala Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465
```

```
<210> SEQ ID NO 41
<211> LENGTH: 1395
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-3 F
<220> FEATURE:
<221> NAME/KEY: CDS
<222> LOCATION: (1)..(1395)

<400> SEQUENCE: 41 atg cag cgg ggc gcc gcg ctg tgc ctg cga ctg tgg ctc tgc ctg gga      48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg      96
Leu Leu Asp Gly Leu Val Ser Gly Tyr Ser Met Thr Pro Pro Thr Leu
            20                  25                  30 aac atc acg gag gag tca cac gtc atc gac acc ggt gac agc ctg tcc    144
Asn Ile Thr Glu Glu Ser His Val Ile Asp Thr Gly Asp Ser Leu Ser
        35                  40                  45 atc tcc tgc agg gga cag cac ccc ctc gag tgg gct tgg cca gga gct    192
Ile Ser Cys Arg Gly Gln His Pro Leu Glu Trp Ala Trp Pro Gly Ala
    50                  55                  60
```

-continued

```
cag gag gcg cca gcc acc gga gac aag gac agc gag gac acg ggg gtg         240
Gln Glu Ala Pro Ala Thr Gly Asp Lys Asp Ser Glu Asp Thr Gly Val
 65              70                  75                  80 gtg cga gac tgc gag ggc aca gac gcc agg ccc tac tgc aag gtg ttg         288
Val Arg Asp Cys Glu Gly Thr Asp Ala Arg Pro Tyr Cys Lys Val Leu
                 85                  90                  95 ctg ctg cac gag gta cat gcc aac gac aca ggc agc tac gtc tgc tac         336
Leu Leu His Glu Val His Ala Asn Asp Thr Gly Ser Tyr Val Cys Tyr
            100                 105                 110 tac aag tac atc aag gca cgc atc gag ggc acc acg gcc gcc agc tcc         384
Tyr Lys Tyr Ile Lys Ala Arg Ile Glu Gly Thr Thr Ala Ala Ser Ser
        115                 120                 125 tac gtg ttc gtg aga gac ttt gag cag cca ttc atc aac aag cct gac         432
Tyr Val Phe Val Arg Asp Phe Glu Gln Pro Phe Ile Asn Lys Pro Asp
130                 135                 140 acg ctc ttg gtc aac agg aag gac gcc atg tgg gtg ccc tgt ctg gtg         480
Thr Leu Leu Val Asn Arg Lys Asp Ala Met Trp Val Pro Cys Leu Val
145                 150                 155                 160 tcc atc ccc ggc ctc aat gtc acg ctg cgc tcg caa agc tcg gtg ctg         528
Ser Ile Pro Gly Leu Asn Val Thr Leu Arg Ser Gln Ser Ser Val Leu
                165                 170                 175 tgg cca gac ggg cag gag gtg gtg tgg gat gac cgg cgg ggc atg ctc         576
Trp Pro Asp Gly Gln Glu Val Val Trp Asp Asp Arg Arg Gly Met Leu
            180                 185                 190 gtg tcc acg cca ctg ctg cac gat gcc ctg tac ctg cag tgc gag acc         624
Val Ser Thr Pro Leu Leu His Asp Ala Leu Tyr Leu Gln Cys Glu Thr
        195                 200                 205 acc tgg gga gac cag gac ttc ctt tcc aac ccc ttc gcg gat ccc atc         672
Thr Trp Gly Asp Gln Asp Phe Leu Ser Asn Pro Phe Ala Asp Pro Ile
210                 215                 220 gaa ggt cgt ggt ggt ggt ggt ggt gat ccc aaa tct tgt gac aaa cct         720
Glu Gly Arg Gly Gly Gly Gly Gly Asp Pro Lys Ser Cys Asp Lys Pro
225                 230                 235                 240 cac aca tgc cca ctg tgc cca gca cct gaa ctc ctg ggg gga ccg tca         768
His Thr Cys Pro Leu Cys Pro Ala Pro Glu Leu Leu Gly Gly Pro Ser
                245                 250                 255 gtc ttc ctc ttc ccc cca aaa ccc aag gac acc ctc atg atc tcc cgg         816
Val Phe Leu Phe Pro Pro Lys Pro Lys Asp Thr Leu Met Ile Ser Arg
            260                 265                 270 acc cct gag gtc aca tgc gtg gtg gtg gac gtg agc cac gaa gac cct         864
Thr Pro Glu Val Thr Cys Val Val Val Asp Val Ser His Glu Asp Pro
        275                 280                 285 gag gtc aag ttc aac tgg tac gtg gac ggc gtg gag gtg cat aat gcc         912
Glu Val Lys Phe Asn Trp Tyr Val Asp Gly Val Glu Val His Asn Ala
290                 295                 300 aag aca aag ccg cgg gag gag cag tac aac agc acg tac cgt gtg gtc         960
Lys Thr Lys Pro Arg Glu Glu Gln Tyr Asn Ser Thr Tyr Arg Val Val
305                 310                 315                 320 agc gtc ctc acc gtc ctg cac cag gac tgg ctg aat ggc aag gag tac        1008
Ser Val Leu Thr Val Leu His Gln Asp Trp Leu Asn Gly Lys Glu Tyr
                325                 330                 335 aag tgc aag gtc tcc aac aaa gcc ctc cca gcc ccc atc gag aaa acc        1056
Lys Cys Lys Val Ser Asn Lys Ala Leu Pro Ala Pro Ile Glu Lys Thr
            340                 345                 350 atc tcc aaa gcc aaa ggg cag ccc cga gaa cca cag gtg tac acc ctg        1104
Ile Ser Lys Ala Lys Gly Gln Pro Arg Glu Pro Gln Val Tyr Thr Leu
        355                 360                 365 ccc cca tcc cgg gat gag ctg acc aag aac cag gtc agc ctg acc tgc        1152
Pro Pro Ser Arg Asp Glu Leu Thr Lys Asn Gln Val Ser Leu Thr Cys
```

-continued

```
          370                 375                 380
cta gtc aaa ggc ttc tat ccc agc gac atc gcc gtg gag tgg gag agc   1200
Leu Val Lys Gly Phe Tyr Pro Ser Asp Ile Ala Val Glu Trp Glu Ser
385                 390                 395                 400 aat ggg cag ccg gag aac aac tac aag gcc acg cct ccc gtg ctg gac   1248
Asn Gly Gln Pro Glu Asn Asn Tyr Lys Ala Thr Pro Pro Val Leu Asp
            405                 410                 415 tcc gac ggc tcc ttc ttc ctc tac agc aag ctc acc gtg gac aag agc   1296
Ser Asp Gly Ser Phe Phe Leu Tyr Ser Lys Leu Thr Val Asp Lys Ser
        420                 425                 430 agg tgg cag cag ggg aac gtc ttc tca tgc tcc gtg atg cat gag gct   1344
Arg Trp Gln Gln Gly Asn Val Phe Ser Cys Ser Val Met His Glu Ala
    435                 440                 445 ctg cac aac cac tac acg cag aag agc ctc tcc ctg tct ccg ggt aaa   1392
Leu His Asn His Tyr Thr Gln Lys Ser Leu Ser Leu Ser Pro Gly Lys
450                 455                 460 tga                                                               1395
```

<210> SEQ ID NO 42
<211> LENGTH: 464
<212> TYPE: PRT
<213> ORGANISM: Artificial sequence
<220> FEATURE:
<223> OTHER INFORMATION: Synthetic polypeptide

<400> SEQUENCE: 42

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Ala Asp Pro Ile
    210                 215                 220

Glu Gly Arg Gly Gly Gly Gly Asp Pro Lys Ser Cys Asp Lys Pro
225                 230                 235                 240
```

```
His Thr Cys Pro Leu Cys Pro Ala Pro Glu Leu Leu Gly Gly Pro Ser
            245                 250                 255

Val Phe Leu Phe Pro Lys Pro Lys Asp Thr Leu Met Ile Ser Arg
            260                 265                 270

Thr Pro Glu Val Thr Cys Val Val Val Asp Val Ser His Glu Asp Pro
            275                 280                 285

Glu Val Lys Phe Asn Trp Tyr Val Asp Gly Val Glu Val His Asn Ala
            290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
            355                 360                 365

Pro Pro Ser Arg Asp Glu Leu Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Ala Thr Pro Pro Val Leu Asp
            405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Lys
            450                 455                 460

<210> SEQ ID NO 43
<211> LENGTH: 1719
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-3 G
<220> FEATURE:
<221> NAME/KEY: CDS
<222> LOCATION: (1)..(1719)

<400> SEQUENCE: 43 atg cag cgg ggc gcc gcg ctg tgc ctg cga ctg tgg ctc tgc ctg gga      48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg      96
Leu Leu Asp Gly Leu Val Ser Gly Tyr Ser Met Thr Pro Pro Thr Leu
            20                  25                  30 aac atc acg gag gag tca cac gtc atc gac acc ggt gac agc ctg tcc     144
Asn Ile Thr Glu Glu Ser His Val Ile Asp Thr Gly Asp Ser Leu Ser
        35                  40                  45 atc tcc tgc agg gga cag cac ccc ctc gag tgg gct tgg cca gga gct     192
Ile Ser Cys Arg Gly Gln His Pro Leu Glu Trp Ala Trp Pro Gly Ala
    50                  55                  60 cag gag gcg cca gcc acc gga gac aag gac agc gag gac acg ggg gtg     240
Gln Glu Ala Pro Ala Thr Gly Asp Lys Asp Ser Glu Asp Thr Gly Val
65                  70                  75                  80 gtg cga gac tgc gag ggc aca gac gcc agg ccc tac tgc aag gtg ttg     288
```

```
                                    -continued

Val Arg Asp Cys Glu Gly Thr Asp Ala Arg Pro Tyr Cys Lys Val Leu
                85                  90                  95 ctg ctg cac gag gta cat gcc aac gac aca ggc agc tac gtc tgc tac       336
Leu Leu His Glu Val His Ala Asn Asp Thr Gly Ser Tyr Val Cys Tyr
        100                 105                 110 tac aag tac atc aag gca cgc atc gag ggc acc acg gcc gcc agc tcc       384
Tyr Lys Tyr Ile Lys Ala Arg Ile Glu Gly Thr Thr Ala Ala Ser Ser
        115                 120                 125 tac gtg ttc gtg aga gac ttt gag cag cca ttc atc aac aag cct gac       432
Tyr Val Phe Val Arg Asp Phe Glu Gln Pro Phe Ile Asn Lys Pro Asp
        130                 135                 140 acg ctc ttg gtc aac agg aag gac gcc atg tgg gtg ccc tgt ctg gtg       480
Thr Leu Leu Val Asn Arg Lys Asp Ala Met Trp Val Pro Cys Leu Val
145                 150                 155                 160 tcc atc ccc ggc ctc aat gtc acg ctg cgc tcg caa agc tcg gtg ctg       528
Ser Ile Pro Gly Leu Asn Val Thr Leu Arg Ser Gln Ser Ser Val Leu
                165                 170                 175 tgg cca gac ggg cag gag gtg gtg tgg gat gac cgg cgg ggc atg ctc       576
Trp Pro Asp Gly Gln Glu Val Val Trp Asp Asp Arg Arg Gly Met Leu
        180                 185                 190 gtg tcc acg cca ctg ctg cac gat gcc ctg tac ctg cag tgc gag acc       624
Val Ser Thr Pro Leu Leu His Asp Ala Leu Tyr Leu Gln Cys Glu Thr
        195                 200                 205 acc tgg gga gac cag gac ttc ctt tcc aac ccc ttc ctg gtg cac atc       672
Thr Trp Gly Asp Gln Asp Phe Leu Ser Asn Pro Phe Leu Val His Ile
210                 215                 220 aca ggc aac gag ctc tat gac atc cag ctg ttg ccc agg aag tcg ctg       720
Thr Gly Asn Glu Leu Tyr Asp Ile Gln Leu Leu Pro Arg Lys Ser Leu
225                 230                 235                 240 gag ctg ctg gta ggg gag aag ctg gtc ctg aac tgc acc gtg tgg gct       768
Glu Leu Leu Val Gly Glu Lys Leu Val Leu Asn Cys Thr Val Trp Ala
                245                 250                 255 gag ttt aac tca ggt gtc acc ttt gac tgg gac tac cca ggg aag cag       816
Glu Phe Asn Ser Gly Val Thr Phe Asp Trp Asp Tyr Pro Gly Lys Gln
        260                 265                 270 gca gag cgg ggt aag tgg gtg ccc gag cga cgc tcc cag cag acc cac       864
Ala Glu Arg Gly Lys Trp Val Pro Glu Arg Arg Ser Gln Gln Thr His
        275                 280                 285 aca gaa ctc tcc agc atc ctg acc atc cac aac gtc agc cag cac gac       912
Thr Glu Leu Ser Ser Ile Leu Thr Ile His Asn Val Ser Gln His Asp
        290                 295                 300 ctg ggc tcg tat gtg tgc aag gcc aac aac ggc atc cag cga ttt cgg       960
Leu Gly Ser Tyr Val Cys Lys Ala Asn Asn Gly Ile Gln Arg Phe Arg
305                 310                 315                 320 gag agc acc gag gtc att gtg cat gag gat ccc atc gaa ggt cgt ggt      1008
Glu Ser Thr Glu Val Ile Val His Glu Asp Pro Ile Glu Gly Arg Gly
                325                 330                 335 ggt ggt ggt ggt gat ccc aaa tct tgt gac aaa cct cac aca tgc cca      1056
Gly Gly Gly Gly Asp Pro Lys Ser Cys Asp Lys Pro His Thr Cys Pro
        340                 345                 350 ctg tgc cca gca cct gaa ctc ctg gga gga ccg tca gtc ttc ctc ttc      1104
Leu Cys Pro Ala Pro Glu Leu Leu Gly Gly Pro Ser Val Phe Leu Phe
        355                 360                 365 ccc cca aaa ccc aag gac acc ctc atg atc tcc cgg acc cct gag gtc      1152
Pro Pro Lys Pro Lys Asp Thr Leu Met Ile Ser Arg Thr Pro Glu Val
370                 375                 380 aca tgc gtg gtg gtg gac gtg agc cac gaa gac cct gag gtc aag ttc      1200
Thr Cys Val Val Val Asp Val Ser His Glu Asp Pro Glu Val Lys Phe
385                 390                 395                 400
```

-continued

```
aac tgg tac gtg gac ggc gtg gag gtg cat aat gcc aag aca aag ccg        1248
Asn Trp Tyr Val Asp Gly Val Glu Val His Asn Ala Lys Thr Lys Pro
            405                 410                 415 cgg gag gag cag tac aac agc acg tac cgt gtg gtc agc gtc ctc acc        1296
Arg Glu Glu Gln Tyr Asn Ser Thr Tyr Arg Val Val Ser Val Leu Thr
        420                 425                 430 gtc ctg cac cag gac tgg ctg aat ggc aag gag tac aag tgc aag gtc        1344
Val Leu His Gln Asp Trp Leu Asn Gly Lys Glu Tyr Lys Cys Lys Val
    435                 440                 445 tcc aac aaa gcc ctc cca gcc ccc atc gag aaa acc atc tcc aaa gcc        1392
Ser Asn Lys Ala Leu Pro Ala Pro Ile Glu Lys Thr Ile Ser Lys Ala
450                 455                 460 aaa ggg cag ccc cga gaa cca cag gtg tac acc ctg ccc cca tcc cgg        1440
Lys Gly Gln Pro Arg Glu Pro Gln Val Tyr Thr Leu Pro Pro Ser Arg
465                 470                 475                 480 gat gag ctg acc aag aac cag gtc agc ctg acc tgc cta gtc aaa ggc        1488
Asp Glu Leu Thr Lys Asn Gln Val Ser Leu Thr Cys Leu Val Lys Gly
            485                 490                 495 ttc tat ccc agc gac atc gcc gtg gag tgg gag agc aat ggg cag ccg        1536
Phe Tyr Pro Ser Asp Ile Ala Val Glu Trp Glu Ser Asn Gly Gln Pro
        500                 505                 510 gag aac aac tac aag gcc acg cct ccc gtg ctg gac tcc gac ggc tcc        1584
Glu Asn Asn Tyr Lys Ala Thr Pro Pro Val Leu Asp Ser Asp Gly Ser
    515                 520                 525 ttc ttc ctc tac agc aag ctc acc gtg gac aag agc agg tgg cag cag        1632
Phe Phe Leu Tyr Ser Lys Leu Thr Val Asp Lys Ser Arg Trp Gln Gln
530                 535                 540 ggg aac gtc ttc tca tgc tcc gtg atg cat gag gct ctg cac aac cac        1680
Gly Asn Val Phe Ser Cys Ser Val Met His Glu Ala Leu His Asn His
545                 550                 555                 560 tac acg cag aag agc ctc tcc ctg tct ccg ggt aaa tga                    1719
Tyr Thr Gln Lys Ser Leu Ser Leu Ser Pro Gly Lys
            565                 570

<210> SEQ ID NO 44
<211> LENGTH: 572
<212> TYPE: PRT
<213> ORGANISM: Artificial sequence
<220> FEATURE:
<223> OTHER INFORMATION: Synthetic polypeptide

<400> SEQUENCE: 44

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
```

-continued

```
            130                 135                 140
Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Arg Arg Gly Met Leu
                180                 185                 190

Val Ser Thr Pro Leu Leu His Asp Ala Leu Tyr Leu Gln Cys Glu Thr
                195                 200                 205

Thr Trp Gly Asp Gln Asp Phe Leu Ser Asn Pro Phe Leu Val His Ile
                210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
                260                 265                 270

Ala Glu Arg Gly Lys Trp Val Pro Glu Arg Arg Ser Gln Gln Thr His
                275                 280                 285

Thr Glu Leu Ser Ser Ile Leu Thr Ile His Asn Val Ser Gln His Asp
                290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asp Pro Ile Glu Gly Arg Gly
                325                 330                 335

Gly Gly Gly Gly Asp Pro Lys Ser Cys Asp Lys Pro His Thr Cys Pro
                340                 345                 350

Leu Cys Pro Ala Pro Glu Leu Leu Gly Gly Pro Ser Val Phe Leu Phe
                355                 360                 365

Pro Pro Lys Pro Lys Asp Thr Leu Met Ile Ser Arg Thr Pro Glu Val
                370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
                420                 425                 430

Val Leu His Gln Asp Trp Leu Asn Gly Lys Glu Tyr Lys Cys Lys Val
                435                 440                 445

Ser Asn Lys Ala Leu Pro Ala Pro Ile Glu Lys Thr Ile Ser Lys Ala
450                 455                 460

Lys Gly Gln Pro Arg Glu Pro Gln Val Tyr Thr Leu Pro Pro Ser Arg
465                 470                 475                 480

Asp Glu Leu Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
                500                 505                 510

Glu Asn Asn Tyr Lys Ala Thr Pro Pro Val Leu Asp Ser Asp Gly Ser
                515                 520                 525

Phe Phe Leu Tyr Ser Lys Leu Thr Val Asp Lys Ser Arg Trp Gln Gln
                530                 535                 540

Gly Asn Val Phe Ser Cys Ser Val Met His Glu Ala Leu His Asn His
545                 550                 555                 560
```

<210> SEQ ID NO 45
<211> LENGTH: 1131
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-3 H
<220> FEATURE:
<221> NAME/KEY: CDS
<222> LOCATION: (1)..(1131)

<400> SEQUENCE: 45

| | | | | | | | | | | | | | | | | |
|---|---|---|---|---|---|---|---|---|---|---|---|---|---|---|---|---|
| atg | cag | cgg | ggc | gcc | gcg | ctg | tgc | ctg | cga | ctg | tgg | ctc | tgc | ctg | gga | 48 |
| Met | Gln | Arg | Gly | Ala | Ala | Leu | Cys | Leu | Arg | Leu | Trp | Leu | Cys | Leu | Gly | |
| 1 | | | 5 | | | | 10 | | | | | 15 | | | | |
| ctc | ctg | gac | ggc | ctg | gtg | agt | ggc | tac | tcc | atg | acc | ccc | ccg | acc | ttg | 96 |
| Leu | Leu | Asp | Gly | Leu | Val | Ser | Gly | Tyr | Ser | Met | Thr | Pro | Pro | Thr | Leu | |
| | | | 20 | | | | 25 | | | | | 30 | | | | |
| aac | atc | acg | gag | gag | tca | cac | gtc | atc | gac | acc | ggt | gac | agc | ctg | tcc | 144 |
| Asn | Ile | Thr | Glu | Glu | Ser | His | Val | Ile | Asp | Thr | Gly | Asp | Ser | Leu | Ser | |
| | 35 | | | | | 40 | | | | | 45 | | | | | |
| atc | tcc | tgc | agg | gga | cag | cac | ccc | ctc | gag | tgg | gct | tgg | cca | gga | gct | 192 |
| Ile | Ser | Cys | Arg | Gly | Gln | His | Pro | Leu | Glu | Trp | Ala | Trp | Pro | Gly | Ala | |
| | 50 | | | | | 55 | | | | | 60 | | | | | |
| cag | gag | gcg | cca | gcc | acc | gga | gac | aag | gac | agc | gag | gac | acg | ggg | gtg | 240 |
| Gln | Glu | Ala | Pro | Ala | Thr | Gly | Asp | Lys | Asp | Ser | Glu | Asp | Thr | Gly | Val | |
| 65 | | | | | 70 | | | | | 75 | | | | | 80 | |
| gtg | cga | gac | tgc | gag | ggc | aca | gac | gcc | agg | ccc | tac | tgc | aag | gtg | ttg | 288 |
| Val | Arg | Asp | Cys | Glu | Gly | Thr | Asp | Ala | Arg | Pro | Tyr | Cys | Lys | Val | Leu | |
| | | | | 85 | | | | | 90 | | | | | 95 | | |
| ctg | ctg | cac | gag | gta | cat | gcc | aac | gac | aca | ggc | agc | tac | gtc | tgc | tac | 336 |
| Leu | Leu | His | Glu | Val | His | Ala | Asn | Asp | Thr | Gly | Ser | Tyr | Val | Cys | Tyr | |
| | | | 100 | | | | | 105 | | | | | 110 | | | |
| tac | aag | tac | atc | aag | gca | cgc | atc | gag | ggc | acc | acg | gcc | gcc | agc | tcc | 384 |
| Tyr | Lys | Tyr | Ile | Lys | Ala | Arg | Ile | Glu | Gly | Thr | Thr | Ala | Ala | Ser | Ser | |
| | | 115 | | | | | 120 | | | | | 125 | | | | |
| tac | gtg | ttc | gtg | agg | gat | ccc | atc | gaa | ggt | cgt | ggt | ggt | ggt | ggt | ggt | 432 |
| Tyr | Val | Phe | Val | Arg | Asp | Pro | Ile | Glu | Gly | Arg | Gly | Gly | Gly | Gly | Gly | |
| | 130 | | | | | 135 | | | | | 140 | | | | | |
| gat | ccc | aaa | tct | tgt | gac | aaa | cct | cac | aca | tgc | cca | ctg | tgc | cca | gca | 480 |
| Asp | Pro | Lys | Ser | Cys | Asp | Lys | Pro | His | Thr | Cys | Pro | Leu | Cys | Pro | Ala | |
| 145 | | | | | 150 | | | | | 155 | | | | | 160 | |
| cct | gaa | ctc | ctg | ggg | gga | ccg | tca | gtc | ttc | ctc | ttc | ccc | cca | aaa | ccc | 528 |
| Pro | Glu | Leu | Leu | Gly | Gly | Pro | Ser | Val | Phe | Leu | Phe | Pro | Pro | Lys | Pro | |
| | | | | 165 | | | | | 170 | | | | | 175 | | |
| aag | gac | acc | ctc | atg | atc | tcc | cgg | acc | cct | gag | gtc | aca | tgc | gtg | gtg | 576 |
| Lys | Asp | Thr | Leu | Met | Ile | Ser | Arg | Thr | Pro | Glu | Val | Thr | Cys | Val | Val | |
| | | | 180 | | | | | 185 | | | | | 190 | | | |
| gtg | gac | gtg | agc | cac | gaa | gac | cct | gag | gtc | aag | ttc | aac | tgg | tac | gtg | 624 |
| Val | Asp | Val | Ser | His | Glu | Asp | Pro | Glu | Val | Lys | Phe | Asn | Trp | Tyr | Val | |
| | | 195 | | | | | 200 | | | | | 205 | | | | |
| gac | ggc | gtg | gag | gtg | cat | aat | gcc | aag | aca | aag | ccg | cgg | gag | gag | cag | 672 |
| Asp | Gly | Val | Glu | Val | His | Asn | Ala | Lys | Thr | Lys | Pro | Arg | Glu | Glu | Gln | |
| | 210 | | | | | 215 | | | | | 220 | | | | | |
| tac | aac | agc | acg | tac | cgt | gtg | gtc | agc | gtc | ctc | acc | gtc | ctg | cac | cag | 720 |
| Tyr | Asn | Ser | Thr | Tyr | Arg | Val | Val | Ser | Val | Leu | Thr | Val | Leu | His | Gln | |
| 225 | | | | | 230 | | | | | 235 | | | | | 240 | |

```
gac tgg ctg aat ggc aag gag tac aag tgc aag gtc tcc aac aaa gcc    768
Asp Trp Leu Asn Gly Lys Glu Tyr Lys Cys Lys Val Ser Asn Lys Ala
            245                 250                 255 ctc cca gcc ccc atc gag aaa acc atc tcc aaa gcc aaa ggg cag ccc    816
Leu Pro Ala Pro Ile Glu Lys Thr Ile Ser Lys Ala Lys Gly Gln Pro
        260                 265                 270 cga gaa cca cag gtg tac acc ctg ccc cca tcc cgg gat gag ctg acc    864
Arg Glu Pro Gln Val Tyr Thr Leu Pro Pro Ser Arg Asp Glu Leu Thr
    275                 280                 285 aag aac cag gtc agc ctg acc tgc cta gtc aaa ggc ttc tat ccc agc    912
Lys Asn Gln Val Ser Leu Thr Cys Leu Val Lys Gly Phe Tyr Pro Ser
290                 295                 300 gac atc gcc gtg gag tgg gag agc aat ggg cag ccg gag aac aac tac    960
Asp Ile Ala Val Glu Trp Glu Ser Asn Gly Gln Pro Glu Asn Asn Tyr
305                 310                 315                 320 aag gcc acg cct ccc gtg ctg gac tcc gac ggc tcc ttc ttc ctc tac   1008
Lys Ala Thr Pro Pro Val Leu Asp Ser Asp Gly Ser Phe Phe Leu Tyr
                325                 330                 335 agc aag ctc acc gtg gac aag agc agg tgg cag cag ggg aac gtc ttc   1056
Ser Lys Leu Thr Val Asp Lys Ser Arg Trp Gln Gln Gly Asn Val Phe
            340                 345                 350 tca tgc tcc gtg atg cat gag gct ctg cac aac cac tac acg cag aag   1104
Ser Cys Ser Val Met His Glu Ala Leu His Asn His Tyr Thr Gln Lys
        355                 360                 365 agc ctc tcc ctg tct ccg ggt aaa tga                               1131
Ser Leu Ser Leu Ser Pro Gly Lys
    370                 375

<210> SEQ ID NO 46
<211> LENGTH: 376
<212> TYPE: PRT
<213> ORGANISM: Artificial sequence
<220> FEATURE:
<223> OTHER INFORMATION: Synthetic polypeptide

<400> SEQUENCE: 46

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Pro Ile Glu Gly Arg Gly Gly Gly Gly Gly
    130                 135                 140

Asp Pro Lys Ser Cys Asp Lys Pro His Thr Cys Pro Leu Cys Pro Ala
145                 150                 155                 160

Pro Glu Leu Leu Gly Gly Pro Ser Val Phe Leu Phe Pro Pro Lys Pro
                165                 170                 175
```

```
Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
            195                 200                 205

Asp Gly Val Glu Val His Asn Ala Lys Thr Lys Pro Arg Glu Glu Gln
            210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
            260                 265                 270

Arg Glu Pro Gln Val Tyr Thr Leu Pro Pro Ser Arg Asp Glu Leu Thr
            275                 280                 285

Lys Asn Gln Val Ser Leu Thr Cys Leu Val Lys Gly Phe Tyr Pro Ser
            290                 295                 300

Asp Ile Ala Val Glu Trp Glu Ser Asn Gly Gln Pro Glu Asn Asn Tyr
305                 310                 315                 320

Lys Ala Thr Pro Pro Val Leu Asp Ser Asp Gly Ser Phe Phe Leu Tyr
                325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
            355                 360                 365

Ser Leu Ser Leu Ser Pro Gly Lys
            370                 375

<210> SEQ ID NO 47
<211> LENGTH: 1443
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-3 I
<220> FEATURE:
<221> NAME/KEY: CDS
<222> LOCATION: (1)..(1443)

<400> SEQUENCE: 47 atg cag cgg ggc gcc gcg ctg tgc ctg cga ctg tgg ctc tgc ctg gga      48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg      96
Leu Leu Asp Gly Leu Val Ser Gly Tyr Ser Met Thr Pro Pro Thr Leu
            20                  25                  30 aac atc acg gag gag tca cac gtc aga gac ttt gag cag cca ttc atc     144
Asn Ile Thr Glu Glu Ser His Val Arg Asp Phe Glu Gln Pro Phe Ile
        35                  40                  45 aac aag cct gac acg ctc ttg gtc aac agg aag gac gcc atg tgg gtg     192
Asn Lys Pro Asp Thr Leu Leu Val Asn Arg Lys Asp Ala Met Trp Val
    50                  55                  60 ccc tgt ctg gtg tcc atc ccc ggc ctc aat gtc acg ctg cgc tcg caa     240
Pro Cys Leu Val Ser Ile Pro Gly Leu Asn Val Thr Leu Arg Ser Gln
65                  70                  75                  80 agc tcg gtg ctg tgg cca gac ggg cag gag gtg gtg tgg gat gac cgg     288
Ser Ser Val Leu Trp Pro Asp Gly Gln Glu Val Val Trp Asp Asp Arg
                85                  90                  95
```

-continued

| | |
|---|---|
| cgg ggc atg ctc gtg tcc acg cca ctg ctg cac gat gcc ctg tac ctg<br>Arg Gly Met Leu Val Ser Thr Pro Leu Leu His Asp Ala Leu Tyr Leu<br>100 105 110 | 336 |
| cag tgc gag acc acc tgg gga gac cag gac ttc ctt tcc aac ccc ttc<br>Gln Cys Glu Thr Thr Trp Gly Asp Gln Asp Phe Leu Ser Asn Pro Phe<br>115 120 125 | 384 |
| ctg gtg cac atc aca ggc aac gag ctc tat gac atc cag ctg ttg ccc<br>Leu Val His Ile Thr Gly Asn Glu Leu Tyr Asp Ile Gln Leu Leu Pro<br>130 135 140 | 432 |
| agg aag tcg ctg gag ctg ctg gta ggg gag aag ctg gtc ctg aac tgc<br>Arg Lys Ser Leu Glu Leu Leu Val Gly Glu Lys Leu Val Leu Asn Cys<br>145 150 155 160 | 480 |
| acc gtg tgg gct gag ttt aac tca ggt gtc acc ttt gac tgg gac tac<br>Thr Val Trp Ala Glu Phe Asn Ser Gly Val Thr Phe Asp Trp Asp Tyr<br>165 170 175 | 528 |
| cca ggg aag cag gca gag cgg ggt aag tgg gtg ccc gag cga cgc tcc<br>Pro Gly Lys Gln Ala Glu Arg Gly Lys Trp Val Pro Glu Arg Arg Ser<br>180 185 190 | 576 |
| cag cag acc cac aca gaa ctc tcc agc atc ctg acc atc cac aac gtc<br>Gln Gln Thr His Thr Glu Leu Ser Ser Ile Leu Thr Ile His Asn Val<br>195 200 205 | 624 |
| agc cag cac gac ctg ggc tcg tat gtg tgc aag gcc aac aac ggc atc<br>Ser Gln His Asp Leu Gly Ser Tyr Val Cys Lys Ala Asn Asn Gly Ile<br>210 215 220 | 672 |
| cag cga ttt cgg gag agc acc gag gtc att gtg cat gag gat ccc atc<br>Gln Arg Phe Arg Glu Ser Thr Glu Val Ile Val His Glu Asp Pro Ile<br>225 230 235 240 | 720 |
| gaa ggt cgt ggt ggt ggt ggt ggt gat ccc aaa tct tgt gac aaa cct<br>Glu Gly Arg Gly Gly Gly Gly Gly Asp Pro Lys Ser Cys Asp Lys Pro<br>245 250 255 | 768 |
| cac aca tgc cca ctg tgc cca gca cct gaa ctc ctg ggg gga ccg tca<br>His Thr Cys Pro Leu Cys Pro Ala Pro Glu Leu Leu Gly Gly Pro Ser<br>260 265 270 | 816 |
| gtc ttc ctc ttc ccc cca aaa ccc aag gac acc ctc atg atc tcc cgg<br>Val Phe Leu Phe Pro Pro Lys Pro Lys Asp Thr Leu Met Ile Ser Arg<br>275 280 285 | 864 |
| acc cct gag gtc aca tgc gtg gtg gtg gac gtg agc cac gaa gac cct<br>Thr Pro Glu Val Thr Cys Val Val Val Asp Val Ser His Glu Asp Pro<br>290 295 300 | 912 |
| gag gtc aag ttc aac tgg tac gtg gac ggc gtg gag gtg cat aat gcc<br>Glu Val Lys Phe Asn Trp Tyr Val Asp Gly Val Glu Val His Asn Ala<br>305 310 315 320 | 960 |
| aag aca aag ccg cgg gag gag cag tac aac agc acg tac cgt gtg gtc<br>Lys Thr Lys Pro Arg Glu Glu Gln Tyr Asn Ser Thr Tyr Arg Val Val<br>325 330 335 | 1008 |
| agc gtc ctc acc gtc ctg cac cag gac tgg ctg aat ggc aag gag tac<br>Ser Val Leu Thr Val Leu His Gln Asp Trp Leu Asn Gly Lys Glu Tyr<br>340 345 350 | 1056 |
| aag tgc aag gtc tcc aac aaa gcc ctc cca gcc ccc atc gag aaa acc<br>Lys Cys Lys Val Ser Asn Lys Ala Leu Pro Ala Pro Ile Glu Lys Thr<br>355 360 365 | 1104 |
| atc tcc aaa gcc aaa ggg cag ccc cga gaa cca cag gtg tac acc ctg<br>Ile Ser Lys Ala Lys Gly Gln Pro Arg Glu Pro Gln Val Tyr Thr Leu<br>370 375 380 | 1152 |
| ccc cca tcc cgg gat gag ctg acc aag aac cag gtc agc ctg acc tgc<br>Pro Pro Ser Arg Asp Glu Leu Thr Lys Asn Gln Val Ser Leu Thr Cys<br>385 390 395 400 | 1200 |
| cta gtc aaa ggc ttc tat ccc agc gac atc gcc gtg gag tgg gag agc<br>Leu Val Lys Gly Phe Tyr Pro Ser Asp Ile Ala Val Glu Trp Glu Ser | 1248 |

```
                    405                 410                 415
aat ggg cag ccg gag aac aac tac aag gcc acg cct ccc gtg ctg gac      1296
Asn Gly Gln Pro Glu Asn Asn Tyr Lys Ala Thr Pro Pro Val Leu Asp
            420                 425                 430 tcc gac ggc tcc ttc ttc ctc tac agc aag ctc acc gtg gac aag agc      1344
Ser Asp Gly Ser Phe Phe Leu Tyr Ser Lys Leu Thr Val Asp Lys Ser
        435                 440                 445 agg tgg cag cag ggg aac gtc ttc tca tgc tcc gtg atg cat gag gct      1392
Arg Trp Gln Gln Gly Asn Val Phe Ser Cys Ser Val Met His Glu Ala
    450                 455                 460 ctg cac aac cac tac acg cag aag agc ctc tcc ctg tct ccg ggt aaa      1440
Leu His Asn His Tyr Thr Gln Lys Ser Leu Ser Leu Ser Pro Gly Lys
465                 470                 475                 480 tga                                                                   1443

<210> SEQ ID NO 48
<211> LENGTH: 480
<212> TYPE: PRT
<213> ORGANISM: Artificial sequence
<220> FEATURE:
<223> OTHER INFORMATION: Synthetic polypeptide

<400> SEQUENCE: 48

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Arg Asp Phe Glu Gln Pro Phe Ile
        35                  40                  45

Asn Lys Pro Asp Thr Leu Leu Val Asn Arg Lys Asp Ala Met Trp Val
    50                  55                  60

Pro Cys Leu Val Ser Ile Pro Gly Leu Asn Val Thr Leu Arg Ser Gln
65                  70                  75                  80

Ser Ser Val Leu Trp Pro Asp Gly Gln Glu Val Val Trp Asp Asp Arg
                85                  90                  95

Arg Gly Met Leu Val Ser Thr Pro Leu Leu His Asp Ala Leu Tyr Leu
            100                 105                 110

Gln Cys Glu Thr Thr Trp Gly Asp Gln Asp Phe Leu Ser Asn Pro Phe
        115                 120                 125

Leu Val His Ile Thr Gly Asn Glu Leu Tyr Asp Ile Gln Leu Leu Pro
    130                 135                 140

Arg Lys Ser Leu Glu Leu Leu Val Gly Glu Lys Leu Val Leu Asn Cys
145                 150                 155                 160

Thr Val Trp Ala Glu Phe Asn Ser Gly Val Thr Phe Asp Trp Asp Tyr
                165                 170                 175

Pro Gly Lys Gln Ala Glu Arg Gly Lys Trp Val Pro Glu Arg Arg Ser
            180                 185                 190

Gln Gln Thr His Thr Glu Leu Ser Ser Ile Leu Thr Ile His Asn Val
        195                 200                 205

Ser Gln His Asp Leu Gly Ser Tyr Val Cys Lys Ala Asn Asn Gly Ile
    210                 215                 220

Gln Arg Phe Arg Glu Ser Thr Glu Val Ile Val His Glu Asp Pro Ile
225                 230                 235                 240

Glu Gly Arg Gly Gly Gly Gly Asp Pro Lys Ser Cys Asp Lys Pro
                245                 250                 255

His Thr Cys Pro Leu Cys Pro Ala Pro Glu Leu Leu Gly Gly Pro Ser
```

```
                260                 265                 270
Val Phe Leu Phe Pro Pro Lys Pro Lys Asp Thr Leu Met Ile Ser Arg
            275                 280                 285

Thr Pro Glu Val Thr Cys Val Val Asp Val Ser His Glu Asp Pro
        290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
            325                 330                 335

Ser Val Leu Thr Val Leu His Gln Asp Trp Leu Asn Gly Lys Glu Tyr
        340                 345                 350

Lys Cys Lys Val Ser Asn Lys Ala Leu Pro Ala Pro Ile Glu Lys Thr
            355                 360                 365

Ile Ser Lys Ala Lys Gly Gln Pro Arg Glu Pro Gln Val Tyr Thr Leu
        370                 375                 380

Pro Pro Ser Arg Asp Glu Leu Thr Lys Asn Gln Val Ser Leu Thr Cys
385                 390                 395                 400

Leu Val Lys Gly Phe Tyr Pro Ser Asp Ile Ala Val Glu Trp Glu Ser
            405                 410                 415

Asn Gly Gln Pro Glu Asn Asn Tyr Lys Ala Thr Pro Pro Val Leu Asp
        420                 425                 430

Ser Asp Gly Ser Phe Phe Leu Tyr Ser Lys Leu Thr Val Asp Lys Ser
            435                 440                 445

Arg Trp Gln Gln Gly Asn Val Phe Ser Cys Ser Val Met His Glu Ala
        450                 455                 460

Leu His Asn His Tyr Thr Gln Lys Ser Leu Ser Leu Ser Pro Gly Lys
465                 470                 475                 480

<210> SEQ ID NO 49
<211> LENGTH: 1197
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-3 J
<220> FEATURE:
<221> NAME/KEY: CDS
<222> LOCATION: (1)..(1197)

<400> SEQUENCE: 49 atg cag cgg ggc gcc gcg ctg tgc ctg cga ctg tgg ctc tgc ctg gga      48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg      96
Leu Leu Asp Gly Leu Val Ser Gly Tyr Ser Met Thr Pro Pro Thr Leu
            20                  25                  30 aac atc acg gag gag tca cac gtc aga gac ttt gag cag cca ttc atc     144
Asn Ile Thr Glu Glu Ser His Val Arg Asp Phe Glu Gln Pro Phe Ile
        35                  40                  45 aac aag cct gac acg ctc ttg gtc aac agg aag gac gcc atg tgg gtg     192
Asn Lys Pro Asp Thr Leu Leu Val Asn Arg Lys Asp Ala Met Trp Val
    50                  55                  60 ccc tgt ctg gtg tcc atc ccc ggc ctc aat gtc acg ctg cgc tcg caa     240
Pro Cys Leu Val Ser Ile Pro Gly Leu Asn Val Thr Leu Arg Ser Gln
65                  70                  75                  80 agc tcg gtg ctg tgg cca gac ggg cag gag gtg gtg tgg gat gac cgg     288
Ser Ser Val Leu Trp Pro Asp Gly Gln Glu Val Val Trp Asp Asp Arg
```

```
                       85                  90                  95
cgg ggc atg ctc gtg tcc acg cca ctg ctg cac gat gcc ctg tac ctg      336
Arg Gly Met Leu Val Ser Thr Pro Leu Leu His Asp Ala Leu Tyr Leu
            100                 105                 110 cag tgc gag acc acc tgg gga gac cag gac ttc ctt tcc aac ccc ttc      384
Gln Cys Glu Thr Thr Trp Gly Asp Gln Asp Phe Leu Ser Asn Pro Phe
            115                 120                 125 ctg gtg cac atc aca ggc aac gag ctc tat gac atc cag ctg ttg ccc      432
Leu Val His Ile Thr Gly Asn Glu Leu Tyr Asp Ile Gln Leu Leu Pro
        130                 135                 140 agg aag tcg ctg gag ctg ctg gta ggg gag aag gat ccc atc gaa ggt      480
Arg Lys Ser Leu Glu Leu Leu Val Gly Glu Lys Asp Pro Ile Glu Gly
145                 150                 155                 160 cgt ggt ggt ggt ggt ggt gat ccc aaa tct tgt gac aaa cct cac aca      528
Arg Gly Gly Gly Gly Gly Asp Pro Lys Ser Cys Asp Lys Pro His Thr
                165                 170                 175 tgc cca ctg tgc cca gca cct gaa ctc ctg ggg gga ccg tca gtc ttc      576
Cys Pro Leu Cys Pro Ala Pro Glu Leu Leu Gly Gly Pro Ser Val Phe
            180                 185                 190 ctc ttc ccc cca aaa ccc aag gac acc ctc atg atc tcc cgg acc cct      624
Leu Phe Pro Pro Lys Pro Lys Asp Thr Leu Met Ile Ser Arg Thr Pro
            195                 200                 205 gag gtc aca tgc gtg gtg gtg gac gtg agc cac gaa gac cct gag gtc      672
Glu Val Thr Cys Val Val Val Asp Val Ser His Glu Asp Pro Glu Val
        210                 215                 220 aag ttc aac tgg tac gtg gac ggc gtg gag gtg cat aat gcc aag aca      720
Lys Phe Asn Trp Tyr Val Asp Gly Val Glu Val His Asn Ala Lys Thr
225                 230                 235                 240 aag ccg cgg gag gag cag tac aac agc acg tac cgt gtg gtc agc gtc      768
Lys Pro Arg Glu Glu Gln Tyr Asn Ser Thr Tyr Arg Val Val Ser Val
                245                 250                 255 ctc acc gtc ctg cac cag gac tgg ctg aat ggc aag gag tac aag tgc      816
Leu Thr Val Leu His Gln Asp Trp Leu Asn Gly Lys Glu Tyr Lys Cys
            260                 265                 270 aag gtc tcc aac aaa gcc ctc cca gcc ccc atc gag aaa acc atc tcc      864
Lys Val Ser Asn Lys Ala Leu Pro Ala Pro Ile Glu Lys Thr Ile Ser
            275                 280                 285 aaa gcc aaa ggg cag ccc cga gaa cca cag gtg tac acc ctg ccc cca      912
Lys Ala Lys Gly Gln Pro Arg Glu Pro Gln Val Tyr Thr Leu Pro Pro
        290                 295                 300 tcc cgg gat gag ctg acc aag aac cag gtc agc ctg acc tgc cta gtc      960
Ser Arg Asp Glu Leu Thr Lys Asn Gln Val Ser Leu Thr Cys Leu Val
305                 310                 315                 320 aaa ggc ttc tat ccc agc gac atc gcc gtg gag tgg gag agc aat ggg     1008
Lys Gly Phe Tyr Pro Ser Asp Ile Ala Val Glu Trp Glu Ser Asn Gly
                325                 330                 335 cag ccg gag aac aac tac aag gcc acg cct ccc gtg ctg gac tcc gac     1056
Gln Pro Glu Asn Asn Tyr Lys Ala Thr Pro Pro Val Leu Asp Ser Asp
            340                 345                 350 ggc tcc ttc ttc ctc tac agc aag ctc acc gtg gac aag agc agg tgg     1104
Gly Ser Phe Phe Leu Tyr Ser Lys Leu Thr Val Asp Lys Ser Arg Trp
            355                 360                 365 cag cag ggg aac gtc ttc tca tgc tcc gtg atg cat gag gct ctg cac     1152
Gln Gln Gly Asn Val Phe Ser Cys Ser Val Met His Glu Ala Leu His
        370                 375                 380 aac cac tac acg cag aag agc ctc tcc ctg tct ccg ggt aaa tga        1197
Asn His Tyr Thr Gln Lys Ser Leu Ser Leu Ser Pro Gly Lys
385                 390                 395
```

<210> SEQ ID NO 50
<211> LENGTH: 398
<212> TYPE: PRT
<213> ORGANISM: Artificial sequence
<220> FEATURE:
<223> OTHER INFORMATION: Synthetic polypeptide

<400> SEQUENCE: 50

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Arg Asp Phe Glu Gln Pro Phe Ile
        35                  40                  45

Asn Lys Pro Asp Thr Leu Leu Val Asn Arg Lys Asp Ala Met Trp Val
    50                  55                  60

Pro Cys Leu Val Ser Ile Pro Gly Leu Asn Val Thr Leu Arg Ser Gln
65                  70                  75                  80

Ser Ser Val Leu Trp Pro Asp Gly Gln Glu Val Val Trp Asp Asp Arg
                85                  90                  95

Arg Gly Met Leu Val Ser Thr Pro Leu Leu His Asp Ala Leu Tyr Leu
            100                 105                 110

Gln Cys Glu Thr Thr Trp Gly Asp Gln Asp Phe Leu Ser Asn Pro Phe
        115                 120                 125

Leu Val His Ile Thr Gly Asn Glu Leu Tyr Asp Ile Gln Leu Leu Pro
    130                 135                 140

Arg Lys Ser Leu Glu Leu Leu Val Gly Glu Lys Asp Pro Ile Glu Gly
145                 150                 155                 160

Arg Gly Gly Gly Gly Asp Pro Lys Ser Cys Asp Lys Pro His Thr
                165                 170                 175

Cys Pro Leu Cys Pro Ala Pro Glu Leu Leu Gly Gly Pro Ser Val Phe
            180                 185                 190

Leu Phe Pro Pro Lys Pro Lys Asp Thr Leu Met Ile Ser Arg Thr Pro
        195                 200                 205

Glu Val Thr Cys Val Val Asp Val Ser His Glu Asp Pro Glu Val
    210                 215                 220

Lys Phe Asn Trp Tyr Val Asp Gly Val Glu Val His Asn Ala Lys Thr
225                 230                 235                 240

Lys Pro Arg Glu Glu Gln Tyr Asn Ser Thr Tyr Arg Val Val Ser Val
                245                 250                 255

Leu Thr Val Leu His Gln Asp Trp Leu Asn Gly Lys Glu Tyr Lys Cys
            260                 265                 270

Lys Val Ser Asn Lys Ala Leu Pro Ala Pro Ile Glu Lys Thr Ile Ser
        275                 280                 285

Lys Ala Lys Gly Gln Pro Arg Glu Pro Gln Val Tyr Thr Leu Pro Pro
    290                 295                 300

Ser Arg Asp Glu Leu Thr Lys Asn Gln Val Ser Leu Thr Cys Leu Val
305                 310                 315                 320

Lys Gly Phe Tyr Pro Ser Asp Ile Ala Val Glu Trp Glu Ser Asn Gly
                325                 330                 335

Gln Pro Glu Asn Asn Tyr Lys Ala Thr Pro Pro Val Leu Asp Ser Asp
            340                 345                 350

Gly Ser Phe Phe Leu Tyr Ser Lys Leu Thr Val Asp Lys Ser Arg Trp
        355                 360                 365

Gln Gln Gly Asn Val Phe Ser Cys Ser Val Met His Glu Ala Leu His
```

-continued

```
            370                 375                 380
Asn His Tyr Thr Gln Lys Ser Leu Ser Leu Ser Pro Gly Lys
385                 390                 395

<210> SEQ ID NO 51
<211> LENGTH: 1146
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-3 K
<220> FEATURE:
<221> NAME/KEY: CDS
<222> LOCATION: (1)..(1146)

<400> SEQUENCE: 51 atg cag cgg ggc gcc gcg ctg tgc ctg cga ctg tgg ctc tgc ctg gga      48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg      96
Leu Leu Asp Gly Leu Val Ser Gly Tyr Ser Met Thr Pro Pro Thr Leu
                20                  25                  30 aac atc acg gag gag tca cac gtc aga gac ttt gag cag cca ttc atc     144
Asn Ile Thr Glu Glu Ser His Val Arg Asp Phe Glu Gln Pro Phe Ile
            35                  40                  45 aac aag cct gac acg ctc ttg gtc aac agg aag gac gcc atg tgg gtg     192
Asn Lys Pro Asp Thr Leu Leu Val Asn Arg Lys Asp Ala Met Trp Val
        50                  55                  60 ccc tgt ctg gtg tcc atc ccc ggc ctc aat gtc acg ctg cgc tcg caa     240
Pro Cys Leu Val Ser Ile Pro Gly Leu Asn Val Thr Leu Arg Ser Gln
65                  70                  75                  80 agc tcg gtg ctg tgg cca gac ggg cag gag gtg gtg tgg gat gac cgg     288
Ser Ser Val Leu Trp Pro Asp Gly Gln Glu Val Val Trp Asp Asp Arg
                85                  90                  95 cgg ggc atg ctc gtg tcc acg cca ctg ctg cac gat gcc ctg tac ctg     336
Arg Gly Met Leu Val Ser Thr Pro Leu Leu His Asp Ala Leu Tyr Leu
                100                 105                 110 cag tgc gag acc acc tgg gga gac cag gac ttc ctt tcc aac ccc ttc     384
Gln Cys Glu Thr Thr Trp Gly Asp Gln Asp Phe Leu Ser Asn Pro Phe
            115                 120                 125 ctg gtg cac atc aca ggc aac gag ctc gcg gat ccc atc gaa ggt cgt     432
Leu Val His Ile Thr Gly Asn Glu Leu Ala Asp Pro Ile Glu Gly Arg
        130                 135                 140 ggt ggt ggt ggt gat ccc aaa tct tgt gac aaa cct cac aca tgc         480
Gly Gly Gly Gly Asp Pro Lys Ser Cys Asp Lys Pro His Thr Cys
145                 150                 155                 160 cca ctg tgc cca gca cct gaa ctc ctg ggg gga ccg tca gtc ttc ctc     528
Pro Leu Cys Pro Ala Pro Glu Leu Leu Gly Gly Pro Ser Val Phe Leu
                165                 170                 175 ttc ccc cca aaa ccc aag gac acc ctc atg atc tcc cgg acc cct gag     576
Phe Pro Pro Lys Pro Lys Asp Thr Leu Met Ile Ser Arg Thr Pro Glu
                180                 185                 190 gtc aca tgc gtg gtg gtg gac gtg agc cac gaa gac cct gag gtc aag     624
Val Thr Cys Val Val Val Asp Val Ser His Glu Asp Pro Glu Val Lys
            195                 200                 205 ttc aac tgg tac gtg gac ggc gtg gag gtg cat aat gcc aag aca aag     672
Phe Asn Trp Tyr Val Asp Gly Val Glu Val His Asn Ala Lys Thr Lys
        210                 215                 220 ccg cgg gag gag cag tac aac agc acg tac cgt gtg gtc agc gtc ctc     720
Pro Arg Glu Glu Gln Tyr Asn Ser Thr Tyr Arg Val Val Ser Val Leu
```

```
acc gtc ctg cac cag gac tgg ctg aat ggc aag gag tac aag tgc aag    768
Thr Val Leu His Gln Asp Trp Leu Asn Gly Lys Glu Tyr Lys Cys Lys
                245                 250                 255 gtc tcc aac aaa gcc ctc cca gcc ccc atc gag aaa acc atc tcc aaa    816
Val Ser Asn Lys Ala Leu Pro Ala Pro Ile Glu Lys Thr Ile Ser Lys
            260                 265                 270 gcc aaa ggg cag ccc cga gaa cca cag gtg tac acc ctg ccc cca tcc    864
Ala Lys Gly Gln Pro Arg Glu Pro Gln Val Tyr Thr Leu Pro Pro Ser
        275                 280                 285 cgg gat gag ctg acc aag aac cag gtc agc ctg acc tgc cta gtc aaa    912
Arg Asp Glu Leu Thr Lys Asn Gln Val Ser Leu Thr Cys Leu Val Lys
    290                 295                 300 ggc ttc tat ccc agc gac atc gcc gtg gag tgg gag agc aat ggg cag    960
Gly Phe Tyr Pro Ser Asp Ile Ala Val Glu Trp Glu Ser Asn Gly Gln
305                 310                 315                 320 ccg gag aac aac tac aag gcc acg cct ccc gtg ctg gac tcc gac ggc   1008
Pro Glu Asn Asn Tyr Lys Ala Thr Pro Pro Val Leu Asp Ser Asp Gly
                325                 330                 335 tcc ttc ttc ctc tac agc aag ctc acc gtg gac aag agc agg tgg cag   1056
Ser Phe Phe Leu Tyr Ser Lys Leu Thr Val Asp Lys Ser Arg Trp Gln
            340                 345                 350 cag ggg aac gtc ttc tca tgc tcc gtg atg cat gag gct ctg cac aac   1104
Gln Gly Asn Val Phe Ser Cys Ser Val Met His Glu Ala Leu His Asn
        355                 360                 365 cac tac acg cag aag agc ctc tcc ctg tct ccg ggt aaa tga           1146
His Tyr Thr Gln Lys Ser Leu Ser Leu Ser Pro Gly Lys
    370                 375                 380

<210> SEQ ID NO 52
<211> LENGTH: 381
<212> TYPE: PRT
<213> ORGANISM: Artificial sequence
<220> FEATURE:
<223> OTHER INFORMATION: Synthetic polynucleotide

<400> SEQUENCE: 52

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Arg Asp Phe Glu Gln Pro Phe Ile
        35                  40                  45

Asn Lys Pro Asp Thr Leu Leu Val Asn Arg Lys Asp Ala Met Trp Val
    50                  55                  60

Pro Cys Leu Val Ser Ile Pro Gly Leu Asn Val Thr Leu Arg Ser Gln
65                  70                  75                  80

Ser Ser Val Leu Trp Pro Asp Gly Gln Glu Val Val Trp Asp Asp Arg
                85                  90                  95

Arg Gly Met Leu Val Ser Thr Pro Leu Leu His Asp Ala Leu Tyr Leu
            100                 105                 110

Gln Cys Glu Thr Thr Trp Gly Asp Gln Asp Phe Leu Ser Asn Pro Phe
        115                 120                 125

Leu Val His Ile Thr Gly Asn Glu Leu Ala Asp Pro Ile Glu Gly Arg
    130                 135                 140

Gly Gly Gly Gly Gly Asp Pro Lys Ser Cys Asp Lys Pro His Thr Cys
145                 150                 155                 160

Pro Leu Cys Pro Ala Pro Glu Leu Leu Gly Gly Pro Ser Val Phe Leu
```

```
                    165                 170                 175
Phe Pro Pro Lys Pro Lys Asp Thr Leu Met Ile Ser Arg Thr Pro Glu
                180                 185                 190

Val Thr Cys Val Val Val Asp Val Ser His Glu Asp Pro Glu Val Lys
            195                 200                 205

Phe Asn Trp Tyr Val Asp Gly Val Glu Val His Asn Ala Lys Thr Lys
        210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
290                 295                 300

Gly Phe Tyr Pro Ser Asp Ile Ala Val Glu Trp Glu Ser Asn Gly Gln
305                 310                 315                 320

Pro Glu Asn Asn Tyr Lys Ala Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly Lys
    370                 375                 380

<210> SEQ ID NO 53
<211> LENGTH: 1128
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-3 L
<220> FEATURE:
<221> NAME/KEY: CDS
<222> LOCATION: (1)..(1128)

<400> SEQUENCE: 53 atg cag cgg ggc gcc gcg ctg tgc ctg cga ctg tgg ctc tgc ctg gga    48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg    96
Leu Leu Asp Gly Leu Val Ser Gly Tyr Ser Met Thr Pro Pro Thr Leu
            20                  25                  30 aac atc acg gag gag tca cac gtc aga gac ttt gag cag cca ttc atc   144
Asn Ile Thr Glu Glu Ser His Val Arg Asp Phe Glu Gln Pro Phe Ile
        35                  40                  45 aac aag cct gac acg ctc ttg gtc aac agg aag gac gcc atg tgg gtg   192
Asn Lys Pro Asp Thr Leu Leu Val Asn Arg Lys Asp Ala Met Trp Val
    50                  55                  60 ccc tgt ctg gtg tcc atc ccc ggc ctc aat gtc acg ctg cgc tcg caa   240
Pro Cys Leu Val Ser Ile Pro Gly Leu Asn Val Thr Leu Arg Ser Gln
65                  70                  75                  80 agc tcg gtg ctg tgg cca gac ggg cag gag gtg gtg tgg gat gac cgg   288
Ser Ser Val Leu Trp Pro Asp Gly Gln Glu Val Val Trp Asp Asp Arg
```

```
                         85                  90                  95
cgg ggc atg ctc gtg tcc acg cca ctg ctg cac gat gcc ctg tac ctg       336
Arg Gly Met Leu Val Ser Thr Pro Leu Leu His Asp Ala Leu Tyr Leu
            100                 105                 110 cag tgc gag acc acc tgg gga gac cag gac ttc ctt tcc aac ccc ttc       384
Gln Cys Glu Thr Thr Trp Gly Asp Gln Asp Phe Leu Ser Asn Pro Phe
        115                 120                 125 ctg gtg cac gcg gat ccc atc gaa ggt cgt ggt ggt ggt ggt gat           432
Leu Val His Ala Asp Pro Ile Glu Gly Arg Gly Gly Gly Gly Asp
    130                 135                 140 ccc aaa tct tgt gac aaa cct cac aca tgc cca ctg tgc cca gca cct       480
Pro Lys Ser Cys Asp Lys Pro His Thr Cys Pro Leu Cys Pro Ala Pro
145                 150                 155                 160 gaa ctc ctg ggg gga ccg tca gtc ttc ctc ttc ccc cca aaa ccc aag       528
Glu Leu Leu Gly Gly Pro Ser Val Phe Leu Phe Pro Pro Lys Pro Lys
                165                 170                 175 gac acc ctc atg atc tcc cgg acc cct gag gtc aca tgc gtg gtg gtg       576
Asp Thr Leu Met Ile Ser Arg Thr Pro Glu Val Thr Cys Val Val Val
            180                 185                 190 gac gtg agc cac gaa gac cct gag gtc aag ttc aac tgg tac gtg gac       624
Asp Val Ser His Glu Asp Pro Glu Val Lys Phe Asn Trp Tyr Val Asp
        195                 200                 205 ggc gtg gag gtg cat aat gcc aag aca aag ccg cgg gag gag cag tac       672
Gly Val Glu Val His Asn Ala Lys Thr Lys Pro Arg Glu Glu Gln Tyr
    210                 215                 220 aac agc acg tac cgt gtg gtc agc gtc ctc acc gtc ctg cac cag gac       720
Asn Ser Thr Tyr Arg Val Val Ser Val Leu Thr Val Leu His Gln Asp
225                 230                 235                 240 tgg ctg aat ggc aag gag tac aag tgc aag gtc tcc aac aaa gcc ctc       768
Trp Leu Asn Gly Lys Glu Tyr Lys Cys Lys Val Ser Asn Lys Ala Leu
                245                 250                 255 cca gcc ccc atc gag aaa acc atc tcc aaa gcc aaa ggg cag ccc cga       816
Pro Ala Pro Ile Glu Lys Thr Ile Ser Lys Ala Lys Gly Gln Pro Arg
            260                 265                 270 gaa cca cag gtg tac acc ctg ccc cca tcc cgg gat gag ctg acc aag       864
Glu Pro Gln Val Tyr Thr Leu Pro Pro Ser Arg Asp Glu Leu Thr Lys
        275                 280                 285 aac cag gtc agc ctg acc tgc cta gtc aaa ggc ttc tat ccc agc gac       912
Asn Gln Val Ser Leu Thr Cys Leu Val Lys Gly Phe Tyr Pro Ser Asp
    290                 295                 300 atc gcc gtg gag tgg gag agc aat ggg cag ccg gag aac aac tac aag       960
Ile Ala Val Glu Trp Glu Ser Asn Gly Gln Pro Glu Asn Asn Tyr Lys
305                 310                 315                 320 gcc acg cct ccc gtg ctg gac tcc gac ggc tcc ttc ttc ctc tac agc      1008
Ala Thr Pro Pro Val Leu Asp Ser Asp Gly Ser Phe Phe Leu Tyr Ser
                325                 330                 335 aag ctc acc gtg gac aag agc agg tgg cag cag ggg aac gtc ttc tca      1056
Lys Leu Thr Val Asp Lys Ser Arg Trp Gln Gln Gly Asn Val Phe Ser
            340                 345                 350 tgc tcc gtg atg cat gag gct ctg cac aac cac tac acg cag aag agc      1104
Cys Ser Val Met His Glu Ala Leu His Asn His Tyr Thr Gln Lys Ser
        355                 360                 365 ctc tcc ctg tct ccg ggt aaa tga                                      1128
Leu Ser Leu Ser Pro Gly Lys
    370                 375

<210> SEQ ID NO 54
<211> LENGTH: 375
<212> TYPE: PRT
<213> ORGANISM: Artificial sequence
```

```
<220> FEATURE:
<223> OTHER INFORMATION: Synthetic polypeptide

<400> SEQUENCE: 54

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Arg Asp Phe Glu Gln Pro Phe Ile
        35                  40                  45

Asn Lys Pro Asp Thr Leu Leu Val Asn Arg Lys Asp Ala Met Trp Val
50                  55                  60

Pro Cys Leu Val Ser Ile Pro Gly Leu Asn Val Thr Leu Arg Ser Gln
65                  70                  75                  80

Ser Ser Val Leu Trp Pro Asp Gly Gln Glu Val Val Trp Asp Asp Arg
                85                  90                  95

Arg Gly Met Leu Val Ser Thr Pro Leu Leu His Asp Ala Leu Tyr Leu
            100                 105                 110

Gln Cys Glu Thr Thr Trp Gly Asp Gln Asp Phe Leu Ser Asn Pro Phe
        115                 120                 125

Leu Val His Ala Asp Pro Ile Glu Gly Arg Gly Gly Gly Gly Gly Asp
    130                 135                 140

Pro Lys Ser Cys Asp Lys Pro His Thr Cys Pro Leu Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Asp Glu Leu Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Ala Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
    370                 375

<210> SEQ ID NO 55
```

<211> LENGTH: 1119
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-3 M
<220> FEATURE:
<221> NAME/KEY: CDS
<222> LOCATION: (1)..(1119)

<400> SEQUENCE: 55

| | | | | | | | | | | | | | | | | |
|---|---|---|---|---|---|---|---|---|---|---|---|---|---|---|---|---|
| atg | cag | cgg | ggc | gcc | gcg | ctg | tgc | ctg | cga | ctg | tgg | ctc | tgc | ctg | gga | 48 |
| Met | Gln | Arg | Gly | Ala | Ala | Leu | Cys | Leu | Arg | Leu | Trp | Leu | Cys | Leu | Gly | |
| 1 | | | | 5 | | | | | 10 | | | | | 15 | | |
| ctc | ctg | gac | ggc | ctg | gtg | agt | ggc | tac | tcc | atg | acc | ccc | ccg | acc | ttg | 96 |
| Leu | Leu | Asp | Gly | Leu | Val | Ser | Gly | Tyr | Ser | Met | Thr | Pro | Pro | Thr | Leu | |
| | | | 20 | | | | | 25 | | | | | 30 | | | |
| aac | atc | acg | gag | gag | tca | cac | gtc | aga | gac | ttt | gag | cag | cca | ttc | atc | 144 |
| Asn | Ile | Thr | Glu | Glu | Ser | His | Val | Arg | Asp | Phe | Glu | Gln | Pro | Phe | Ile | |
| | | 35 | | | | | 40 | | | | | 45 | | | | |
| aac | aag | cct | gac | acg | ctc | ttg | gtc | aac | agg | aag | gac | gcc | atg | tgg | gtg | 192 |
| Asn | Lys | Pro | Asp | Thr | Leu | Leu | Val | Asn | Arg | Lys | Asp | Ala | Met | Trp | Val | |
| | 50 | | | | | 55 | | | | | 60 | | | | | |
| ccc | tgt | ctg | gtg | tcc | atc | ccc | ggc | ctc | aat | gtc | acg | ctg | cgc | tcg | caa | 240 |
| Pro | Cys | Leu | Val | Ser | Ile | Pro | Gly | Leu | Asn | Val | Thr | Leu | Arg | Ser | Gln | |
| 65 | | | | | 70 | | | | | 75 | | | | | 80 | |
| agc | tcg | gtg | ctg | tgg | cca | gac | ggg | cag | gag | gtg | gtg | tgg | gat | gac | cgg | 288 |
| Ser | Ser | Val | Leu | Trp | Pro | Asp | Gly | Gln | Glu | Val | Val | Trp | Asp | Asp | Arg | |
| | | | | 85 | | | | | 90 | | | | | 95 | | |
| cgg | ggc | atg | ctc | gtg | tcc | acg | cca | ctg | ctg | cac | gat | gcc | ctg | tac | ctg | 336 |
| Arg | Gly | Met | Leu | Val | Ser | Thr | Pro | Leu | Leu | His | Asp | Ala | Leu | Tyr | Leu | |
| | | | 100 | | | | | 105 | | | | | 110 | | | |
| cag | tgc | gag | acc | acc | tgg | gga | gac | cag | gac | ttc | ctt | tcc | aac | ccc | ttc | 384 |
| Gln | Cys | Glu | Thr | Thr | Trp | Gly | Asp | Gln | Asp | Phe | Leu | Ser | Asn | Pro | Phe | |
| | | 115 | | | | | 120 | | | | | 125 | | | | |
| gcg | gat | ccc | atc | gaa | ggt | cgt | ggt | ggt | ggt | ggt | ggt | gat | ccc | aaa | tct | 432 |
| Ala | Asp | Pro | Ile | Glu | Gly | Arg | Gly | Gly | Gly | Gly | Gly | Asp | Pro | Lys | Ser | |
| | 130 | | | | | 135 | | | | | 140 | | | | | |
| tgt | gac | aaa | cct | cac | aca | tgc | cca | ctg | tgc | cca | gca | cct | gaa | ctc | ctg | 480 |
| Cys | Asp | Lys | Pro | His | Thr | Cys | Pro | Leu | Cys | Pro | Ala | Pro | Glu | Leu | Leu | |
| 145 | | | | | 150 | | | | | 155 | | | | | 160 | |
| ggg | gga | ccg | tca | gtc | ttc | ctc | ttc | ccc | cca | aaa | ccc | aag | gac | acc | ctc | 528 |
| Gly | Gly | Pro | Ser | Val | Phe | Leu | Phe | Pro | Pro | Lys | Pro | Lys | Asp | Thr | Leu | |
| | | | | 165 | | | | | 170 | | | | | 175 | | |
| atg | atc | tcc | cgg | acc | cct | gag | gtc | aca | tgc | gtg | gtg | gtg | gac | gtg | agc | 576 |
| Met | Ile | Ser | Arg | Thr | Pro | Glu | Val | Thr | Cys | Val | Val | Val | Asp | Val | Ser | |
| | | | 180 | | | | | 185 | | | | | 190 | | | |
| cac | gaa | gac | cct | gag | gtc | aag | ttc | aac | tgg | tac | gtg | gac | ggc | gtg | gag | 624 |
| His | Glu | Asp | Pro | Glu | Val | Lys | Phe | Asn | Trp | Tyr | Val | Asp | Gly | Val | Glu | |
| | | 195 | | | | | 200 | | | | | 205 | | | | |
| gtg | cat | aat | gcc | aag | aca | aag | ccg | cgg | gag | gag | cag | tac | aac | agc | acg | 672 |
| Val | His | Asn | Ala | Lys | Thr | Lys | Pro | Arg | Glu | Glu | Gln | Tyr | Asn | Ser | Thr | |
| | 210 | | | | | 215 | | | | | 220 | | | | | |
| tac | cgt | gtg | gtc | agc | gtc | ctc | acc | gtc | ctg | cac | cag | gac | tgg | ctg | aat | 720 |
| Tyr | Arg | Val | Val | Ser | Val | Leu | Thr | Val | Leu | His | Gln | Asp | Trp | Leu | Asn | |
| 225 | | | | | 230 | | | | | 235 | | | | | 240 | |
| ggc | aag | gag | tac | aag | tgc | aag | gtc | tcc | aac | aaa | gcc | ctc | cca | gcc | ccc | 768 |
| Gly | Lys | Glu | Tyr | Lys | Cys | Lys | Val | Ser | Asn | Lys | Ala | Leu | Pro | Ala | Pro | |
| | | | | 245 | | | | | 250 | | | | | 255 | | |
| atc | gag | aaa | acc | atc | tcc | aaa | gcc | aaa | ggg | cag | ccc | cga | gaa | cca | cag | 816 |

-continued

```
Ile Glu Lys Thr Ile Ser Lys Ala Lys Gly Gln Pro Arg Glu Pro Gln
            260                 265                 270 gtg tac acc ctg ccc cca tcc cgg gat gag ctg acc aag aac cag gtc      864
Val Tyr Thr Leu Pro Pro Ser Arg Asp Glu Leu Thr Lys Asn Gln Val
    275                 280                 285 agc ctg acc tgc cta gtc aaa ggc ttc tat ccc agc gac atc gcc gtg      912
Ser Leu Thr Cys Leu Val Lys Gly Phe Tyr Pro Ser Asp Ile Ala Val
290                 295                 300 gag tgg gag agc aat ggg cag ccg gag aac aac tac aag gcc acg cct      960
Glu Trp Glu Ser Asn Gly Gln Pro Glu Asn Asn Tyr Lys Ala Thr Pro
305                 310                 315                 320 ccc gtg ctg gac tcc gac ggc tcc ttc ttc ctc tac agc aag ctc acc     1008
Pro Val Leu Asp Ser Asp Gly Ser Phe Phe Leu Tyr Ser Lys Leu Thr
                325                 330                 335 gtg gac aag agc agg tgg cag cag ggg aac gtc ttc tca tgc tcc gtg     1056
Val Asp Lys Ser Arg Trp Gln Gln Gly Asn Val Phe Ser Cys Ser Val
            340                 345                 350 atg cat gag gct ctg cac aac cac tac acg cag aag agc ctc tcc ctg     1104
Met His Glu Ala Leu His Asn His Tyr Thr Gln Lys Ser Leu Ser Leu
        355                 360                 365 tct ccg ggt aaa tga                                                  1119
Ser Pro Gly Lys
    370

<210> SEQ ID NO 56
<211> LENGTH: 372
<212> TYPE: PRT
<213> ORGANISM: Artificial sequence
<220> FEATURE:
<223> OTHER INFORMATION: Synthetic polypeptide

<400> SEQUENCE: 56

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Arg Asp Phe Glu Gln Pro Phe Ile
        35                  40                  45

Asn Lys Pro Asp Thr Leu Leu Val Asn Arg Lys Asp Ala Met Trp Val
    50                  55                  60

Pro Cys Leu Val Ser Ile Pro Gly Leu Asn Val Thr Leu Arg Ser Gln
65                  70                  75                  80

Ser Ser Val Leu Trp Pro Asp Gly Gln Glu Val Val Trp Asp Asp Arg
                85                  90                  95

Arg Gly Met Leu Val Ser Thr Pro Leu Leu His Asp Ala Leu Tyr Leu
            100                 105                 110

Gln Cys Glu Thr Thr Trp Gly Asp Gln Asp Phe Leu Ser Asn Pro Phe
        115                 120                 125

Ala Asp Pro Ile Glu Gly Arg Gly Gly Gly Asp Pro Lys Ser
    130                 135                 140

Cys Asp Lys Pro His Thr Cys Pro Leu Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205
```

```
Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Asp Glu Leu Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Ala Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
    370

<210> SEQ ID NO 57
<211> LENGTH: 1161
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R-3 N
<220> FEATURE:
<221> NAME/KEY: CDS
<222> LOCATION: (1)..(1161)

<400> SEQUENCE: 57 atg cag cgg ggc gcc gcg ctg tgc ctg cga ctg tgg ctc tgc ctg gga      48
Met Gln Arg Gly Ala Ala Leu Cys Leu Arg Leu Trp Leu Cys Leu Gly
1               5                   10                  15 ctc ctg gac ggc ctg gtg agt ggc tac tcc atg acc ccc ccg acc ttg      96
Leu Leu Asp Gly Leu Val Ser Gly Tyr Ser Met Thr Pro Pro Thr Leu
            20                  25                  30 aac atc acg gag gag tca cac gtc aac gag ctc tat gac atc cag ctg     144
Asn Ile Thr Glu Glu Ser His Val Asn Glu Leu Tyr Asp Ile Gln Leu
        35                  40                  45 ttg ccc agg aag tcg ctg gag ctg ctg gta ggg gag aag ctg gtc ctg     192
Leu Pro Arg Lys Ser Leu Glu Leu Leu Val Gly Glu Lys Leu Val Leu
    50                  55                  60 aac tgc acc gtg tgg gct gag ttt aac tca ggt gtc acc ttt gac tgg     240
Asn Cys Thr Val Trp Ala Glu Phe Asn Ser Gly Val Thr Phe Asp Trp
65                  70                  75                  80 gac tac cca ggg aag cag gca gag cgg ggt aag tgg gtg ccc gag cga     288
Asp Tyr Pro Gly Lys Gln Ala Glu Arg Gly Lys Trp Val Pro Glu Arg
                85                  90                  95 cgc tcc cag cag acc cac aca gaa ctc tcc agc atc ctg acc atc cac     336
Arg Ser Gln Gln Thr His Thr Glu Leu Ser Ser Ile Leu Thr Ile His
            100                 105                 110 aac gtc agc cag cac gac ctg ggc tcg tat gtg tgc aag gcc aac aac     384
```

```
                Asn Val Ser Gln His Asp Leu Gly Ser Tyr Val Cys Lys Ala Asn Asn
                                115                 120                 125 ggc atc cag cga ttt cgg gag agc acc gag gtc att gtg cat gag gat          432
Gly Ile Gln Arg Phe Arg Glu Ser Thr Glu Val Ile Val His Glu Asp
            130                 135                 140 ccc atc gaa ggt cgt ggt ggt ggt ggt gat ccc aaa tct tgt gac              480
Pro Ile Glu Gly Arg Gly Gly Gly Gly Asp Pro Lys Ser Cys Asp
145                 150                 155                 160 aaa cct cac aca tgc cca ctg tgc cca gca cct gaa ctc ctg ggg gga          528
Lys Pro His Thr Cys Pro Leu Cys Pro Ala Pro Glu Leu Leu Gly Gly
                165                 170                 175 ccg tca gtc ttc ctc ttc ccc cca aaa ccc aag gac acc ctc atg atc          576
Pro Ser Val Phe Leu Phe Pro Pro Lys Pro Lys Asp Thr Leu Met Ile
            180                 185                 190 tcc cgg acc cct gag gtc aca tgc gtg gtg gtg gac gtg agc cac gaa          624
Ser Arg Thr Pro Glu Val Thr Cys Val Val Val Asp Val Ser His Glu
        195                 200                 205 gac cct gag gtc aag ttc aac tgg tac gtg gac ggc gtg gag gtg cat          672
Asp Pro Glu Val Lys Phe Asn Trp Tyr Val Asp Gly Val Glu Val His
    210                 215                 220 aat gcc aag aca aag ccg cgg gag gag cag tac aac agc acg tac cgt          720
Asn Ala Lys Thr Lys Pro Arg Glu Glu Gln Tyr Asn Ser Thr Tyr Arg
225                 230                 235                 240 gtg gtc agc gtc ctc acc gtc ctg cac cag gac tgg ctg aat ggc aag          768
Val Val Ser Val Leu Thr Val Leu His Gln Asp Trp Leu Asn Gly Lys
                245                 250                 255 gag tac aag tgc aag gtc tcc aac aaa gcc ctc cca gcc ccc atc gag          816
Glu Tyr Lys Cys Lys Val Ser Asn Lys Ala Leu Pro Ala Pro Ile Glu
            260                 265                 270 aaa acc atc tcc aaa gcc aaa ggg cag ccc cga gaa cca cag gtg tac          864
Lys Thr Ile Ser Lys Ala Lys Gly Gln Pro Arg Glu Pro Gln Val Tyr
        275                 280                 285 acc ctg ccc cca tcc cgg gat gag ctg acc aag aac cag gtc agc ctg          912
Thr Leu Pro Pro Ser Arg Asp Glu Leu Thr Lys Asn Gln Val Ser Leu
    290                 295                 300 acc tgc cta gtc aaa ggc ttc tat ccc agc gac atc gcc gtg gag tgg          960
Thr Cys Leu Val Lys Gly Phe Tyr Pro Ser Asp Ile Ala Val Glu Trp
305                 310                 315                 320 gag agc aat ggg cag ccg gag aac aac tac aag gcc acg cct ccc gtg         1008
Glu Ser Asn Gly Gln Pro Glu Asn Asn Tyr Lys Ala Thr Pro Pro Val
                325                 330                 335 ctg gac tcc gac ggc tcc ttc ttc ctc tac agc aag ctc acc gtg gac         1056
Leu Asp Ser Asp Gly Ser Phe Phe Leu Tyr Ser Lys Leu Thr Val Asp
            340                 345                 350 aag agc agg tgg cag cag ggg aac gtc ttc tca tgc tcc gtg atg cat         1104
Lys Ser Arg Trp Gln Gln Gly Asn Val Phe Ser Cys Ser Val Met His
        355                 360                 365 gag gct ctg cac aac cac tac acg cag aag agc ctc tcc ctg tct ccg         1152
Glu Ala Leu His Asn His Tyr Thr Gln Lys Ser Leu Ser Leu Ser Pro
    370                 375                 380 ggt aaa tga                                                              1161
Gly Lys
385

<210> SEQ ID NO 58
<211> LENGTH: 386
<212> TYPE: PRT
<213> ORGANISM: Artificial sequence
<220> FEATURE:
<223> OTHER INFORMATION: Synthetic polypeptide
```

<400> SEQUENCE: 58

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Asn Glu Leu Tyr Asp Ile Gln Leu
        35                  40                  45

Leu Pro Arg Lys Ser Leu Glu Leu Leu Val Gly Glu Lys Leu Val Leu
    50                  55                  60

Asn Cys Thr Val Trp Ala Glu Phe Asn Ser Gly Val Thr Phe Asp Trp
65                  70                  75                  80

Asp Tyr Pro Gly Lys Gln Ala Glu Arg Gly Lys Trp Val Pro Glu Arg
                85                  90                  95

Arg Ser Gln Gln Thr His Thr Glu Leu Ser Ser Ile Leu Thr Ile His
            100                 105                 110

Asn Val Ser Gln His Asp Leu Gly Ser Tyr Val Cys Lys Ala Asn Asn
        115                 120                 125

Gly Ile Gln Arg Phe Arg Glu Ser Thr Glu Val Ile Val His Glu Asp
    130                 135                 140

Pro Ile Glu Gly Arg Gly Gly Gly Gly Asp Pro Lys Ser Cys Asp
145                 150                 155                 160

Lys Pro His Thr Cys Pro Leu Cys Pro Ala Pro Glu Leu Leu Gly Gly
                165                 170                 175

Pro Ser Val Phe Leu Phe Pro Pro Lys Pro Lys Asp Thr Leu Met Ile
            180                 185                 190

Ser Arg Thr Pro Glu Val Thr Cys Val Val Asp Val Ser His Glu
        195                 200                 205

Asp Pro Glu Val Lys Phe Asn Trp Tyr Val Asp Gly Val Glu Val His
    210                 215                 220

Asn Ala Lys Thr Lys Pro Arg Glu Glu Gln Tyr Asn Ser Thr Tyr Arg
225                 230                 235                 240

Val Val Ser Val Leu Thr Val Leu His Gln Asp Trp Leu Asn Gly Lys
                245                 250                 255

Glu Tyr Lys Cys Lys Val Ser Asn Lys Ala Leu Pro Ala Pro Ile Glu
            260                 265                 270

Lys Thr Ile Ser Lys Ala Lys Gly Gln Pro Arg Glu Pro Gln Val Tyr
        275                 280                 285

Thr Leu Pro Pro Ser Arg Asp Glu Leu Thr Lys Asn Gln Val Ser Leu
    290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Ala Thr Pro Pro Val
                325                 330                 335

Leu Asp Ser Asp Gly Ser Phe Phe Leu Tyr Ser Lys Leu Thr Val Asp
            340                 345                 350

Lys Ser Arg Trp Gln Gln Gly Asn Val Phe Ser Cys Ser Val Met His
        355                 360                 365

Glu Ala Leu His Asn His Tyr Thr Gln Lys Ser Leu Ser Leu Ser Pro
    370                 375                 380

Gly Lys
385
```

<210> SEQ ID NO 59

<211> LENGTH: 27
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-2 D1 reverse primer

<400> SEQUENCE: 59
gctggatctt gaacatagac ataaatg        27

<210> SEQ ID NO 60
<211> LENGTH: 27
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-2 D1-2 reverse primer #1

<400> SEQUENCE: 60
ctaggatccc ctacaacgac aactatg        27

<210> SEQ ID NO 61
<211> LENGTH: 27
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-2 D1-2 reverse primer #2

<400> SEQUENCE: 61
ctaggatcca catcataaat cctatac        27

<210> SEQ ID NO 62
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-2 D1-2 reverse primer #3

<400> SEQUENCE: 62
gcatggtctc ggatcatgag aagacggact cagaac        36

<210> SEQ ID NO 63
<211> LENGTH: 26
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-2 D1-2 reverse primer #4

<400> SEQUENCE: 63
ctaggatcct tttctccaac agatag        26

<210> SEQ ID NO 64
<211> LENGTH: 29
<212> TYPE: DNA
<213> ORGANISM: Artificial sequence
<220> FEATURE:

```
<223> OTHER INFORMATION: Synthetic polynucleotide
<220> FEATURE:
<221> NAME/KEY: misc_feature
<223> OTHER INFORMATION: VEGFR-2 D2 forward primer

<400> SEQUENCE: 64
agcgctagcg ttcaagatta cagatctcc                                    29

<210> SEQ ID NO 65
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-2 D2-3 reverse primer

<400> SEQUENCE: 65
atgtgtgagg ttttgcacaa g                                            21

<210> SEQ ID NO 66
<211> LENGTH: 27
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-2 D2 reverse primer #1

<400> SEQUENCE: 66
ctaggatccc ctacaacgac aactatg                                      27

<210> SEQ ID NO 67
<211> LENGTH: 27
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-2 D2 reverse primer #2

<400> SEQUENCE: 67
ctaggatcca catcataaat cctatac                                      27

<210> SEQ ID NO 68
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-2 D2 reverse primer #3

<400> SEQUENCE: 68
gcatggtctc ggatcatgag aagacggact cagaac                            36

<210> SEQ ID NO 69
<211> LENGTH: 26
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-2 D2 reverse primer #4
```

```
<400> SEQUENCE: 69
ctaggatcct tttctccaac agatag                                    26

<210> SEQ ID NO 70
<211> LENGTH: 27
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-2 D3 forward primer

<400> SEQUENCE: 70
agcgctagct ataggattta tgatgtg                                   27

<210> SEQ ID NO 71
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-2 D3 reverse primer

<400> SEQUENCE: 71
atgtgtgagg ttttgcacaa g                                         21

<210> SEQ ID NO 72
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-2 D1-3 reverse primer 1

<400> SEQUENCE: 72
gcggatcctt gcctagtgtt tctcttgatc                                30

<210> SEQ ID NO 73
<211> LENGTH: 40
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-2 D1-3 reverse primer 2

<400> SEQUENCE: 73
ccagtcacct gctccggatc ttcatggacc ctgacaaatg                     40

<210> SEQ ID NO 74
<211> LENGTH: 25
<212> TYPE: DNA
<213> ORGANISM: Artificial sequence
<220> FEATURE:
<221> NAME/KEY: misc_feature
<223> OTHER INFORMATION: VEGFR-3 D1-2 reverse primer 1

<400> SEQUENCE: 74
tcaggatccg cgagctcgtt gcctg                                     25
```

```
<210> SEQ ID NO 75
<211> LENGTH: 27
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-3 D1-2 reverse primer 2

<400> SEQUENCE: 75
tacaggatcc cctgtgatgt gcaccag                                27

<210> SEQ ID NO 76
<211> LENGTH: 25
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-3 D1-2 reverse primer 3

<400> SEQUENCE: 76
tcaggatccg cgtgcaccag gaagg                                  25

<210> SEQ ID NO 77
<211> LENGTH: 26
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-3 D1-2 reverse primer 4

<400> SEQUENCE: 77
tcaggatccg cgaaggggtt ggaaag                                 26

<210> SEQ ID NO 78
<211> LENGTH: 60
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-3 Delta D1 primer 1

<400> SEQUENCE: 78
ccttgaacat cacggaggag tcacacgtca gagactttga gcagccattc atcaacaagc    60

<210> SEQ ID NO 79
<211> LENGTH: 42
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFR-3 Delta D1 primer 2

<400> SEQUENCE: 79
agctgctggt aggggagaag gatcctgaac tgcaccgtgt gg               42

<210> SEQ ID NO 80
<211> LENGTH: 990
<212> TYPE: DNA
<213> ORGANISM: Homo sapiens
```

```
<220> FEATURE:
<221> NAME/KEY: misc_feature
<223> OTHER INFORMATION: VEGF-A
<220> FEATURE:
<221> NAME/KEY: CDS
<222> LOCATION: (57)..(629)

<400> SEQUENCE: 80
cagtgtgctg gcggcccggc gcgagccggc ccggccccgg tcgggcctcc gaaacc atg      59
                                                                 Met
                                                                  1 aac ttt ctg ctg tct tgg gtg cat tgg agc ctc gcc ttg ctg ctc tac       107
Asn Phe Leu Leu Ser Trp Val His Trp Ser Leu Ala Leu Leu Leu Tyr
         5                  10                  15 ctc cac cat gcc aag tgg tcc cag gct gca ccc atg gca gaa gga gga       155
Leu His His Ala Lys Trp Ser Gln Ala Ala Pro Met Ala Glu Gly Gly
             20                  25                  30 ggg cag aat cat cac gaa gtg gtg aag ttc atg gat gtc tat cag cgc       203
Gly Gln Asn His His Glu Val Val Lys Phe Met Asp Val Tyr Gln Arg
 35                  40                  45 agc tac tgc cat cca atc gag acc ctg gtg gac atc ttc cag gag tac       251
Ser Tyr Cys His Pro Ile Glu Thr Leu Val Asp Ile Phe Gln Glu Tyr
 50                  55                  60                  65 cct gat gag atc gag tac atc ttc aag cca tcc tgt gtg ccc ctg atg       299
Pro Asp Glu Ile Glu Tyr Ile Phe Lys Pro Ser Cys Val Pro Leu Met
                 70                  75                  80 cga tgc ggg ggc tgc tgc aat gac gag ggc ctg gag tgt gtg ccc act       347
Arg Cys Gly Gly Cys Cys Asn Asp Glu Gly Leu Glu Cys Val Pro Thr
             85                  90                  95 gag gag tcc aac atc acc atg cag att atg cgg atc aaa cct cac caa       395
Glu Glu Ser Asn Ile Thr Met Gln Ile Met Arg Ile Lys Pro His Gln
        100                 105                 110 ggc cag cac ata gga gag atg agc ttc cta cag cac aac aaa tgt gaa       443
Gly Gln His Ile Gly Glu Met Ser Phe Leu Gln His Asn Lys Cys Glu
    115                 120                 125 tgc aga cca aag aaa gat aga gca aga caa gaa aat ccc tgt ggg cct       491
Cys Arg Pro Lys Lys Asp Arg Ala Arg Gln Glu Asn Pro Cys Gly Pro
130                 135                 140                 145 tgc tca gag cgg aga aag cat ttg ttt gta caa gat ccg cag acg tgt       539
Cys Ser Glu Arg Arg Lys His Leu Phe Val Gln Asp Pro Gln Thr Cys
                150                 155                 160 aaa tgt tcc tgc aaa aac aca gac tcg cgt tgc aag gcg agg cag ctt       587
Lys Cys Ser Cys Lys Asn Thr Asp Ser Arg Cys Lys Ala Arg Gln Leu
            165                 170                 175 gag tta aac gaa cgt act tgc aga tgt gac aag ccg agg cgg                629
Glu Leu Asn Glu Arg Thr Cys Arg Cys Asp Lys Pro Arg Arg
        180                 185                 190 tgagccgggc aggaggaagg agcctccctc agggtttcgg gaaccagatc tctcaccagg      689
aaagactgat acagaacgat cgatacagaa accacgctgc cgccaccaca ccatcaccat      749
cgacagaaca gtccttaatc cagaaacctg aaatgaagga agaggagact ctgcgcagag      809
cactttgggt ccgagggcg agactccggc ggaagcattc ccgggcgggt gacccagcac       869
ggtccctctt ggaattggat tcgccatttt attttcttg ctgctaaatc accgagcccg       929
gaagattaga gagttttatt tctgggattc ctgtagacac accgcggccg ccagcacact      989
g                                                                     990

<210> SEQ ID NO 81
<211> LENGTH: 191
<212> TYPE: PRT
```

<213> ORGANISM: Homo sapiens

<400> SEQUENCE: 81

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190
```

<210> SEQ ID NO 82
<211> LENGTH: 1997
<212> TYPE: DNA
<213> ORGANISM: Homo sapiens
<220> FEATURE:
<221> NAME/KEY: misc_feature
<223> OTHER INFORMATION: VEGF-C
<220> FEATURE:
<221> NAME/KEY: CDS
<222> LOCATION: (352)..(1608)

<400> SEQUENCE: 82

```
cccgccccgc ctctccaaaa agctacaccg acgcggaccg cggcggcgtc ctccctcgcc      60
ctcgcttcac ctcgcgggct ccgaatgcgg ggagctcgga tgtccggttt cctgtgaggc     120
ttttacctga cacccgccgc ctttccccgg cactggctgg gagggcgccc tgcaaagttg     180
ggaacgcgga gccccggacc cgctcccgcc gcctccggct cgcccagggg gggtcgccgg     240
gaggagcccg ggggagaggg accaggaggg gcccgcggcc tcgcaggggc gcccgcgccc     300 ccaccctgc ccccgccagc ggaccggtcc cccacccccg gtccttccac c atg cac    357
                                                        Met His
                                                        1 ttg ctg ggc ttc ttc tct gtg gcg tgt tct ctg ctc gcc gct gcg ctg      405
Leu Leu Gly Phe Phe Ser Val Ala Cys Ser Leu Leu Ala Ala Ala Leu
        5                   10                  15 ctc ccg ggt cct cgc gag gcg ccc gcc gcc gcc gcc ttc gag tcc          453
Leu Pro Gly Pro Arg Glu Ala Pro Ala Ala Ala Ala Phe Glu Ser
    20                  25                  30 gga ctc gac ctc tcg gac gcg gag ccc gac gcg ggc gag gcc acg gct      501
Gly Leu Asp Leu Ser Asp Ala Glu Pro Asp Ala Gly Glu Ala Thr Ala
35                  40                  45                  50
```

-continued

| | |
|---|---|
| tat gca agc aaa gat ctg gag gag cag tta cgg tct gtg tcc agt gta<br>Tyr Ala Ser Lys Asp Leu Glu Glu Gln Leu Arg Ser Val Ser Ser Val<br>55              60              65 | 549 |
| gat gaa ctc atg act gta ctc tac cca gaa tat tgg aaa atg tac aag<br>Asp Glu Leu Met Thr Val Leu Tyr Pro Glu Tyr Trp Lys Met Tyr Lys<br>70              75              80 | 597 |
| tgt cag cta agg aaa ggc tgg caa cat aac aga gaa cag gcc aac<br>Cys Gln Leu Arg Lys Gly Gly Trp Gln His Asn Arg Glu Gln Ala Asn<br>85              90              95 | 645 |
| ctc aac tca agg aca gaa gag act ata aaa ttt gct gca gca cat tat<br>Leu Asn Ser Arg Thr Glu Glu Thr Ile Lys Phe Ala Ala Ala His Tyr<br>100              105              110 | 693 |
| aat aca gag atc ttg aaa agt att gat aat gag tgg aga aag act caa<br>Asn Thr Glu Ile Leu Lys Ser Ile Asp Asn Glu Trp Arg Lys Thr Gln<br>115              120              125              130 | 741 |
| tgc atg cca cgg gag gtg tgt ata gat gtg ggg aag gag ttt gga gtc<br>Cys Met Pro Arg Glu Val Cys Ile Asp Val Gly Lys Glu Phe Gly Val<br>135              140              145 | 789 |
| gcg aca aac acc ttc ttt aaa cct cca tgt gtg tcc gtc tac aga tgt<br>Ala Thr Asn Thr Phe Phe Lys Pro Pro Cys Val Ser Val Tyr Arg Cys<br>150              155              160 | 837 |
| ggg ggt tgc tgc aat agt gag ggg ctg cag tgc atg aac acc agc acg<br>Gly Gly Cys Cys Asn Ser Glu Gly Leu Gln Cys Met Asn Thr Ser Thr<br>165              170              175 | 885 |
| agc tac ctc agc aag acg tta ttt gaa att aca gtg cct ctc tct caa<br>Ser Tyr Leu Ser Lys Thr Leu Phe Glu Ile Thr Val Pro Leu Ser Gln<br>180              185              190 | 933 |
| ggc ccc aaa cca gta aca atc agt ttt gcc aat cac act tcc tgc cga<br>Gly Pro Lys Pro Val Thr Ile Ser Phe Ala Asn His Thr Ser Cys Arg<br>195              200              205              210 | 981 |
| tgc atg tct aaa ctg gat gtt tac aga caa gtt cat tcc att att aga<br>Cys Met Ser Lys Leu Asp Val Tyr Arg Gln Val His Ser Ile Ile Arg<br>215              220              225 | 1029 |
| cgt tcc ctg cca gca aca cta cca cag tgt cag gca gcg aac aag acc<br>Arg Ser Leu Pro Ala Thr Leu Pro Gln Cys Gln Ala Ala Asn Lys Thr<br>230              235              240 | 1077 |
| tgc ccc acc aat tac atg tgg aat aat cac atc tgc aga tgc ctg gct<br>Cys Pro Thr Asn Tyr Met Trp Asn Asn His Ile Cys Arg Cys Leu Ala<br>245              250              255 | 1125 |
| cag gaa gat ttt atg ttt tcc tcg gat gct gga gat gac tca aca gat<br>Gln Glu Asp Phe Met Phe Ser Ser Asp Ala Gly Asp Asp Ser Thr Asp<br>260              265              270 | 1173 |
| gga ttc cat gac atc tgt gga cca aac aag gag ctg gat gaa gag acc<br>Gly Phe His Asp Ile Cys Gly Pro Asn Lys Glu Leu Asp Glu Glu Thr<br>275              280              285              290 | 1221 |
| tgt cag tgt gtc tgc aga gcg ggg ctt cgg cct gcc agc tgt gga ccc<br>Cys Gln Cys Val Cys Arg Ala Gly Leu Arg Pro Ala Ser Cys Gly Pro<br>295              300              305 | 1269 |
| cac aaa gaa cta gac aga aac tca tgc cag tgt gtc tgt aaa aac aaa<br>His Lys Glu Leu Asp Arg Asn Ser Cys Gln Cys Val Cys Lys Asn Lys<br>310              315              320 | 1317 |
| ctc ttc ccc agc caa tgt ggg gcc aac cga gaa ttt gat gaa aac aca<br>Leu Phe Pro Ser Gln Cys Gly Ala Asn Arg Glu Phe Asp Glu Asn Thr<br>325              330              335 | 1365 |
| tgc cag tgt gta tgt aaa aga acc tgc ccc aga aat caa ccc cta aat<br>Cys Gln Cys Val Cys Lys Arg Thr Cys Pro Arg Asn Gln Pro Leu Asn<br>340              345              350 | 1413 |
| cct gga aaa tgt gcc tgt gaa tgt aca gaa agt cca cag aaa tgc ttg<br>Pro Gly Lys Cys Ala Cys Glu Cys Thr Glu Ser Pro Gln Lys Cys Leu | 1461 |

```
                   355                 360                 365                 370
tta aaa gga aag aag ttc cac cac caa aca tgc agc tgt tac aga cgg        1509
Leu Lys Gly Lys Lys Phe His His Gln Thr Cys Ser Cys Tyr Arg Arg
                375                 380                 385 cca tgt acg aac cgc cag aag gct tgt gag cca gga ttt tca tat agt        1557
Pro Cys Thr Asn Arg Gln Lys Ala Cys Glu Pro Gly Phe Ser Tyr Ser
                390                 395                 400 gaa gaa gtg tgt cgt tgt gtc cct tca tat tgg aaa aga cca caa atg        1605
Glu Glu Val Cys Arg Cys Val Pro Ser Tyr Trp Lys Arg Pro Gln Met
            405                 410                 415 agc taagattgta ctgttttcca gttcatcgat tttctattat ggaaaactgt             1658
Ser gttgccacag tagaactgtc tgtgaacaga gagaccttg tgggtccatg ctaacaaga         1718 caaaagtctg tctttcctga accatgtgga taactttaca gaatggact ggagctcatc       1778 tgcaaaaggc ctcttgtaaa gactggtttt ctgccaatga ccaaacagcc aagattttcc      1838
tcttgtgatt tctttaaaag aatgactata taatttattt ccactaaaaa tattgtttct      1898
gcattcattt ttatagcaac aacaattggt aaaactcact gtgatcaata ttttatatc       1958 atgcaaaata tgtttaaaat aaaatgaaaa ttgtattat                             1997

<210> SEQ ID NO 83
<211> LENGTH: 419
<212> TYPE: PRT
<213> ORGANISM: Homo sapiens

<400> SEQUENCE: 83

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
                20                  25                  30

Glu Ser Gly Leu Asp Leu Ser Asp Ala Glu Pro Asp Ala Gly Glu Ala
            35                  40                  45

Thr Ala Tyr Ala Ser Lys Asp Leu Glu Glu Gln Leu Arg Ser Val Ser
        50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
                100                 105                 110

His Tyr Asn Thr Glu Ile Leu Lys Ser Ile Asp Asn Glu Trp Arg Lys
            115                 120                 125

Thr Gln Cys Met Pro Arg Glu Val Cys Ile Asp Val Gly Lys Glu Phe
        130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
                180                 185                 190

Ser Gln Gly Pro Lys Pro Val Thr Ile Ser Phe Ala Asn His Thr Ser
            195                 200                 205

Cys Arg Cys Met Ser Lys Leu Asp Val Tyr Arg Gln Val His Ser Ile
        210                 215                 220
```

```
Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
            245                 250                 255

Leu Ala Gln Glu Asp Phe Met Phe Ser Ser Asp Ala Gly Asp Asp Ser
        260                 265                 270

Thr Asp Gly Phe His Asp Ile Cys Gly Pro Asn Lys Glu Leu Asp Glu
    275                 280                 285

Glu Thr Cys Gln Cys Val Cys Arg Ala Gly Leu Arg Pro Ala Ser Cys
290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
    370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 84
<211> LENGTH: 1645
<212> TYPE: DNA
<213> ORGANISM: Homo sapiens
<220> FEATURE:
<221> NAME/KEY: misc_feature
<223> OTHER INFORMATION: PIGF
<220> FEATURE:
<221> NAME/KEY: CDS
<222> LOCATION: (322)..(768)

<400> SEQUENCE: 84
gggattcggg ccgcccagct acgggaggac ctggagtggc actgggcgcc cgacggacca      60
tccccgggac ccgcctgccc ctcggcgccc cgccccgccg ggccgctccc cgtcgggttc     120
cccagccaca gccttaccta cgggctcctg actccgcaag cttccagaa gatgctcgaa     180 ccaccggccg gggcctcggg gcagcagtga gggaggcgtc cagcccccca ctcagctctt     240
ctcctcctgt gccaggggct ccccggggga tgagcatggt ggttttccct cggagccccc     300
tggctcggga cgtctgagaa g atg ccg gtc atg agg ctg ttc cct tgc ttc       351
                        Met Pro Val Met Arg Leu Phe Pro Cys Phe
                        1               5                   10 ctg cag ctc ctg gcc ggg ctg gcg ctg cct gct gtg ccc ccc cag cag       399
Leu Gln Leu Leu Ala Gly Leu Ala Leu Pro Ala Val Pro Pro Gln Gln
                15                  20                  25 tgg gcc ttg tct gct ggg aac ggc tcg tca gag gtg gaa gtg gta ccc       447
Trp Ala Leu Ser Ala Gly Asn Gly Ser Ser Glu Val Glu Val Val Pro
            30                  35                  40 ttc cag gaa gtg tgg ggc cgc agc tac tgc cgg gcg ctg gag agg ctg       495
Phe Gln Glu Val Trp Gly Arg Ser Tyr Cys Arg Ala Leu Glu Arg Leu
        45                  50                  55 gtg gac gtc gtg tcc gag tac ccc agc gag gtg gag cac atg ttc agc       543
```

| | | | | | | | | | | | | | | | |
|---|---|---|---|---|---|---|---|---|---|---|---|---|---|---|---|
|Val|Asp|Val|Val|Ser|Glu|Tyr|Pro|Ser|Glu|Val|Glu|His|Met|Phe|Ser|
| |60| | | |65| | | |70| | | | | | |

```
cca tcc tgt gtc tcc ctg ctg cgc tgc acc ggc tgc tgc ggc gat gag      591
Pro Ser Cys Val Ser Leu Leu Arg Cys Thr Gly Cys Cys Gly Asp Glu
75              80                  85                  90 aat ctg cac tgt gtg ccg gtg gag acg gcc aat gtc acc atg cag ctc      639
Asn Leu His Cys Val Pro Val Glu Thr Ala Asn Val Thr Met Gln Leu
                95                  100                 105 cta aag atc cgt tct ggg gac cgg ccc tcc tac gtg gag ctg acg ttc      687
Leu Lys Ile Arg Ser Gly Asp Arg Pro Ser Tyr Val Glu Leu Thr Phe
        110                 115                 120 tct cag cac gtt cgc tgc gaa tgc cgg cct ctg cgg gag aag atg aag      735
Ser Gln His Val Arg Cys Glu Cys Arg Pro Leu Arg Glu Lys Met Lys
            125                 130                 135 ccg gaa agg tgc ggc gat gct gtt ccc cgg agg taacccaccc cttggaggag    788
Pro Glu Arg Cys Gly Asp Ala Val Pro Arg Arg
        140                 145 agagaccccg cacccggctc gtgtatttat taccgtcaca ctcttcagtg actcctgctg    848
gtacctgccc tctatttatt agccaactgt ttccctgctg aatgcctcgc tcccttcaag    908 acgagggggca gggaaggaca ggaccctcag gaattcagtg ccttcaacaa cgtgagagaa   968
agagagaagc cagccacaga cccctgggag cttccgcttt gaaagaagca agacacgtgg   1028
cctcgtgagg ggcaagctag gccccagagg ccctggaggt ctccaggggc ctgcagaagg   1088
aaagaagggg gccctgctac ctgttcttgg gcctcaggct ctgcacagac aagcagccct   1148
tgctttcgga gctcctgtcc aaagtaggga tgcggattct gctggggccg ccacggcctg   1208
gtggtgggaa ggccggcagc gggcggaggg gattcagcca cttccccctc ttcttctgaa   1268
gatcagaaca ttcagctctg gagaacagtg gttgcctggg ggcttttgcc actccttgtc   1328
ccccgtgatc tcccctcaca ctttgccatt tgcttgtact gggacattgt tctttccggc   1388
cgaggtgcca ccaccctgcc cccactaaga gacacataca gagtgggccc cgggctggag   1448
aaagagctgc ctggatgaga aacagctcag ccagtgggga tgaggtcacc aggggaggag   1508
cctgtgcgtc ccagctgaag gcagtggcag gggagcaggt tccccaaggg ccctggcacc   1568
cccacaagct gtccctgcag ggccatctga ctgccaagcc agattctctt gaataaagta   1628
ttctagtgtg gaaacgc                                                  1645

<210> SEQ ID NO 85
<211> LENGTH: 149
<212> TYPE: PRT
<213> ORGANISM: Homo sapiens

<400> SEQUENCE: 85

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
                20                  25                  30

Asn Gly Ser Ser Glu Val Glu Val Pro Phe Gln Glu Val Trp Gly
            35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95
```

```
Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg Pro Leu Arg Glu Lys Met Lys Pro Glu Arg Cys Gly Asp
    130                 135                 140

Ala Val Pro Arg Arg
145

<210> SEQ ID NO 86
<211> LENGTH: 2029
<212> TYPE: DNA
<213> ORGANISM: Homo sapiens
<220> FEATURE:
<221> NAME/KEY: misc_feature
<223> OTHER INFORMATION: VEGF-D
<220> FEATURE:
<221> NAME/KEY: CDS
<222> LOCATION: (411)..(1472)

<400> SEQUENCE: 86
gttgggttcc agctttctgt agctgtaagc attggtggcc acaccacctc cttacaaagc      60
aactagaacc tgcggcatac attggagaga ttttttttaat tttctggaca tgaagtaaat    120
ttagagtgct ttctaatttc aggtagaaga catgtccacc ttctgattat ttttggagaa    180
cattttgatt ttttcatct ctctctcccc accctaaga ttgtgcaaaa aaagcgtacc      240
ttgcctaatt gaataattt cattggattt tgatcagaac tgattattg gttttctgtg      300 tgaagttttg aggtttcaaa ctttccttct ggagaatgcc ttttgaaaca attttctcta    360
gctgcctgat gtcaactgct tagtaatcag tggatattga atattcaaa atg tac        416
                                                        Met Tyr
                                                         1 aga gag tgg gta gtg gtg aat gtt ttc atg atg ttg tac gtc cag ctg      464
Arg Glu Trp Val Val Val Asn Val Phe Met Met Leu Tyr Val Gln Leu
        5                   10                  15 gtg cag ggc tcc agt aat gaa cat gga cca gtg aag cga tca tct cag      512
Val Gln Gly Ser Ser Asn Glu His Gly Pro Val Lys Arg Ser Ser Gln
    20                  25                  30 tcc aca ttg gaa cga tct gaa cag cag atc agg gct gct tct agt ttg      560
Ser Thr Leu Glu Arg Ser Glu Gln Gln Ile Arg Ala Ala Ser Ser Leu
35                  40                  45                  50 gag gaa cta ctt cga att act cac tct gag gac tgg aag ctg tgg aga      608
Glu Glu Leu Leu Arg Ile Thr His Ser Glu Asp Trp Lys Leu Trp Arg
                55                  60                  65 tgc agg ctg agg ctc aaa agt ttt acc agt atg gac tct cgc tca gca      656
Cys Arg Leu Arg Leu Lys Ser Phe Thr Ser Met Asp Ser Arg Ser Ala
            70                  75                  80 tcc cat cgg tcc act agg ttt gcg gca act ttc tat gac att gaa aca      704
Ser His Arg Ser Thr Arg Phe Ala Ala Thr Phe Tyr Asp Ile Glu Thr
        85                  90                  95 cta aaa gtt ata gat gaa gaa tgg caa aga act cag tgc agc cct aga      752
Leu Lys Val Ile Asp Glu Glu Trp Gln Arg Thr Gln Cys Ser Pro Arg
    100                 105                 110 gaa acg tgc gtg gag gtg gcc agt gag ctg ggg aag agt acc aac aca      800
Glu Thr Cys Val Glu Val Ala Ser Glu Leu Gly Lys Ser Thr Asn Thr
115                 120                 125                 130 ttc ttc aag ccc cct tgt gtg aac gtg ttc cga tgt ggt ggc tgt tgc      848
Phe Phe Lys Pro Pro Cys Val Asn Val Phe Arg Cys Gly Gly Cys Cys
                135                 140                 145 aat gaa gag agc ctt atc tgt atg aac acc agc acc tcg tac att tcc      896
```

-continued

| | | |
|---|---|---|
| Asn Glu Glu Ser Leu Ile Cys Met Asn Thr Ser Thr Ser Tyr Ile Ser<br>150 155 160 | | |
| aaa cag ctc ttt gag ata tca gtg cct ttg aca tca gta cct gaa tta<br>Lys Gln Leu Phe Glu Ile Ser Val Pro Leu Thr Ser Val Pro Glu Leu<br>165 170 175 | 944 | |
| gtg cct gtt aaa gtt gcc aat cat aca ggt tgt aag tgc ttg cca aca<br>Val Pro Val Lys Val Ala Asn His Thr Gly Cys Lys Cys Leu Pro Thr<br>180 185 190 | 992 | |
| gcc ccc cgc cat cca tac tca att atc aga aga tcc atc cag atc cct<br>Ala Pro Arg His Pro Tyr Ser Ile Ile Arg Arg Ser Ile Gln Ile Pro<br>195 200 205 210 | 1040 | |
| gaa gaa gat cgc tgt tcc cat tcc aag aaa ctc tgt cct att gac atg<br>Glu Glu Asp Arg Cys Ser His Ser Lys Lys Leu Cys Pro Ile Asp Met<br>215 220 225 | 1088 | |
| cta tgg gat agc aac aaa tgt aaa tgt gtt ttg cag gag gaa aat cca<br>Leu Trp Asp Ser Asn Lys Cys Lys Cys Val Leu Gln Glu Glu Asn Pro<br>230 235 240 | 1136 | |
| ctt gct gga aca gaa gac cac tct cat ctc cag gaa cca gct ctc tgt<br>Leu Ala Gly Thr Glu Asp His Ser His Leu Gln Glu Pro Ala Leu Cys<br>245 250 255 | 1184 | |
| ggg cca cac atg atg ttt gac gaa gat cgt tgc gag tgt gtc tgt aaa<br>Gly Pro His Met Met Phe Asp Glu Asp Arg Cys Glu Cys Val Cys Lys<br>260 265 270 | 1232 | |
| aca cca tgt ccc aaa gat cta atc cag cac ccc aaa aac tgc agt tgc<br>Thr Pro Cys Pro Lys Asp Leu Ile Gln His Pro Lys Asn Cys Ser Cys<br>275 280 285 290 | 1280 | |
| ttt gag tgc aaa gaa agt ctg gag acc tgc tgc cag aag cac aag cta<br>Phe Glu Cys Lys Glu Ser Leu Glu Thr Cys Cys Gln Lys His Lys Leu<br>295 300 305 | 1328 | |
| ttt cac cca gac acc tgc agc tgt gag gac aga tgc ccc ttt cat acc<br>Phe His Pro Asp Thr Cys Ser Cys Glu Asp Arg Cys Pro Phe His Thr<br>310 315 320 | 1376 | |
| aga cca tgt gca agt ggc aaa aca gca tgt gca aag cat tgc cgc ttt<br>Arg Pro Cys Ala Ser Gly Lys Thr Ala Cys Ala Lys His Cys Arg Phe<br>325 330 335 | 1424 | |
| cca aag gag aaa agg gct gcc cag ggg ccc cac agc cga aag aat cct<br>Pro Lys Glu Lys Arg Ala Ala Gln Gly Pro His Ser Arg Lys Asn Pro<br>340 345 350 | 1472 | |
| tgattcagcg ttccaagttc cccatccctg tcatttttaa cagcatgctg ctttgccaag | 1532 | |
| ttgctgtcac tgttttttc ccaggtgtta aaaaaaaaat ccattttaca cagcaccaca | 1592 | |
| gtgaatccag accaaccttc cattcacacc agctaaggag tccctggttc attgatggat | 1652 | |
| gtcttctagc tgcagatgcc tctgcgcacc aaggaatgga gaggagggga cccatgtaat | 1712 | |
| cctttgttt agttttgttt ttgttttttg gtgaatgaga aaggtgtgct ggtcatggaa | 1772 | |
| tggcaggtgt catatgactg attactcaga gcagatgagg aaaactgtag tctctgagtc | 1832 | |
| ctttgctaat cgcaactctt gtgaattatt ctgattcttt tttatgcaga atttgattcg | 1892 | |
| tatgatcagt actgactttc tgattactgt ccagcttata gtcttccagt ttaatgaact | 1952 | |
| accatctgat gtttcatatt taagtgtatt taaagaaaat aaacaccatt attcaagcca | 2012 | |
| aaaaaaaaaa aaaaaa | 2029 | |

<210> SEQ ID NO 87
<211> LENGTH: 354
<212> TYPE: PRT
<213> ORGANISM: Homo sapiens

<400> SEQUENCE: 87

-continued

```
Met Tyr Arg Glu Trp Val Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro
```

<210> SEQ ID NO 88
<211> LENGTH: 1830
<212> TYPE: DNA
<213> ORGANISM: ORF Virus
<220> FEATURE:
<221> NAME/KEY: misc_feature
<223> OTHER INFORMATION: VEGF-E
<220> FEATURE:
<221> NAME/KEY: CDS
<222> LOCATION: (312)..(755)

<400> SEQUENCE: 88

```
cggccacgcg gccgcgaact gcgcgctcgc gcgcgtggcg accgcgctga cgcgccgcgt      60
gcccgcgagc cggcacggcc tcgcggaggg cggcacgccg ccgtggacgc tgctgctggc     120
ggtggccgcg gtggcggtgc tcggcgtggt ggcaatttcg ctgctgcgcc gcgcgctaag     180
aatacggttt agatactcaa agtctatcca gacacttaga gtgtaacttt gagtaaaaaa     240
tgtaaatact aacgccaaaa tttcgatagt tgttaagcaa tatataacat ttttaaaacg     300
tcatcaccag c atg aag tta aca gct acg tta caa gtt gtt gtt gca ttg     350
            Met Lys Leu Thr Ala Thr Leu Gln Val Val Val Ala Leu
              1               5                  10 tta ata tgt atg tat aat ttg cca gaa tgc gtg tct cag agt aat gat     398
Leu Ile Cys Met Tyr Asn Leu Pro Glu Cys Val Ser Gln Ser Asn Asp
     15                  20                  25 tca cct cct tca acc aat gac tgg atg cgt aca cta gac aaa agt ggt     446
Ser Pro Pro Ser Thr Asn Asp Trp Met Arg Thr Leu Asp Lys Ser Gly
 30                  35                  40                  45 tgt aaa cct aga gat act gtt gtt tat ttg gga gaa gaa tat cca gaa     494
Cys Lys Pro Arg Asp Thr Val Val Tyr Leu Gly Glu Glu Tyr Pro Glu
                 50                  55                  60 agc act aac cta caa tat aat ccc cgg tgc gta act gtt aaa cga tgc     542
Ser Thr Asn Leu Gln Tyr Asn Pro Arg Cys Val Thr Val Lys Arg Cys
             65                  70                  75 agt ggt tgc tgt aac ggt gac ggt caa ata tgt aca gcg gtt gaa aca     590
Ser Gly Cys Cys Asn Gly Asp Gly Gln Ile Cys Thr Ala Val Glu Thr
         80                  85                  90 aga aat aca act gta aca gtt tca gta acc ggc gtg tct agt tcg tct     638
Arg Asn Thr Thr Val Thr Val Ser Val Thr Gly Val Ser Ser Ser Ser
     95                 100                 105 ggt act aat agt ggt gta tct act aac ctt caa aga ata agt gtt aca     686
Gly Thr Asn Ser Gly Val Ser Thr Asn Leu Gln Arg Ile Ser Val Thr
110                 115                 120                 125 gaa cac aca aag tgc gat tgt att ggt aga aca acg aca aca cct acg     734
Glu His Thr Lys Cys Asp Cys Ile Gly Arg Thr Thr Thr Thr Pro Thr
                130                 135                 140 acc act agg gaa cct aga cga taactaataa caaaaaatgt ttattttgt          785
Thr Thr Arg Glu Pro Arg Arg
                145 aaatacttaa ttattacaca ctttacaata atctcaaaaa taaattgcgt gcccggacgg     845 ctgcagctgg tgacgctgct gtgtcacaca ctgcgtattc gattcaagtt cactaacgcc     905 actaaactag ttgtgcgtgt ccgagtgtta accgtacgtc aaactaacat cttacctgtc     965 cgtgacaaga actaaaactt gaaccacata tttttaaagt atatttaaca aaatcactca    1025 cactcacaca atcataaaca ccacaaccac aaccaaacac gcatgagaat taatattctt    1085 acttatccgt aacactctat gctgtacatc aacgcatcag agcagtctga gtctgactaa    1145 tggcggcaaa cgggaacgca ggcgcgacat aatcactgag aatctccgca gcaaccgctc    1205 aaggacatct ctagcgctaa cggctgtttg tcattccccc gtgtgttcat ctcacacgac    1265 attgtgaccg tcgcaaagca cacattcaaa gtgccgcatg tggaagaatt caccgtcgag    1325 acacacacca taattaaaca agatcagtgc ataagagaga ttagcattct acagcacacc    1385 acgtgcgaat acggacctcg taattgttta gactagaaca cctctggtct aaacaacatg    1445 tccgatctta gaacagagtt tatgacgcat atgtaactgt gttctttatg tagaagttat    1505 cttttatgtc actcccttgt cttagatgag ttatacatga catgatgtat gtgtcgcccg    1565
```

```
cggcggcgcg gggcgctcgg cggcgggget getgegegeg gegggeccgc ggtggcggcg      1625 gctggcgcgg cgctgcggcc gcgggcgcgc ggcgggtag cggcccgccc gcccgggcgc       1685
ccgccgcagc ccttgccccg gaccaggcgc cacggagcaa agtgaaaaag gaccgcctag      1745
cagtcgagac cctcccgccg cagccgcgac accccacacc cgccttccac ccgccagacg      1805
ccaacaccac agccaacaag catgc                                           1830
```

<210> SEQ ID NO 89
<211> LENGTH: 148
<212> TYPE: PRT
<213> ORGANISM: ORF Virus

<400> SEQUENCE: 89

```
Met Lys Leu Thr Ala Thr Leu Gln Val Val Ala Leu Leu Ile Cys
1               5                   10                  15

Met Tyr Asn Leu Pro Glu Cys Val Ser Gln Ser Asn Asp Ser Pro Pro
            20                  25                  30

Ser Thr Asn Asp Trp Met Arg Thr Leu Asp Lys Ser Gly Cys Lys Pro
        35                  40                  45

Arg Asp Thr Val Val Tyr Leu Gly Glu Glu Tyr Pro Glu Ser Thr Asn
    50                  55                  60

Leu Gln Tyr Asn Pro Arg Cys Val Thr Lys Arg Cys Ser Gly Cys
65                  70                  75                  80

Cys Asn Gly Asp Gly Gln Ile Cys Thr Ala Val Glu Thr Arg Asn Thr
                85                  90                  95

Thr Val Thr Val Ser Val Thr Gly Val Ser Ser Ser Gly Thr Asn
            100                 105                 110

Ser Gly Val Ser Thr Asn Leu Gln Arg Ile Ser Val Thr Glu His Thr
        115                 120                 125

Lys Cys Asp Cys Ile Gly Arg Thr Thr Thr Thr Pro Thr Thr Thr Arg
    130                 135                 140

Glu Pro Arg Arg
145
```

<210> SEQ ID NO 90
<211> LENGTH: 815
<212> TYPE: DNA
<213> ORGANISM: Homo sapiens
<220> FEATURE:
<221> NAME/KEY: misc_feature
<223> OTHER INFORMATION: 232 amino acid isoform of VEGF-A
<220> FEATURE:
<221> NAME/KEY: CDS
<222> LOCATION: (69)..(767)

<400> SEQUENCE: 90

```
gaattcgaat tccagtgtgc tggcggccgc gcgcgagccg cgccggcccc ggtcgggcct       60 ccgaaacc atg aac ttt ctg ctg tct tgg gtg cat tgg agc ctc gcc ttg       110
         Met Asn Phe Leu Leu Ser Trp Val His Trp Ser Leu Ala Leu
         1               5                   10 ctg ctc tac ctc cac cat gcc aag tgg tcc cag gct gca ccc atg gca       158
Leu Leu Tyr Leu His His Ala Lys Trp Ser Gln Ala Ala Pro Met Ala
15                  20                  25                  30 gaa gga gga ggg cag aat cat cac gaa gtg gtg aag ttc atg gat gtc       206
Glu Gly Gly Gly Gln Asn His His Glu Val Val Lys Phe Met Asp Val
                35                  40                  45 tat cag cgc agc tac tgc cat cca atc gag acc ctg gtg gac atc ttc       254
Tyr Gln Arg Ser Tyr Cys His Pro Ile Glu Thr Leu Val Asp Ile Phe
            50                  55                  60
```

-continued

```
cag gag tac cct gat gag atc gag tac atc ttc aag cca tcc tgt gtg       302
Gln Glu Tyr Pro Asp Glu Ile Glu Tyr Ile Phe Lys Pro Ser Cys Val
            65                  70                  75 ccc ctg atg cga tgc ggg ggc tgc tgc aat gac gag ggc ctg gag tgt       350
Pro Leu Met Arg Cys Gly Gly Cys Cys Asn Asp Glu Gly Leu Glu Cys
        80                  85                  90 gtg ccc act gag gag tcc aac atc acc atg cag att atg cgg atc aaa       398
Val Pro Thr Glu Glu Ser Asn Ile Thr Met Gln Ile Met Arg Ile Lys
95                  100                 105                 110 cct cac caa ggc cag cac ata gga gag atg agc ttc cta cag cac aac       446
Pro His Gln Gly Gln His Ile Gly Glu Met Ser Phe Leu Gln His Asn
                115                 120                 125 aaa tgt gaa tgc aga cca aag aaa gat aga gca aga caa gaa aaa aaa       494
Lys Cys Glu Cys Arg Pro Lys Lys Asp Arg Ala Arg Gln Glu Lys Lys
            130                 135                 140 tca gtt cga gga aag gga aag ggg caa aaa cga aag cgc aag aaa tcc       542
Ser Val Arg Gly Lys Gly Lys Gly Gln Lys Arg Lys Arg Lys Lys Ser
145                 150                 155 cgg tat aag tcc tgg agc gtg tac gtt ggt gcc cgc tgc tgt cta atg       590
Arg Tyr Lys Ser Trp Ser Val Tyr Val Gly Ala Arg Cys Cys Leu Met
        160                 165                 170 ccc tgg agc ctc cct ggc ccc cat ccc tgt ggg cct tgc tca gag cgg       638
Pro Trp Ser Leu Pro Gly Pro His Pro Cys Gly Pro Cys Ser Glu Arg
175                 180                 185                 190 aga aag cat ttg ttt gta caa gat ccg cag acg tgt aaa tgt tcc tgc       686
Arg Lys His Leu Phe Val Gln Asp Pro Gln Thr Cys Lys Cys Ser Cys
                195                 200                 205 aaa aac aca gac tcg cgt tgc aag gcg agg cag ctt gag tta aac gaa       734
Lys Asn Thr Asp Ser Arg Cys Lys Ala Arg Gln Leu Glu Leu Asn Glu
            210                 215                 220 cgt act tgc aga tgt gac aag ccg agg cgg tga gccgggctgg aggaaggagc    787
Arg Thr Cys Arg Cys Asp Lys Pro Arg Arg
                225                 230 ctccctcagg gtttcgggaa ccagatcc                                       815
```

<210> SEQ ID NO 91
<211> LENGTH: 232
<212> TYPE: PRT
<213> ORGANISM: Homo sapiens

<400> SEQUENCE: 91

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125
```

```
Glu Cys Arg Pro Lys Lys Asp Arg Ala Arg Gln Glu Lys Lys Ser Val
    130                 135                 140
Arg Gly Lys Gly Lys Gly Gln Lys Arg Lys Arg Lys Lys Ser Arg Tyr
145                 150                 155                 160
Lys Ser Trp Ser Val Tyr Val Gly Ala Arg Cys Cys Leu Met Pro Trp
                165                 170                 175
Ser Leu Pro Gly Pro His Pro Cys Gly Pro Cys Ser Glu Arg Arg Lys
            180                 185                 190
His Leu Phe Val Gln Asp Pro Gln Thr Cys Lys Cys Ser Cys Lys Asn
        195                 200                 205
Thr Asp Ser Arg Cys Lys Ala Arg Gln Leu Glu Leu Asn Glu Arg Thr
    210                 215                 220
Cys Arg Cys Asp Lys Pro Arg Arg
225                 230
```

<210> SEQ ID NO 92
<211> LENGTH: 399
<212> TYPE: DNA
<213> ORGANISM: ORF virus
<220> FEATURE:
<221> NAME/KEY: misc_feature
<223> OTHER INFORMATION: D1701 VEGF
<220> FEATURE:
<221> NAME/KEY: CDS
<222> LOCATION: (1)..(399)

<400> SEQUENCE: 92

```
atg aag ttt ctc gtc ggc ata ctg gta gct gtg tgc ttg cac cag tat        48
Met Lys Phe Leu Val Gly Ile Leu Val Ala Val Cys Leu His Gln Tyr
1               5                   10                  15 ctg ctg aac gcg gac agc acg aaa aca tgg tcc gaa gtg ttt gaa aac        96
Leu Leu Asn Ala Asp Ser Thr Lys Thr Trp Ser Glu Val Phe Glu Asn
            20                  25                  30 agc ggg tgc aag cca agg ccg atg gtc ttt cga gta cac gac gag cac       144
Ser Gly Cys Lys Pro Arg Pro Met Val Phe Arg Val His Asp Glu His
        35                  40                  45 ccg gag cta act tct cag cgg ttc aac ccg ccg tgt gtc acg ttg atg       192
Pro Glu Leu Thr Ser Gln Arg Phe Asn Pro Pro Cys Val Thr Leu Met
    50                  55                  60 cga tgc ggc ggg tgc tgc aac gac gag agc tta gaa tgc gtc ccc acg       240
Arg Cys Gly Gly Cys Cys Asn Asp Glu Ser Leu Glu Cys Val Pro Thr
65                  70                  75                  80 gaa gag gca aac gta acg atg caa ctc atg gga gcg tcg gtc tcc ggt       288
Glu Glu Ala Asn Val Thr Met Gln Leu Met Gly Ala Ser Val Ser Gly
                85                  90                  95 ggt aac ggg atg caa cat ctg agc ttc gta gag cat aag aaa tgc gat       336
Gly Asn Gly Met Gln His Leu Ser Phe Val Glu His Lys Lys Cys Asp
            100                 105                 110 tgt aaa cca cca ctc acg acc acg cca ccg acg acc aca agg ccg ccc       384
Cys Lys Pro Pro Leu Thr Thr Thr Pro Pro Thr Thr Thr Arg Pro Pro
        115                 120                 125 aga aga cgc cgc tag                                                   399
Arg Arg Arg Arg
    130
```

<210> SEQ ID NO 93
<211> LENGTH: 132
<212> TYPE: PRT
<213> ORGANISM: ORF virus

<400> SEQUENCE: 93

```
Met Lys Phe Leu Val Gly Ile Leu Val Ala Val Cys Leu His Gln Tyr
1               5                   10                  15

Leu Leu Asn Ala Asp Ser Thr Lys Thr Trp Ser Glu Val Phe Glu Asn
            20                  25                  30

Ser Gly Cys Lys Pro Arg Pro Met Val Phe Arg Val His Asp Glu His
        35                  40                  45

Pro Glu Leu Thr Ser Gln Arg Phe Asn Pro Pro Cys Val Thr Leu Met
    50                  55                  60

Arg Cys Gly Gly Cys Cys Asn Asp Glu Ser Leu Glu Cys Val Pro Thr
65              70                  75                  80

Glu Glu Ala Asn Val Thr Met Gln Leu Met Gly Ala Ser Val Ser Gly
                85                  90                  95

Gly Asn Gly Met Gln His Leu Ser Phe Val Glu His Lys Lys Cys Asp
            100                 105                 110

Cys Lys Pro Pro Leu Thr Thr Thr Pro Pro Thr Thr Thr Arg Pro Pro
        115                 120                 125

Arg Arg Arg Arg
        130

<210> SEQ ID NO 94
<211> LENGTH: 570
<212> TYPE: DNA
<213> ORGANISM: Homo sapiens
<220> FEATURE:
<221> NAME/KEY: misc_feature
<223> OTHER INFORMATION: VEGF-B Isoform 1

<400> SEQUENCE: 94
accatgagcc ctctgctccg ccgcctgctg ctcgccgcac tcctgcagct ggccccgcc      60 caggcccctg tctcccagcc tgatgcccct ggccaccaga ggaaagtggt gtcatggata    120
gatgtgtata ctcgcgctac ctgccagccc cgggaggtgg tggtgccctt gactgtggag    180
ctcatgggca ccgtggccaa acagctggtg cccagctgcg tgactgtgca gcgctgtggt    240
ggctgctgcc ctgacgatgg cctggagtgt gtgcccactg gcagcacca agtccggatg    300 cagatcctca tgatccggta cccgagcagt cagctggggg agatgtccct ggaagaacac    360
agccagtgtg aatgcagacc taaaaaaaag gacagtgctg tgaagccaga cagccccagg    420 ccctctgcc cacgctgcac ccagcaccac cagcgccctg accccggac ctgccgctgc      480 cgctgccgac gccgcagctt cctccgttgc caagggcggg gcttagagct caacccagac    540
acctgcaggt gccggaagct gcgaaggtga                                      570

<210> SEQ ID NO 95
<211> LENGTH: 188
<212> TYPE: PRT
<213> ORGANISM: Homo sapiens
<220> FEATURE:
<221> NAME/KEY: MISC_FEATURE
<223> OTHER INFORMATION: VEGF-B Isoform 1
<220> FEATURE:
<221> NAME/KEY: mat_peptide
<222> LOCATION: (22)..(188)

<400> SEQUENCE: 95

Met Ser Pro Leu Leu Arg Arg Leu Leu Leu Ala Ala Leu Leu Gln Leu
        -20                 -15                 -10

Ala Pro Ala Gln Ala Pro Val Ser Gln Pro Asp Ala Pro Gly His Gln
-5              -1  1               5                   10

Arg Lys Val Val Ser Trp Ile Asp Val Tyr Thr Arg Ala Thr Cys Gln
```

-continued

```
                 15                  20                  25
Pro Arg Glu Val Val Pro Leu Thr Val Glu Leu Met Gly Thr Val
             30                  35                  40
Ala Lys Gln Leu Val Pro Ser Cys Val Thr Val Gln Arg Cys Gly Gly
         45                  50                  55
Cys Cys Pro Asp Asp Gly Leu Glu Cys Val Pro Thr Gly Gln His Gln
 60                  65                  70                  75
Val Arg Met Gln Ile Leu Met Ile Arg Tyr Pro Ser Ser Gln Leu Gly
                 80                  85                  90
Glu Met Ser Leu Glu Glu His Ser Gln Cys Glu Cys Arg Pro Lys Lys
             95                 100                 105
Lys Asp Ser Ala Val Lys Pro Asp Ser Pro Arg Pro Leu Cys Pro Arg
         110                 115                 120
Cys Thr Gln His His Gln Arg Pro Asp Pro Arg Thr Cys Arg Cys Arg
     125                 130                 135
Cys Arg Arg Arg Ser Phe Leu Arg Cys Gln Gly Arg Gly Leu Glu Leu
140                 145                 150                 155
Asn Pro Asp Thr Cys Arg Cys Arg Lys Leu Arg Arg
                160                 165
```

<210> SEQ ID NO 96
<211> LENGTH: 624
<212> TYPE: DNA
<213> ORGANISM: Homo sapiens
<220> FEATURE:
<221> NAME/KEY: misc_feature
<223> OTHER INFORMATION: VEGF-B Isoform 2

<400> SEQUENCE: 96

```
atgagccctc tgctccgccg cctgctgctc gccgcactcc tgcagctggc ccccgcccag    60
gcccctgtct cccagcctga tgccctggc caccagagga agtggtgtc atggatagat     120
gtgtatactc gcgctacctg ccagccccgg gaggtggtgg tgcccttgac tgtggagctc    180
atgggcaccg tggccaaaca gctggtgccc agctgcgtga ctgtgcagcg ctgtggtggc    240
tgctgccctg acgatggcct ggagtgtgtg cccactgggc agcaccaagt ccggatgcag    300
atcctcatga tccggtaccc gagcagtcag ctggggagaa tgtccctgga agaacacagc    360
cagtgtgaat gcagacctaa aaaaaaggac agtgctgtga agccagacag ggctgccact    420
ccccaccacc gtccccagcc ccgttctgtt ccgggctggg actctgcccc cggagcaccc    480
tccccagctg acatcacccca tcccactcca gcccaggcc ctctgccca cgctgcaccc    540
agcaccacca gcgccctgac ccccggacct gccgccgccg ctgccgacgc cgcagcttcc    600
tccgttgcca agggcggggc ttag                                          624
```

<210> SEQ ID NO 97
<211> LENGTH: 207
<212> TYPE: PRT
<213> ORGANISM: Homo sapiens
<220> FEATURE:
<221> NAME/KEY: MISC_FEATURE
<223> OTHER INFORMATION: VEGF-B Isoform 2
<220> FEATURE:
<221> NAME/KEY: mat_peptide
<222> LOCATION: (22)..(207)

<400> SEQUENCE: 97

```
Met Ser Pro Leu Leu Arg Arg Leu Leu Leu Ala Ala Leu Leu Gln Leu
    -20                 -15                 -10
```

```
Ala Pro Ala Gln Ala Pro Val Ser Gln Pro Asp Ala Pro Gly His Gln
 -5          -1   1               5                  10

Arg Lys Val Val Ser Trp Ile Asp Val Tyr Thr Arg Ala Thr Cys Gln
             15              20              25

Pro Arg Glu Val Val Pro Leu Thr Val Glu Leu Met Gly Thr Val
         30              35              40

Ala Lys Gln Leu Val Pro Ser Cys Val Thr Val Gln Arg Cys Gly Gly
         45              50              55

Cys Cys Pro Asp Asp Gly Leu Glu Cys Val Pro Thr Gly Gln His Gln
 60              65              70              75

Val Arg Met Gln Ile Leu Met Ile Arg Tyr Pro Ser Ser Gln Leu Gly
                 80              85              90

Glu Met Ser Leu Glu Glu His Ser Gln Cys Glu Cys Arg Pro Lys Lys
             95              100             105

Lys Asp Ser Ala Val Lys Pro Asp Arg Ala Ala Thr Pro His His Arg
         110             115             120

Pro Gln Pro Arg Ser Val Pro Gly Trp Asp Ser Ala Pro Gly Ala Pro
         125             130             135

Ser Pro Ala Asp Ile Thr His Pro Thr Pro Ala Pro Gly Pro Ser Ala
140             145             150             155

His Ala Ala Pro Ser Thr Thr Ser Ala Leu Thr Pro Gly Pro Ala Ala
                160             165             170

Ala Ala Ala Asp Ala Ala Ala Ser Ser Val Ala Lys Gly Gly Ala
                175             180             185

<210> SEQ ID NO 98
<211> LENGTH: 2305
<212> TYPE: DNA
<213> ORGANISM: Homo sapiens
<220> FEATURE:
<221> NAME/KEY: misc_feature
<223> OTHER INFORMATION: PDGF-A
<220> FEATURE:
<221> NAME/KEY: CDS
<222> LOCATION: (404)..(991)
<223> OTHER INFORMATION: PDGF-A

<400> SEQUENCE: 98
ttcttggggc tgatgtccgc aaatatgcag aattaccggc cgggtcgctc ctgaagccag      60
cgcggggagc gagcgcggcg gcggccagca ccgggaacgc accgaggaag aagcccagcc     120
cccgccctcc gccccttccg tccccacccc ctaccggcg gcccaggagg ctccccggct      180
gcggcgcgca ctccctgttt ctcctcctcc tggctggcgc tgcctgcctc tccgcactca     240
ctgctcgccg ggcgccgtcc gccagctccg tgctccccgc gccacccctcc tccgggccgc    300 gctccctaag ggatggtact gaatttcgcc gccacaggag accggctgga gcgcccgccc    360
cgcgcctcgc ctctcctccg agcagccagc gcctcgggac gcg atg agg acc ttg      415
                                               Met Arg Thr Leu
                                                1 gct tgc ctg ctg ctc ctc ggc tgc gga tac ctc gcc cat gtt ctg gcc      463
Ala Cys Leu Leu Leu Leu Gly Cys Gly Tyr Leu Ala His Val Leu Ala
 5              10              15              20 gag gaa gcc gag atc ccc cgc gag gtg atc gag agg ctg gcc cgc agt      511
Glu Glu Ala Glu Ile Pro Arg Glu Val Ile Glu Arg Leu Ala Arg Ser
             25              30              35 cag atc cac agc atc cgg gac ctc cag cga ctc ctg gag ata gac tcc      559
Gln Ile His Ser Ile Arg Asp Leu Gln Arg Leu Leu Glu Ile Asp Ser
         40              45              50
```

```
gta ggg agt gag gat tct ttg gac acc agc ctg aga gct cac ggg gtc        607
Val Gly Ser Glu Asp Ser Leu Asp Thr Ser Leu Arg Ala His Gly Val
         55                  60                  65 cac gcc act aag cat gtg ccc gag aag cgg ccc ctg ccc att cgg agg        655
His Ala Thr Lys His Val Pro Glu Lys Arg Pro Leu Pro Ile Arg Arg
 70                  75                  80 aag aga agc atc gag gaa gct gtc ccc gct gtc tgc aag acc agg acg        703
Lys Arg Ser Ile Glu Glu Ala Val Pro Ala Val Cys Lys Thr Arg Thr
 85                  90                  95                 100 gtc att tac gag att cct cgg agt cag gtc gac ccc acg tcc gcc aac        751
Val Ile Tyr Glu Ile Pro Arg Ser Gln Val Asp Pro Thr Ser Ala Asn
                105                 110                 115 ttc ctg atc tgg ccc ccg tgc gtg gag gtg aaa cgc tgc acc ggc tgc        799
Phe Leu Ile Trp Pro Pro Cys Val Glu Val Lys Arg Cys Thr Gly Cys
                120                 125                 130 tgc aac acg agc agt gtc aag tgc cag ccc tcc cgc gtc cac cac cgc        847
Cys Asn Thr Ser Ser Val Lys Cys Gln Pro Ser Arg Val His His Arg
        135                 140                 145 agc gtc aag gtg gcc aag gtg gaa tac gtc agg aag aag cca aaa tta        895
Ser Val Lys Val Ala Lys Val Glu Tyr Val Arg Lys Lys Pro Lys Leu
    150                 155                 160 aaa gaa gtc cag gtg agg tta gag gag cat ttg gag tgc gcc tgc gcg        943
Lys Glu Val Gln Val Arg Leu Glu Glu His Leu Glu Cys Ala Cys Ala
165                 170                 175                 180 acc aca agc ctg aat ccg gat tat cgg gaa gag gac acg gat gtg agg        991
Thr Thr Ser Leu Asn Pro Asp Tyr Arg Glu Glu Asp Thr Asp Val Arg
                185                 190                 195 tgaggatgag ccgcagccct tcctgggac atggatgtac atggcgtgtt acattcctga      1051
acctactatg tacggtgctt tattgccagt gtgcggtctt tgttctcctc cgtgaaaaac     1111
tgtgtccgag aacactcggg agaacaaaga gacagtgcac atttgtttaa tgtgacatca     1171
aagcaagtat tgtagcactc ggtgaagcag taagaagctt ccttgtcaaa agagagaga     1231 gagagagaga gagagaaaac aaaaccacaa atgacaaaaa caaaacggac tcacaaaaat     1291
atctaaactc gatgagatgg agggtcgccc cgtgggatgg aagtgcagag gtctcagcag     1351
actggatttc tgtccgggtg gtcacaggtg cttttttgcc gaggatgcag agcctgcttt     1411
gggaacgact ccagaggggt gctggtgggc tctgcagggc ccgcaggaag caggaatgtc     1471
ttggaaaccg ccacgcgaac tttagaaacc acacctcctc gctgtagtat ttaagcccat     1531
acagaaacct tcctgagagc cttaagtggt tttttttttt gttttgtttt tgttttttt     1591 tttttttgttt tttttttttt tttttttttt tacaccataa agtgattatt aagcttcctt     1651
ttactctttg gctagctttt tttttttttt tttttttttt tttttttaat tatctcttgg     1711
atgacattta caccgataac acacaggctg ctgtaactgt caggacagtg cgacggtatt     1771
tttcctagca agatgcaaac taatgagatg tattaaaata aacatggtat acctacctat     1831
gcatcatttc ctaaatgttt ctggctttgt gtttctccct tacccctgctt tatttgttaa     1891 tttaagccat tttgaaagaa ctatgcgtca accaatcgta cgccgtccct gcggcacctg     1951
ccccagagcc cgtttgtggc tgagtgacaa cttgttcccc gcagtgcaca cctagaatgc     2011
tgtgttccca cgcggcacgt gagatgcatt gccgcttctg tctgtgttgt tggtgtgccc     2071
tggtgccgtg gtggcggtca ctccctctgc tgccagtgtt tggacagaac ccaaattctt     2131
tatttttggt aagatattgt gctttacctg tattaacaga aatgtgtgtg tgtggtttgt     2191 tttttttgtaa aggtgaagtt tgtatgttta cctaatatta cctgttttgt atacctgaga     2251
gcctgctatg ttcttctttt gttgatccaa aattaaaaaa aaaataccac caac            2305
```

<210> SEQ ID NO 99
<211> LENGTH: 196
<212> TYPE: PRT
<213> ORGANISM: Homo sapiens

<400> SEQUENCE: 99

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
        35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
    130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Asp Val Arg
        195

<210> SEQ ID NO 100
<211> LENGTH: 2137
<212> TYPE: DNA
<213> ORGANISM: Homo sapiens
<220> FEATURE:
<221> NAME/KEY: misc_feature
<223> OTHER INFORMATION: PDGF-B
<220> FEATURE:
<221> NAME/KEY: CDS
<222> LOCATION: (983)..(1705)

<400> SEQUENCE: 100
ccctgcctgc ctccctgcgc acccgcagcc tccccgctg cctccctagg gctcccctcc      60
ggccgccagc gccattttt cattccctag atagagatac tttgcgcgca cacacataca    120
tacgcgcgca aaaggaaaa aaaaaaaaaa agcccaccc tccagcctcg ctgcaaagag     180
aaaaccggag cagccgcagc tcgcagctcg cagcccgcag cccgcagagg acgcccagag   240
cggcgagcgg gcgggcagac ggaccgacgg actcgcgccg cgtccacctg tcggccgggc   300
ccagccgagc gcgcagcggg cacgccgcgc gcgggagca gccgtgcccg ccgcccgggc    360
ccgccgccag ggcgcacacg ctcccgcccc cctacccggc ccgggcggga gtttgcacct   420
ctccctgccc gggtgctcga gctgccgttg caaagccaac tttggaaaaa gttttttggg   480
ggagacttgg gccttgaggt gcccagctcc gcgctttccg attttggggg cctttccaga   540

```
aaatgttgca aaaaagctaa gccggcgggc agaggaaaac gcctgtagcc ggcgagtgaa    600
gacgaaccat cgactgccgt gttccttttc ctcttggagg ttggagtccc ctgggcgccc    660
ccacacggct agacgcctcg gctggttcgc gacgcagccc cccggccgtg gatgctgcac    720
tcgggctcgg gatccgccca ggtagcggcc tcggacccag gtcctgcgcc caggtcctcc    780 cctgccccc agcgacggag ccgggccgg gggcggcggc gccgggggca tgcgggtgag    840
ccgcggctgc agaggcctga gcgcctgatc gccgcggacc cgagccgagc ccaccccct    900 ccccagcccc ccaccctggc cgcggggggcg gcgcgctcga tctacgcgtt cggggccccg    960
cggggccggg cccggagtcg gc atg aat cgc tgc tgg gcg ctc ttc ctg tct   1012
              Met Asn Arg Cys Trp Ala Leu Phe Leu Ser
              1           5                        10 ctc tgc tgc tac ctg cgt ctg gtc agc gcc gag ggg gac ccc att ccc   1060
Leu Cys Cys Tyr Leu Arg Leu Val Ser Ala Glu Gly Asp Pro Ile Pro
            15                  20                  25 gag gag ctt tat gag atg ctg agt gac cac tcg atc cgc tcc ttt gat   1108
Glu Glu Leu Tyr Glu Met Leu Ser Asp His Ser Ile Arg Ser Phe Asp
            30                  35                  40 gat ctc caa cgc ctg ctg cac gga gac ccc gga gag gaa gat ggg gcc   1156
Asp Leu Gln Arg Leu Leu His Gly Asp Pro Gly Glu Glu Asp Gly Ala
            45                  50                  55 gag ttg gac ctg aac atg acc cgc tcc cac tct gga ggc gag ctg gag   1204
Glu Leu Asp Leu Asn Met Thr Arg Ser His Ser Gly Gly Glu Leu Glu
    60                  65                  70 agc ttg gct cgt gga aga agg agc ctg ggt tcc ctg acc att gct gag   1252
Ser Leu Ala Arg Gly Arg Arg Ser Leu Gly Ser Leu Thr Ile Ala Glu
75                  80                  85                  90 ccg gcc atg atc gcc gag tgc aag acg cgc acc gag gtg ttc gag atc   1300
Pro Ala Met Ile Ala Glu Cys Lys Thr Arg Thr Glu Val Phe Glu Ile
                95                  100                 105 tcc cgg cgc ctc ata gac cgc acc aac gcc aac ttc ctg gtg tgg ccg   1348
Ser Arg Arg Leu Ile Asp Arg Thr Asn Ala Asn Phe Leu Val Trp Pro
            110                 115                 120 ccc tgt gtg gag gtg cag cgc tgc tcc ggc tgc tgc aac aac cgc aac   1396
Pro Cys Val Glu Val Gln Arg Cys Ser Gly Cys Cys Asn Asn Arg Asn
            125                 130                 135 gtg cag tgc cgc ccc acc cag gtg cag ctg cga cct gtc cag gtg aga   1444
Val Gln Cys Arg Pro Thr Gln Val Gln Leu Arg Pro Val Gln Val Arg
        140                 145                 150 aag atc gag att gtg cgg aag aag cca atc ttt aag aag gcc acg gtg   1492
Lys Ile Glu Ile Val Arg Lys Lys Pro Ile Phe Lys Lys Ala Thr Val
155                 160                 165                 170 acg ctg gaa gac cac ctg gca tgc aag tgt gag aca gtg gca gct gca   1540
Thr Leu Glu Asp His Leu Ala Cys Lys Cys Glu Thr Val Ala Ala Ala
                175                 180                 185 cgg cct gtg acc cga agc ccg ggg ggt tcc cag gag cag cga gcc aaa   1588
Arg Pro Val Thr Arg Ser Pro Gly Gly Ser Gln Glu Gln Arg Ala Lys
            190                 195                 200 acg ccc caa act cgg gtg acc att cgg acg gtg cga gtc cgc cgg ccc   1636
Thr Pro Gln Thr Arg Val Thr Ile Arg Thr Val Arg Val Arg Arg Pro
        205                 210                 215 ccc aag ggc aag cac cgg aaa ttc aag cac acg cat gac aag acg gca   1684
Pro Lys Gly Lys His Arg Lys Phe Lys His Thr His Asp Lys Thr Ala
        220                 225                 230 ctg aag gag acc ctt gga gcc tagggcatc ggcaggagag tgtgtgggca        1735
Leu Lys Glu Thr Leu Gly Ala
235                 240
```

-continued

```
gggttatttta atatggtatt tgctgtattg cccccatggg gccttggagt agataatatt    1795
gtttccctcg tccgtctgtc tcgatgcctg attcggacgg ccaatggtgc ctcccccacc    1855
cctccacgtg tccgtccacc cttccatcag cgggtctcct cccagcggcc tccggctctt    1915
gcccagcagc tcaagaagaa aaagaaggac tgaactccat cgccatcttc ttcccttaac    1975
tccaagaact tgggataaga gtgtgagaga gactgatggg gtcgctcttt ggggaaacg     2035 ggttccttcc cctgcacctg gcctgggcca cacctgagcg ctgtggactg tcctgaggag    2095
ccctgaggac ctctcagcat agcctgcctg atccctgaac cc                       2137
```

<210> SEQ ID NO 101
<211> LENGTH: 241
<212> TYPE: PRT
<213> ORGANISM: Homo sapiens

<400> SEQUENCE: 101

```
Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala
```

<210> SEQ ID NO 102
<211> LENGTH: 2108
<212> TYPE: DNA
<213> ORGANISM: Homo sapiens
<220> FEATURE:
<221> NAME/KEY: misc_feature
<223> OTHER INFORMATION: PDGF-C
<220> FEATURE:
<221> NAME/KEY: misc_feature
<222> LOCATION: (2002)..(2002)
<223> OTHER INFORMATION: n = a, c, g, or t
<220> FEATURE:
<221> NAME/KEY: misc_feature
<222> LOCATION: (2065)..(2065)
<223> OTHER INFORMATION: n = a, c, g, or t
<220> FEATURE:
<221> NAME/KEY: misc_feature
<222> LOCATION: (2070)..(2070)
<223> OTHER INFORMATION: n = a, c, g, or t
<220> FEATURE:
<221> NAME/KEY: misc_feature
<222> LOCATION: (2089)..(2089)
<223> OTHER INFORMATION: n = a, c, g, or t

<400> SEQUENCE: 102

```
ccccgccgtg agtgagctct caccccagtc agccaaatga gcctcttcgg gcttctcctg      60
gtgacatctg ccctggccgg ccagagacga gggactcagg cggaatccaa cctgagtagt     120
aaattccagt tttccagcaa caaggaacag aacggagtac aagatcctca gcatgagaga     180
attattactg tgtctactaa tggaagtatt cacagcccaa ggtttcctca tacttatcca     240
agaaatacgg tcttggtatg agattagta gcagtagagg aaaatgtatg gatacaactt      300
acgtttgatg aaagatttgg gcttgaagac ccagaagatg acatatgcaa gtatgatttt     360
gtagaagttg aggaacccag tgatggaact atattagggc gctggtgtgg ttctggtact     420
gtaccaggaa acagatttc taaggaaat caaattagga taagatttgt atctgatgaa       480
tatttttcctt ctgaaccagg gttctgcatc cactacaaca ttgtcatgcc acaattcaca    540
gaagctgtga gtccttcagt gctacccct tcagctttgc cactggacct gcttaataat      600
gctataactg cctttagtac cttggaagac cttattcgat atcttgaacc agagagatgg     660
cagttggact tagaagatct atataggcca acttggcaac ttcttggcaa ggcttttgtt    720
tttggaagaa aatccagagt ggtggatctg aaccttctaa cagaggaggt aagattatac    780
agctgcacac ctcgtaactt ctcagtgtcc ataagggaag aactaaagag aaccgatacc    840
attttctggc caggttgtct cctggttaaa cgctgtggtg ggaactgtgc ctgttgtctc    900
cacaattgca atgaatgtca atgtgtccca agcaaagtta ctaaaaaata ccacgaggtc    960
cttcagttga gaccaaagac cggtgtcagg ggattgcaca atcactcac cgacgtggcc   1020
ctggagcacc atgaggagtg tgactgtgtg tgcagaggga gcacaggagg atagccgcat   1080
caccaccagc agctcttgcc cagagctgtg cagtgcagtg gctgattcta ttagagaacg   1140
tatgcgttat ctccatcctt aatctcagtt gtttgcttca aggacctttc atcttcagga   1200
tttacagtgc attctgaaag aggagacatc aaacagaatt aggagttgtg caacagctct   1260
tttgagagga ggcctaaagg acaggagaaa aggtcttcaa tcgtggaaag aaaattaaat   1320
gttgtattaa atagatcacc agctagtttc agagttacca tgtacgtatt ccactagctg   1380
ggttctgtat ttcagttctt tcgatacggc ttagggtaat gtcagtacag gaaaaaaact   1440
gtgcaagtga gcacctgatt ccgttgcctt gcttaactct aaagctccat gtcctgggcc   1500
taaaatcgta taaatctgg attttttttt ttttttttgc tcatattcac atatgtaaac    1560
cagaacattc tatgtactac aaacctggtt tttaaaaagg aactatgttg ctatgaatta   1620
aacttgtgtc rtgctgatag gacagactgg attttcata tttcttatta aaatttctgc    1680
catttagaag aagagaacta cattcatggt ttggaagaga taaacctgaa aagaagagtg   1740
gccttatctt cactttatcg ataagtcagt ttatttgttt cattgtgtac attttttatat   1800
tctcctttg acattataac tgttggcttt tctaatcttg ttaaatatat ctattttac     1860
```

-continued

```
caaaggtatt taatattctt ttttatgaca acttagatca actattttta gcttggtaaa    1920
tttttctaaa cacaattgtt atagccagag gaacaaagat ggatataaaa atattgttgc    1980
cctggacaaa aatacatgta tntccatccc ggaatggtgc tagagttgga ttaaacctgc    2040
attttaaaaa acctgaattg ggaanggaan ttggtaaggt tggccaaanc tttttgaaa     2100 ataattaa                                                            2108
```

<210> SEQ ID NO 103
<211> LENGTH: 345
<212> TYPE: PRT
<213> ORGANISM: Homo sapiens
<220> FEATURE:
<221> NAME/KEY: MISC_FEATURE
<223> OTHER INFORMATION: PDGF-C

<400> SEQUENCE: 103

```
Met Ser Leu Phe Gly Leu Leu Leu Val Thr Ser Ala Leu Ala Gly Gln
 1               5                  10                  15

Arg Arg Gly Thr Gln Ala Glu Ser Asn Leu Ser Ser Lys Phe Gln Phe
             20                  25                  30

Ser Ser Asn Lys Glu Gln Asn Gly Val Gln Asp Pro Gln His Glu Arg
         35                  40                  45

Ile Ile Thr Val Ser Thr Asn Gly Ser Ile His Ser Pro Arg Phe Pro
     50                  55                  60

His Thr Tyr Pro Arg Asn Thr Val Leu Val Trp Arg Leu Val Ala Val
 65                  70                  75                  80

Glu Glu Asn Val Trp Ile Gln Leu Thr Phe Asp Glu Arg Phe Gly Leu
                 85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
```

| | | | | 305 | | | | | 310 | | | | | 315 | | | | | 320 |
|---|---|---|---|---|---|---|---|---|---|---|---|---|---|---|---|---|---|---|---|
| His | Lys | Ser | Leu | Thr | Asp | Val | Ala | Leu | Glu | His | His | Glu | Glu | Cys | Asp |
| | | | | 325 | | | | | 330 | | | | | 335 | |

| Cys | Val | Cys | Arg | Gly | Ser | Thr | Gly | Gly |
|---|---|---|---|---|---|---|---|---|
| | | | 340 | | | | | 345 |

<210> SEQ ID NO 104
<211> LENGTH: 2253
<212> TYPE: DNA
<213> ORGANISM: Homo sapiens
<220> FEATURE:
<221> NAME/KEY: misc_feature
<223> OTHER INFORMATION: PDGF-D

<400> SEQUENCE: 104

```
cgctcggaaa gttcagcatg caggaagttt ggggagagct cggcgattag cacagcgacc        60
cgggccagcg cagggcgagc gcaggcggcg agagcgcagg gcggcgcggc gtcggtcccg       120
ggagcagaac ccggcttttt cttggagcga cgctgtctct agtcgctgat cccaaatgca       180
ccggctcatc tttgtctaca ctctaatctg cgcaaacttt tgcagctgtc gggacacttc       240
tgcaaccccg cagagcgcat ccatcaaagc tttgcgcaac gccaacctca ggcgagatga       300
gagcaatcac ctcacagact tgtaccgaag agatgagacc atccaggtga aaggaaacgg       360
ctacgtgcag agtcctagat cccgaacaga ctaccccagg aacctgctcc tgacatggcg       420
gcttcactct caggagaata cacgataca gctagtgttt gacaatcagt ttggattaga       480
ggaagcagaa aatgatatct gtaggtatga ttttgtggaa gttgaagata tatccgaaac       540
cagtaccatt attagaggac gatggtgtgg acacaaggaa gttcctccaa ggataaaatc       600
aagaacgaac caaattaaaa tcacattcaa gtccgatgac tactttgtgg ctaaacctgg       660
attcaagatt tattattctt tgctggaaga tttccaaccc gcagcagctt cagagaccaa       720
ctgggaatct gtcacaagct ctatttcagg ggtatcctat aactctccat cagtaacgga       780
tcccactctg attgcggatg ctctggacaa aaaaattgca gaatttgata cagtggaaga       840
tctgctcaag tacttcaatc cagagtcatg gcaagaagat cttgagaata tgtatctgga       900
caccccctcgg tatcgaggca ggtcatacca tgaccggaag tcaaaagttg acctggatag       960
gctcaatgat gatgccaagc gttacagttg cactcccagg aattactcgg tcaatataag      1020
agaagagctg aagttggcca atgtggtctt cttttccacgt tgcctcctcg tgcagcgctg      1080
tggaggaaat tgtggctgtg aactgtcaa ctggaggtcc tgcacatgca attcagggaa      1140
aaccgtgaaa aagtatcatg aggtattaca gtttgagcct ggccacatca gaggagggg      1200
tagagctaag accatggctc tagttgacat ccagttggat caccatgaac gatgcgattg      1260
tatctgcagc tcaagaccac ctcgataaga gaatgtgcac atccttacat taagcctgaa      1320
agaaccttta gtttaaggag ggtgagataa gagacccttt tcctaccagc aaccaaactt      1380
actactagcc tgcaatgcaa tgaacacaag tggttgctga gtctcagcct tgctttgtta      1440
atgccatggc aagtagaaag gtatatcatc aacttctata cctaagaata taggattgca      1500
tttaataata gtgtttgagg ttatatatgc acaaacacac acagaaatat attcatgtct      1560
atgtgtatat agatcaaatg ttttttttgg tatatataac caggtacacc agagcttaca      1620
tatgtttgag ttagactctt aaaatccttt gccaaaataa gggatggtca aatatatgaa      1680
acatgtcttt agaaaattta ggagataaat tatttttaa attttgaaac acaaaacaat      1740
tttgaatctt gctctcttaa agaaagcatc ttgtatatta aaaatcaaaa gatgaggctt      1800
```

```
tcttacatat acatcttagt tgattattaa aaaaggaaaa aggtttccag agaaaaggcc    1860
aatacctaag catttttttcc atgagaagca ctgcatactt acctatgtgg actgtaataa   1920
cctgtctcca aaaccatgcc ataataatat aagtgcttta gaaattaaat cattgtgttt   1980
tttatgcatt ttgctgaggc atccttattc atttaacacc tatctcaaaa acttacttag   2040
aaggtttttt attatagtcc tacaaaagac aatgtataag ctgtaacaga attttgaatt   2100
gtttttcttt gcaaaacccc tccacaaaag caaatccttt caagaatggc atgggcattc   2160
tgtatgaacc tttccagatg gtgttcagtg aaagatgtgg gtagttgaga acttaaaaag   2220
tgaacattga aacatcgacg taactggaaa ccg                                2253

<210> SEQ ID NO 105
<211> LENGTH: 116
<212> TYPE: PRT
<213> ORGANISM: Homo sapiens
<220> FEATURE:
<221> NAME/KEY: MISC_FEATURE
<223> OTHER INFORMATION: PDGF-D

<400> SEQUENCE: 105

Gly Arg Lys Ser Arg Val Val Asp Leu Asn Leu Leu Thr Glu Glu Val
1               5                   10                  15

Arg Leu Tyr Ser Cys Thr Pro Arg Asn Phe Ser Val Ser Ile Arg Glu
            20                  25                  30

Glu Leu Lys Arg Thr Asp Thr Ile Phe Trp Pro Gly Cys Leu Leu Val
        35                  40                  45

Lys Arg Cys Gly Gly Asn Cys Ala Cys Cys Leu His Asn Cys Asn Glu
    50                  55                  60

Cys Gln Cys Val Pro Ser Lys Val Thr Lys Lys Tyr His Glu Val Leu
65                  70                  75                  80

Gln Leu Arg Pro Lys Thr Gly Val Arg Gly Leu His Lys Ser Leu Thr
                85                  90                  95

Asp Val Ala Leu Glu His His Glu Glu Cys Asp Cys Val Cys Arg Gly
            100                 105                 110

Ser Thr Gly Gly
        115

<210> SEQ ID NO 106
<211> LENGTH: 456
<212> TYPE: DNA
<213> ORGANISM: Artificial sequence
<220> FEATURE:
<221> NAME/KEY: misc_feature
<223> OTHER INFORMATION: hVEGFA109

<400> SEQUENCE: 106
atggagacag acacactcct gctatgggta ctgctgctct ggttccagg ttccactggt     60 gacgcggccc aggatcctgg gcagaatcat acgaagtgg tgaaattcat ggatgtctat    120
cagcgcagct actgccatcc gatcgagaca ctggtggaca tcttccagga tacccctgat   180
gagatcgagt acatcttcaa gccatcctgc gtgcccctga tgagatgtgg gggttgctgc    240
aatgacgaag gctggagtg cgttcccacc gaggagtcca acatcaccat gcagattatg    300
agaattaaac ctcaccaagg gcagcacatc ggagagatga gctttctcca gcataacaaa   360
tgtgaatgta gaccaaagaa agatttggtc ttcgaacaaa aactcatctc agaagaggat   420
ctgaatagcg ccgtcgacca tcatcatcat catcat                              456
```

<210> SEQ ID NO 107
<211> LENGTH: 152
<212> TYPE: PRT
<213> ORGANISM: Artificial sequence
<220> FEATURE:
<221> NAME/KEY: MISC_FEATURE
<223> OTHER INFORMATION: hVEGFA109

<400> SEQUENCE: 107

```
Met Glu Thr Asp Thr Leu Leu Leu Trp Val Leu Leu Leu Trp Val Pro
1               5                   10                  15

Gly Ser Thr Gly Asp Ala Ala Gln Asp Pro Gly Gln Asn His His Glu
            20                  25                  30

Val Val Lys Phe Met Asp Val Tyr Gln Arg Ser Tyr Cys His Pro Ile
        35                  40                  45

Glu Thr Leu Val Asp Ile Phe Gln Glu Tyr Pro Asp Glu Ile Glu Tyr
    50                  55                  60

Ile Phe Lys Pro Ser Cys Val Pro Leu Met Arg Cys Gly Gly Cys Cys
65                  70                  75                  80

Asn Asp Glu Gly Leu Glu Cys Val Pro Thr Glu Glu Ser Asn Ile Thr
                85                  90                  95

Met Gln Ile Met Arg Ile Lys Pro His Gln Gly Gln His Ile Gly Glu
            100                 105                 110

Met Ser Phe Leu Gln His Asn Lys Cys Glu Cys Arg Pro Lys Lys Asp
        115                 120                 125

Leu Val Phe Glu Gln Lys Leu Ile Ser Glu Glu Asp Leu Asn Ser Ala
    130                 135                 140

Val Asp His His His His His His
145                 150
```

<210> SEQ ID NO 108
<211> LENGTH: 504
<212> TYPE: DNA
<213> ORGANISM: Artificial sequence
<220> FEATURE:
<221> NAME/KEY: misc_feature
<223> OTHER INFORMATION: hVEGFC109

<400> SEQUENCE: 108

| | | | | | |
|---|---|---|---|---|---|
| atggagacag | acacactcct | gctatgggta | ctgctgctct | gggttccagg | ttccactggt | 60 |
| gacgcggccc | agccggccag | gcgcgccgta | cgaagcttgg | taccgagctc | ggatccagca | 120 |
| cattataata | cagagatctt | gaaaagtatt | gataatgagt | ggagaaagac | tcaatgcatg | 180 |
| ccacgggagg | tgtgtataga | tgtggggaag | gagtttggag | tcgcgacaaa | caccttcttt | 240 |
| aaacctccat | gtgtgtccgt | ctacagatgt | gggggttgct | gcaatagtga | ggggctgcag | 300 |
| tgcatgaaca | ccagcacgag | ctacctcagc | aagacgttat | ttgaaattac | agtgcctctc | 360 |
| tctcaaggcc | ccaaaccagt | aacaatcagt | tttgccaatc | acacttcctg | ccgatgcatg | 420 |
| tctaagctgg | atttggtctt | cgaacaaaaa | ctcatctcag | aagaggatct | gaatagcgcc | 480 |
| gtcgaccatc | atcatcatca | tcat | | | | 504 |

<210> SEQ ID NO 109
<211> LENGTH: 168
<212> TYPE: PRT
<213> ORGANISM: Artificial sequence
<220> FEATURE:
<221> NAME/KEY: MISC_FEATURE
<223> OTHER INFORMATION: hVEGFC109

<400> SEQUENCE: 109

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Val Arg Ser
            20                  25                  30

Leu Val Pro Ser Ser Asp Pro Ala His Tyr Asn Thr Glu Ile Leu Lys
            35                  40                  45

Ser Ile Asp Asn Glu Trp Arg Lys Thr Gln Cys Met Pro Arg Glu Val
50                  55                  60

Cys Ile Asp Val Gly Lys Glu Phe Gly Val Ala Thr Asn Thr Phe Phe
65                  70                  75                  80

Lys Pro Pro Cys Val Ser Val Tyr Arg Cys Gly Cys Cys Asn Ser
                85                  90                  95

Glu Gly Leu Gln Cys Met Asn Thr Ser Thr Ser Tyr Leu Ser Lys Thr
            100                 105                 110

Leu Phe Glu Ile Thr Val Pro Leu Ser Gln Gly Pro Lys Pro Val Thr
            115                 120                 125

Ile Ser Phe Ala Asn His Thr Ser Cys Arg Cys Met Ser Lys Leu Asp
130                 135                 140

Leu Val Phe Glu Gln Lys Leu Ile Ser Glu Glu Asp Leu Asn Ser Ala
145                 150                 155                 160

Val Asp His His His His His His
                165
```

<210> SEQ ID NO 110
<211> LENGTH: 87
<212> TYPE: PRT
<213> ORGANISM: Artificial sequence
<220> FEATURE:
<221> NAME/KEY: MISC_FEATURE
<223> OTHER INFORMATION: VHD motif
<220> FEATURE:
<221> NAME/KEY: misc_feature
<222> LOCATION: (2)..(23)
<223> OTHER INFORMATION: Xaa = any or unknown amino acid
<220> FEATURE:
<221> NAME/KEY: misc_feature
<222> LOCATION: (24)..(25)
<223> OTHER INFORMATION: Xaa = any amino acid or unknown amino acid or
      nothing
<220> FEATURE:
<221> NAME/KEY: misc_feature
<222> LOCATION: (27)..(27)
<223> OTHER INFORMATION: Xaa = Proline, Serine or Arginine
<220> FEATURE:
<221> NAME/KEY: misc_feature
<222> LOCATION: (30)..(32)
<223> OTHER INFORMATION: Xaa = any or unknown amino acid
<220> FEATURE:
<221> NAME/KEY: misc_feature
<222> LOCATION: (35)..(35)
<223> OTHER INFORMATION: Xaa = Guanine, Serine, Threonine or Alanine
<220> FEATURE:
<221> NAME/KEY: misc_feature
<222> LOCATION: (39)..(44)
<223> OTHER INFORMATION: Xaa = any or unknown amino acid
<220> FEATURE:
<221> NAME/KEY: misc_feature
<222> LOCATION: (46)..(77)
<223> OTHER INFORMATION: Xaa = any or unknown amino acid
<220> FEATURE:
<221> NAME/KEY: misc_feature
<222> LOCATION: (78)..(86)
<223> OTHER INFORMATION: Xaa = any amino acid or unknown amino acid or
      nothing

<400> SEQUENCE: 110

```
Cys Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Pro Xaa Cys Val Xaa Xaa Xaa
                20                  25                  30

Arg Cys Xaa Gly Cys Cys Xaa Xaa Xaa Xaa Cys Xaa Xaa Xaa
            35                  40                  45

Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa
65                  70                  75                  80

Xaa Xaa Xaa Xaa Xaa Xaa Cys
            85

<210> SEQ ID NO 111
<211> LENGTH: 13
<212> TYPE: PRT
<213> ORGANISM: Artificial sequence
<220> FEATURE:
<221> NAME/KEY: MISC_FEATURE
<223> OTHER INFORMATION: PDGF motif
<220> FEATURE:
<221> NAME/KEY: misc_feature
<222> LOCATION: (2)..(2)
<223> OTHER INFORMATION: Xaa = Proline or Serine
<220> FEATURE:
<221> NAME/KEY: misc_feature
<222> LOCATION: (5)..(7)
<223> OTHER INFORMATION: Xaa = any or unknown amino acid
<220> FEATURE:
<221> NAME/KEY: misc_feature
<222> LOCATION: (10)..(10)
<223> OTHER INFORMATION: Xaa = Arginine, Serine, Threonine or Alanine

<400> SEQUENCE: 111

Pro Xaa Cys Val Xaa Xaa Xaa Arg Cys Xaa Gly Cys Cys
1               5                   10

<210> SEQ ID NO 112
<211> LENGTH: 2772
<212> TYPE: DNA
<213> ORGANISM: Homo sapiens
<220> FEATURE:
<221> NAME/KEY: CDS
<222> LOCATION: (1)..(2772)

<400> SEQUENCE: 112
```

| | | | | | | | | | | | | | | | | |
|---|---|---|---|---|---|---|---|---|---|---|---|---|---|---|---|---|
| atg | gag | agg | ggg | ctg | ccg | ctc | ctc | tgc | gcc | gtg | ctc | gcc | ctc | gtc | ctc | 48 |
| Met | Glu | Arg | Gly | Leu | Pro | Leu | Leu | Cys | Ala | Val | Leu | Ala | Leu | Val | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gcc | ccg | gcc | ggc | gct | ttt | cgc | aac | gat | gaa | tgt | ggc | gat | act | ata | aaa | 96 |
| Ala | Pro | Ala | Gly | Ala | Phe | Arg | Asn | Asp | Glu | Cys | Gly | Asp | Thr | Ile | Lys | |
| | | 20 | | | | | 25 | | | | | 30 | | | | |

| | | | | | | | | | | | | | | | | |
|---|---|---|---|---|---|---|---|---|---|---|---|---|---|---|---|---|
| att | gaa | agc | ccc | ggg | tac | ctt | aca | tct | cct | ggt | tat | cct | cat | tct | tat | 144 |
| Ile | Glu | Ser | Pro | Gly | Tyr | Leu | Thr | Ser | Pro | Gly | Tyr | Pro | His | Ser | Tyr | |
| | | | 35 | | | | | 40 | | | | | 45 | | | |

| | | | | | | | | | | | | | | | | |
|---|---|---|---|---|---|---|---|---|---|---|---|---|---|---|---|---|
| cac | cca | agt | gaa | aaa | tgc | gaa | tgg | ctg | att | cag | gct | ccg | gac | cca | tac | 192 |
| His | Pro | Ser | Glu | Lys | Cys | Glu | Trp | Leu | Ile | Gln | Ala | Pro | Asp | Pro | Tyr | |
| | 50 | | | | | 55 | | | | | 60 | | | | | |

| | | | | | | | | | | | | | | | | |
|---|---|---|---|---|---|---|---|---|---|---|---|---|---|---|---|---|
| cag | aga | att | atg | atc | aac | ttc | aac | cct | cac | ttc | gat | ttg | gag | gac | aga | 240 |
| Gln | Arg | Ile | Met | Ile | Asn | Phe | Asn | Pro | His | Phe | Asp | Leu | Glu | Asp | Arg | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gac | tgc | aag | tat | gac | tac | gtg | gaa | gtc | ttc | gat | gga | gaa | aat | gaa | aat | 288 |
| Asp | Cys | Lys | Tyr | Asp | Tyr | Val | Glu | Val | Phe | Asp | Gly | Glu | Asn | Glu | Asn | |
| | | | | 85 | | | | | 90 | | | | | 95 | | |

-continued

```
gga cat ttt agg gga aag ttc tgt gga aag ata gcc cct cct cct gtt      336
Gly His Phe Arg Gly Lys Phe Cys Gly Lys Ile Ala Pro Pro Pro Val
        100                 105                 110 gtg tct tca ggg cca ttt ctt ttt atc aaa ttt gtc tct gac tac gaa      384
Val Ser Ser Gly Pro Phe Leu Phe Ile Lys Phe Val Ser Asp Tyr Glu
115                 120                 125 aca cat ggt gca gga ttt tcc ata cgt tat gaa att ttc aag aga ggt      432
Thr His Gly Ala Gly Phe Ser Ile Arg Tyr Glu Ile Phe Lys Arg Gly
    130                 135                 140 cct gaa tgt tcc cag aac tac aca aca cct agt gga gtg ata aag tcc      480
Pro Glu Cys Ser Gln Asn Tyr Thr Thr Pro Ser Gly Val Ile Lys Ser
145                 150                 155                 160 ccc gga ttc cct gaa aaa tat ccc aac agc ctt gaa tgc act tat att      528
Pro Gly Phe Pro Glu Lys Tyr Pro Asn Ser Leu Glu Cys Thr Tyr Ile
                165                 170                 175 gtc ttt gcg cca aag atg tca gag att atc ctg gaa ttt gaa agc ttt      576
Val Phe Ala Pro Lys Met Ser Glu Ile Ile Leu Glu Phe Glu Ser Phe
            180                 185                 190 gac ctg gag cct gac tca aat cct cca ggg ggg atg ttc tgt cgc tac      624
Asp Leu Glu Pro Asp Ser Asn Pro Pro Gly Gly Met Phe Cys Arg Tyr
        195                 200                 205 gac cgg cta gaa atc tgg gat gga ttc cct gat gtt ggc cct cac att      672
Asp Arg Leu Glu Ile Trp Asp Gly Phe Pro Asp Val Gly Pro His Ile
    210                 215                 220 ggg cgt tac tgt gga cag aaa aca cca ggt cga atc cga tcc tca tcg      720
Gly Arg Tyr Cys Gly Gln Lys Thr Pro Gly Arg Ile Arg Ser Ser Ser
225                 230                 235                 240 ggc att ctc tcc atg gtt ttt tac acc gac agc gcg ata gca aaa gaa      768
Gly Ile Leu Ser Met Val Phe Tyr Thr Asp Ser Ala Ile Ala Lys Glu
                245                 250                 255 ggt ttc tca gca aac tac agt gtc ttg cag agc agt gtc tca gaa gat      816
Gly Phe Ser Ala Asn Tyr Ser Val Leu Gln Ser Ser Val Ser Glu Asp
            260                 265                 270 ttc aaa tgt atg gaa gct ctg ggc atg gaa tca gga gaa att cat tct      864
Phe Lys Cys Met Glu Ala Leu Gly Met Glu Ser Gly Glu Ile His Ser
        275                 280                 285 gac cag atc aca gct tct tcc cag tat agc acc aac tgg tct gca gag      912
Asp Gln Ile Thr Ala Ser Ser Gln Tyr Ser Thr Asn Trp Ser Ala Glu
    290                 295                 300 cgc tcc cgc ctg aac tac cct gag aat ggg tgg act ccc gga gag gat      960
Arg Ser Arg Leu Asn Tyr Pro Glu Asn Gly Trp Thr Pro Gly Glu Asp
305                 310                 315                 320 tcc tac cga gag tgg ata cag gta gac ttg ggc ctt ctg cgc ttt gtc     1008
Ser Tyr Arg Glu Trp Ile Gln Val Asp Leu Gly Leu Leu Arg Phe Val
                325                 330                 335 acg gct gtc ggg aca cag ggc gcc att tca aaa gaa acc aag aag aaa     1056
Thr Ala Val Gly Thr Gln Gly Ala Ile Ser Lys Glu Thr Lys Lys Lys
            340                 345                 350 tat tat gtc aag act tac aag atc gac gtt agc tcc aac ggg gaa gac     1104
Tyr Tyr Val Lys Thr Tyr Lys Ile Asp Val Ser Ser Asn Gly Glu Asp
        355                 360                 365 tgg atc acc ata aaa gaa gga aac aaa cct gtt ctc ttt cag gga aac     1152
Trp Ile Thr Ile Lys Glu Gly Asn Lys Pro Val Leu Phe Gln Gly Asn
    370                 375                 380 acc aac ccc aca gat gtt gtg gtt gca gta ttc ccc aaa cca ctg ata     1200
Thr Asn Pro Thr Asp Val Val Val Ala Val Phe Pro Lys Pro Leu Ile
385                 390                 395                 400 act cga ttt gtc cga atc aag cct gca act tgg gaa act ggc ata tct     1248
Thr Arg Phe Val Arg Ile Lys Pro Ala Thr Trp Glu Thr Gly Ile Ser
                405                 410                 415
```

```
atg aga ttt gaa gta tac ggt tgc aag ata aca gat tat cct tgc tct      1296
Met Arg Phe Glu Val Tyr Gly Cys Lys Ile Thr Asp Tyr Pro Cys Ser
            420                 425                 430 gga atg ttg ggt atg gtg tct gga ctt att tct gac tcc cag atc aca      1344
Gly Met Leu Gly Met Val Ser Gly Leu Ile Ser Asp Ser Gln Ile Thr
        435                 440                 445 tca tcc aac caa gga gac aga aac tgg atg cct gaa aac atc cgc ctg      1392
Ser Ser Asn Gln Gly Asp Arg Asn Trp Met Pro Glu Asn Ile Arg Leu
450                 455                 460 gta acc agt cgc tct ggc tgg gca ctt cca ccc gca cct cat tcc tac      1440
Val Thr Ser Arg Ser Gly Trp Ala Leu Pro Pro Ala Pro His Ser Tyr
465                 470                 475                 480 atc aat gag tgg ctc caa ata gac ctg ggg gag gag aag atc gtg agg      1488
Ile Asn Glu Trp Leu Gln Ile Asp Leu Gly Glu Glu Lys Ile Val Arg
                485                 490                 495 ggc atc atc att cag ggt ggg aag cac cga gag aac aag gtg ttc atg      1536
Gly Ile Ile Ile Gln Gly Gly Lys His Arg Glu Asn Lys Val Phe Met
            500                 505                 510 agg aag ttc aag atc ggg tac agc aac aac ggc tcg gac tgg aag atg      1584
Arg Lys Phe Lys Ile Gly Tyr Ser Asn Asn Gly Ser Asp Trp Lys Met
        515                 520                 525 atc atg gat gac agc aaa cgc aag gcg aag tct ttt gag ggc aac aac      1632
Ile Met Asp Asp Ser Lys Arg Lys Ala Lys Ser Phe Glu Gly Asn Asn
530                 535                 540 aac tat gat aca cct gag ctg cgg act ttt cca gct ctc tcc acg cga      1680
Asn Tyr Asp Thr Pro Glu Leu Arg Thr Phe Pro Ala Leu Ser Thr Arg
545                 550                 555                 560 ttc atc agg atc tac ccc gag aga gcc act cat ggc gga ctg ggg ctc      1728
Phe Ile Arg Ile Tyr Pro Glu Arg Ala Thr His Gly Gly Leu Gly Leu
                565                 570                 575 aga atg gag ctg ctg ggc tgt gaa gtg gaa gcc cct aca gct gga ccg      1776
Arg Met Glu Leu Leu Gly Cys Glu Val Glu Ala Pro Thr Ala Gly Pro
            580                 585                 590 acc act ccc aac ggg aac ttg gtg gat gaa tgt gat gac gac cag gcc      1824
Thr Thr Pro Asn Gly Asn Leu Val Asp Glu Cys Asp Asp Asp Gln Ala
        595                 600                 605 aac tgc cac agt gga aca ggt gat gac ttc cag ctc aca ggt ggc acc      1872
Asn Cys His Ser Gly Thr Gly Asp Asp Phe Gln Leu Thr Gly Gly Thr
610                 615                 620 act gtg ctg gcc aca gaa aag ccc acg gtc ata gac agc acc ata caa      1920
Thr Val Leu Ala Thr Glu Lys Pro Thr Val Ile Asp Ser Thr Ile Gln
625                 630                 635                 640 tca gag ttt cca aca tat ggt ttt aac tgt gaa ttt ggc tgg ggc tct      1968
Ser Glu Phe Pro Thr Tyr Gly Phe Asn Cys Glu Phe Gly Trp Gly Ser
                645                 650                 655 cac aag acc ttc tgc cac tgg gaa cat gac aat cac gtg cag ctc aag      2016
His Lys Thr Phe Cys His Trp Glu His Asp Asn His Val Gln Leu Lys
            660                 665                 670 tgg agt gtg ttg acc agc aag acg gga ccc att cag gat cac aca gga      2064
Trp Ser Val Leu Thr Ser Lys Thr Gly Pro Ile Gln Asp His Thr Gly
        675                 680                 685 gat ggc aac ttc atc tat tcc caa gct gac gaa aat cag aag ggc aaa      2112
Asp Gly Asn Phe Ile Tyr Ser Gln Ala Asp Glu Asn Gln Lys Gly Lys
690                 695                 700 gtg gct cgc ctg gtg agc cct gtg gtt tat tcc cag aac tct gcc cac      2160
Val Ala Arg Leu Val Ser Pro Val Val Tyr Ser Gln Asn Ser Ala His
705                 710                 715                 720 tgc atg acc ttc tgg tat cac atg tct ggg tcc cac gtc ggc aca ctc      2208
Cys Met Thr Phe Trp Tyr His Met Ser Gly Ser His Val Gly Thr Leu
```

-continued

```
                725                 730                 735
agg gtc aaa ctg cgc tac cag aag cca gag gag tac gat cag ctg gtc    2256
Arg Val Lys Leu Arg Tyr Gln Lys Pro Glu Glu Tyr Asp Gln Leu Val
        740                 745                 750 tgg atg gcc att gga cac caa ggt gac cac tgg aag gaa ggg cgt gtc    2304
Trp Met Ala Ile Gly His Gln Gly Asp His Trp Lys Glu Gly Arg Val
            755                 760                 765 ttg ctc cac aag tct ctg aaa ctt tat cag gtg att ttc gag ggc gaa    2352
Leu Leu His Lys Ser Leu Lys Leu Tyr Gln Val Ile Phe Glu Gly Glu
    770                 775                 780 atc gga aaa gga aac ctt ggt ggg att gct gtg gat gac att agt att    2400
Ile Gly Lys Gly Asn Leu Gly Gly Ile Ala Val Asp Asp Ile Ser Ile
785                 790                 795                 800 aat aac cac att tca caa gaa gat tgt gca aaa cca gca gac ctg gat    2448
Asn Asn His Ile Ser Gln Glu Asp Cys Ala Lys Pro Ala Asp Leu Asp
                805                 810                 815 aaa aag aac cca gaa att aaa att gat gaa aca ggg agc acg cca gga    2496
Lys Lys Asn Pro Glu Ile Lys Ile Asp Glu Thr Gly Ser Thr Pro Gly
            820                 825                 830 tac gaa ggt gaa gga gaa ggt gac aag aac atc tcc agg aag cca ggc    2544
Tyr Glu Gly Glu Gly Glu Gly Asp Lys Asn Ile Ser Arg Lys Pro Gly
        835                 840                 845 aat gtg ttg aag acc tta gaa ccc atc ctc atc acc atc ata gcc atg    2592
Asn Val Leu Lys Thr Leu Glu Pro Ile Leu Ile Thr Ile Ile Ala Met
850                 855                 860 agc gcc ctg ggg gtc ctc ctg ggg gct gtc tgt ggg gtc gtg ctg tac    2640
Ser Ala Leu Gly Val Leu Leu Gly Ala Val Cys Gly Val Val Leu Tyr
865                 870                 875                 880 tgt gcc tgt tgg cat aat ggg atg tca gaa aga aac ttg tct gcc ctg    2688
Cys Ala Cys Trp His Asn Gly Met Ser Glu Arg Asn Leu Ser Ala Leu
                885                 890                 895 gag aac tat aac ttt gaa ctt gtg gat ggt gtg aag ttg aaa aaa gac    2736
Glu Asn Tyr Asn Phe Glu Leu Val Asp Gly Val Lys Leu Lys Lys Asp
            900                 905                 910 aaa ctg aat aca cag agt act tat tcg gag gca tga                    2772
Lys Leu Asn Thr Gln Ser Thr Tyr Ser Glu Ala
        915                 920
```

<210> SEQ ID NO 113
<211> LENGTH: 923
<212> TYPE: PRT
<213> ORGANISM: Homo sapiens

<400> SEQUENCE: 113

```
Met Glu Arg Gly Leu Pro Leu Leu Cys Ala Val Leu Ala Leu Val Leu
1               5                   10                  15

Ala Pro Ala Gly Ala Phe Arg Asn Asp Glu Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110
```

```
Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
        130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Gly Gly Met Phe Cys Arg Tyr
        195                 200                 205

Asp Arg Leu Glu Ile Trp Asp Gly Phe Pro Asp Val Gly Pro His Ile
210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
        435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
        515                 520                 525

Ile Met Asp Asp Ser Lys Arg Lys Ala Lys Ser Phe Glu Gly Asn Asn
```

```
                530             535             540
Asn Tyr Asp Thr Pro Glu Leu Arg Thr Phe Pro Ala Leu Ser Thr Arg
545                 550             555                 560

Phe Ile Arg Ile Tyr Pro Glu Arg Ala Thr His Gly Gly Leu Gly Leu
                565             570                 575

Arg Met Glu Leu Leu Gly Cys Glu Val Glu Ala Pro Thr Ala Gly Pro
            580             585             590

Thr Thr Pro Asn Gly Asn Leu Val Asp Glu Cys Asp Asp Gln Ala
        595             600             605

Asn Cys His Ser Gly Thr Gly Asp Asp Phe Gln Leu Thr Gly Gly Thr
610             615             620

Thr Val Leu Ala Thr Glu Lys Pro Thr Val Ile Asp Ser Thr Ile Gln
625             630             635             640

Ser Glu Phe Pro Thr Tyr Gly Phe Asn Cys Glu Phe Gly Trp Gly Ser
                645             650             655

His Lys Thr Phe Cys His Trp Glu His Asp Asn His Val Gln Leu Lys
            660             665             670

Trp Ser Val Leu Thr Ser Lys Thr Gly Pro Ile Gln Asp His Thr Gly
        675             680             685

Asp Gly Asn Phe Ile Tyr Ser Gln Ala Asp Glu Asn Gln Lys Gly Lys
        690             695             700

Val Ala Arg Leu Val Ser Pro Val Val Tyr Ser Gln Asn Ser Ala His
705             710             715             720

Cys Met Thr Phe Trp Tyr His Met Ser Gly Ser His Val Gly Thr Leu
                725             730             735

Arg Val Lys Leu Arg Tyr Gln Lys Pro Glu Glu Tyr Asp Gln Leu Val
            740             745             750

Trp Met Ala Ile Gly His Gln Gly Asp His Trp Lys Glu Gly Arg Val
            755             760             765

Leu His Lys Ser Leu Lys Leu Tyr Gln Val Ile Phe Glu Gly Glu
        770             775             780

Ile Gly Lys Gly Asn Leu Gly Gly Ile Ala Val Asp Asp Ile Ser Ile
785             790             795             800

Asn Asn His Ile Ser Gln Glu Asp Cys Ala Lys Pro Ala Asp Leu Asp
            805             810             815

Lys Lys Asn Pro Glu Ile Lys Ile Asp Glu Thr Gly Ser Thr Pro Gly
            820             825             830

Tyr Glu Gly Glu Gly Glu Gly Asp Lys Asn Ile Ser Arg Lys Pro Gly
            835             840             845

Asn Val Leu Lys Thr Leu Glu Pro Ile Leu Ile Thr Ile Ala Met
        850             855             860

Ser Ala Leu Gly Val Leu Leu Gly Ala Val Cys Gly Val Val Leu Tyr
865             870             875             880

Cys Ala Cys Trp His Asn Gly Met Ser Glu Arg Asn Leu Ser Ala Leu
            885             890             895

Glu Asn Tyr Asn Phe Glu Leu Val Asp Gly Val Lys Leu Lys Lys Asp
            900             905             910

Lys Leu Asn Thr Gln Ser Thr Tyr Ser Glu Ala
            915             920

<210> SEQ ID NO 114
<211> LENGTH: 2781
<212> TYPE: DNA
<213> ORGANISM: Homo sapiens
```

```
<220> FEATURE:
<221> NAME/KEY: CDS
<222> LOCATION: (1)..(2781)

<400> SEQUENCE: 114
```

| | | | | | | | | | | | | | | | | |
|---|---|---|---|---|---|---|---|---|---|---|---|---|---|---|---|---|
| atg | gat | atg | ttt | cct | ctc | acc | tgg | gtt | ttc | tta | gcc | ctc | tac | ttt | tca | 48 |
| Met | Asp | Met | Phe | Pro | Leu | Thr | Trp | Val | Phe | Leu | Ala | Leu | Tyr | Phe | Ser | |
| 1 | | | | 5 | | | | | 10 | | | | | 15 | | |
| aga | cac | caa | gtg | aga | ggc | caa | cca | gac | cca | ccg | tgc | gga | ggt | cgt | ttg | 96 |
| Arg | His | Gln | Val | Arg | Gly | Gln | Pro | Asp | Pro | Pro | Cys | Gly | Gly | Arg | Leu | |
| | | | 20 | | | | | 25 | | | | | 30 | | | |
| aat | tcc | aaa | gat | gct | ggc | tat | atc | acc | tct | ccc | ggt | tac | ccc | cag | gac | 144 |
| Asn | Ser | Lys | Asp | Ala | Gly | Tyr | Ile | Thr | Ser | Pro | Gly | Tyr | Pro | Gln | Asp | |
| | | 35 | | | | | 40 | | | | | 45 | | | | |
| tac | ccc | tcc | cac | cag | aac | tgc | gag | tgg | att | gtt | tac | gcc | ccc | gaa | ccc | 192 |
| Tyr | Pro | Ser | His | Gln | Asn | Cys | Glu | Trp | Ile | Val | Tyr | Ala | Pro | Glu | Pro | |
| 50 | | | | | 55 | | | | | 60 | | | | | | |
| aac | cag | aag | att | gtc | ctc | aac | ttc | aac | cct | cac | ttt | gaa | atc | gag | aag | 240 |
| Asn | Gln | Lys | Ile | Val | Leu | Asn | Phe | Asn | Pro | His | Phe | Glu | Ile | Glu | Lys | |
| 65 | | | | | 70 | | | | | 75 | | | | | 80 | |
| cac | gac | tgc | aag | tat | gac | ttt | atc | gag | att | cgg | gat | ggg | gac | agt | gaa | 288 |
| His | Asp | Cys | Lys | Tyr | Asp | Phe | Ile | Glu | Ile | Arg | Asp | Gly | Asp | Ser | Glu | |
| | | | | 85 | | | | | 90 | | | | | 95 | | |
| tcc | gca | gac | ctc | ctg | ggc | aaa | cac | tgt | ggg | aac | atc | gcc | ccg | ccc | acc | 336 |
| Ser | Ala | Asp | Leu | Leu | Gly | Lys | His | Cys | Gly | Asn | Ile | Ala | Pro | Pro | Thr | |
| | | | 100 | | | | | 105 | | | | | 110 | | | |
| atc | atc | tcc | tcg | ggc | tcc | atg | ctc | tac | atc | aag | ttc | acc | tcc | gac | tac | 384 |
| Ile | Ile | Ser | Ser | Gly | Ser | Met | Leu | Tyr | Ile | Lys | Phe | Thr | Ser | Asp | Tyr | |
| | | 115 | | | | | 120 | | | | | 125 | | | | |
| gcc | cgg | cag | ggg | gca | ggc | ttc | tct | ctg | cgc | tac | gag | atc | ttc | aag | aca | 432 |
| Ala | Arg | Gln | Gly | Ala | Gly | Phe | Ser | Leu | Arg | Tyr | Glu | Ile | Phe | Lys | Thr | |
| 130 | | | | | 135 | | | | | 140 | | | | | | |
| ggc | tct | gaa | gat | tgc | tca | aaa | aac | ttc | aca | agc | ccc | aac | ggg | acc | atc | 480 |
| Gly | Ser | Glu | Asp | Cys | Ser | Lys | Asn | Phe | Thr | Ser | Pro | Asn | Gly | Thr | Ile | |
| 145 | | | | | 150 | | | | | 155 | | | | | 160 | |
| gaa | tct | cct | ggg | ttt | cct | gag | aag | tat | cca | cac | aac | ttg | gac | tgc | acc | 528 |
| Glu | Ser | Pro | Gly | Phe | Pro | Glu | Lys | Tyr | Pro | His | Asn | Leu | Asp | Cys | Thr | |
| | | | | 165 | | | | | 170 | | | | | 175 | | |
| ttt | acc | atc | ctg | gcc | aaa | ccc | aag | atg | gag | atc | atc | ctg | cag | ttc | ctg | 576 |
| Phe | Thr | Ile | Leu | Ala | Lys | Pro | Lys | Met | Glu | Ile | Ile | Leu | Gln | Phe | Leu | |
| | | | 180 | | | | | 185 | | | | | 190 | | | |
| atc | ttt | gac | ctg | gag | cat | gac | cct | ttg | cag | gtg | gga | gag | ggg | gac | tgc | 624 |
| Ile | Phe | Asp | Leu | Glu | His | Asp | Pro | Leu | Gln | Val | Gly | Glu | Gly | Asp | Cys | |
| | | 195 | | | | | 200 | | | | | 205 | | | | |
| aag | tac | gat | tgg | ctg | gac | atc | tgg | gat | ggc | att | cca | cat | gtt | ggc | ccc | 672 |
| Lys | Tyr | Asp | Trp | Leu | Asp | Ile | Trp | Asp | Gly | Ile | Pro | His | Val | Gly | Pro | |
| | 210 | | | | | 215 | | | | | 220 | | | | | |
| ctg | att | ggc | aag | tac | tgt | ggg | acc | aaa | aca | ccc | tct | gaa | ctt | cgt | tca | 720 |
| Leu | Ile | Gly | Lys | Tyr | Cys | Gly | Thr | Lys | Thr | Pro | Ser | Glu | Leu | Arg | Ser | |
| 225 | | | | | 230 | | | | | 235 | | | | | 240 | |
| tcg | acg | ggg | atc | ctc | tcc | ctg | acc | ttt | cac | acg | gac | atg | gcg | gtg | gcc | 768 |
| Ser | Thr | Gly | Ile | Leu | Ser | Leu | Thr | Phe | His | Thr | Asp | Met | Ala | Val | Ala | |
| | | | | 245 | | | | | 250 | | | | | 255 | | |
| aag | gat | ggc | ttc | tct | gcg | cgt | tac | tac | ctg | gtc | cac | caa | gag | cca | cta | 816 |
| Lys | Asp | Gly | Phe | Ser | Ala | Arg | Tyr | Tyr | Leu | Val | His | Gln | Glu | Pro | Leu | |
| | | | 260 | | | | | 265 | | | | | 270 | | | |
| gag | aac | ttt | cag | tgc | aat | gtt | cct | ctg | ggc | atg | gag | tct | ggc | cgg | att | 864 |
| Glu | Asn | Phe | Gln | Cys | Asn | Val | Pro | Leu | Gly | Met | Glu | Ser | Gly | Arg | Ile | |
| | | 275 | | | | | 280 | | | | | 285 | | | | |
| gct | aat | gaa | cag | atc | agt | gcc | tca | tct | acc | tac | tct | gat | ggg | agg | tgg | 912 |

-continued

```
                Ala Asn Glu Gln Ile Ser Ala Ser Ser Thr Tyr Ser Asp Gly Arg Trp
                    290                 295                 300 acc cct caa caa agc cgg ctc cat ggt gac gac aat ggc tgg acc ccc              960
Thr Pro Gln Gln Ser Arg Leu His Gly Asp Asp Asn Gly Trp Thr Pro
305                 310                 315                 320 aac ttg gat tcc aac aag gag tat ctc cag gtg gac ctg cgc ttt tta            1008
Asn Leu Asp Ser Asn Lys Glu Tyr Leu Gln Val Asp Leu Arg Phe Leu
                325                 330                 335 acc atg ctc acg gcc atc gca aca cag gga gcg att tcc agg gaa aca            1056
Thr Met Leu Thr Ala Ile Ala Thr Gln Gly Ala Ile Ser Arg Glu Thr
            340                 345                 350 cag aat ggc tac tac gtc aaa tcc tac aag ctg gaa gtc agc act aat            1104
Gln Asn Gly Tyr Tyr Val Lys Ser Tyr Lys Leu Glu Val Ser Thr Asn
        355                 360                 365 gga gag gac tgg atg gtg tac cgg cat ggc aaa aac cac aag gta ttt            1152
Gly Glu Asp Trp Met Val Tyr Arg His Gly Lys Asn His Lys Val Phe
    370                 375                 380 caa gcc aac aac gat gca act gag gtg gtt ctg aac aag ctc cac gct            1200
Gln Ala Asn Asn Asp Ala Thr Glu Val Val Leu Asn Lys Leu His Ala
385                 390                 395                 400 cca ctg ctg aca agg ttt gtt aga atc cgc cct cag acc tgg cac tca            1248
Pro Leu Leu Thr Arg Phe Val Arg Ile Arg Pro Gln Thr Trp His Ser
                405                 410                 415 ggt atc gcc ctc cgg ctg gag ctc ttc ggc tgc cgg gtc aca gat gct            1296
Gly Ile Ala Leu Arg Leu Glu Leu Phe Gly Cys Arg Val Thr Asp Ala
            420                 425                 430 ccc tgc tcc aac atg ctg ggg atg ctc tca ggc ctc att gca gac tcc            1344
Pro Cys Ser Asn Met Leu Gly Met Leu Ser Gly Leu Ile Ala Asp Ser
        435                 440                 445 cag atc tcc gcc tct tcc acc cag gaa tac ctc tgg agc ccc agt gca            1392
Gln Ile Ser Ala Ser Ser Thr Gln Glu Tyr Leu Trp Ser Pro Ser Ala
    450                 455                 460 gcc cgc ctg gtc agc agc cgc tcg ggc tgg ttc cct cga atc cct cag            1440
Ala Arg Leu Val Ser Ser Arg Ser Gly Trp Phe Pro Arg Ile Pro Gln
465                 470                 475                 480 gcc cag ccc ggt gag gag tgg ctt cag gta gat ctg gga aca ccc aag            1488
Ala Gln Pro Gly Glu Glu Trp Leu Gln Val Asp Leu Gly Thr Pro Lys
                485                 490                 495 aca gtg aaa ggt gtc atc atc cag gga gcc cgc gga gga gac agt atc            1536
Thr Val Lys Gly Val Ile Ile Gln Gly Ala Arg Gly Gly Asp Ser Ile
            500                 505                 510 act gct gtg gaa gcc aga gca ttt gtg cgc aag ttc aaa gtc tcc tac            1584
Thr Ala Val Glu Ala Arg Ala Phe Val Arg Lys Phe Lys Val Ser Tyr
        515                 520                 525 agc cta aac ggc aag gac tgg gaa tac att cag gac ccc agg acc cag            1632
Ser Leu Asn Gly Lys Asp Trp Glu Tyr Ile Gln Asp Pro Arg Thr Gln
    530                 535                 540 cag cca aag ctg ttc gaa ggg aac atg cac tat gac acc cct gac atc            1680
Gln Pro Lys Leu Phe Glu Gly Asn Met His Tyr Asp Thr Pro Asp Ile
545                 550                 555                 560 cga agg ttt gac ccc att ccg gca cag tat gtg cgg gta tac ccg gag            1728
Arg Arg Phe Asp Pro Ile Pro Ala Gln Tyr Val Arg Val Tyr Pro Glu
                565                 570                 575 agg tgg tcg ccg gcg ggg att ggg atg cgg ctg gag gtg ctg ggc tgt            1776
Arg Trp Ser Pro Ala Gly Ile Gly Met Arg Leu Glu Val Leu Gly Cys
            580                 585                 590 gac tgg aca gac tcc aag ccc acg gta aaa acg ctg gga ccc act gtg            1824
Asp Trp Thr Asp Ser Lys Pro Thr Val Lys Thr Leu Gly Pro Thr Val
        595                 600                 605
```

```
aag agc gaa gag aca acc acc ccc tac ccc acc gaa gag gag gcc aca    1872
Lys Ser Glu Glu Thr Thr Thr Pro Tyr Pro Thr Glu Glu Glu Ala Thr
610                 615                 620 gag tgt ggg gag aac tgc agc ttt gag gat gac aaa gat ttg cag ctc    1920
Glu Cys Gly Glu Asn Cys Ser Phe Glu Asp Asp Lys Asp Leu Gln Leu
625                 630                 635                 640 cct tcg gga ttc aat tgc aac ttc gat ttc ctc gag gag ccc tgt ggt    1968
Pro Ser Gly Phe Asn Cys Asn Phe Asp Phe Leu Glu Glu Pro Cys Gly
                645                 650                 655 tgg atg tat gac cat gcc aag tgg ctc cgg acc acc tgg gcc agc agc    2016
Trp Met Tyr Asp His Ala Lys Trp Leu Arg Thr Thr Trp Ala Ser Ser
                660                 665                 670 tcc agc cca aac gac cgg acg ttt cca gat gac agg aat ttc ttg cgg    2064
Ser Ser Pro Asn Asp Arg Thr Phe Pro Asp Asp Arg Asn Phe Leu Arg
                675                 680                 685 ctg cag agt gac agc cag aga gag ggc cag tat gcc cgg ctc atc agc    2112
Leu Gln Ser Asp Ser Gln Arg Glu Gly Gln Tyr Ala Arg Leu Ile Ser
690                 695                 700 ccc cct gtc cac ctg ccc cga agc ccg gtg tgc atg gag ttc cag tac    2160
Pro Pro Val His Leu Pro Arg Ser Pro Val Cys Met Glu Phe Gln Tyr
705                 710                 715                 720 cag gcc acg ggc ggc cgc ggg gtg gcg ctg cag gtg gtg cgg gaa gcc    2208
Gln Ala Thr Gly Gly Arg Gly Val Ala Leu Gln Val Val Arg Glu Ala
                725                 730                 735 agc cag gag agc aag ttg ctg tgg gtc atc cgt gag gac cag ggc ggc    2256
Ser Gln Glu Ser Lys Leu Leu Trp Val Ile Arg Glu Asp Gln Gly Gly
                740                 745                 750 gag tgg aag cac ggg cgg atc atc ctg ccc agc tac gac atg gag tac    2304
Glu Trp Lys His Gly Arg Ile Ile Leu Pro Ser Tyr Asp Met Glu Tyr
                755                 760                 765 cag att gtg ttc gag gga gtg ata ggg aaa gga cgt tcc gga gag att    2352
Gln Ile Val Phe Glu Gly Val Ile Gly Lys Gly Arg Ser Gly Glu Ile
770                 775                 780 gcc att gat gac att cgg ata agc act gat gtc cca ctg gag aac tgc    2400
Ala Ile Asp Asp Ile Arg Ile Ser Thr Asp Val Pro Leu Glu Asn Cys
785                 790                 795                 800 atg gaa ccc atc tcg gct ttt gca gtg gac atc cca gaa ata cat gag    2448
Met Glu Pro Ile Ser Ala Phe Ala Val Asp Ile Pro Glu Ile His Glu
                805                 810                 815 aga gaa gga tat gaa gat gaa att gat gat gaa tac gag gtg gac tgg    2496
Arg Glu Gly Tyr Glu Asp Glu Ile Asp Asp Glu Tyr Glu Val Asp Trp
                820                 825                 830 agc aat tct tct tct gca acc tca ggg tct ggc gcc ccc tcg acc gac    2544
Ser Asn Ser Ser Ser Ala Thr Ser Gly Ser Gly Ala Pro Ser Thr Asp
                835                 840                 845 aaa gaa aag agc tgg ctg tac acc ctg gat ccc atc ctc atc acc atc    2592
Lys Glu Lys Ser Trp Leu Tyr Thr Leu Asp Pro Ile Leu Ile Thr Ile
850                 855                 860 atc gcc atg agc tca ctg ggc gtc ctc ctg ggg gcc acc tgt gca ggc    2640
Ile Ala Met Ser Ser Leu Gly Val Leu Leu Gly Ala Thr Cys Ala Gly
865                 870                 875                 880 ctc ctg ctc tac tgc acc tgt tcc tac tcg ggc ctg agc tcc cga agc    2688
Leu Leu Leu Tyr Cys Thr Cys Ser Tyr Ser Gly Leu Ser Ser Arg Ser
                885                 890                 895 tgc acc aca ctg gag aac tac aac ttc gag ctc tac gat ggc ctt aag    2736
Cys Thr Thr Leu Glu Asn Tyr Asn Phe Glu Leu Tyr Asp Gly Leu Lys
                900                 905                 910 cac aag gtc aag atg aac cac caa aag tgc tgc tcc gag gca tga        2781
His Lys Val Lys Met Asn His Gln Lys Cys Cys Ser Glu Ala
                915                 920                 925
```

<210> SEQ ID NO 115
<211> LENGTH: 926
<212> TYPE: PRT
<213> ORGANISM: Homo sapiens

<400> SEQUENCE: 115

```
Met Asp Met Phe Pro Leu Thr Trp Val Phe Leu Ala Leu Tyr Phe Ser
1               5                   10                  15

Arg His Gln Val Arg Gly Gln Pro Asp Pro Cys Gly Gly Arg Leu
            20                  25                  30

Asn Ser Lys Asp Ala Gly Tyr Ile Thr Ser Pro Gly Tyr Pro Gln Asp
            35                  40                  45

Tyr Pro Ser His Gln Asn Cys Glu Trp Ile Val Tyr Ala Pro Glu Pro
        50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Met Leu Tyr Ile Lys Phe Thr Ser Asp Tyr
            115                 120                 125

Ala Arg Gln Gly Ala Gly Phe Ser Leu Arg Tyr Glu Ile Phe Lys Thr
        130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
            195                 200                 205

Lys Tyr Asp Trp Leu Asp Ile Trp Asp Gly Ile Pro His Val Gly Pro
        210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
            260                 265                 270

Glu Asn Phe Gln Cys Asn Val Pro Leu Gly Met Glu Ser Gly Arg Ile
            275                 280                 285

Ala Asn Glu Gln Ile Ser Ala Ser Ser Thr Tyr Ser Asp Gly Arg Trp
        290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Asn Gly Tyr Tyr Val Lys Ser Tyr Lys Leu Glu Val Ser Thr Asn
            355                 360                 365

Gly Glu Asp Trp Met Val Tyr Arg His Gly Lys Asn His Lys Val Phe
```

```
             370                 375                 380
Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                405                 410                 415

Gly Ile Ala Leu Arg Leu Glu Leu Phe Gly Cys Arg Val Thr Asp Ala
                420                 425                 430

Pro Cys Ser Asn Met Leu Gly Met Leu Ser Gly Leu Ile Ala Asp Ser
                435                 440                 445

Gln Ile Ser Ala Ser Ser Thr Gln Glu Tyr Leu Trp Ser Pro Ser Ala
450                 455                 460

Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
                500                 505                 510

Thr Ala Val Glu Ala Arg Ala Phe Val Arg Lys Phe Lys Val Ser Tyr
                515                 520                 525

Ser Leu Asn Gly Lys Asp Trp Glu Tyr Ile Gln Asp Pro Arg Thr Gln
530                 535                 540

Gln Pro Lys Leu Phe Glu Gly Asn Met His Tyr Asp Thr Pro Asp Ile
545                 550                 555                 560

Arg Arg Phe Asp Pro Ile Pro Ala Gln Tyr Val Arg Val Tyr Pro Glu
                565                 570                 575

Arg Trp Ser Pro Ala Gly Ile Gly Met Arg Leu Glu Val Leu Gly Cys
                580                 585                 590

Asp Trp Thr Asp Ser Lys Pro Thr Val Lys Thr Leu Gly Pro Thr Val
                595                 600                 605

Lys Ser Glu Glu Thr Thr Thr Pro Tyr Pro Thr Glu Glu Ala Thr
610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Leu Glu Glu Pro Cys Gly
                645                 650                 655

Trp Met Tyr Asp His Ala Lys Trp Leu Arg Thr Thr Trp Ala Ser Ser
                660                 665                 670

Ser Ser Pro Asn Asp Arg Thr Phe Pro Asp Asp Arg Asn Phe Leu Arg
                675                 680                 685

Leu Gln Ser Asp Ser Gln Arg Glu Gly Gln Tyr Ala Arg Leu Ile Ser
                690                 695                 700

Pro Pro Val His Leu Pro Arg Ser Pro Val Cys Met Glu Phe Gln Tyr
705                 710                 715                 720

Gln Ala Thr Gly Gly Arg Gly Val Ala Leu Gln Val Val Arg Glu Ala
                725                 730                 735

Ser Gln Glu Ser Lys Leu Leu Trp Val Ile Arg Glu Asp Gln Gly Gly
                740                 745                 750

Glu Trp Lys His Gly Arg Ile Ile Leu Pro Ser Tyr Asp Met Glu Tyr
                755                 760                 765

Gln Ile Val Phe Glu Gly Val Ile Gly Lys Gly Arg Ser Gly Glu Ile
                770                 775                 780

Ala Ile Asp Asp Ile Arg Ile Ser Thr Asp Val Pro Leu Glu Asn Cys
785                 790                 795                 800
```

```
Met Glu Pro Ile Ser Ala Phe Ala Val Asp Ile Pro Glu Ile His Glu
                805                 810                 815

Arg Glu Gly Tyr Glu Asp Glu Ile Asp Asp Glu Tyr Glu Val Asp Trp
            820                 825                 830

Ser Asn Ser Ser Ser Ala Thr Ser Gly Ser Gly Ala Pro Ser Thr Asp
        835                 840                 845

Lys Glu Lys Ser Trp Leu Tyr Thr Leu Asp Pro Ile Leu Ile Thr Ile
    850                 855                 860

Ile Ala Met Ser Ser Leu Gly Val Leu Leu Gly Ala Thr Cys Ala Gly
865                 870                 875                 880

Leu Leu Leu Tyr Cys Thr Cys Ser Tyr Ser Gly Leu Ser Ser Arg Ser
                885                 890                 895

Cys Thr Thr Leu Glu Asn Tyr Asn Phe Glu Leu Tyr Asp Gly Leu Lys
            900                 905                 910

His Lys Val Lys Met Asn His Gln Lys Cys Cys Ser Glu Ala
        915                 920                 925

<210> SEQ ID NO 116
<211> LENGTH: 6375
<212> TYPE: DNA
<213> ORGANISM: Homo sapiens
<220> FEATURE:
<221> NAME/KEY: CDS
<222> LOCATION: (129)..(3398)
<220> FEATURE:
<221> NAME/KEY: misc_feature
<222> LOCATION: (4476)..(4476)
<223> OTHER INFORMATION: n is a, c, g, or t
<220> FEATURE:
<221> NAME/KEY: misc_feature
<222> LOCATION: (4499)..(4499)
<223> OTHER INFORMATION: n is a, c, g, or t

<400> SEQUENCE: 116
ttggagctac agggagagaa acagaggagg agactgcaag agatcattgg aggccgtggg      60
cacgctcttt actccatgtg tgggacattc attgcggaat aacatcggag gagaagtttc     120 ccagagct atg ggg act tcc cat ccg gcg ttc ctg gtc tta ggc tgt ctt      170
         Met Gly Thr Ser His Pro Ala Phe Leu Val Leu Gly Cys Leu
           1               5                  10 ctc aca ggg ctg agc cta atc ctc tgc cag ctt tca tta ccc tct atc      218
Leu Thr Gly Leu Ser Leu Ile Leu Cys Gln Leu Ser Leu Pro Ser Ile
 15                  20                  25                  30 ctt cca aat gaa aat gaa aag gtt gtg cag ctg aat tca tcc ttt tct      266
Leu Pro Asn Glu Asn Glu Lys Val Val Gln Leu Asn Ser Ser Phe Ser
                 35                  40                  45 ctg aga tgc ttt ggg gag agt gaa gtg agc tgg cag tac ccc atg tct      314
Leu Arg Cys Phe Gly Glu Ser Glu Val Ser Trp Gln Tyr Pro Met Ser
             50                  55                  60 gaa gaa gag agc tcc gat gtg gaa atc aga aat gaa gaa aac aac agc      362
Glu Glu Glu Ser Ser Asp Val Glu Ile Arg Asn Glu Glu Asn Asn Ser
         65                  70                  75 ggc ctt ttt gtg acg gtc ttg gaa gtg agc agt gcc tcg gcg gcc cac      410
Gly Leu Phe Val Thr Val Leu Glu Val Ser Ser Ala Ser Ala Ala His
     80                  85                  90 aca ggg ttg tac act tgc tat tac aac cac act cag aca gaa gag aat      458
Thr Gly Leu Tyr Thr Cys Tyr Tyr Asn His Thr Gln Thr Glu Glu Asn
 95                 100                 105                 110 gag ctt gaa ggc agg cac att tac atc tat gtg cca gac cca gat gta      506
Glu Leu Glu Gly Arg His Ile Tyr Ile Tyr Val Pro Asp Pro Asp Val
                115                 120                 125
```

```
gcc ttt gta cct cta gga atg acg gat tat tta gtc atc gtg gag gat      554
Ala Phe Val Pro Leu Gly Met Thr Asp Tyr Leu Val Ile Val Glu Asp
        130                 135                 140 gat gat tct gcc att ata cct tgt cgc aca act gat ccc gag act cct      602
Asp Asp Ser Ala Ile Ile Pro Cys Arg Thr Thr Asp Pro Glu Thr Pro
            145                 150                 155 gta acc tta cac aac agt gag ggg gtg gta cct gcc tcc tac gac agc      650
Val Thr Leu His Asn Ser Glu Gly Val Val Pro Ala Ser Tyr Asp Ser
        160                 165                 170 aga cag ggc ttt aat ggg acc ttc act gta ggg ccc tat atc tgt gag      698
Arg Gln Gly Phe Asn Gly Thr Phe Thr Val Gly Pro Tyr Ile Cys Glu
175                 180                 185                 190 gcc acc gtc aaa gga aag aag ttc cag acc atc cca ttt aat gtt tat      746
Ala Thr Val Lys Gly Lys Lys Phe Gln Thr Ile Pro Phe Asn Val Tyr
        195                 200                 205 gct tta aaa gca aca tca gag ctg gat cta gaa atg gaa gct ctt aaa      794
Ala Leu Lys Ala Thr Ser Glu Leu Asp Leu Glu Met Glu Ala Leu Lys
            210                 215                 220 acc gtg tat aag tca ggg gaa acg att gtg gtc acc tgt gct gtt ttt      842
Thr Val Tyr Lys Ser Gly Glu Thr Ile Val Val Thr Cys Ala Val Phe
        225                 230                 235 aac aat gag gtg gtt gac ctt caa tgg act tac cct gga gaa gtg aaa      890
Asn Asn Glu Val Val Asp Leu Gln Trp Thr Tyr Pro Gly Glu Val Lys
240                 245                 250 ggc aaa ggc atc aca atg ctg gaa gaa atc aaa gtc cca tcc atc aaa      938
Gly Lys Gly Ile Thr Met Leu Glu Glu Ile Lys Val Pro Ser Ile Lys
255                 260                 265                 270 ttg gtg tac act ttg acg gtc ccc gag gcc acg gtg aaa gac agt gga      986
Leu Val Tyr Thr Leu Thr Val Pro Glu Ala Thr Val Lys Asp Ser Gly
            275                 280                 285 gat tac gaa tgt gct gcc cgc cag gct acc agg gag gtc aaa gaa atg     1034
Asp Tyr Glu Cys Ala Ala Arg Gln Ala Thr Arg Glu Val Lys Glu Met
        290                 295                 300 aag aaa gtc act att tct gtc cat gag aaa ggt ttc att gaa atc aaa     1082
Lys Lys Val Thr Ile Ser Val His Glu Lys Gly Phe Ile Glu Ile Lys
            305                 310                 315 ccc acc ttc agc cag ttg gaa gct gtc aac ctg cat gaa gtc aaa cat     1130
Pro Thr Phe Ser Gln Leu Glu Ala Val Asn Leu His Glu Val Lys His
320                 325                 330 ttt gtt gta gag gtg cgg gcc tac cca cct ccc agg ata tcc tgg ctg     1178
Phe Val Val Glu Val Arg Ala Tyr Pro Pro Pro Arg Ile Ser Trp Leu
335                 340                 345                 350 aaa aac aat ctg act ctg att gaa aat ctc act gag atc acc act gat     1226
Lys Asn Asn Leu Thr Leu Ile Glu Asn Leu Thr Glu Ile Thr Thr Asp
            355                 360                 365 gtg gaa aag att cag gaa ata agg tat cga agc aaa tta aag ctg atc     1274
Val Glu Lys Ile Gln Glu Ile Arg Tyr Arg Ser Lys Leu Lys Leu Ile
        370                 375                 380 cgt gct aag gaa gaa gac agt ggc cat tat act att gta gct caa aat     1322
Arg Ala Lys Glu Glu Asp Ser Gly His Tyr Thr Ile Val Ala Gln Asn
            385                 390                 395 gaa gat gct gtg aag agc tat act ttt gaa ctg tta act caa gtt cct     1370
Glu Asp Ala Val Lys Ser Tyr Thr Phe Glu Leu Leu Thr Gln Val Pro
        400                 405                 410 tca tcc att ctg gac ttg gtc gat gat cac cat ggc tca act ggg gga     1418
Ser Ser Ile Leu Asp Leu Val Asp Asp His His Gly Ser Thr Gly Gly
415                 420                 425                 430 cag acg gtg agg tgc aca gct gaa ggc acg ccg ctt cct gat att gag     1466
Gln Thr Val Arg Cys Thr Ala Glu Gly Thr Pro Leu Pro Asp Ile Glu
```

-continued

```
              435                 440                 445
tgg atg ata tgc aaa gat att aag aaa tgt aat aat gaa act tcc tgg    1514
Trp Met Ile Cys Lys Asp Ile Lys Lys Cys Asn Asn Glu Thr Ser Trp
            450                 455                 460 act att ttg gcc aac aat gtc tca aac atc atc acg gag atc cac tcc    1562
Thr Ile Leu Ala Asn Asn Val Ser Asn Ile Ile Thr Glu Ile His Ser
            465                 470                 475 cga gac agg agt acc gtg gag ggc cgt gtg act ttc gcc aaa gtg gag    1610
Arg Asp Arg Ser Thr Val Glu Gly Arg Val Thr Phe Ala Lys Val Glu
        480                 485                 490 gag acc atc gcc gtg cga tgc ctg gct aag aat ctc ctt gga gct gag    1658
Glu Thr Ile Ala Val Arg Cys Leu Ala Lys Asn Leu Leu Gly Ala Glu
495                 500                 505                 510 aac cga gag ctg aag ctg gtg gct ccc acc ctg cgt tct gaa ctc acg    1706
Asn Arg Glu Leu Lys Leu Val Ala Pro Thr Leu Arg Ser Glu Leu Thr
                515                 520                 525 gtg gct gct gca gtc ctg gtg ctg ttg gtg att gtg atc atc tca ctt    1754
Val Ala Ala Ala Val Leu Val Leu Leu Val Ile Val Ile Ile Ser Leu
            530                 535                 540 att gtc ctg gtt gtc att tgg aaa cag aaa ccg agg tat gaa att cgc    1802
Ile Val Leu Val Val Ile Trp Lys Gln Lys Pro Arg Tyr Glu Ile Arg
            545                 550                 555 tgg agg gtc att gaa tca atc agc cca gat gga cat gaa tat att tat    1850
Trp Arg Val Ile Glu Ser Ile Ser Pro Asp Gly His Glu Tyr Ile Tyr
        560                 565                 570 gtg gac ccg atg cag ctg cct tat gac tca aga tgg gag ttt cca aga    1898
Val Asp Pro Met Gln Leu Pro Tyr Asp Ser Arg Trp Glu Phe Pro Arg
575                 580                 585                 590 gat gga cta gtg ctt ggt cgg gtc ttg ggg tct gga gcg ttt ggg aag    1946
Asp Gly Leu Val Leu Gly Arg Val Leu Gly Ser Gly Ala Phe Gly Lys
                595                 600                 605 gtg gtt gaa gga aca gcc tat gga tta agc cgg tcc caa cct gtc atg    1994
Val Val Glu Gly Thr Ala Tyr Gly Leu Ser Arg Ser Gln Pro Val Met
            610                 615                 620 aaa gtt gca gtg aag atg cta aaa ccc acg gcc aga tcc agt gaa aaa    2042
Lys Val Ala Val Lys Met Leu Lys Pro Thr Ala Arg Ser Ser Glu Lys
            625                 630                 635 caa gct ctc atg tct gaa ctg aag ata atg act cac ctg ggg cca cat    2090
Gln Ala Leu Met Ser Glu Leu Lys Ile Met Thr His Leu Gly Pro His
        640                 645                 650 ttg aac att gta aac ttg ctg gga gcc tgc acc aag tca ggc ccc att    2138
Leu Asn Ile Val Asn Leu Leu Gly Ala Cys Thr Lys Ser Gly Pro Ile
655                 660                 665                 670 tac atc atc aca gag tat tgc ttc tat gga gat ttg gtc aac tat ttg    2186
Tyr Ile Ile Thr Glu Tyr Cys Phe Tyr Gly Asp Leu Val Asn Tyr Leu
                675                 680                 685 cat aag aat agg gat agc ttc ctg agc cac cac cca gag aag cca aag    2234
His Lys Asn Arg Asp Ser Phe Leu Ser His His Pro Glu Lys Pro Lys
            690                 695                 700 aaa gag ctg gat atc ttt gga ttg aac cct gct gat gaa agc aca cgg    2282
Lys Glu Leu Asp Ile Phe Gly Leu Asn Pro Ala Asp Glu Ser Thr Arg
            705                 710                 715 agc tat gtt att tta tct ttt gaa aac aat ggt gac tac atg gac atg    2330
Ser Tyr Val Ile Leu Ser Phe Glu Asn Asn Gly Asp Tyr Met Asp Met
        720                 725                 730 aag cag gct gat act aca cag tat gtc ccc atg cta gaa agg aaa gag    2378
Lys Gln Ala Asp Thr Thr Gln Tyr Val Pro Met Leu Glu Arg Lys Glu
735                 740                 745                 750 gtt tct aaa tat tcc gac atc cag aga tca ctc tat gat cgt cca gcc    2426
```

```
                                               -continued

Val Ser Lys Tyr Ser Asp Ile Gln Arg Ser Leu Tyr Asp Arg Pro Ala
            755                 760                 765 tca tat aag aag aaa tct atg tta gac tca gaa gtc aaa aac ctc ctt    2474
Ser Tyr Lys Lys Lys Ser Met Leu Asp Ser Glu Val Lys Asn Leu Leu
            770                 775                 780 tca gat gat aac tca gaa ggc ctt act tta ttg gat ttg ttg agc ttc    2522
Ser Asp Asp Asn Ser Glu Gly Leu Thr Leu Leu Asp Leu Leu Ser Phe
            785                 790                 795 acc tat caa gtt gcc cga gga atg gag ttt ttg gct tca aaa aat tgt    2570
Thr Tyr Gln Val Ala Arg Gly Met Glu Phe Leu Ala Ser Lys Asn Cys
        800                 805                 810 gtc cac cgt gat ctg gct gct cgc aac gtt ctc ctg gca caa gga aaa    2618
Val His Arg Asp Leu Ala Ala Arg Asn Val Leu Leu Ala Gln Gly Lys
815                 820                 825                 830 att gtg aag atc tgt gac ttt ggc ctg gcc aga gac atc atg cat gat    2666
Ile Val Lys Ile Cys Asp Phe Gly Leu Ala Arg Asp Ile Met His Asp
                835                 840                 845 tcg aac tat gtg tcg aaa ggc agt acc ttt ctg ccc gtg aag tgg atg    2714
Ser Asn Tyr Val Ser Lys Gly Ser Thr Phe Leu Pro Val Lys Trp Met
            850                 855                 860 gct cct gag agc atc ttt gac aac ctc tac acc aca ctg agt gat gtc    2762
Ala Pro Glu Ser Ile Phe Asp Asn Leu Tyr Thr Thr Leu Ser Asp Val
        865                 870                 875 tgg tct tat ggc att ctg ctc tgg gag atc ttt tcc ctt ggt ggc acc    2810
Trp Ser Tyr Gly Ile Leu Leu Trp Glu Ile Phe Ser Leu Gly Gly Thr
        880                 885                 890 cct tac ccc ggc atg atg gtg gat tct act ttc tac aat aag atc aag    2858
Pro Tyr Pro Gly Met Met Val Asp Ser Thr Phe Tyr Asn Lys Ile Lys
895                 900                 905                 910 agt ggg tac cgg atg gcc aag cct gac cac gct acc agt gaa gtc tac    2906
Ser Gly Tyr Arg Met Ala Lys Pro Asp His Ala Thr Ser Glu Val Tyr
                915                 920                 925 gag atc atg gtg aaa tgc tgg aac agt gag ccg gag aag aga ccc tcc    2954
Glu Ile Met Val Lys Cys Trp Asn Ser Glu Pro Glu Lys Arg Pro Ser
            930                 935                 940 ttt tac cac ctg agt gag att gtg gag aat ctg ctg cct gga caa tat    3002
Phe Tyr His Leu Ser Glu Ile Val Glu Asn Leu Leu Pro Gly Gln Tyr
        945                 950                 955 aaa aag agt tat gaa aaa att cac ctg gac ttc ctg aag agt gac cat    3050
Lys Lys Ser Tyr Glu Lys Ile His Leu Asp Phe Leu Lys Ser Asp His
        960                 965                 970 cct gct gtg gca cgc atg cgt gtg gac tca gac aat gca tac att ggt    3098
Pro Ala Val Ala Arg Met Arg Val Asp Ser Asp Asn Ala Tyr Ile Gly
975                 980                 985                 990 gtc acc tac aaa aac gag gaa gac aag ctg  aag gac tgg gag ggt  ggt  3146
Val Thr Tyr Lys Asn Glu Glu Asp Lys Leu  Lys Asp Trp Glu Gly  Gly
                995                 1000                1005 ctg gat gag cag  aga ctg agc gct gac  agt ggc tac atc att  cct       3191
Leu Asp Glu Gln  Arg Leu Ser Ala Asp  Ser Gly Tyr Ile Ile  Pro
                1010                1015                1020 ctg cct gac att  gac cct gtc cct gag  gag gag gac ctg ggc  aag       3236
Leu Pro Asp Ile  Asp Pro Val Pro Glu  Glu Glu Asp Leu Gly  Lys
                1025                1030                1035 agg aac aga cac  agc tcg cag acc tct  gaa gag agt gcc att  gag       3281
Arg Asn Arg His  Ser Ser Gln Thr Ser  Glu Glu Ser Ala Ile  Glu
                1040                1045                1050 acg ggt tcc agc  agt tcc acc ttc atc  aag aga gag gac gag  acc       3326
Thr Gly Ser Ser  Ser Ser Thr Phe Ile  Lys Arg Glu Asp Glu  Thr
                1055                1060                1065
```

|  |  |  |  |  |  |  |  |  |  |  |  |  |
|---|---|---|---|---|---|---|---|---|---|---|---|---|
| att | gaa | gac | atc | gac | atg | atg | gac | gac | atc | ggc | ata | gac | tct | tca | 3371 |
| Ile | Glu | Asp | Ile | Asp | Met | Met | Asp | Asp | Ile | Gly | Ile | Asp | Ser | Ser |  |
|  |  | 1070 |  |  |  |  |  | 1075 |  |  |  | 1080 |  |  |  | gac ctg gtg gaa gac agc ttc ctg taa ctggcggatt cgaggggttc　　　3418
Asp Leu Val Glu Asp Ser Phe Leu
　　　　　1085 cttccacttc tggggccacc tctggatccc gttcagaaaa ccactttatt gcaatgcgga　　3478
ggttgagagg aggacttggt tgatgtttaa agagaagttc ccagccaagg gcctcgggga　　3538
gcctttctaa atatgaatga atgggatatt ttgaaatgaa ctttgtcagt gttgcctctt　　3598
gcaatgcctc agtagcatct cagtggtgtg tgaagtttgg agatagatgg ataagggaat　　3658
aataggccac agaaggtgaa ctttctgctt caaggacatt ggtgagagtc aacagacac　　3718
aatttatact gcgacagaac ttcagcattg taattatgta ataactcta accacggctg　　3778
tgtttagatt gtattaacta tcttctttgg acttctgaag agaccactca atccatccat　　3838
gtacttccct cttgaaacct gatgtcagct gctgttgaac tttttaaaga agtgcatgaa　　3898
aaaccatttt tgaccttaaa aggtactggt actatagcat tttgctatct tttttagtgt　　3958
taaagagata aagaataata attaaccaac cttgtttaat agatttgggt catttagaag　　4018
cctgacaact catttcata ttgtaatcta tgtttataat actactactg ttatcagtaa　　4078
tgctaaatgt gtaataatgt aacatgattt ccctccacac aaagcacaat ttaaaaacaa　　4138
tccttactaa gtaggtgatg agtttgacag ttttgacat ttatattaaa taacatgttt　　4198
ctctataaag tatggtaata gcttagtga attaaattta gttgagcata gagaacaaag　　4258
taaaagtagt gttgtccagg aagtcagaat ttttaactgt actgaatagg ttccccaatc　　4318
catcgtatta aaaacaatt aactgccctc tgaaataatg ggattagaaa caaacaaaac　　4378
tcttaagtcc taaagttct caatgtagag gcataaacct gtgctgaaca taacttctca　　4438
tgtatattac ccaatggaaa atataatgat cagcgcanaa agactggatt tgcagaagtt　　4498
nttttttttt tttcttcttg cctgatgaaa gctttggcga ccccaatata tgtatttttt　　4558
gaatctatga acctgaaaag ggtcacaaag gatgcccaga catcagcctc cttcttcac　　4618
cccttaccc aaagagaaag agtttgaaac tcgagaccat aaagatattc tttagtggag　　4678
gctggaagtg cattagcctg atcctcagtt ctcaaatgtg tgtggcagcc aggtagacta　　4738
gtacctgggt ttccatcctt gagattctga agtatgaagt ctgagggaaa ccagagtctg　　4798
tatttttcta aactccctgg ctgttctgat cggccaggtt tcggaaacac tgacttaggt　　4858
ttcaggaagt tgccatggga aacaaataat ttgaactttg gaacagggtt cttaagttgg　　4918
tgcgtccttc ggatgataaa tttaggaacc gaagtccaat cactgtaaat tacggtagat　　4978
cgatcgttaa cgctggaatt aaattgaaag gtcagaatcg actccgactc tttcgatttc　　5038
aaaccaaaac tgtccaaaag gttttcattt ctacgatgaa gggtgacata cccctctaa　　5098
cttgaaaggg gcagagggca gaagagcgga gggtgaggta tggggcggtt cctttccgta　　5158
catgttttta atacgttaag tcacaaggtt cagagacaca ttggtcgagt cacaaaacca　　5218
cctttttgt aaaattcaaa atgactatta aactccaatc taccctccta cttaacagtg　　5278
tagataggtg tgacagtttg tccaaccaca cccaagtaac cgtaagaaac gttatgacga　　5338
attaacgact atggtatact tactttgtac ccgacactaa tgcgttagt gacacgatag　　5398
ccgtctacta cgaaaccttc tacgtcttcg ttattatttc atgaactgat ggatgaccac　　5458
attagagtta cgttcgggt tgaaagaata ggttgaaaaa gtatcattca cgcttctgac　　5518
tcggtctaac cggttaattt ttcttttgga ctgatccaag acatctcggt taatctgaac　　5578

-continued

```
tttatgcaaa cacaaagatc ttagtgtcga gttcgtaaga caaatagcga gtgagaggga    5638
acatgtcgga ataaaacaac cacgaaacgt aaaactataa cgacactcgg aacgtactgt    5698
agtactccgg cctactttga agagtcaggt cgtcaaaggt caggattgtt tacgagggtg    5758
gacttaaaca tatactgacg taaacaccca cacacacaca aaagtcgttt aaggtctaaa    5818
caaaggaaaa ccggaggacg tttcagaggt cttcttttaa acggttagaa aggatgaaag    5878
ataaaaatac tactgttagt ttcggccgga ctctttgtga taaacactga aaaatttgct    5938
aatcactaca ggaattttac accagacggt tagacatgtt ttaccaggat aaaaacactt    5998
ctccctgtat tctattttac tacaatatgt agttatacat atatacataa agatatatct    6058
gaacctctta tgacggtttt gtaaatactg ttcgacatag tgacggaagc aaatataaaa    6118
aaattgacac tattaggggt gtccgtgtaa ttgacaacgt gaaaacttac aggttttaaa    6178
tataaaatct ttattatttt tctttctatg aatgtacaag ggttttgtta ccacaccact    6238
tacacactct ttttgattga actatcccag atggttatgt tttacataat gcttacgggg    6298
acaagtacaa aaacaaaatt ttgcacattt acttctagaa atataaagtt atttactata    6358
tattaaattt ccttaag                                                   6375
```

<210> SEQ ID NO 117
<211> LENGTH: 1089
<212> TYPE: PRT
<213> ORGANISM: Homo sapiens

<400> SEQUENCE: 117

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220
```

-continued

```
Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
            245                 250                 255

Gly Ile Thr Met Leu Glu Glu Ile Lys Val Pro Ser Ile Lys Leu Val
        260                 265                 270

Tyr Thr Leu Thr Val Pro Glu Ala Thr Val Lys Asp Ser Gly Asp Tyr
    275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
            325                 330                 335

Val Glu Val Arg Ala Tyr Pro Pro Arg Ile Ser Trp Leu Lys Asn
        340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
            405                 410                 415

Ile Leu Asp Leu Val Asp Asp His His Gly Ser Thr Gly Gly Gln Thr
        420                 425                 430

Val Arg Cys Thr Ala Glu Gly Thr Pro Leu Pro Asp Ile Glu Trp Met
    435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
            485                 490                 495

Ile Ala Val Arg Cys Leu Ala Lys Asn Leu Leu Gly Ala Glu Asn Arg
        500                 505                 510

Glu Leu Lys Leu Val Ala Pro Thr Leu Arg Ser Glu Leu Thr Val Ala
    515                 520                 525

Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
            565                 570                 575

Pro Met Gln Leu Pro Tyr Asp Ser Arg Trp Glu Phe Pro Arg Asp Gly
        580                 585                 590

Leu Val Leu Gly Arg Val Leu Gly Ser Gly Ala Phe Gly Lys Val Val
    595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
```

-continued

```
                645                 650                 655
Ile Val Asn Leu Leu Gly Ala Cys Thr Lys Ser Gly Pro Ile Tyr Ile
            660                 665                 670
Ile Thr Glu Tyr Cys Phe Tyr Gly Asp Leu Val Asn Tyr Leu His Lys
            675                 680                 685
Asn Arg Asp Ser Phe Leu Ser His His Pro Glu Lys Pro Lys Lys Glu
            690                 695                 700
Leu Asp Ile Phe Gly Leu Asn Pro Ala Asp Glu Ser Thr Arg Ser Tyr
705                 710                 715                 720
Val Ile Leu Ser Phe Glu Asn Asn Gly Asp Tyr Met Asp Met Lys Gln
                725                 730                 735
Ala Asp Thr Thr Gln Tyr Val Pro Met Leu Glu Arg Lys Glu Val Ser
            740                 745                 750
Lys Tyr Ser Asp Ile Gln Arg Ser Leu Tyr Asp Arg Pro Ala Ser Tyr
                755                 760                 765
Lys Lys Lys Ser Met Leu Asp Ser Glu Val Lys Asn Leu Leu Ser Asp
770                 775                 780
Asp Asn Ser Glu Gly Leu Thr Leu Leu Asp Leu Leu Ser Phe Thr Tyr
785                 790                 795                 800
Gln Val Ala Arg Gly Met Glu Phe Leu Ala Ser Lys Asn Cys Val His
                805                 810                 815
Arg Asp Leu Ala Ala Arg Asn Val Leu Leu Ala Gln Gly Lys Ile Val
            820                 825                 830
Lys Ile Cys Asp Phe Gly Leu Ala Arg Asp Ile Met His Asp Ser Asn
            835                 840                 845
Tyr Val Ser Lys Gly Ser Thr Phe Leu Pro Val Lys Trp Met Ala Pro
850                 855                 860
Glu Ser Ile Phe Asp Asn Leu Tyr Thr Thr Leu Ser Asp Val Trp Ser
865                 870                 875                 880
Tyr Gly Ile Leu Leu Trp Glu Ile Phe Ser Leu Gly Gly Thr Pro Tyr
                885                 890                 895
Pro Gly Met Met Val Asp Ser Thr Phe Tyr Asn Lys Ile Lys Ser Gly
                900                 905                 910
Tyr Arg Met Ala Lys Pro Asp His Ala Thr Ser Glu Val Tyr Glu Ile
            915                 920                 925
Met Val Lys Cys Trp Asn Ser Glu Pro Glu Lys Arg Pro Ser Phe Tyr
930                 935                 940
His Leu Ser Glu Ile Val Glu Asn Leu Leu Pro Gly Gln Tyr Lys Lys
945                 950                 955                 960
Ser Tyr Glu Lys Ile His Leu Asp Phe Leu Lys Ser Asp His Pro Ala
                965                 970                 975
Val Ala Arg Met Arg Val Asp Ser Asp Asn Ala Tyr Ile Gly Val Thr
            980                 985                 990
Tyr Lys Asn Glu Glu Asp Lys Leu Lys Asp Trp Glu Gly Gly Leu Asp
                995                 1000                1005
Glu Gln Arg Leu Ser Ala Asp Ser Gly Tyr Ile Ile Pro Leu Pro
            1010                1015                1020
Asp Ile Asp Pro Val Pro Glu Glu Asp Leu Gly Lys Arg Asn
            1025                1030                1035
Arg His Ser Ser Gln Thr Ser Glu Glu Ser Ala Ile Glu Thr Gly
            1040                1045                1050
Ser Ser Ser Ser Thr Phe Ile Lys Arg Glu Asp Glu Thr Ile Glu
            1055                1060                1065
```

```
Asp Ile  Asp Met Met Asp Asp  Ile Gly Ile Asp Ser  Ser Asp Leu
    1070             1075             1080

Val Glu  Asp Ser Phe Leu
    1085

<210> SEQ ID NO 118
<211> LENGTH: 5427
<212> TYPE: DNA
<213> ORGANISM: Homo sapiens
<220> FEATURE:
<221> NAME/KEY: CDS
<222> LOCATION: (187)..(3507)

<400> SEQUENCE: 118
tgttctcctg agccttcagg agcctgcacc agtcctgcct gtccttctac tcagctgtta      60
cccactctgg gaccagcagt ctttctgata actgggagag ggcagtaagg aggacttcct     120 ggaggggtg actgtccaga gcctggaact gtgcccacac cagaagccat cagcagcaag      180 gacacc atg cgg ctt ccg ggt gcg atg cca gct ctg gcc ctc aaa ggc        228
       Met Arg Leu Pro Gly Ala Met Pro Ala Leu Ala Leu Lys Gly
       1               5                   10 gag ctg ctg ttg ctg tct ctc ctg tta ctt ctg gaa cca cag atc tct       276
Glu Leu Leu Leu Leu Ser Leu Leu Leu Leu Leu Glu Pro Gln Ile Ser
15                  20                  25                  30 cag ggc ctg gtc gtc aca ccc ccg ggg cca gag ctt gtc ctc aat gtc       324
Gln Gly Leu Val Val Thr Pro Pro Gly Pro Glu Leu Val Leu Asn Val
                35                  40                  45 tcc agc acc ttc gtt ctg acc tgc tcg ggt tca gct ccg gtg gtg tgg       372
Ser Ser Thr Phe Val Leu Thr Cys Ser Gly Ser Ala Pro Val Val Trp
            50                  55                  60 gaa cgg atg tcc cag gag ccc cca cag gaa atg gcc aag gcc cag gat       420
Glu Arg Met Ser Gln Glu Pro Pro Gln Glu Met Ala Lys Ala Gln Asp
65                  70                  75 ggc acc ttc tcc agc gtg ctc aca ctg acc aac ctc act ggg cta gac       468
Gly Thr Phe Ser Ser Val Leu Thr Leu Thr Asn Leu Thr Gly Leu Asp
        80                  85                  90 acg gga gaa tac ttt tgc acc cac aat gac tcc cgt gga ctg gag acc       516
Thr Gly Glu Tyr Phe Cys Thr His Asn Asp Ser Arg Gly Leu Glu Thr
95                  100                 105                 110 gat gag cgg aaa cgg ctc tac atc ttt gtg cca gat ccc acc gtg ggc       564
Asp Glu Arg Lys Arg Leu Tyr Ile Phe Val Pro Asp Pro Thr Val Gly
                115                 120                 125 ttc ctc cct aat gat gcc gag gaa cta ttc atc ttt ctc acg gaa ata       612
Phe Leu Pro Asn Asp Ala Glu Glu Leu Phe Ile Phe Leu Thr Glu Ile
            130                 135                 140 act gag atc acc att cca tgc cga gta aca gac cca cag ctg gtg gtg       660
Thr Glu Ile Thr Ile Pro Cys Arg Val Thr Asp Pro Gln Leu Val Val
        145                 150                 155 aca ctg cac gag aag aaa ggg gac gtt gca ctg cct gtc ccc tat gat       708
Thr Leu His Glu Lys Lys Gly Asp Val Ala Leu Pro Val Pro Tyr Asp
    160                 165                 170 cac caa cgt ggc ttt tct ggt atc ttt gag gac aga agc tac atc tgc       756
His Gln Arg Gly Phe Ser Gly Ile Phe Glu Asp Arg Ser Tyr Ile Cys
175                 180                 185                 190 aaa acc acc att ggg gac agg gag gtg gat tct gat gcc tac tat gtc       804
Lys Thr Thr Ile Gly Asp Arg Glu Val Asp Ser Asp Ala Tyr Tyr Val
                195                 200                 205 tac aga ctc cag gtg tca tcc atc aac gtc tct gtg aac gca gtg cag       852
Tyr Arg Leu Gln Val Ser Ser Ile Asn Val Ser Val Asn Ala Val Gln
            210                 215                 220
```

-continued

| | | |
|---|---|---|
| act gtg gtc cgc cag ggt gag aac atc acc ctc atg tgc att gtg atc<br>Thr Val Val Arg Gln Gly Glu Asn Ile Thr Leu Met Cys Ile Val Ile<br>225 230 235 | | 900 |
| ggg aat gat gtg gtc aac ttc gag tgg aca tac ccc cgc aaa gaa agt<br>Gly Asn Asp Val Val Asn Phe Glu Trp Thr Tyr Pro Arg Lys Glu Ser<br>240 245 250 | | 948 |
| ggg cgg ctg gtg gag ccg gtg act gac ttc ctc ttg gat atg cct tac<br>Gly Arg Leu Val Glu Pro Val Thr Asp Phe Leu Leu Asp Met Pro Tyr<br>255 260 265 270 | | 996 |
| cac atc cgc tcc atc ctg cac atc ccc agt gcc gag tta gaa gac tcg<br>His Ile Arg Ser Ile Leu His Ile Pro Ser Ala Glu Leu Glu Asp Ser<br>275 280 285 | | 1044 |
| ggg acc tac acc tgc aat gtg acg gag agt gtg aat gac cat cag gat<br>Gly Thr Tyr Thr Cys Asn Val Thr Glu Ser Val Asn Asp His Gln Asp<br>290 295 300 | | 1092 |
| gaa aag gcc atc aac atc acc gtg gtt gag agc ggc tac gtg cgg ctc<br>Glu Lys Ala Ile Asn Ile Thr Val Val Glu Ser Gly Tyr Val Arg Leu<br>305 310 315 | | 1140 |
| ctg gga gag gtg ggc aca cta caa ttt gct gag ctg cat cgg agc cgg<br>Leu Gly Glu Val Gly Thr Leu Gln Phe Ala Glu Leu His Arg Ser Arg<br>320 325 330 | | 1188 |
| aca ctg cag gta gtg ttc gag gcc tac cca ccg ccc act gtc ctg tgg<br>Thr Leu Gln Val Val Phe Glu Ala Tyr Pro Pro Pro Thr Val Leu Trp<br>335 340 345 350 | | 1236 |
| ttc aaa gac aac cgc acc ctg ggc gac tcc agc gct ggc gaa atc gcc<br>Phe Lys Asp Asn Arg Thr Leu Gly Asp Ser Ser Ala Gly Glu Ile Ala<br>355 360 365 | | 1284 |
| ctg tcc acg cgc aac gtg tcg gag acc cgg tat gtg tca gag ctg aca<br>Leu Ser Thr Arg Asn Val Ser Glu Thr Arg Tyr Val Ser Glu Leu Thr<br>370 375 380 | | 1332 |
| ctg gtt cgc gtg aag gtg gca gag gct ggc cac tac acc atg cgg gcc<br>Leu Val Arg Val Lys Val Ala Glu Ala Gly His Tyr Thr Met Arg Ala<br>385 390 395 | | 1380 |
| ttc cat gag gat gct gag gtc cag ctc tcc ttc cag cta cag atc aat<br>Phe His Glu Asp Ala Glu Val Gln Leu Ser Phe Gln Leu Gln Ile Asn<br>400 405 410 | | 1428 |
| gtc cct gtc cga gtg ctg gag cta agt gag agc cac cct gac agt ggg<br>Val Pro Val Arg Val Leu Glu Leu Ser Glu Ser His Pro Asp Ser Gly<br>415 420 425 430 | | 1476 |
| gaa cag aca gtc cgc tgt cgt ggc cgg ggc atg ccg cag ccg aac atc<br>Glu Gln Thr Val Arg Cys Arg Gly Arg Gly Met Pro Gln Pro Asn Ile<br>435 440 445 | | 1524 |
| atc tgg tct gcc tgc aga gac ctc aaa agg tgt cca cgt gag ctg ccg<br>Ile Trp Ser Ala Cys Arg Asp Leu Lys Arg Cys Pro Arg Glu Leu Pro<br>450 455 460 | | 1572 |
| ccc acg ctg ctg ggg aac agt tcc gaa gag gag agc cag ctg gag act<br>Pro Thr Leu Leu Gly Asn Ser Ser Glu Glu Glu Ser Gln Leu Glu Thr<br>465 470 475 | | 1620 |
| aac gtg acg tac tgg gag gag gag cag gag ttt gag gtg gtg agc aca<br>Asn Val Thr Tyr Trp Glu Glu Glu Gln Glu Phe Glu Val Val Ser Thr<br>480 485 490 | | 1668 |
| ctg cgt ctg cag cac gtg gat cgg cca ctg tcg gtg cgc tgc acg ctg<br>Leu Arg Leu Gln His Val Asp Arg Pro Leu Ser Val Arg Cys Thr Leu<br>495 500 505 510 | | 1716 |
| cgc aac gct gtg ggc cag gac acg cag gag gtc atc gtg gtg cca cac<br>Arg Asn Ala Val Gly Gln Asp Thr Gln Glu Val Ile Val Val Pro His<br>515 520 525 | | 1764 |
| tcc ttg ccc ttt aag gtg gtg gtg atc tca gcc atc ctg gcc ctg gtg<br>Ser Leu Pro Phe Lys Val Val Val Ile Ser Ala Ile Leu Ala Leu Val | | 1812 |

-continued

```
                530                     535                     540
gtg ctc acc atc atc tcc ctt atc atc ctc atc atg ctt tgg cag aag          1860
Val Leu Thr Ile Ile Ser Leu Ile Ile Leu Ile Met Leu Trp Gln Lys
            545                     550                     555 aag cca cgt tac gag atc cga tgg aag gtg att gag tct gtg agc tct          1908
Lys Pro Arg Tyr Glu Ile Arg Trp Lys Val Ile Glu Ser Val Ser Ser
560                     565                     570 gac ggc cat gag tac atc tac gtg gac ccc atg cag ctg ccc tat gac          1956
Asp Gly His Glu Tyr Ile Tyr Val Asp Pro Met Gln Leu Pro Tyr Asp
575                     580                     585                 590 tcc acg tgg gag ctg ccg cgg gac cag ctt gtg ctg gga cgc acc ctc          2004
Ser Thr Trp Glu Leu Pro Arg Asp Gln Leu Val Leu Gly Arg Thr Leu
                595                     600                     605 ggc tct ggg gcc ttt ggg cag gtg gtg gag gcc aca gct cat ggt ctg          2052
Gly Ser Gly Ala Phe Gly Gln Val Val Glu Ala Thr Ala His Gly Leu
            610                     615                     620 agc cat tct cag gcc acg atg aaa gtg gcc gtc aag atg ctt aaa tcc          2100
Ser His Ser Gln Ala Thr Met Lys Val Ala Val Lys Met Leu Lys Ser
            625                     630                     635 aca gcc cgc agc agt gag aag caa gcc ctt atg tcg gag ctg aag atc          2148
Thr Ala Arg Ser Ser Glu Lys Gln Ala Leu Met Ser Glu Leu Lys Ile
        640                     645                     650 atg agt cac ctt ggg ccc cac ctg aac gtg gtc aac ctg ttg ggg gcc          2196
Met Ser His Leu Gly Pro His Leu Asn Val Val Asn Leu Leu Gly Ala
655                     660                     665                 670 tgc acc aaa gga gga ccc atc tat atc atc act gag tac tgc cgc tac          2244
Cys Thr Lys Gly Gly Pro Ile Tyr Ile Ile Thr Glu Tyr Cys Arg Tyr
                675                     680                     685 gga gac ctg gtg gac tac ctg cac cgc aac aaa cac acc ttc ctg cag          2292
Gly Asp Leu Val Asp Tyr Leu His Arg Asn Lys His Thr Phe Leu Gln
            690                     695                     700 cac cac tcc gac aag cgc cgc ccg ccc agc gcg gag ctc tac agc aat          2340
His His Ser Asp Lys Arg Arg Pro Ser Ala Glu Leu Tyr Ser Asn
            705                     710                     715 gct ctg ccc gtt ggg ctc ccc ctg ccc agc cat gtg tcc ttg acc ggg          2388
Ala Leu Pro Val Gly Leu Pro Leu Pro Ser His Val Ser Leu Thr Gly
        720                     725                     730 gag agc gac ggt ggc tac atg gac atg agc aag gac gag tcg gtg gac          2436
Glu Ser Asp Gly Gly Tyr Met Asp Met Ser Lys Asp Glu Ser Val Asp
735                     740                     745                 750 tat gtg ccc atg ctg gac atg aaa gga gac gtc aaa tat gca gac atc          2484
Tyr Val Pro Met Leu Asp Met Lys Gly Asp Val Lys Tyr Ala Asp Ile
                755                     760                     765 gag tcc tcc aac tac atg gcc cct tac gat aac tac gtt ccc tct gcc          2532
Glu Ser Ser Asn Tyr Met Ala Pro Tyr Asp Asn Tyr Val Pro Ser Ala
            770                     775                     780 cct gag agg acc tgc cga gca act ttg atc aac gag tct cca gtg cta          2580
Pro Glu Arg Thr Cys Arg Ala Thr Leu Ile Asn Glu Ser Pro Val Leu
        785                     790                     795 agc tac atg gac ctc gtg ggc ttc agc tac cag gtg gcc aat ggc atg          2628
Ser Tyr Met Asp Leu Val Gly Phe Ser Tyr Gln Val Ala Asn Gly Met
800                     805                     810 gag ttt ctg gcc tcc aag aac tgc gtc cac aga gac ctg gcg gct agg          2676
Glu Phe Leu Ala Ser Lys Asn Cys Val His Arg Asp Leu Ala Ala Arg
815                     820                     825                 830 aac gtg ctc atc tgt gaa ggc aag ctg gtc aag atc tgt gac ttt ggc          2724
Asn Val Leu Ile Cys Glu Gly Lys Leu Val Lys Ile Cys Asp Phe Gly
                835                     840                     845 ctg gct cga gac atc atg cgg gac tcg aat tac atc tcc aaa ggc agc          2772
Leu Ala Arg Asp Ile Met Arg Asp Ser Asn Tyr Ile Ser Lys Gly Ser
```

```
                Leu Ala Arg Asp Ile Met Arg Asp Ser Asn Tyr Ile Ser Lys Gly Ser
                                850                 855                 860 acc ttt ttg cct tta aag tgg atg gct ccg gag agc atc ttc aac agc              2820
Thr Phe Leu Pro Leu Lys Trp Met Ala Pro Glu Ser Ile Phe Asn Ser
            865                 870                 875 ctc tac acc acc ctg agc gac gtg tgg tcc ttc ggg atc ctg ctc tgg              2868
Leu Tyr Thr Thr Leu Ser Asp Val Trp Ser Phe Gly Ile Leu Leu Trp
    880                 885                 890 gag atc ttc acc ttg ggt ggc acc cct tac cca gag ctg ccc atg aac              2916
Glu Ile Phe Thr Leu Gly Gly Thr Pro Tyr Pro Glu Leu Pro Met Asn
895                 900                 905                 910 gag cag ttc tac aat gcc atc aaa cgg ggt tac cgc atg gcc cag cct              2964
Glu Gln Phe Tyr Asn Ala Ile Lys Arg Gly Tyr Arg Met Ala Gln Pro
                915                 920                 925 gcc cat gcc tcc gac gag atc tat gag atc atg cag aag tgc tgg gaa              3012
Ala His Ala Ser Asp Glu Ile Tyr Glu Ile Met Gln Lys Cys Trp Glu
            930                 935                 940 gag aag ttt gag att cgg ccc ccc ttc tcc cag ctg gtg ctg ctt ctc              3060
Glu Lys Phe Glu Ile Arg Pro Pro Phe Ser Gln Leu Val Leu Leu Leu
    945                 950                 955 gag aga ctg ttg ggc gaa ggt tac aaa aag aag tac cag cag gtg gat              3108
Glu Arg Leu Leu Gly Glu Gly Tyr Lys Lys Lys Tyr Gln Gln Val Asp
960                 965                 970 gag gag ttt ctg agg agt gac cac cca gcc atc ctt cgg tcc cag gcc              3156
Glu Glu Phe Leu Arg Ser Asp His Pro Ala Ile Leu Arg Ser Gln Ala
975                 980                 985                 990 cgc ttg cct ggg ttc cat ggc ctc cga tct ccc ctg gac acc agc tcc              3204
Arg Leu Pro Gly Phe His Gly Leu Arg Ser Pro Leu Asp Thr Ser Ser
                995                 1000                1005 gtc ctc tat act gcc gtg cag ccc aat gag ggt gac aac gac tat                  3249
Val Leu Tyr Thr Ala Val Gln Pro Asn Glu Gly Asp Asn Asp Tyr
            1010                1015                1020 atc atc ccc ctg cct gac ccc aaa cct gag gtt gct gac gag ggc                  3294
Ile Ile Pro Leu Pro Asp Pro Lys Pro Glu Val Ala Asp Glu Gly
    1025                1030                1035 cca ctg gag ggt tcc ccc agc cta gcc agc tcc acc ctg aat gaa                  3339
Pro Leu Glu Gly Ser Pro Ser Leu Ala Ser Ser Thr Leu Asn Glu
1040                1045                1050 gtc aac acc tcc tca acc atc tcc tgt gac agc ccc ctg gag ccc                  3384
Val Asn Thr Ser Ser Thr Ile Ser Cys Asp Ser Pro Leu Glu Pro
            1055                1060                1065 cag gac gaa cca gag cca gag ccc cag ctt gag ctc cag gtg gag                  3429
Gln Asp Glu Pro Glu Pro Glu Pro Gln Leu Glu Leu Gln Val Glu
    1070                1075                1080 ccg gag ccg gag ctg gaa cag ttg ccg gat tcg ggg tgc cct gcg                  3474
Pro Glu Pro Glu Leu Glu Gln Leu Pro Asp Ser Gly Cys Pro Ala
1085                1090                1095 cct cgg gcg gaa gca gag gat agc ttc ctg tag ggggctggcc                       3517
Pro Arg Ala Glu Ala Glu Asp Ser Phe Leu
            1100                1105 cctaccctgc cctgcctgaa gctccccgc tgccagcacc cagcatctcc tggcctggcc             3577
tggccgggct tcctgtcagc caggctgccc ttatcagctg tccccttctg gaagctttct            3637
gctcctgacg tgttgtgccc caaaccctgg ggctggctta ggaggcaaga aaactgcagg            3697
ggccgtgacc agccctctgc ctccagggag gccaactgac tctgagccag ggttccccca            3757
gggaactcag ttttcccata tgtaagatgg gaaagttagg cttgatgacc cagaatctag            3817
gattctctcc ctggctgaca ggtggggaga ccgaatccct ccctgggaag attcttggag            3877
```

```
ttactgaggt ggtaaattaa ctttttttctg ttcagccagc tacccctcaa ggaatcatag    3937
ctctctcctc gcacttttat ccacccagga gctagggaag agaccctagc ctccctggct    3997
gctggctgag ctagggccta gccttgagca gtgttgcctc atccagaaga aagccagtct    4057
cctccctatg atgccagtcc ctgcgttccc tggcccgagc tggtctgggg ccattaggca    4117
gcctaattaa tgctggaggc tgagccaagt acaggacacc cccagcctgc agcccttgcc    4177
cagggcactt ggagcacacg cagccatagc aagtgcctgt gtccctgtcc ttcaggccca    4237
tcagtcctgg ggcttttttct ttatcaccct cagtcttaat ccatccacca gagtctagaa    4297
ggccagacgg gccccgcatc tgtgatgaga atgtaaatgt gccagtgtgg agtggccacg    4357
tgtgtgtgcc agatatggcc ctggctctgc attggacctg ctatgaggct ttggaggaat    4417
ccctcaccct ctctgggcct cagtttcccc ttcaaaaaat gaataagtcg gacttattaa    4477
ctctgagtgc cttgccagca ctaacattct agagtatcca ggtggttgca catttgtcca    4537
gatgaagcaa ggccatatac cctaaacttc catcctgggg gtcagctggg ctcctgggag    4597
attccagatc acacatcaca ctctggggac tcaggaacca tgccccttcc ccaggccccc    4657
agcaagtctc aagaacacag ctgcacaggc cttgacttag agtgacagcc ggtgtcctgg    4717
aaagccccca gcagctgccc cagggacatg ggaagaccac gggacctctt tcactaccca    4777
cgatgacctc cggggtatc ctgggcaaaa gggacaaaga gggcaaatga gatcacctcc    4837
tgcagcccac cactccagca cctgtgccga ggtctgcgtc gaagacagaa tggacagtga    4897
ggacagttat gtcttgtaaa agacaagaag cttcagatgg gtaccccaag aaggatgtga    4957
gaggtgggcg cttttggaggt ttgcccctca cccaccagct gccccatccc tgaggcagcg    5017
ctccatgggg gtatggtttt gtcactgccc agacctagca gtgacatctc attgtcccca    5077
gcccagtggg cattggaggt gccaggggag tcagggttgt agccaagacg cccccgcacg    5137
gggagggttg ggaaggggggt gcaggaagct caacccctct gggcaccaac cctgcattgc    5197
aggttggcac cttacttccc tgggatccca gagttggtcc aaggagggag agtgggttct    5257
caatacggta ccaaagatat aatcacctag gtttacaaat attttttagga ctcacgttaa    5317
ctcacattta tacagcagaa atgctattttt gtatgctgtt aagttttttct atctgtgtac    5377
tttttttttaa gggaaagatt ttaatattaa acctggtgct tctcactcac                5427
```

<210> SEQ ID NO 119  
<211> LENGTH: 1106  
<212> TYPE: PRT  
<213> ORGANISM: Homo sapiens

<400> SEQUENCE: 119

```
Met Arg Leu Pro Gly Ala Met Pro Ala Leu Ala Leu Lys Gly Glu Leu
 1               5                  10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
```

-continued

```
            100                 105                 110
Arg Lys Arg Leu Tyr Ile Phe Val Pro Asp Pro Thr Val Gly Phe Leu
            115                 120                 125
Pro Asn Asp Ala Glu Glu Leu Phe Ile Phe Leu Thr Glu Ile Thr Glu
130                 135                 140
Ile Thr Ile Pro Cys Arg Val Thr Asp Pro Gln Leu Val Val Thr Leu
145                 150                 155                 160
His Glu Lys Lys Gly Asp Val Ala Leu Pro Val Pro Tyr Asp His Gln
                165                 170                 175
Arg Gly Phe Ser Gly Ile Phe Glu Asp Arg Ser Tyr Ile Cys Lys Thr
            180                 185                 190
Thr Ile Gly Asp Arg Glu Val Asp Ser Asp Ala Tyr Tyr Val Tyr Arg
        195                 200                 205
Leu Gln Val Ser Ser Ile Asn Val Ser Val Asn Ala Val Gln Thr Val
    210                 215                 220
Val Arg Gln Gly Glu Asn Ile Thr Leu Met Cys Ile Val Ile Gly Asn
225                 230                 235                 240
Asp Val Val Asn Phe Glu Trp Thr Tyr Pro Arg Lys Glu Ser Gly Arg
                245                 250                 255
Leu Val Glu Pro Val Thr Asp Phe Leu Leu Asp Met Pro Tyr His Ile
            260                 265                 270
Arg Ser Ile Leu His Ile Pro Ser Ala Glu Leu Glu Asp Ser Gly Thr
        275                 280                 285
Tyr Thr Cys Asn Val Thr Glu Ser Val Asn Asp His Gln Asp Glu Lys
    290                 295                 300
Ala Ile Asn Ile Thr Val Val Glu Ser Gly Tyr Val Arg Leu Leu Gly
305                 310                 315                 320
Glu Val Gly Thr Leu Gln Phe Ala Glu Leu His Arg Ser Arg Thr Leu
                325                 330                 335
Gln Val Val Phe Glu Ala Tyr Pro Pro Thr Val Leu Trp Phe Lys
            340                 345                 350
Asp Asn Arg Thr Leu Gly Asp Ser Ser Ala Gly Glu Ile Ala Leu Ser
        355                 360                 365
Thr Arg Asn Val Ser Glu Thr Arg Tyr Val Ser Glu Leu Thr Leu Val
    370                 375                 380
Arg Val Lys Val Ala Glu Ala Gly His Tyr Thr Met Arg Ala Phe His
385                 390                 395                 400
Glu Asp Ala Glu Val Gln Leu Ser Phe Gln Leu Gln Ile Asn Val Pro
                405                 410                 415
Val Arg Val Leu Glu Leu Ser Glu Ser His Pro Asp Ser Gly Glu Gln
            420                 425                 430
Thr Val Arg Cys Arg Gly Arg Gly Met Pro Gln Pro Asn Ile Ile Trp
        435                 440                 445
Ser Ala Cys Arg Asp Leu Lys Arg Cys Pro Arg Glu Leu Pro Pro Thr
    450                 455                 460
Leu Leu Gly Asn Ser Ser Glu Glu Glu Ser Gln Leu Glu Thr Asn Val
465                 470                 475                 480
Thr Tyr Trp Glu Glu Glu Gln Glu Phe Glu Val Val Ser Thr Leu Arg
                485                 490                 495
Leu Gln His Val Asp Arg Pro Leu Ser Val Arg Cys Thr Leu Arg Asn
            500                 505                 510
Ala Val Gly Gln Asp Thr Gln Glu Val Ile Val Val Pro His Ser Leu
        515                 520                 525
```

```
Pro Phe Lys Val Val Ile Ser Ala Ile Leu Ala Leu Val Val Leu
    530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
                565                 570                 575

His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
        595                 600                 605

Gly Ala Phe Gly Gln Val Val Glu Ala Thr Ala His Gly Leu Ser His
    610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
        675                 680                 685

Leu Val Asp Tyr Leu His Arg Asn Lys His Thr Phe Leu Gln His His
    690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
        755                 760                 765

Ser Asn Tyr Met Ala Pro Tyr Asp Asn Tyr Val Pro Ser Ala Pro Glu
770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
        835                 840                 845

Arg Asp Ile Met Arg Asp Ser Asn Tyr Ile Ser Lys Gly Ser Thr Phe
850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
            900                 905                 910

Phe Tyr Asn Ala Ile Lys Arg Gly Tyr Arg Met Ala Gln Pro Ala His
        915                 920                 925

Ala Ser Asp Glu Ile Tyr Glu Ile Met Gln Lys Cys Trp Glu Glu Lys
930                 935                 940
```

```
Phe Glu Ile Arg Pro Pro Phe Ser Gln Leu Val Leu Leu Glu Arg
945                 950                 955                 960

Leu Leu Gly Glu Gly Tyr Lys Lys Tyr Gln Gln Val Asp Glu Glu
            965                 970                 975

Phe Leu Arg Ser Asp His Pro Ala Ile Leu Arg Ser Asn Ala Arg Leu
        980                 985                 990

Pro Gly Phe His Gly Leu Arg Ser Pro Leu Asp Thr Ser Ser Val Leu
        995                 1000                1005

Tyr Thr Ala Val Gln Pro Asn Glu Gly Asp Asn Asp Tyr Ile Ile
    1010                1015                1020

Pro Leu Pro Asp Pro Lys Pro Glu Val Ala Asp Glu Gly Pro Leu
    1025                1030                1035

Glu Gly Ser Pro Ser Leu Ala Ser Ser Thr Leu Asn Glu Val Asn
    1040                1045                1050

Thr Ser Ser Thr Ile Ser Cys Asp Ser Pro Leu Glu Pro Gln Asp
    1055                1060                1065

Glu Pro Glu Pro Glu Pro Gln Leu Glu Leu Gln Val Glu Pro Glu
    1070                1075                1080

Pro Glu Leu Glu Gln Leu Pro Asp Ser Gly Cys Pro Ala Pro Arg
    1085                1090                1095

Ala Glu Ala Glu Asp Ser Phe Leu
    1100                1105

<210> SEQ ID NO 120
<211> LENGTH: 4795
<212> TYPE: DNA
<213> ORGANISM: Homo sapiens
<220> FEATURE:
<221> NAME/KEY: CDS
<222> LOCATION: (20)..(4111)

<400> SEQUENCE: 120
ccacgcgcag cggccggag atg cag cgg ggc gcc gcg ctg tgc ctg cga ctg       52
                    Met Gln Arg Gly Ala Ala Leu Cys Leu Arg Leu
                     1               5                  10 tgg ctc tgc ctg gga ctc ctg gac ggc ctg gtg agt ggc tac tcc atg       100
Trp Leu Cys Leu Gly Leu Leu Asp Gly Leu Val Ser Gly Tyr Ser Met
            15                  20                  25 acc ccc ccg acc ttg aac atc acg gag gag tca cac gtc atc gac acc       148
Thr Pro Pro Thr Leu Asn Ile Thr Glu Glu Ser His Val Ile Asp Thr
        30                  35                  40 ggt gac agc ctg tcc atc tcc tgc agg gga cag cac ccc ctc gag tgg       196
Gly Asp Ser Leu Ser Ile Ser Cys Arg Gly Gln His Pro Leu Glu Trp
    45                  50                  55 gct tgg cca gga gct cag gag gcg cca gcc acc gga gac aag gac agc       244
Ala Trp Pro Gly Ala Gln Glu Ala Pro Ala Thr Gly Asp Lys Asp Ser
60                  65                  70                  75 gag gac acg ggg gtg gtg cga gac tgc gag ggc aca gac gcc agg ccc       292
Glu Asp Thr Gly Val Val Arg Asp Cys Glu Gly Thr Asp Ala Arg Pro
                80                  85                  90 tac tgc aag gtg ttg ctg ctg cac gag gta cat gcc aac gac aca ggc       340
Tyr Cys Lys Val Leu Leu Leu His Glu Val His Ala Asn Asp Thr Gly
            95                  100                 105 agc tac gtc tgc tac tac aag tac atc aag gca cgc atc gag ggc acc       388
Ser Tyr Val Cys Tyr Tyr Lys Tyr Ile Lys Ala Arg Ile Glu Gly Thr
        110                 115                 120 acg gcc gcc agc tcc tac gtg ttc gtg aga gac ttt gag cag cca ttc       436
Thr Ala Ala Ser Ser Tyr Val Phe Val Arg Asp Phe Glu Gln Pro Phe
    125                 130                 135
```

```
atc aac aag cct gac acg ctc ttg gtc aac agg aag gac gcc atg tgg      484
Ile Asn Lys Pro Asp Thr Leu Leu Val Asn Arg Lys Asp Ala Met Trp
140                 145                 150                 155 gtg ccc tgt ctg gtg tcc atc ccc ggc ctc aat gtc acg ctg cgc tcg      532
Val Pro Cys Leu Val Ser Ile Pro Gly Leu Asn Val Thr Leu Arg Ser
                160                 165                 170 caa agc tcg gtg ctg tgg cca gac ggg cag gag gtg gtg tgg gat gac      580
Gln Ser Ser Val Leu Trp Pro Asp Gly Gln Glu Val Val Trp Asp Asp
            175                 180                 185 cgg cgg ggc atg ctc gtg tcc acg cca ctg ctg cac gat gcc ctg tac      628
Arg Arg Gly Met Leu Val Ser Thr Pro Leu Leu His Asp Ala Leu Tyr
        190                 195                 200 ctg cag tgc gag acc acc tgg gga gac cag gac ttc ctt tcc aac ccc      676
Leu Gln Cys Glu Thr Thr Trp Gly Asp Gln Asp Phe Leu Ser Asn Pro
    205                 210                 215 ttc ctg gtg cac atc aca ggc aac gag ctc tat gac atc cag ctg ttg      724
Phe Leu Val His Ile Thr Gly Asn Glu Leu Tyr Asp Ile Gln Leu Leu
220                 225                 230                 235 ccc agg aag tcg ctg gag ctg ctg gta ggg gag aag ctg gtc ctg aac      772
Pro Arg Lys Ser Leu Glu Leu Leu Val Gly Glu Lys Leu Val Leu Asn
                240                 245                 250 tgc acc gtg tgg gct gag ttt aac tca ggt gtc acc ttt gac tgg gac      820
Cys Thr Val Trp Ala Glu Phe Asn Ser Gly Val Thr Phe Asp Trp Asp
            255                 260                 265 tac cca ggg aag cag gca gag cgg ggt aag tgg gtg ccc gag cga cgc      868
Tyr Pro Gly Lys Gln Ala Glu Arg Gly Lys Trp Val Pro Glu Arg Arg
        270                 275                 280 tcc cag cag acc cac aca gaa ctc tcc agc atc ctg acc atc cac aac      916
Ser Gln Gln Thr His Thr Glu Leu Ser Ser Ile Leu Thr Ile His Asn
    285                 290                 295 gtc agc cag cac gac ctg ggc tcg tat gtg tgc aag gcc aac aac ggc      964
Val Ser Gln His Asp Leu Gly Ser Tyr Val Cys Lys Ala Asn Asn Gly
300                 305                 310                 315 atc cag cga ttt cgg gag agc acc gag gtc att gtg cat gaa aat ccc     1012
Ile Gln Arg Phe Arg Glu Ser Thr Glu Val Ile Val His Glu Asn Pro
                320                 325                 330 ttc atc agc gtc gag tgg ctc aaa gga ccc atc ctg gag gcc acg gca     1060
Phe Ile Ser Val Glu Trp Leu Lys Gly Pro Ile Leu Glu Ala Thr Ala
            335                 340                 345 gga gac gag ctg gtg aag ctg ccc gtg aag ctg gca gcg tac ccc ccg     1108
Gly Asp Glu Leu Val Lys Leu Pro Val Lys Leu Ala Ala Tyr Pro Pro
        350                 355                 360 ccc gag ttc cag tgg tac aag gat gga aag gca ctg tcc ggg cgc cac     1156
Pro Glu Phe Gln Trp Tyr Lys Asp Gly Lys Ala Leu Ser Gly Arg His
    365                 370                 375 agt cca cat gcc ctg gtg ctc aag gag gtg aca gag gcc agc aca ggc     1204
Ser Pro His Ala Leu Val Leu Lys Glu Val Thr Glu Ala Ser Thr Gly
380                 385                 390                 395 acc tac acc ctc gcc ctg tgg aac tcc gct gct ggc ctg agg cgc aac     1252
Thr Tyr Thr Leu Ala Leu Trp Asn Ser Ala Ala Gly Leu Arg Arg Asn
                400                 405                 410 atc agc ctg gag ctg gtg gtg aat gtg ccc ccc cag ata cat gag aag     1300
Ile Ser Leu Glu Leu Val Val Asn Val Pro Pro Gln Ile His Glu Lys
            415                 420                 425 gag gcc tcc tcc ccc agc atc tac tcg cgt cac agc cgc cag gcc ctc     1348
Glu Ala Ser Ser Pro Ser Ile Tyr Ser Arg His Ser Arg Gln Ala Leu
        430                 435                 440 acc tgc acg gcc tac ggg gtg ccc ctg cct ctc agc atc cag tgg cac     1396
Thr Cys Thr Ala Tyr Gly Val Pro Leu Pro Leu Ser Ile Gln Trp His
```

```
                        445                 450                 455
tgg cgg ccc tgg aca ccc tgc aag atg ttt gcc cag cgt agt ctc cgg    1444
Trp Arg Pro Trp Thr Pro Cys Lys Met Phe Ala Gln Arg Ser Leu Arg
460                 465                 470                 475 cgg cgg cag cag caa gac ctc atg cca cag tgc cgt gac tgg agg gcg    1492
Arg Arg Gln Gln Gln Asp Leu Met Pro Gln Cys Arg Asp Trp Arg Ala
                480                 485                 490 gtg acc acg cag gat gcc gtg aac ccc atc gag agc ctg gac acc tgg    1540
Val Thr Thr Gln Asp Ala Val Asn Pro Ile Glu Ser Leu Asp Thr Trp
        495                 500                 505 acc gag ttt gtg gag gga aag aat aag act gtg agc aag ctg gtg atc    1588
Thr Glu Phe Val Glu Gly Lys Asn Lys Thr Val Ser Lys Leu Val Ile
            510                 515                 520 cag aat gcc aac gtg tct gcc atg tac aag tgt gtg gtc tcc aac aag    1636
Gln Asn Ala Asn Val Ser Ala Met Tyr Lys Cys Val Val Ser Asn Lys
525                 530                 535 gtg ggc cag gat gag cgg ctc atc tac ttc tat gtg acc acc atc ccc    1684
Val Gly Gln Asp Glu Arg Leu Ile Tyr Phe Tyr Val Thr Thr Ile Pro
540                 545                 550                 555 gac ggc ttc acc atc gaa tcc aag cca tcc gag gag cta cta gag ggc    1732
Asp Gly Phe Thr Ile Glu Ser Lys Pro Ser Glu Glu Leu Leu Glu Gly
                560                 565                 570 cag ccg gtg ctc ctg agc tgc caa gcc gac agc tac aag tac gag cat    1780
Gln Pro Val Leu Leu Ser Cys Gln Ala Asp Ser Tyr Lys Tyr Glu His
        575                 580                 585 ctg cgc tgg tac cgc ctc aac ctg tcc acg ctg cac gat gcg cac ggg    1828
Leu Arg Trp Tyr Arg Leu Asn Leu Ser Thr Leu His Asp Ala His Gly
            590                 595                 600 aac ccg ctt ctg ctc gac tgc aag aac gtg cat ctg ttc gcc acc cct    1876
Asn Pro Leu Leu Leu Asp Cys Lys Asn Val His Leu Phe Ala Thr Pro
605                 610                 615 ctg gcc gcc agc ctg gag gag gtg gca cct ggg gcg cgc cac gcc acg    1924
Leu Ala Ala Ser Leu Glu Glu Val Ala Pro Gly Ala Arg His Ala Thr
620                 625                 630                 635 ctc agc ctg agt atc ccc cgc gtc gcg ccc gag cac gag ggc cac tat    1972
Leu Ser Leu Ser Ile Pro Arg Val Ala Pro Glu His Glu Gly His Tyr
                640                 645                 650 gtg tgc gaa gtg caa gac cgg cgc agc cat gac aag cac tgc cac aag    2020
Val Cys Glu Val Gln Asp Arg Arg Ser His Asp Lys His Cys His Lys
        655                 660                 665 aag tac ctg tcg gtg cag gcc ctg gaa gcc cct cgg ctc acg cag aac    2068
Lys Tyr Leu Ser Val Gln Ala Leu Glu Ala Pro Arg Leu Thr Gln Asn
            670                 675                 680 ttg acc gac ctc ctg gtg aac gtg agc gac tcg ctg gag atg cag tgc    2116
Leu Thr Asp Leu Leu Val Asn Val Ser Asp Ser Leu Glu Met Gln Cys
685                 690                 695 ttg gtg gcc gga gcg cac gcg ccc agc atc gtg tgg tac aaa gac gag    2164
Leu Val Ala Gly Ala His Ala Pro Ser Ile Val Trp Tyr Lys Asp Glu
700                 705                 710                 715 agg ctg ctg gag gaa aag tct gga gtc gac ttg gcg gac tcc aac cag    2212
Arg Leu Leu Glu Glu Lys Ser Gly Val Asp Leu Ala Asp Ser Asn Gln
                720                 725                 730 aag ctg agc atc cag cgc gtg cgc gag gag gat gcg gga cgc tat ctg    2260
Lys Leu Ser Ile Gln Arg Val Arg Glu Glu Asp Ala Gly Arg Tyr Leu
        735                 740                 745 tgc agc gtg tgc aac gcc aag ggc tgc gtc aac tcc tcc gcc agc gtg    2308
Cys Ser Val Cys Asn Ala Lys Gly Cys Val Asn Ser Ser Ala Ser Val
            750                 755                 760 gcc gtg gaa ggc tcc gag gat aag ggc agc atg gag atc gtg atc ctt    2356
```

-continued

| | | |
|---|---|---|
| Ala Val Glu Gly Ser Glu Asp Lys Gly Ser Met Glu Ile Val Ile Leu<br>765                           770                         775 | |
| gtc ggt acc ggc gtc atc gct gtc ttc ttc tgg gtc ctc ctc ctc<br>Val Gly Thr Gly Val Ile Ala Val Phe Phe Trp Val Leu Leu Leu Leu<br>780                         785                         790                        795 | 2404 |
| atc ttc tgt aac atg agg agg ccg gcc cac gca gac atc aag acg ggc<br>Ile Phe Cys Asn Met Arg Arg Pro Ala His Ala Asp Ile Lys Thr Gly<br>                      800                         805                         810 | 2452 |
| tac ctg tcc atc atc atg gac ccc ggg gag gtg cct ctg gag gag caa<br>Tyr Leu Ser Ile Ile Met Asp Pro Gly Glu Val Pro Leu Glu Glu Gln<br>                  815                       820                        825 | 2500 |
| tgc gaa tac ctg tcc tac gat gcc agc cag tgg gaa ttc ccc cga gag<br>Cys Glu Tyr Leu Ser Tyr Asp Ala Ser Gln Trp Glu Phe Pro Arg Glu<br>         830                     835                      840 | 2548 |
| cgg ctg cac ctg ggg aga gtg ctc ggc tac ggc gcc ttc ggg aag gtg<br>Arg Leu His Leu Gly Arg Val Leu Gly Tyr Gly Ala Phe Gly Lys Val<br>         845                     850                      855 | 2596 |
| gtg gaa gcc tcc gct ttc ggc atc cac aag ggc agc agc tgt gac acc<br>Val Glu Ala Ser Ala Phe Gly Ile His Lys Gly Ser Ser Cys Asp Thr<br>860                       865                       870                      875 | 2644 |
| gtg gcc gtg aaa atg ctg aaa gag ggc gcc acg gcc agc gag cac cgc<br>Val Ala Val Lys Met Leu Lys Glu Gly Ala Thr Ala Ser Glu His Arg<br>                      880                         885                         890 | 2692 |
| gcg ctg atg tcg gag ctc aag atc ctc att cac atc ggc aac cac ctc<br>Ala Leu Met Ser Glu Leu Lys Ile Leu Ile His Ile Gly Asn His Leu<br>         895                     900                      905 | 2740 |
| aac gtg gtc aac ctc ctc ggg gcg tgc acc aag ccg cag ggc ccc ctc<br>Asn Val Val Asn Leu Leu Gly Ala Cys Thr Lys Pro Gln Gly Pro Leu<br>                  910                       915                      920 | 2788 |
| atg gtg atc gtg gag ttc tgc aag tac ggc aac ctc tcc aac ttc ctg<br>Met Val Ile Val Glu Phe Cys Lys Tyr Gly Asn Leu Ser Asn Phe Leu<br>925                       930                       935 | 2836 |
| cgc gcc aag cgg gac gcc ttc agc ccc tgc gcg gag aag tct ccc gag<br>Arg Ala Lys Arg Asp Ala Phe Ser Pro Cys Ala Glu Lys Ser Pro Glu<br>940                       945                       950                      955 | 2884 |
| cag cgc gga cgc ttc cgc gcc atg gtg gag ctc gcc agg ctg gat cgg<br>Gln Arg Gly Arg Phe Arg Ala Met Val Glu Leu Ala Arg Leu Asp Arg<br>                  960                       965                      970 | 2932 |
| agg cgg ccg ggg agc agc gac agg gtc ctc ttc gcg cgg ttc tcg aag<br>Arg Arg Pro Gly Ser Ser Asp Arg Val Leu Phe Ala Arg Phe Ser Lys<br>                  975                       980                      985 | 2980 |
| acc gag ggc gga gcg agg cgg gct tct cca gac caa gaa gct gag gac<br>Thr Glu Gly Gly Ala Arg Arg Ala Ser Pro Asp Gln Glu Ala Glu Asp<br>         990                     995                     1000 | 3028 |
| ctg tgg ctg agc ccg ctg acc atg gaa gat ctt gtc tgc tac agc<br>Leu Trp Leu Ser Pro Leu Thr Met Glu Asp Leu Val Cys Tyr Ser<br>    1005                       1010                      1015 | 3073 |
| ttc cag gtg gcc aga ggg atg gag ttc ctg gct tcc cga aag tgc<br>Phe Gln Val Ala Arg Gly Met Glu Phe Leu Ala Ser Arg Lys Cys<br>    1020                       1025                      1030 | 3118 |
| atc cac aga gac ctg gct gct cgg aac att ctg ctg tcg gaa agc<br>Ile His Arg Asp Leu Ala Ala Arg Asn Ile Leu Leu Ser Glu Ser<br>    1035                       1040                      1045 | 3163 |
| gac gtg gtg aag atc tgt gac ttt ggc ctt gcc cgg gac atc tac<br>Asp Val Val Lys Ile Cys Asp Phe Gly Leu Ala Arg Asp Ile Tyr<br>    1050                       1055                      1060 | 3208 |
| aaa gac cct gac tac gtc cgc aag ggc agt gcc cgg ctg ccc ctg<br>Lys Asp Pro Asp Tyr Val Arg Lys Gly Ser Ala Arg Leu Pro Leu<br>    1065                       1070                      1075 | 3253 |

```
aag tgg atg gcc cct gaa agc atc ttc gac aag gtg tac acc acg    3298
Lys Trp Met Ala Pro Glu Ser Ile Phe Asp Lys Val Tyr Thr Thr
    1080            1085                1090 cag agt gac gtg tgg tcc ttt ggg gtg ctt ctc tgg gag atc ttc    3343
Gln Ser Asp Val Trp Ser Phe Gly Val Leu Leu Trp Glu Ile Phe
1095                1100                1105 tct ctg ggg gcc tcc ccg tac cct ggg gtg cag atc aat gag gag    3388
Ser Leu Gly Ala Ser Pro Tyr Pro Gly Val Gln Ile Asn Glu Glu
    1110            1115                1120 ttc tgc cag cgg ctg aga gac ggc aca agg atg agg gcc ccg gag    3433
Phe Cys Gln Arg Leu Arg Asp Gly Thr Arg Met Arg Ala Pro Glu
1125                1130                1135 ctg gcc act ccc gcc ata cgc cgc atc atg ctg aac tgc tgg tcc    3478
Leu Ala Thr Pro Ala Ile Arg Arg Ile Met Leu Asn Cys Trp Ser
    1140            1145                1150 gga gac ccc aag gcg aga cct gca ttc tcg gag ctg gtg gag atc    3523
Gly Asp Pro Lys Ala Arg Pro Ala Phe Ser Glu Leu Val Glu Ile
1155                1160                1165 ctg ggg gac ctg ctc cag ggc agg ggc ctg caa gag gaa gag gag    3568
Leu Gly Asp Leu Leu Gln Gly Arg Gly Leu Gln Glu Glu Glu Glu
    1170            1175                1180 gtc tgc atg gcc ccg cgc agc tct cag agc tca gaa gag ggc agc    3613
Val Cys Met Ala Pro Arg Ser Ser Gln Ser Ser Glu Glu Gly Ser
1185                1190                1195 ttc tcg cag gtg tcc acc atg gcc cta cac atc gcc cag gct gac    3658
Phe Ser Gln Val Ser Thr Met Ala Leu His Ile Ala Gln Ala Asp
    1200            1205                1210 gct gag gac agc ccg cca agc ctg cag cgc cac agc ctg gcc gcc    3703
Ala Glu Asp Ser Pro Pro Ser Leu Gln Arg His Ser Leu Ala Ala
1215                1220                1225 agg tat tac aac tgg gtg tcc ttt ccc ggg tgc ctg gcc aga ggg    3748
Arg Tyr Tyr Asn Trp Val Ser Phe Pro Gly Cys Leu Ala Arg Gly
    1230            1235                1240 gct gag acc cgt ggt tcc tcc agg atg aag aca ttt gag gaa ttc    3793
Ala Glu Thr Arg Gly Ser Ser Arg Met Lys Thr Phe Glu Glu Phe
1245                1250                1255 ccc atg acc cca acg acc tac aaa ggc tct gtg gac aac cag aca    3838
Pro Met Thr Pro Thr Thr Tyr Lys Gly Ser Val Asp Asn Gln Thr
    1260            1265                1270 gac agt ggg atg gtg ctg gcc tcg gag gag ttt gag cag ata gag    3883
Asp Ser Gly Met Val Leu Ala Ser Glu Glu Phe Glu Gln Ile Glu
1275                1280                1285 agc agg cat aga caa gaa agc ggc ttc agc tgt aaa gga cct ggc    3928
Ser Arg His Arg Gln Glu Ser Gly Phe Ser Cys Lys Gly Pro Gly
    1290            1295                1300 cag aat gtg gct gtg acc agg gca cac cct gac tcc caa ggg agg    3973
Gln Asn Val Ala Val Thr Arg Ala His Pro Asp Ser Gln Gly Arg
1305                1310                1315 cgg cgg cgg cct gag cgg ggg gcc cga gga ggc cag gtg ttt tac    4018
Arg Arg Arg Pro Glu Arg Gly Ala Arg Gly Gly Gln Val Phe Tyr
    1320            1325                1330 aac agc gag tat ggg gag ctg tcg gag cca agc gag gag gac cac    4063
Asn Ser Glu Tyr Gly Glu Leu Ser Glu Pro Ser Glu Glu Asp His
1335                1340                1345 tgc tcc ccg tct gcc cgc gtg act ttc ttc aca gac aac agc tac    4108
Cys Ser Pro Ser Ala Arg Val Thr Phe Phe Thr Asp Asn Ser Tyr
    1350            1355                1360 taa gcagcatcgg acaagacccc cagcacttgg gggttcaggc ccggcagggc    4161
gggcagaggg ctggaggccc aggctgggaa ctcatctggt tgaactctgg tggcacagga  4221
```

-continued

```
gtgtcctctt ccctctctgc agacttccca gctaggaaga gcaggactcc aggcccaagg    4281
ctcccggaat tccgtcacca cgactggcca gggcacgctc cagctgcccc ggcccctccc    4341
cctgagattc agatgtcatt tagttcagca tccgcaggtg ctggtcccgg ggccagcact    4401
tccatgggaa tgtctctttg gcgacctcct ttcatcacac tgggtggtgg cctggtccct    4461
gttttcccac gaggaatctg tgggtctggg agtcacacag tgttggaggt taaggcatac    4521
gagagcagag gtctcccaaa cgcccttttcc tcctcaggca cacagctact ctccccacga    4581
gggctggctg gcctcaccca cccctgcaca gttgaaggga ggggctgtgt ttccatctca    4641
aagaaggcat ttgcagggtc ctcttctggg cctgaccaaa cagccaacta gcccctgggg    4701
tggccaccag tatgacagta ttatacgctg gcaacacaga ggcagcccgc acacctgcgc    4761
ctgggtgttg agagccatcc tgcaagtctt tttc                                4795
```

<210> SEQ ID NO 121
<211> LENGTH: 1363
<212> TYPE: PRT
<213> ORGANISM: Homo sapiens

<400> SEQUENCE: 121

```
Met Gln Arg Gly Ala Ala Leu Cys Leu Arg Leu Trp Leu Cys Leu Gly
1               5                   10                  15
Leu Leu Asp Gly Leu Val Ser Gly Tyr Ser Met Thr Pro Pro Thr Leu
            20                  25                  30
Asn Ile Thr Glu Glu Ser His Val Ile Asp Thr Gly Asp Ser Leu Ser
        35                  40                  45
Ile Ser Cys Arg Gly Gln His Pro Leu Glu Trp Ala Trp Pro Gly Ala
    50                  55                  60
Gln Glu Ala Pro Ala Thr Gly Asp Lys Asp Ser Glu Asp Thr Gly Val
65                  70                  75                  80
Val Arg Asp Cys Glu Gly Thr Asp Ala Arg Pro Tyr Cys Lys Val Leu
                85                  90                  95
Leu Leu His Glu Val His Ala Asn Asp Thr Gly Ser Tyr Val Cys Tyr
            100                 105                 110
Tyr Lys Tyr Ile Lys Ala Arg Ile Glu Gly Thr Thr Ala Ala Ser Ser
        115                 120                 125
Tyr Val Phe Val Arg Asp Phe Glu Gln Pro Phe Ile Asn Lys Pro Asp
    130                 135                 140
Thr Leu Leu Val Asn Arg Lys Asp Ala Met Trp Val Pro Cys Leu Val
145                 150                 155                 160
Ser Ile Pro Gly Leu Asn Val Thr Leu Arg Ser Gln Ser Ser Val Leu
                165                 170                 175
Trp Pro Asp Gly Gln Glu Val Val Trp Asp Asp Arg Arg Gly Met Leu
            180                 185                 190
Val Ser Thr Pro Leu Leu His Asp Ala Leu Tyr Leu Gln Cys Glu Thr
        195                 200                 205
Thr Trp Gly Asp Gln Asp Phe Leu Ser Asn Pro Phe Leu Val His Ile
    210                 215                 220
Thr Gly Asn Glu Leu Tyr Asp Ile Gln Leu Leu Pro Arg Lys Ser Leu
225                 230                 235                 240
Glu Leu Leu Val Gly Glu Lys Leu Val Leu Asn Cys Thr Val Trp Ala
                245                 250                 255
Glu Phe Asn Ser Gly Val Thr Phe Asp Trp Asp Tyr Pro Gly Lys Gln
            260                 265                 270
```

-continued

```
Ala Glu Arg Gly Lys Trp Val Pro Glu Arg Ser Gln Gln Thr His
        275                 280                 285
Thr Glu Leu Ser Ser Ile Leu Thr Ile His Asn Val Ser Gln His Asp
    290                 295                 300
Leu Gly Ser Tyr Val Cys Lys Ala Asn Asn Gly Ile Gln Arg Phe Arg
305                 310                 315                 320
Glu Ser Thr Glu Val Ile Val His Glu Asn Pro Phe Ile Ser Val Glu
                325                 330                 335
Trp Leu Lys Gly Pro Ile Leu Glu Ala Thr Ala Gly Asp Glu Leu Val
            340                 345                 350
Lys Leu Pro Val Lys Leu Ala Ala Tyr Pro Pro Glu Phe Gln Trp
        355                 360                 365
Tyr Lys Asp Gly Lys Ala Leu Ser Gly Arg His Ser Pro His Ala Leu
    370                 375                 380
Val Leu Lys Glu Val Thr Glu Ala Ser Thr Gly Thr Tyr Thr Leu Ala
385                 390                 395                 400
Leu Trp Asn Ser Ala Ala Gly Leu Arg Arg Asn Ile Ser Leu Glu Leu
                405                 410                 415
Val Val Asn Val Pro Pro Gln Ile His Glu Lys Glu Ala Ser Ser Pro
            420                 425                 430
Ser Ile Tyr Ser Arg His Ser Arg Gln Ala Leu Thr Cys Thr Ala Tyr
        435                 440                 445
Gly Val Pro Leu Pro Leu Ser Ile Gln Trp His Trp Arg Pro Trp Thr
    450                 455                 460
Pro Cys Lys Met Phe Ala Gln Arg Ser Leu Arg Arg Arg Gln Gln Gln
465                 470                 475                 480
Asp Leu Met Pro Gln Cys Arg Asp Trp Arg Ala Val Thr Thr Gln Asp
                485                 490                 495
Ala Val Asn Pro Ile Glu Ser Leu Asp Thr Trp Thr Glu Phe Val Glu
            500                 505                 510
Gly Lys Asn Lys Thr Val Ser Lys Leu Val Ile Gln Asn Ala Asn Val
        515                 520                 525
Ser Ala Met Tyr Lys Cys Val Val Ser Asn Lys Val Gly Gln Asp Glu
    530                 535                 540
Arg Leu Ile Tyr Phe Tyr Val Thr Thr Ile Pro Asp Gly Phe Thr Ile
545                 550                 555                 560
Glu Ser Lys Pro Ser Glu Glu Leu Leu Glu Gly Gln Pro Val Leu Leu
                565                 570                 575
Ser Cys Gln Ala Asp Ser Tyr Lys Tyr Glu His Leu Arg Trp Tyr Arg
            580                 585                 590
Leu Asn Leu Ser Thr Leu His Asp Ala His Gly Asn Pro Leu Leu Leu
        595                 600                 605
Asp Cys Lys Asn Val His Leu Phe Ala Thr Pro Leu Ala Ala Ser Leu
    610                 615                 620
Glu Glu Val Ala Pro Gly Ala Arg His Ala Thr Leu Ser Leu Ser Ile
625                 630                 635                 640
Pro Arg Val Ala Pro Glu His Glu Gly His Tyr Val Cys Glu Val Gln
                645                 650                 655
Asp Arg Arg Ser His Asp Lys His Cys His Lys Lys Tyr Leu Ser Val
            660                 665                 670
Gln Ala Leu Glu Ala Pro Arg Leu Thr Gln Asn Leu Thr Asp Leu Leu
        675                 680                 685
```

-continued

```
Val Asn Val Ser Asp Ser Leu Glu Met Gln Cys Leu Val Ala Gly Ala
    690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
                725                 730                 735

Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
        755                 760                 765

Glu Asp Lys Gly Ser Met Glu Ile Val Ile Leu Val Gly Thr Gly Val
    770                 775                 780

Ile Ala Val Phe Phe Trp Val Leu Leu Leu Ile Phe Cys Asn Met
785                 790                 795                 800

Arg Arg Pro Ala His Ala Asp Ile Lys Thr Gly Tyr Leu Ser Ile Ile
                805                 810                 815

Met Asp Pro Gly Glu Val Pro Leu Glu Glu Gln Cys Glu Tyr Leu Ser
            820                 825                 830

Tyr Asp Ala Ser Gln Trp Glu Phe Pro Arg Glu Arg Leu His Leu Gly
        835                 840                 845

Arg Val Leu Gly Tyr Gly Ala Phe Gly Lys Val Val Glu Ala Ser Ala
    850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
                885                 890                 895

Leu Lys Ile Leu Ile His Ile Gly Asn His Leu Asn Val Val Asn Leu
            900                 905                 910

Leu Gly Ala Cys Thr Lys Pro Gln Gly Pro Leu Met Val Ile Val Glu
        915                 920                 925

Phe Cys Lys Tyr Gly Asn Leu Ser Asn Phe Leu Arg Ala Lys Arg Asp
    930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Arg Pro Gly Ser
                965                 970                 975

Ser Asp Arg Val Leu Phe Ala Arg Phe Ser Lys Thr Glu Gly Gly Ala
            980                 985                 990

Arg Arg Ala Ser Pro Asp Gln Glu Ala Glu Asp Leu Trp Leu Ser Pro
        995                 1000                1005

Leu Thr Met Glu Asp Leu Val Cys Tyr Ser Phe Gln Val Ala Arg
    1010                1015                1020

Gly Met Glu Phe Leu Ala Ser Arg Lys Cys Ile His Arg Asp Leu
    1025                1030                1035

Ala Ala Arg Asn Ile Leu Leu Ser Glu Ser Asp Val Val Lys Ile
    1040                1045                1050

Cys Asp Phe Gly Leu Ala Arg Asp Ile Tyr Lys Asp Pro Asp Tyr
    1055                1060                1065

Val Arg Lys Gly Ser Ala Arg Leu Pro Leu Lys Trp Met Ala Pro
    1070                1075                1080

Glu Ser Ile Phe Asp Lys Val Tyr Thr Thr Gln Ser Asp Val Trp
    1085                1090                1095

Ser Phe Gly Val Leu Leu Trp Glu Ile Phe Ser Leu Gly Ala Ser
```

```
                  1100                1105                1110

Pro Tyr Pro Gly Val Gln Ile Asn Glu Glu Phe Cys Gln Arg Leu
    1115                1120                1125

Arg Asp Gly Thr Arg Met Arg Ala Pro Glu Leu Ala Thr Pro Ala
    1130                1135                1140

Ile Arg Arg Ile Met Leu Asn Cys Trp Ser Gly Asp Pro Lys Ala
    1145                1150                1155

Arg Pro Ala Phe Ser Glu Leu Val Glu Ile Leu Gly Asp Leu Leu
    1160                1165                1170

Gln Gly Arg Gly Leu Gln Glu Glu Glu Val Cys Met Ala Pro
    1175                1180                1185

Arg Ser Ser Gln Ser Ser Glu Gly Ser Phe Ser Gln Val Ser
    1190                1195                1200

Thr Met Ala Leu His Ile Ala Gln Ala Asp Ala Glu Asp Ser Pro
    1205                1210                1215

Pro Ser Leu Gln Arg His Ser Leu Ala Ala Arg Tyr Tyr Asn Trp
    1220                1225                1230

Val Ser Phe Pro Gly Cys Leu Ala Arg Gly Ala Glu Thr Arg Gly
    1235                1240                1245

Ser Ser Arg Met Lys Thr Phe Glu Glu Phe Pro Met Thr Pro Thr
    1250                1255                1260

Thr Tyr Lys Gly Ser Val Asp Asn Gln Thr Asp Ser Gly Met Val
    1265                1270                1275

Leu Ala Ser Glu Glu Phe Glu Gln Ile Glu Ser Arg His Arg Gln
    1280                1285                1290

Glu Ser Gly Phe Ser Cys Lys Gly Pro Gly Gln Asn Val Ala Val
    1295                1300                1305

Thr Arg Ala His Pro Asp Ser Gln Gly Arg Arg Arg Pro Glu
    1310                1315                1320

Arg Gly Ala Arg Gly Gly Gln Val Phe Tyr Asn Ser Glu Tyr Gly
    1325                1330                1335

Glu Leu Ser Glu Pro Ser Glu Glu Asp His Cys Ser Pro Ser Ala
    1340                1345                1350

Arg Val Thr Phe Phe Thr Asp Asn Ser Tyr
    1355                1360

<210> SEQ ID NO 122
<211> LENGTH: 33
<212> TYPE: DNA
<213> ORGANISM: Artificial sequence
<220> FEATURE:
<223> OTHER INFORMATION: Synthetic primer

<400> SEQUENCE: 122
tacttggcag tacatctacg tattagtcat cgc                                33

<210> SEQ ID NO 123
<211> LENGTH: 39
<212> TYPE: DNA
<213> ORGANISM: Artificial sequence
<220> FEATURE:
<223> OTHER INFORMATION: Synthetic primer

<400> SEQUENCE: 123
cggagatctg tagtcttgca cgtacacgta ggagctggc                          39

<210> SEQ ID NO 124
```

<211> LENGTH: 1752
<212> TYPE: DNA
<213> ORGANISM: Homo sapiens

<400> SEQUENCE: 124

```
atgcagcggg gcgccgcgct gtgcctgcga ctgtggctct gcctgggact cctggacggc      60
ctggtgagtg gctactccat gaccccccg accttgaaca tcacggagga gtcacacgtc     120
atcgacaccg gtgacagcct gtccatctcc tgcaggggac agcacccct cgagtgggct     180
tggccaggag ctcaggaggc gccagccacc ggagacaagg acagcgagga cacggggtg     240
gtgcgagact gcgagggcac agacgccagg ccctactgca aggtgttgct gctgcacgag     300
gtacatgcca acgacacagg cagctacgtc tgctactaca gtacatcaa ggcacgcatc     360
gagggcacca cggccgccag ctcctacgtg tacgtgcaag actacagatc tccatttatt     420
gcttctgtta gtgaccaaca tggagtcgtg tacattactg agaacaaaaa caaaactgtg     480
gtgattccat gtctcgggtc catttcaaat ctcaacgtgt cactttgtgc aagatacca     540
gaaaagagat tgttcctga tggtaacaga atttcctggg acagcaagaa gggctttact     600
attcccagct acatgatcag ctatgctggc atggtcttct gtgaagcaaa aattaatgat     660
gaaagttacc agtctattat gtacatagtt gtcgttgtag ggtataggat ttatgatgtg     720
gttctgagtc cgtctcatgg aattgaacta tctgttggag aaaagcttgt cttaaattgt     780
acagcaagaa ctgaactaaa tgtggggatt gacttcaact gggaataccc ttcttcgaag     840
catcagcata gaaacttgt aaaccgagac taaaaaccc agtctgggag tgagatgaag     900
aaattttga gcaccttaac tatagatggt gtaacccgga gtgaccaagg attgtacacc     960
tgtgcagcat ccagtgggct gatgaccaag aagaacagca catttgtcag ggtccatgaa    1020
gatcccatcg aaggtcgtgg tggtggtggt ggtgatccca atcttgtga caaacctcac    1080
acatgcccac tgtgcccagc acctgaactc ctgggggac cgtcagtctt cctcttcccc    1140
ccaaaaccca aggacaccct catgatctcc cggacccctg aggtcacatg cgtggtggtg    1200
gacgtgagcc acgaagaccc tgaggtcaag ttcaactggt acgtggacgg cgtggaggtg    1260
cataatgcca agacaaagcc gcgggaggag cagtacaaca gcacgtaccg tgtggtcagc    1320
gtcctcaccg tcctgcacca ggactggctg aatggcaagg agtacaagtg caaggtctcc    1380
aacaaagccc tcccagcccc catcgagaaa accatctcca aagccaaagg gcagccccga    1440
gaaccacagg tgtacaccct gcccccatcc cgggatgagc tgaccaagaa ccaggtcagc    1500
ctgacctgcc tagtcaaagg cttctatccc agcgacatcg ccgtggagtg ggagagcaat    1560
gggcagccgg agaacaacta caaggccacg cctcccgtgc tggactccga cggctccttc    1620
ttcctctaca gcaagctcac cgtggacaag agcaggtggc agcagggaa cgtcttctca    1680
tgctccgtga tgcatgaggc tctgcacaac cactacacgc agaagagcct ctccctgtct    1740
ccgggtaaat ga                                                       1752
```

<210> SEQ ID NO 125
<211> LENGTH: 583
<212> TYPE: PRT
<213> ORGANISM: Homo sapiens

<400> SEQUENCE: 125

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30
```

-continued

```
Asn Ile Thr Glu Glu Ser His Val Ile Asp Thr Gly Asp Ser Leu Ser
         35                  40                  45

Ile Ser Cys Arg Gly Gln His Pro Leu Glu Trp Ala Trp Pro Gly Ala
 50                  55                  60

Gln Glu Ala Pro Ala Thr Gly Asp Lys Asp Ser Glu Asp Thr Gly Val
 65                  70                  75                  80

Val Arg Asp Cys Glu Gly Thr Asp Ala Arg Pro Tyr Cys Lys Val Leu
                 85                  90                  95

Leu Leu His Glu Val His Ala Asn Asp Thr Gly Ser Tyr Val Cys Tyr
             100                 105                 110

Tyr Lys Tyr Ile Lys Ala Arg Ile Glu Gly Thr Thr Ala Ala Ser Ser
         115                 120                 125

Tyr Val Tyr Val Gln Asp Tyr Arg Ser Pro Phe Ile Ala Ser Val Ser
     130                 135                 140

Asp Gln His Gly Val Val Tyr Ile Thr Glu Asn Lys Asn Lys Thr Val
145                 150                 155                 160

Val Ile Pro Cys Leu Gly Ser Ile Ser Asn Leu Asn Val Ser Leu Cys
                 165                 170                 175

Ala Arg Tyr Pro Glu Lys Arg Phe Val Pro Asp Gly Asn Arg Ile Ser
             180                 185                 190

Trp Asp Ser Lys Lys Gly Phe Thr Ile Pro Ser Tyr Met Ile Ser Tyr
         195                 200                 205

Ala Gly Met Val Phe Cys Glu Ala Lys Ile Asn Asp Glu Ser Tyr Gln
     210                 215                 220

Ser Ile Met Tyr Ile Val Val Val Gly Tyr Arg Ile Tyr Asp Val
225                 230                 235                 240

Val Leu Ser Pro Ser His Gly Ile Glu Leu Ser Val Gly Glu Lys Leu
                 245                 250                 255

Val Leu Asn Cys Thr Ala Arg Thr Glu Leu Asn Val Gly Ile Asp Phe
             260                 265                 270

Asn Trp Glu Tyr Pro Ser Ser Lys His Gln His Lys Lys Leu Val Asn
         275                 280                 285

Arg Asp Leu Lys Thr Gln Ser Gly Ser Glu Met Lys Lys Phe Leu Ser
     290                 295                 300

Thr Leu Thr Ile Asp Gly Val Thr Arg Ser Asp Gln Gly Leu Tyr Thr
305                 310                 315                 320

Cys Ala Ala Ser Ser Gly Leu Met Thr Lys Lys Asn Ser Thr Phe Val
                 325                 330                 335

Arg Val His Glu Asp Pro Ile Glu Gly Arg Gly Gly Gly Gly Asp
             340                 345                 350

Pro Lys Ser Cys Asp Lys Pro His Thr Cys Pro Leu Cys Pro Ala Pro
         355                 360                 365

Glu Leu Leu Gly Gly Pro Ser Val Phe Leu Phe Pro Pro Lys Pro Lys
     370                 375                 380

Asp Thr Leu Met Ile Ser Arg Thr Pro Glu Val Thr Cys Val Val Val
385                 390                 395                 400

Asp Val Ser His Glu Asp Pro Glu Val Lys Phe Asn Trp Tyr Val Asp
                 405                 410                 415

Gly Val Glu Val His Asn Ala Lys Thr Lys Pro Arg Glu Glu Gln Tyr
             420                 425                 430

Asn Ser Thr Tyr Arg Val Val Ser Val Leu Thr Val Leu His Gln Asp
         435                 440                 445
```

-continued

| | | | | | | | | | | | | |
|---|---|---|---|---|---|---|---|---|---|---|---|---|
|Trp|Leu|Asn|Gly|Lys|Glu|Tyr|Lys|Cys|Lys|Val|Ser|Asn|Lys|Ala|Leu|
| | |450| | | |455| | | |460| | | | | |
|Pro|Ala|Pro|Ile|Glu|Lys|Thr|Ile|Ser|Lys|Ala|Lys|Gly|Gln|Pro|Arg|
|465| | | | |470| | | | |475| | | | |480|
|Glu|Pro|Gln|Val|Tyr|Thr|Leu|Pro|Pro|Ser|Arg|Asp|Glu|Leu|Thr|Lys|
| | | | |485| | | | |490| | | | |495| |
|Asn|Gln|Val|Ser|Leu|Thr|Cys|Leu|Val|Lys|Gly|Phe|Tyr|Pro|Ser|Asp|
| | | |500| | | | |505| | | | |510| | |
|Ile|Ala|Val|Glu|Trp|Glu|Ser|Asn|Gly|Gln|Pro|Glu|Asn|Asn|Tyr|Lys|
| | |515| | | | |520| | | | |525| | | |
|Ala|Thr|Pro|Pro|Val|Leu|Asp|Ser|Asp|Gly|Ser|Phe|Phe|Leu|Tyr|Ser|
| |530| | | | |535| | | | |540| | | | |
|Lys|Leu|Thr|Val|Asp|Lys|Ser|Arg|Trp|Gln|Gln|Gly|Asn|Val|Phe|Ser|
|545| | | |550| | | | |555| | | | |560| |
|Cys|Ser|Val|Met|His|Glu|Ala|Leu|His|Asn|His|Tyr|Thr|Gln|Lys|Ser|
| | | |565| | | | |570| | | | |575| | |
|Leu|Ser|Leu|Ser|Pro|Gly|Lys| | | | | | | | | |
| | | |580| | | | | | | | | | | | |

<210> SEQ ID NO 126
<211> LENGTH: 81
<212> TYPE: DNA
<213> ORGANISM: Homo sapiens

<400> SEQUENCE: 126

```
tacaattgag acaagcgta tgtccacgaa gtagtttaac tggacgaggc gtgcttattt      60
gcacatcata aatcctatac c                                              81
```

<210> SEQ ID NO 127
<211> LENGTH: 1752
<212> TYPE: DNA
<213> ORGANISM: Homo sapiens

<400> SEQUENCE: 127

```
atgcagcggg gcgccgcgct gtgcctgcga ctgtggctct gcctgggact cctggacggc      60
ctggtgagtg gctactccat gacccccccg accttgaaca tcacggagga gtcacacgtc     120
atcgacaccg gtgacagcct gtccatctcc tgcaggggac agcaccccct cgagtgggct     180
tggccaggag ctcaggaggc gccagccacc ggagacaagg acagcgagga cacggggtg     240
gtgcgagact gcgagggcac agacgccagg ccctactgca aggtgttgct gctgcacgag     300
gtacatgcca acgacacagg cagctacgtc tgctactaca gtacatcaa ggcacgcatc     360
gagggcacca cggccgccag ctcctacgtg tacgtgcaag actacagatc tccatttatt     420
gcttctgtta gtgaccaaca tggagtcgtg tacattactg agaacaaaaa caaaactgtg     480
gtgattccat gtctcgggtc catttcaaat ctcaacgtgt cactttgtgc aagatcccca     540
gaaagagat ttgttcctga tggtaacaga atttcctggg acagcaagaa gggctttact     600
attcccagct acatgatcag ctatgctggc atggtcttct gtgaagcaaa aattaatgat     660
gaaagttacc agtctattat gtacatagtt gtcgttgtag ggtataggat ttatgatgtg     720
gttctgagtc cgtctcatgg aattgaacta tctgttggag aaaagcttgt cttaaattgt     780
acagcaagaa ctgaactaaa tgtggggatt gacttcaact gggaatacccttcttcgaag     840
catcagcata agaaacttgt aaaccgagac ctaaaaaccc agtctgggag tgagatgaag     900
aaatttttga gcaccttaac tatagatggt gtaacccgga gtgaccaagg attgtacacc     960
```

-continued

```
tgtgcagcat ccagtgggct gatgaccaag aagaacagca catttgtcag ggtccatgaa   1020
gatcccatcg aaggtcgtgg tggtggtggt ggtgatccca atcttgtga caaacctcac    1080 acatgcccac tgtgcccagc acctgaactc ctgggggac cgtcagtctt cctcttcccc    1140
ccaaaaccca aggacaccct catgatctcc cggacccctg aggtcacatg cgtggtggtg   1200
gacgtgagcc acgaagaccc tgaggtcaag ttcaactggt acgtggacgg cgtggaggtg   1260
cataatgcca agacaaagcc gcgggaggag cagtacaaca gcacgtaccg tgtggtcagc   1320
gtcctcaccg tcctgcacca ggactggctg aatggcaagg agtacaagtg caaggtctcc   1380
aacaaagccc tcccagcccc catcgagaaa accatctcca agccaaagg gcagccccga    1440 gaaccacagg tgtacaccct gcccccatcc cgggatgagc tgaccaagaa ccaggtcagc   1500
ctgacctgcc tagtcaaagg cttctatccc agcgacatcg ccgtggagtg ggagagcaat   1560
gggcagccgg agaacaacta caaggccacg cctcccgtgc tggactccga cggctccttc   1620
ttcctctaca gcaagctcac cgtggacaag agcaggtggc agcaggggaa cgtcttctca   1680
tgctccgtga tgcatgaggc tctgcacaac cactacacgc agaagagcct ctccctgtct   1740
ccgggtaaat ga                                                       1752
```

<210> SEQ ID NO 128
<211> LENGTH: 583
<212> TYPE: PRT
<213> ORGANISM: Homo sapiens

<400> SEQUENCE: 128

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Tyr Val Gln Asp Tyr Arg Ser Pro Phe Ile Ala Ser Val Ser
    130                 135                 140

Asp Gln His Gly Val Val Tyr Ile Thr Glu Asn Lys Asn Lys Thr Val
145                 150                 155                 160

Val Ile Pro Cys Leu Gly Ser Ile Ser Asn Leu Asn Val Ser Leu Cys
                165                 170                 175

Ala Arg Tyr Pro Glu Lys Arg Phe Val Pro Asp Gly Asn Arg Ile Ser
            180                 185                 190

Trp Asp Ser Lys Lys Gly Phe Thr Ile Pro Ser Tyr Met Ile Ser Tyr
        195                 200                 205

Ala Gly Met Val Phe Cys Glu Ala Lys Ile Asn Asp Glu Ser Tyr Gln
    210                 215                 220

Ser Ile Met Tyr Ile Val Val Val Val Gly Tyr Arg Ile Tyr Asp Val
```

-continued

```
225                 230                 235                 240
Val Leu Ser Pro Ser His Gly Ile Glu Leu Ser Val Gly Glu Lys Leu
                245                 250                 255
Val Leu Asn Cys Thr Ala Arg Thr Glu Leu Asn Val Gly Ile Asp Phe
                260                 265                 270
Asn Trp Glu Tyr Pro Ser Ser Lys His Gln His Lys Lys Leu Val Asn
                275                 280                 285
Arg Asp Leu Lys Thr Gln Ser Gly Ser Glu Met Lys Lys Phe Leu Ser
                290             295                 300
Thr Leu Thr Ile Asp Gly Val Thr Arg Ser Asp Gln Gly Leu Tyr Thr
305                 310                 315                 320
Cys Ala Ala Ser Ser Gly Leu Met Thr Lys Lys Asn Ser Thr Phe Val
                325                 330                 335
Arg Val His Glu Asp Pro Ile Glu Gly Arg Gly Gly Gly Gly Gly Asp
                340                 345                 350
Pro Lys Ser Cys Asp Lys Pro His Thr Cys Pro Leu Cys Pro Ala Pro
                355                 360                 365
Glu Leu Leu Gly Gly Pro Ser Val Phe Leu Phe Pro Pro Lys Pro Lys
    370                 375                 380
Asp Thr Leu Met Ile Ser Arg Thr Pro Glu Val Thr Cys Val Val Val
385                 390                 395                 400
Asp Val Ser His Glu Asp Pro Glu Val Lys Phe Asn Trp Tyr Val Asp
                405                 410                 415
Gly Val Glu Val His Asn Ala Lys Thr Lys Pro Arg Glu Glu Gln Tyr
                420                 425                 430
Asn Ser Thr Tyr Arg Val Val Ser Val Leu Thr Val Leu His Gln Asp
                435                 440                 445
Trp Leu Asn Gly Lys Glu Tyr Lys Cys Lys Val Ser Asn Lys Ala Leu
    450                 455                 460
Pro Ala Pro Ile Glu Lys Thr Ile Ser Lys Ala Lys Gly Gln Pro Arg
465                 470                 475                 480
Glu Pro Gln Val Tyr Thr Leu Pro Pro Ser Arg Asp Glu Leu Thr Lys
                485                 490                 495
Asn Gln Val Ser Leu Thr Cys Leu Val Lys Gly Phe Tyr Pro Ser Asp
                500                 505                 510
Ile Ala Val Glu Trp Glu Ser Asn Gly Gln Pro Glu Asn Asn Tyr Lys
                515                 520                 525
Ala Thr Pro Pro Val Leu Asp Ser Asp Gly Ser Phe Phe Leu Tyr Ser
                530                 535                 540
Lys Leu Thr Val Asp Lys Ser Arg Trp Gln Gln Gly Asn Val Phe Ser
545                 550                 555                 560
Cys Ser Val Met His Glu Ala Leu His Asn His Tyr Thr Gln Lys Ser
                565                 570                 575
Leu Ser Leu Ser Pro Gly Lys
                580
```

GROWTH FACTOR BINDING CONSTRUCTS MATERIALS AND METHODS

This application is a divisional of U.S. patent application Ser. No. 11/075,047, filed Mar. 7, 2005, now U.S. Pat. No. 7,422,741, which the priority benefit of U.S. Provisional Application No. 60/550,907, filed Mar. 5, 2004, incorporated herein by reference in its entirety.

BACKGROUND

The vascular endothelial growth factor (VEGF) proteins and their receptors (VEGFRs) play important roles in both vasculogenesis, the development of the embryonic vasculature from early differentiating endothelial cells, angiogenesis, the process of forming new blood vessels from pre-existing ones, and lymphangiogenesis, the process of forming new lymph vessels. The platelet derived growth factor (PDGF) proteins and their receptors (PDGFRs) are involved in regulation of cell proliferation, survival and migration of several cell types.

Dysfunction of the endothelial cell regulatory system is a key feature of cancer and various diseases associated with abnormal vasculogenesis, angiogenesis, and lymphangiogenesis.

Angiogenesis occurs in embryonic development and normal tissue growth, repair, and regeneration, and also in the female reproductive cycle, establishment and maintenance of pregnancy, and in repair of wounds and fractures. In addition to angiogenesis which takes place in the healthy individual, angiogenic events are involved in a number of pathological processes, notably tumor growth and metastasis, and other conditions in which blood vessel proliferation, especially of the microvascular system, is increased, such as diabetic retinopathy, psoriasis and arthropathies. Inhibition of angiogenesis is useful in preventing or alleviating these pathological processes.

Although therapies directed to blockade of VEGF/PDGF signaling through their receptors has shown promise for inhibition of angiogenesis and tumor growth, medicine needs new compounds and therapies for the treatment of such diseases.

SUMMARY OF THE INVENTION

The present invention relates to novel compositions and methods of use thereof for the inhibition of aberrant angiogenesis and lymphangiogenesis, and inhibition of other effects of members of the PDGF/VEGF family of growth factors: VEGF-A, VEGF-B, VEGF-C, VEGF-D, VEGF-E, PDGF, PDGF-A, PDGF-B, PDGF-C, and PDGF-D, each of which is able to bind at least one growth factor receptor tyrosine kinase and stimulate phosphorylation of the same. The compositions of the invention include binding constructs that bind one or more PDGF/VEGF molecules. The binding constructs include one or more binding units. In some embodiments, the binding unit comprises a polypeptide, e.g., a fragment of a growth factor receptor tyrosine kinase extracellular domain. The invention also provides nucleic acids encoding such binding constructs. Binding units are not limited to receptor fragments, nor are they limited to polypeptides, but rather comprise any species that binds a growth factor. Administration of the compositions of the invention to patients inhibits growth factor stimulation of VEGF receptors and/or PDGF receptors (e.g., inhibits phosphorylation of the receptors) and thereby inhibits biological responses mediated through the receptors including, but not limited to, PDGFR- and/or VEGFR-mediated angiogenesis and lymphangiogenesis.

Each member of the growth factor genus described above binds with high affinity to, and stimulation phosphorylation of, at least one PDGF receptor or VEGF receptor (or receptor heterodimer) selected from VEGFR-1, VEGFR-2, VEGFR-3, PDGFR-alpha, and PDGFR-beta. This statement refers to well known properties of the growth factors toward their cognate receptors, and is not meant as a limiting feature per se of the binding constructs of the invention. (For example, VEGF-A has been shown to bind to VEGFR-1 and VEGFR-2 and induce tyrosine phosphorylation of both receptors and initiate downstream receptor signaling.) However, preferred binding units of the invention do more than simply bind their target growth factors: a preferred binding construct also inhibits the growth factor(s) to which it binds from stimulating phosphorylation of at least one (and preferably all) of the receptor tyrosine kinases to which the growth factor(s) bind. Stimulation of tyrosine phosphorylation is readily measured using in vitro cell-based assays and anti-phosphotyrosine antibodies. Because phosphorylation of the receptor tyrosine kinases is an initial step in a signaling cascade, it is a convenient indicator of whether the binding construct is capable of inhibiting growth factor-mediated signal transduction that leads to cell migration, cell growth, and other responses. A number of other cell based and in vivo assays can be used to confirm the growth factor neutralizing properties of binding constructs of the invention.

As described herein, binding constructs can be chemically modified (e.g., heterologous peptide fusions, glycosylation, pegylation, etc.) to impart desired characteristics, while maintaining their specific growth factor binding properties. An exemplary peptide fusion comprises a immunoglobulin constant domain fragment. Exemplary desired characteristics imparted by chemical modifications include increased serum half life, increased solubility in an aqueous medium, and the ability to target a specific cell population, e.g., cancer cells.

Binding constructs and units that are "specific" for a particular growth factor are binding constructs and units that specifically recognize a circulating, active form of the growth factor. Preferably, the binding constructs specifically bind other forms of the growth factors as well. By way of example, VEGF-A exists in multiple isoforms, some of which circulate and others of which associate with heparin sulfate proteoglycans on cell surfaces. Binding constructs that are specific for VEGF-A bind to at least a circulating isoform, preferably all circulating isoforms, and more preferably, bind other major isoforms as well. By way of another example, VEGF-C is translated as a prepro-molecule with extensive amino-terminal and carboxy-terminal propeptides that are cleaved to yield a "fully processed" form of VEGF-C that binds and stimulates VEGFR-2 and VEGFR-3. Binding constructs specific for VEGF-C bind to at least the fully processed form of VEGF-C, and preferably also bind to partly processed forms and unprocessed forms.

Additional description is used herein when a more specialized meaning is intended. For example, VEGF-B167 is heparin bound whereas VEGF-B186 is freely secreted. An binding construct of the invention that minimally binds the circulating isoform is said to be specific for VEGF-B, and such a binding construct preferably also binds the heparin bound form. A binding construct of the invention that is "specific for heparin-bound VEGF-B" or "specific for VEGF-B167" is a binding construct that differentially recognizes the heparin bound isoform, compared to the freely circulating isoform. A binding construct of the invention that is specific for VEGF-B186" is a binding construct that differentially recognizes the circulating form, compared to the heparin bound form. Binding constructs specific for each isoform of a growth factor are contemplated as components of some embodiments of the binding constructs of the invention.

The designations "first" and "second" and "third" in respect to the binding units of the binding constructs is for ease and clarity in description only, and is not meant to signify a particular order, e.g., order in the amino acid sequence of a polypeptide binding construct.

A binding construct comprising two or more binding units may further comprise a linker connecting adjacent binding units. The linker may take on a number of different forms. Preferably, the linker comprises a peptide which allows adjacent binding units to be linked to form a single polypeptide.

The invention also includes compositions comprising a polypeptide, binding construct, or nucleic acid encoding the same, together with a pharmaceutically acceptable carrier. Such compositions may further comprise a pharmaceutically acceptable diluent, adjuvant, or carrier medium.

Nucleic acids (polynucleotides) of the invention include nucleic acids that constitute binding units, e.g., aptamers, and also nucleic acids that encode polypeptide binding units and constructs, which may be used for such applications as gene therapy and recombinant in vitro expression of polypeptide binding constructs. In some embodiments, nucleic acids are purified or isolated. In some embodiments, polynucleotides further comprise a promoter sequence operatively connected to a nucleotide sequence encoding a polypeptide, wherein the promoter sequence promotes transcription of the sequence that encodes the polypeptide in a host cell. Polynucleotides may also comprise a polyadenylation sequence.

Vectors comprising polynucleotides are also aspects of the invention. Such vectors may comprise an expression control sequence operatively connected to the sequence that encodes the polypeptide, and the vector may be selected from the group consisting of a lentivirus vector, an adeno-associated viral vector, an adenoviral vector, a liposomal vector, and combinations thereof. In some embodiments, the vector comprises a replication-deficient adenovirus, said adenovirus comprising the polynucleotide operatively connected to a promoter and flanked by adenoviral polynucleotide sequences. Host cells comprising the polynucleotides, vectors and other nucleic acids, and methods for using the same to express and isolate the binding constructs and units are also aspects of the invention.

For binding units of a binding construct that comprises an aptamer, the aptamer may be generated by preparing a library of nucleic acids; contacting the library of nucleic acids with a growth factor, wherein nucleic acids having greater binding affinity for the growth factor (relative to other library nucleic acids) are selected and amplified to yield a mixture of nucleic acids enriched for nucleic acids with relatively higher affinity and specificity for binding to the growth factor. The processes may be repeated, and the selected nucleic acids mutated and rescreened, whereby a growth factor aptamer is be identified. Nucleic acids may be screened to select for molecules that bind to more than growth factor.

In one aspect of the invention, the binding construct comprises a purified polypeptide comprising an amino acid sequence at least 95% identical to a vascular endothelial growth factor receptor 3(VEGFR-3) fragment, wherein the VEGFR-3 fragment comprises an amino acid sequence consisting of a portion of SEQ ID NO: 6, wherein the carboxy-terminal residue of the fragment is selected from the group consisting of positions 211 to 247 of SEQ ID NO: 6. The fragment, and the polypeptide comprising the same, specifically bind to at least one growth factor selected from the group consisting of human vascular endothelial growth factor-C (VEGF-C), and human vascular endothelial growth factor-D (VEGF-D). In some embodiments the VEGFR-3 fragments has an amino terminal amino acid selected from the group consisting of positions 1 to 47 of SEQ ID NO: 6. In some embodiments, the polypeptide comprises an amino acid sequence selected from the group consisting of SEQ ID NOS: 36 and 38. In some embodiments, the fragment has an amino acid sequence selected from the group consisting of positions 1-226 and 1-229 of SEQ ID NO: 6. In some embodiments, the polypeptide is part of a binding construct, and the polypeptide is operatively connected with a second polypeptide that binds at least one growth factor selected from the group consisting of VEGF-A, VEGF-B, VEGF-C, VEGF-D, VEGF-E, PDGF, PDGF-A, PDGF-B, PDGF-C, and PDGF-D. In some embodiments, the second polypeptide is selected from the group consisting of a polypeptide comprising a vascular endothelial growth factor receptor extracellular domain fragment, a platelet derived growth factor receptor extracellular domain fragment, and a polypeptide comprising an antigen binding fragment of an antibody that immunoreacts with the at least one of said growth factors. In some embodiments, at least one of the polypeptides is encoded by a polynucleotide comprising a nucleotide sequence selected from the group consisting of SEQ ID NOS: 35 and 37.

In another aspect of the invention, a binding construct comprises a purified polypeptide comprising an amino acid sequence at least 95% identical to a VEGFR-2 fragment, wherein the VEGFR-2 fragment comprises an amino acid sequence consisting of a portion of SEQ ID NO: 4, wherein the amino terminal amino acid of the VEGFR-2 fragment is selected from the group consisting of positions 106-145 of SEQ ID NO: 4, wherein the carboxy terminal amino acid of the VEGFR-2 fragment is selected from the group consisting of positions 203 to 240 of SEQ ID NO: 4, and wherein the VEGFR-2 fragment and the polypeptide bind VEGF-C or VEGF-D. In some embodiments, the polypeptide comprises an amino acid sequence selected from the group consisting of SEQ ID NO: 22, 24, and 26. In some embodiments, the fragment consists of an amino acid sequence selected from the group consisting of residues 118-220, 118-226, and 118-232 of SEQ ID NO: 4. In some embodiments, the polypeptide is part of a binding construct, and the polypeptide is operatively connected with a second polypeptide that binds at least one growth factor selected from the group consisting of VEGF-A, VEGF-B, VEGF-C, VEGF-D, VEGF-E, PDGF, PDGF-A, PDGF-B, PDGF-C, and PDGF-D. In some embodiments, the second polypeptide is selected from the group consisting of a polypeptide comprising a vascular endothelial growth factor receptor extracellular domain fragment, a platelet derived growth factor receptor extracellular domain fragment, and a polypeptide comprising an antigen binding fragment of an antibody that immunoreacts with the at least one of said growth factors. In some embodiments, at least one of the polypeptides is encoded by a polynucleotide comprising a nucleotide sequence selected from the group consisting of SEQ ID NOS: 21, 23, and 25.

In still another aspect, the invention provides a binding construct comprising a first polypeptide operatively connected to a second polypeptide. The first and second polypeptides each binds at least one growth factor selected from the group consisting of VEGF-A, VEGF-B, VEGF-C, VEGF-D, VEGF-E, PDGF, PDGF-A, PDGF-B, PDGF-C, and PDGF-D polypeptides. The amino acid sequence of the first polypeptide differs from the amino acid sequence of the second polypeptide. The first and second polypeptides comprise members independently selected from the group consisting of:

(a) a polypeptide comprising an amino acid sequence at least 90% identical to the VEGFR-1 extracellular domain amino acid sequence comprising positions 27-758 of SEQ ID NO: 2;

(b) a fragment of (a) that binds VEGF-A, VEGF-B, or PlGF;

(c) a polypeptide comprising an amino acid sequence at least 90% identical to the VEGFR-2 extracellular domain amino acid sequence comprising positions 20-764 of SEQ ID NO: 4;

(d) a fragment of (c) that binds VEGF-A, VEGF-C, VEGF-E or VEGF-D;

(e) a polypeptide comprising an amino acid sequence at least 90% identical to the VEGFR-3 extracellular domain amino acid sequence comprising residues 24-775 of SEQ ID NO: 6;

(f) a fragment of (e) that binds VEGF-C or VEGF-D;

(g) a polypeptide comprising an amino acid sequence at least 90% identical to the neuropilin-1 extracellular domain amino acid sequence comprising residues 22-856 of SEQ ID NO: 113;

(h) a fragment of (g) that binds VEGF-A, VEGF-B, VEGF-C, VEGF-E, or PlGF;

(i) a polypeptide comprising an amino acid sequence at least 90% identical to the neuropilin-2 extracellular domain amino acid sequence comprising residues 21-864 of SEQ ID NO: 115;

(j) a fragment of (i) that binds VEGF-A, VEGF-C, or PlGF;

(k) a polypeptide comprising an amino acid sequence at least 90% identical to the platelet derived growth factor receptor alpha extracellular domain amino acid sequence comprising residues 24-524 of SEQ ID NO: 117;

(l) a fragment of (k) that binds PDGF-A, PDGF-B, or PDGF-C;

(m) a polypeptide comprising an amino acid sequence at least 90% identical to the platelet derived growth factor beta extracellular domain amino acid sequence comprising residues 33 to 531 of SEQ ID NO: 119;

(n) a fragment of (m) that binds PDGF-B or PDGF-D; and (o) a polypeptide comprising an antigen binding fragment of an antibody that binds to at least one growth factor selected from the group consisting of VEGF-A, VEGF-B, VEGF-C, VEGF-D, VEGF-E, PDGF, PDGF-A, PDGF-B, PDGF-C, and PDGF-D.

In one embodiment, the binding construct of the invention comprises a first polypeptide comprising a fragment of a polypeptide comprising an amino acid sequence at least 90% identical to the VEGFR-2 extracellular domain amino acid sequence comprising positions 20-764 of SEQ ID NO: 4, wherein the fragment binds VEGF-A, VEGF-C, VEGF-E or VEGF-D. It is contemplated that the binding construct further comprises a second polypeptide comprising a fragment of a polypeptide comprising an amino acid sequence at least 90% identical to the VEGFR-1 extracellular domain amino acid sequence comprising positions 27-758 of SEQ ID NO: 2; wherein the fragment binds VEGF-A, VEGF-B, or PlGF. Additionally, it is contemplated that the binding construct further comprises a third polypeptide operatively connected to the first or second polypeptide, wherein the third polypeptide comprises a fragment of a polypeptide comprising an amino acid sequence at least 90% identical to the VEGFR-3 extracellular domain amino acid sequence comprising residues 24-775 of SEQ ID NO: 6, wherein the fragment binds VEGF-C or VEGF-D.

As described herein in greater detail, the extracellular domain of VEGFR or PDGFR have immunoglobulin-like domain structure. In a related embodiment, the binding construct of the invention comprises a first, second and third polypeptide as described above, wherein: (a) the first polypeptide comprises an amino acid sequence at least 90% identical to a fragment of the VEGFR-2 extracellular domain, wherein the fragment comprises immunoglobulin-like domain 2 amino acid sequence; (b) the second polypeptide comprises an amino acid sequence at least 90% identical to a fragment of the VEGFR-1 extracellular domain, wherein the fragment comprises immunoglobulin-like domain 3 amino acid sequence; and (c) the third polypeptide comprises an amino acid sequence at least 90% identical to a fragment of the VEGFR-3 extracellular domain, wherein said fragment comprises VEGFR-3 immunoglobulin-like domain 1 amino acid sequence.

In another aspect, the invention provides a binding construct comprising: a) a first amino acid sequence at least 90% identical to a fragment of the VEGFR-3 extracellular domain, wherein said fragment comprises VEGFR-3 immunoglobulin-like domain 1 amino acid sequence; (b) a second amino acid sequence at least 90% identical to a fragment of the VEGFR-2 extracellular domain, wherein the fragment comprises immunoglobulin-like domain 2 amino acid sequence; and, (c) a third amino acid sequence at least 90% identical to a fragment of the VEGFR-1 extracellular domain, wherein the fragment comprises immunoglobulin-like domain 3 amino acid sequence; wherein the first, second, and third amino acid sequences are operatively connected, and wherein the binding construct binds to at least VEGF-A and VEGF-C. In one embodiment, the binding construct comprises an amino acid sequence at least 95% identical to the amino acid sequence set out in SEQ ID NO: 128. In a related embodiment, the binding construct comprises the amino acid sequence of SEQ ID NO: 128.

In a second embodiment, the binding construct of the invention comprises a first polypeptide comprising a fragment of a polypeptide comprising an amino acid sequence at least 90% identical to the VEGFR-3 extracellular domain amino acid sequence comprising residues 24-775 of SEQ ID NO: 6, wherein the fragment binds VEGF-C or VEGF-D. It is contemplated that the binding construct of the invention comprises a second polypeptide comprising a fragment of a polypeptide comprising an amino acid sequence at least 90% identical to the VEGFR-2 extracellular domain amino acid sequence comprising positions 20-764 of SEQ ID NO: 4, wherein the fragment binds VEGF-A, VEGF-C, VEGF-E or VEGF-D.

In a related embodiment, the binding construct of the invention comprises a first and second polypeptide as described above, wherein: (a) the first polypeptide comprises an amino acid sequence at least 90% identical to a fragment of the VEGFR-3 extracellular domain, wherein said fragment comprises VEGFR-3 immunoglobulin-like domain 1 amino acid sequence; and, (b) the second polypeptide comprises an amino acid sequence at least 90% identical to a fragment of the VEGFR-2 extracellular domain, wherein the fragment comprises immunoglobulin-like domains 2 and 3 amino acid sequence.

In another aspect, the invention provides a binding construct comprising: a) a first amino acid sequence at least 90% identical to a fragment of the VEGFR-3 extracellular domain, wherein said fragment comprises VEGFR-3 immunoglobulin-like domain 1 amino acid sequence; and, (b) a second amino acid sequence at least 90% identical to a fragment of the VEGFR-2 extracellular domain, wherein the fragment comprises immunoglobulin-like domain 2 amino acid sequence; and an immunoglobulin-like domain 3 amino acid sequence; wherein the first, second, and third amino acid sequences are operatively connected, and wherein the binding construct binds to at least VEGF-A and VEGF-C. It is further contemplated that the construct binds VEGF-D. In one embodiment, the binding construct comprises an amino acid sequence at least 95% identical to the amino acid sequence set out in SEQ ID NO: 125. In a related embodiment, the binding construct comprises the amino acid sequence of SEQ ID NO: 125.

Preferably, the binding units of a binding construct are not exclusively (antibody) antigen binding fragments. In some embodiments, the binding construct comprises at least one non-antigen binding fragment binding unit. In some embodiments, the binding units all comprise antigen binding fragments. Exemplary Bispecific antibodies are provided in co-owned, concurrently (Mar. 5, 2004) filed U.S. Provisional Patent Application No. 60/550,511: "Multivalent Antibody Materials And Methods For VEGF/PDGF Family Of Growth Factors," and related, co-filed International Patent Application No. PCT/US05/07742, both applications incorporated herein by reference it their entirety.

Every method of using binding constructs of the invention, and nucleic acids encoding the same, whether for therapeutic, diagnostic, or research purposes, is another aspect of the invention.

For example, the invention further contemplates use of the binding constructs of the invention as a method for screening for inhibition of growth factor binding to receptor and decrease in receptor activation. In one aspect the invention provides a method of screening a binding construct for growth factor neutralization activity comprising: contacting a growth factor and a growth factor receptor in the presence and absence of a binding construct; and, measuring binding between the growth factor and the growth factor receptor in the presence and absence of the binding construct, wherein reduced binding in the presence of the binding construct indicates growth factor neutralization activity for the binding construct; wherein the growth factor comprises at least one member selected from the group consisting of VEGF-A, VEGF-B, VEGF-C, VEGF-D, VEGF-E, PDGF, PDGF-A, PDGF-B, PDGF-C, and PDGF-D and combinations thereof; wherein the receptor is at least one member selected from the group consisting of VEGFR-1, VEGFR-2, VEGFR-3, PDGFR-α, PDGFR-β; an extracellular domain fragment of any of said receptors that is effective to bind to the growth factor; a chimeric receptor comprising the extracellular domain fragment; and combinations thereof; and wherein the binding construct comprises a polypeptide or binding construct or a polynucleotide or vector according to the invention.

It is further contemplated in the screening method that the contacting is performed in a cell free system and the measuring of the binding comprises: measuring growth factor bound to the growth factor receptor. In a related embodiment, the contacting comprises contacting a cell that expresses the receptor with the growth factor; and wherein the measuring comprises: measuring growth factor receptor phosphorylation, wherein the phosphorylation is indicative of binding; measuring a growth factor-mediated cellular response in the cell, wherein the cellular response is indicative of binding between the growth factor and the receptor.

The substances are useful for any disorder where one PDGF/VEGF family member is overexpressed and especially useful if two or more are overexpressed.

For example, the invention includes a method of inhibiting fibrosis comprising administering to a mammalian subject in need of inhibition of fibrosis a binding construct of the invention.

For example, one aspect of the invention is a method for inhibiting angiogenesis or lymphangiogenesis comprising administering to a mammalian subject in need of inhibition of angiogenesis or lymphangiogenesis a binding construct according to the invention, in an amount effective to inhibit angiogenesis or lymphangiogenesis. Methods to determine the extent of inhibition of angiogenesis and lymphangiogenesis are described herein.

The invention further contemplates a method for inhibiting angiogenesis or lymphangiogenesis comprising administering to a mammalian subject in need of inhibition of angiogenesis or lymphangiogenesis a binding construct according to the invention, wherein the subject has a disease characterized by neoplastic cell growth exhibiting angiogenesis or lymphangiogenesis, and the binding construct is administered in an amount effective to inhibit the neoplastic cell growth. Neoplastic cell growth as used herein refers to multiplication of the cells which is uncontrolled and progressive. Cancers, especially vascularized cancers, are examples of neoplastic cell growth that is treatable using materials and methods of the invention.

It is further contemplated that the method of the invention is used wherein the subject has a disease characterized by aberrant angiogenesis or lymphangiogenesis, wherein the disease is selected from the group consisting of inflammation (chronic or acute), an infection, an immunological disease, arthritis, rheumatoid arthritis, diabetes, retinopathy, psoriasis, arthopathies, congestive heart failure, plasma leakage, fluid accumulation due to vascular permeability, lymphangioma, and lymphangiectasis.

The binding constructs also may be used to treat or prevent cancer associated disorders such as cancer associated ascites formation.

In one aspect, the invention provides a method of inhibiting endothelial or smooth muscle cell proliferation in a mammal, comprising administering to a mammal a composition, said composition comprising a polypeptide or binding construct, or a polynucleotide or vector encoding a binding construct, in an amount effective to inhibit endothelial cell proliferation in the mammal.

In some embodiments, the mammal to which the composition is administered has a neoplastic disease characterized by endothelial or smooth muscle cell growth. In some embodiments the neoplastic disease is selected from the group consisting of carcinomas, squamous cell carcinomas, lymphomas, melanomas, and sarcomas. Other cancers may be targeted as well as discussed herein. The composition is preferably administered in an amount effective to inhibit tumor growth or metastasis.

The method may also comprise the step of screening a mammal to identify a neoplastic disorder characterized by endothelial cell proliferation. In some embodiments, the subject of the method is a human, in other a non-human mammal, and in still others a non-mammalian species. In some embodiments, the screening step comprises screening the mammal for elevated serum levels of at least one growth factor selected from the group consisting of VEGF-A, VEGF-B, VEGF-C, VEGF-D, VEGF-E, PDGF, PDGF-A, PDGF-B, PDGF-C, and PDGF-D polypeptides. In some embodiments, the screening step comprises obtaining a tissue sample from the tumor and detecting elevated levels of at least one growth factor selected from the group consisting of VEGF-A, VEGF-B, VEGF-C, VEGF-D, VEGF-E, PDGF, PDGF-A, PDGF-B, PDGF-C, and PDGF-D polypeptides, or elevated levels of at least one receptor capable of binding the same. The method may also comprise the step of selecting a binding construct, wherein the binding construct binds to one or more of the elevated growth factors identified in the screening step, for use in the administration step.

The methods of the invention may also be carried out with more than one binding construct, or at least one binding construct in combination with another therapeutic. For example, other therapeutics that may be used in combination with the binding constructs of the invention include antisense RNA, RNA interference, bispecific antibodies, other antibody types, and small molecules, e.g., chemotherapeutic agents, which target growth factors and/or their receptors. A cytokine, radiotherapeutic agent, or radiation therapy may also be used in combination with a binding construct. The chemotherapeutic agent or radiotherapeutic agent may be a member of the class of agents including an anti-metabolite; a DNA-damaging agent; a cytokine or growth factor; a covalent DNA-binding drug; a topoisomerase inhibitor; an anti-mitotic agent; an anti-tumor antibiotic; a differentiation agent; an alkylating agent; a methylating agent; a hormone or hormone antagonist; a nitrogen mustard; a radiosensitizer; and a photosensitizer. Specific examples of these agents are described elsewhere in the application. Combination therapies are preferably synergistic, but they need not be, and additive therapies are also considered aspects of the invention.

In addition to their use in methods, the binding constructs may be combined or packaged with other therapeutics in kits or as unit doses. Neoplastic diseases are not the only diseases that may be treated with the binding constructs. The binding constructs may be used as therapeutics for any disease associated with abnormally high levels of growth factor expression.

This summary of the invention is not intended to be limiting or comprehensive, and additional embodiments are described in the drawings and detailed description, including the examples. All such embodiments are aspects of the invention. Moreover, for the sake of brevity, various details that are applicable to multiple embodiments have not been repeated for every embodiment. Variations reflecting combinations and rearrangements of the embodiments described herein are intended as aspects of the invention. In addition to the foregoing, the invention includes, as an additional aspect, all embodiments of the invention narrower in scope in any way than the variations specifically mentioned above. For example, for aspects described as a genus or range, every subgenus, subrange or species is specifically contemplated as an embodiment of the invention.

Figure 1:
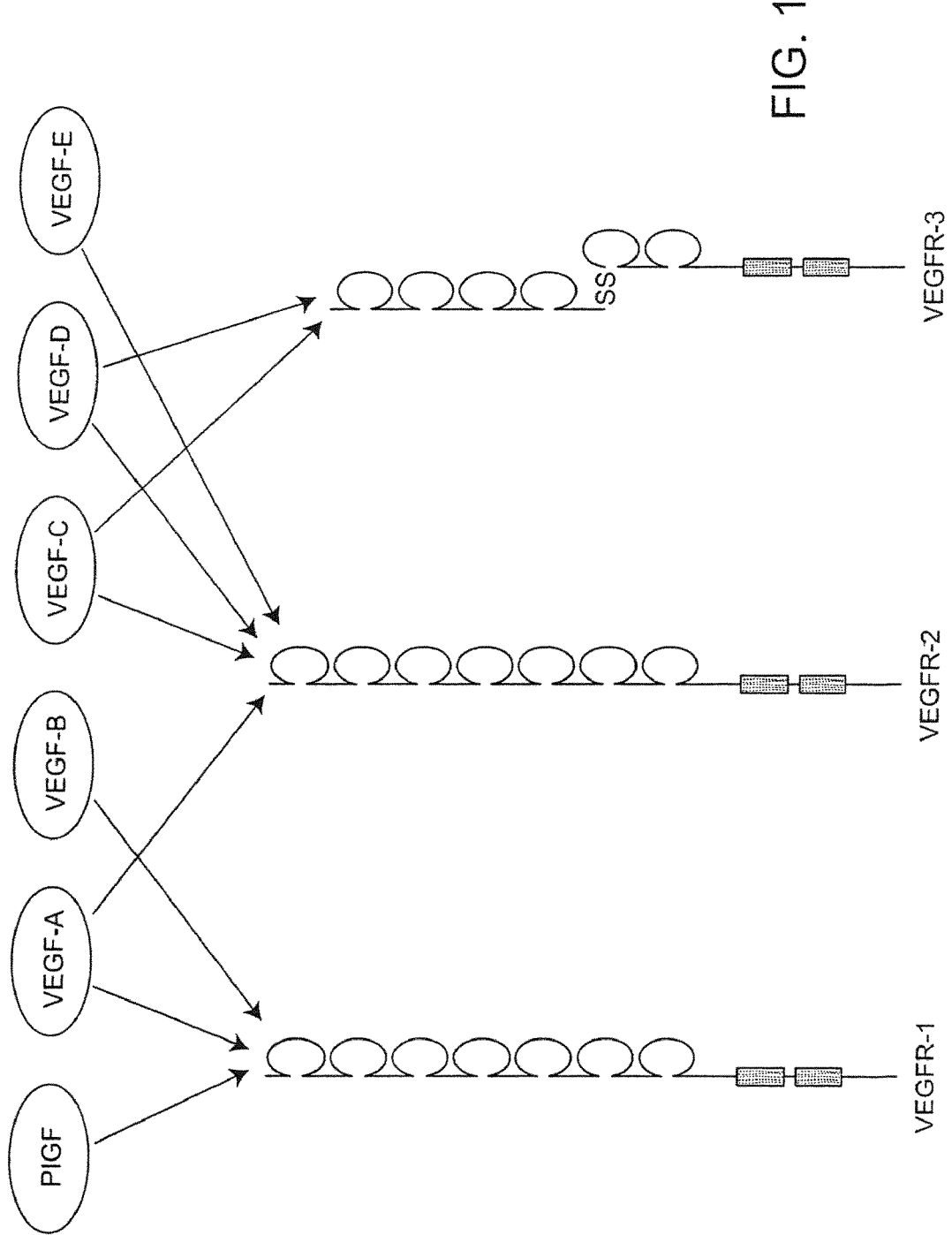
FIG. 1 is a schematic depiction of vascular endothelial growth factor receptors and ligands that bind the same.

While the disclosure is susceptible to various modifications and alternative constructions, certain illustrative embodiments thereof have been shown in the drawings and will be described herein in detail. It should be understood, however, that there is no intention to limit the disclosure to the specific forms disclosed, but on the contrary, the intention is to cover all modifications, alternative constructions, and the equivalents falling within the spirit and scope of the disclosure as defined by the appended claims.

DETAILED DESCRIPTION

The present invention provides novel binding constructs, compositions, and materials and methods for making and using the same. The binding constructs bind growth factors that exert angiogenic, lymphangenic, and other effects in vivo, and are useful for modulating those effects and also for purifying, isolating, and characterizing the growth factors.

I. BINDING CONSTRUCTS

For the purposes of this invention, a "binding construct" comprises one or more binding units associated with each other by covalent or other forms of attachment. A "binding unit" binds a growth factor ligand, i.e., one or more growth factor polypeptides, and preferably does so with high affinity. A binding unit preferably comprises at least one peptide or polypeptide, but other embodiments are possible as well, including organic small molecules, aptamers, and combinations of the same. While a binding unit preferably comprises a single polypeptide, it may comprise multiple polypeptides if a single polypeptide is not sufficient for binding a particular growth factor. When more than one binding unit or polypeptide segment is in a given binding construct, the binding units may be joined directly (i.e., through a covalent bond, e.g., a peptide, ester, or sulfhydryl bond, or non-covalently, e.g., hydrophobically) together via a linker. A binding construct may further include a heterologous peptide or other chemical moieties. Such additions are can modify binding construct properties such as stability, solubility, toxicity, serum half-life, immunogenicity, detectability, or other properties.

The term "high affinity" is used in a physiological context pertaining to the relative affinity of the binding construct for the growth factor ligand(s) in vivo in a mammal, such as a laboratory test animal, a domesticated farm or pet animal, or a human. The targeted growth factors of the invention, e.g., the VEGF/PDGF family members, have characteristic affinities for their receptors in vivo, typically measured in terms of sub-nanomolar dissociation constants ($K_d$). For the purposes of this invention, a binding construct can bind to its target growth factor(s) with a $K_d$ less than or equal to 1000 times the $K_d$ of the natural growth factor-receptor pair, while retaining the specificity of the natural pair. A binding unit that binds a growth factor with a $K_d$ less than or equal to 10 times the $K_d$ of the natural growth factor-receptor pair, while retaining the specificity of the natural pair, is considered high affinity. While high affinity is preferred, it is not a requirement. In a preferred embodiment, the affinity of the binding unit for the growth factor equals or exceeds the affinity of the natural receptor for the growth factor.

By binding activity is meant the ability to bind to a ligand, receptor, or binding construct, and does not require the retention of biological activity in so far as enzymatic activity or signaling is concerned. Binding may include either binding to a monomer or a dimer, homodimers or heterodimers, whether of receptors or ligands. Polypeptides for use according to the present invention can be used in the form of a protein dimer, particularly a disulfide-linked dimer. Mechanistic descriptions of binding constructs, e.g., as ligand traps, are not meant to be limiting. For example, a binding construct comprising a receptor extracellular domain fragment may function by forming inactive dimers with an endogenous receptor monomer.

In some embodiments, a binding construct comprises a first binding unit (e.g., a polypeptide) operatively associated with a second binding unit (e.g., a polypeptide), wherein each binding unit binds a growth factor selected from the group consisting of VEGF-A, VEGF-B, VEGF-C, VEGF-D, VEGF-E, PDGF, PDGF-A, PDGF-B, PDGF-C, PDGF-D, D1701 VEGF, NZ2 VEGF, NZ7 VEGF, and fallotein. In some embodiments the first and second binding units act together to bind a single ligand molecule (wherein the ligand may comprise a monomer or dimer). In some embodiments, the binding units act independently, i.e., each polypeptide binds a separate ligand molecule. In some embodiments, the first and second binding units are capable of either acting together or acting independently to bind one or more ligand polypeptides. In some embodiments, a binding unit of a first binding construct is able to interact with a binding unit on a second binding construct, e.g., to form dimers between binding units.

In some embodiments, the binding construct comprises a first polypeptide operatively connected to a second polypeptide, wherein the first and second polypeptides each binds at least one growth factor selected from the group consisting of VEGF-A, VEGF-B, VEGF-C, VEGF-D, VEGF-E, and PDGF polypeptides; wherein the amino acid sequence of the first polypeptide differs from the amino acid sequence of the second polypeptide; and wherein the first and second polypeptides comprise members independently selected from the group consisting of:

(a) a polypeptide comprising an amino acid sequence at least 35% identical to the VEGFR-1 extracellular domain amino acid sequence comprising positions 27-758 of SEQ ID NO: 2;

(b) a fragment of (a) that binds VEGF-A, VEGF-B, or PDGF;

(c) a polypeptide comprising an amino acid sequence at least 35% identical to the VEGFR-2 extracellular domain amino acid sequence comprising positions 20-764 of SEQ ID NO: 4;

(d) a fragment of (c) that binds VEGF-A, VEGF-C, VEGF-E or VEGF-D;

(e) a polypeptide comprising an amino acid sequence at least 35% identical to the VEGFR-3 extracellular domain amino acid sequence comprising residues 24-775 of SEQ ID NO: 6;

(f) a fragment of (e) that binds VEGF-C or VEGF-D;

(g) a polypeptide comprising an amino acid sequence at least 35% identical to the neuropilin-1 extracellular domain amino acid sequence comprising residues 22-856 of SEQ ID NO: 113;

(h) a fragment of (g) that binds VEGF-A, VEGF-B, VEGF-C, VEGF-E, or PDGF;

(i) a polypeptide comprising an amino acid sequence at least 35% identical to the neuropilin-2 extracellular domain amino acid sequence comprising residues 21-864 of SEQ ID NO: 115;

(j) a fragment of (i) that binds VEGF-A, VEGF-C, or PDGF;

(k) a polypeptide comprising an amino acid sequence at least 35% identical to the platelet derived growth factor receptor alpha extracellular domain amino acid sequence comprising residues 24-524 of SEQ ID NO: 117;

(l) a fragment of (k) that binds PDGF-A, PDGF-B, or PDGF-C;

(m) a polypeptide comprising an amino acid sequence at least 35% identical to the platelet derived growth factor beta extracellular domain amino acid sequence comprising residues 33 to 531 of SEQ ID NO: 119;

(n) a fragment of (m) that binds PDGF-B or PDGF-D;

(o) a polypeptide comprising an antigen binding fragment of an antibody that binds to at least one growth factor selected from the group consisting of VEGF-A, VEGF-B, VEGF-C, VEGF-D, VEGF-E, PDGF, PDGF-A, PDGF-B, PDGF-C, and PDGF-D;

(p) a polypeptide that binds at least one growth factor selected from the group consisting of VEGF-A, VEGF-B, VEGF-C, VEGF-D, VEGF-E, PDGF, PDGF-A, PDGF-B, PDGF-C, and PDGF-D polypeptides, wherein the polypeptide is generated using phage display; and (q) an organic molecule that mimics the binding properties of (a)-(p).

Preferably, the binding units of a binding construct are not exclusively polypeptides comprising (antibody) antigen binding fragments. In some embodiments, the binding construct comprises at least one non-antigen binding fragment comprising binding unit. In some embodiments, the binding construct comprises two or more receptor fragments. In some embodiments, the binding construct comprising at least one receptor fragment and at least one polypeptide comprising an antigen binding fragment.

In some embodiments, the binding units all comprise antigen binding fragments. Exemplary bispecific antibodies are provided in co-owned, concurrently (Mar. 5, 2004) filed U.S. Provisional Patent Application No. 60/550,511: "Multivalent Antibody Materials And Methods For VEGF/PDGF Family Of Growth Factors," and related, co-filed International Patent Application No. PCT/US05/07742, both applications incorporated herein by reference it their entirety.

In some embodiments, one or more of the polypeptides of a binding construct is replaced with another type of molecule, e.g., a nucleic acid, that mimics the binding properties of any of the polypeptides described above in (a) through (p). Such nucleic acids include, for example, aptamers.

A. Binding Units

The growth factors that are the targets of the binding constructs of the invention exert their physiological effects in vivo by binding to the extracellular domains of growth factor receptors. Accordingly, growth factor receptors and fragments thereof constitute examples of binding units. Exemplary human nucleotide and amino acid sequences, for relevant ligands and receptors are set forth in the sequence listing as summarized below:

TABLE 1A

RECEPTOR SEQUENCES

| RECEPTOR | SEQ ID NOS: |
|---|---|
| VEGFR-1 | 1 and 2 |
| VEGFR-2 | 3 and 4 |
| VEGFR-3 short | 5 and 6 |
| VEGFR-3 long | 120 and 121 |
| PDGFR-α | 116 and 117 |
| PDGFR-β | 118 and 119 |
| Neuropilin-1 | 112 and 113 |
| Neuropilin-2 | 114 and 115 |

TABLE 1B

RECEPTOR SEQUENCES

| LIGAND | SEQ ID NOS: |
|---|---|
| VEGF-A | 80 and 81 |
| VEGF-A 232 isoform | 90 and 91 |
| VEGF-B isoform 1 | 94 and 95 |
| VEGF-B isoform 2 | 96 and 97 |

TABLE 1B-continued

RECEPTOR SEQUENCES

| LIGAND | SEQ ID NOS: |
| --- | --- |
| VEGF-C | 82 and 83 |
| VEGF-D | 86 and 87 |
| VEGF-E (NZ7) | 88 and 89 |
| PlGF | 84 and 85 |
| D1701 VEGF | 92 and 93 |
| PDGF-A | 98 and 99 |
| PDGF-B | 100 and 101 |
| PDGF-C | 102 and 103 |
| PDGF-D | 104 and 105 |

Other VEGF growth factors members include snake venom VEGFs (e.g., EMBL. AY033151, AY033152, and AY42981), various VEGF-E (orf virus VEGF homologs, some of which are presented in Table 1B) molecules including VEGF-E NZ2 [S67520], VEGF-E NZ7, VEGF-E D1701, VEGF-E Orf-11, and VEGF-E OV-IA82. [See generally, WO 00/25085.]

Members of the PDGF/VEGF family are characterized by a number of structural motifs including a conserved PDGF motif defined by the sequence: P—[PS]—C—V—X(3)-R—C-[GSTA]-G-C—C (SEQ ID NO: 111), where the brackets indicate a variable position that can be any one of the amino acids within the brackets. The number contained within the parentheses indicates the number of amino acids that separate the "V" and "R" residues. This conserved motif falls within a large domain of 70-150 amino acids defined in part by eight highly conserved cysteine residues that form inter- and intramolecular disulfide bonds. This domain forms a cysteine knot motif composed of two disulfide bonds which form a covalently linked ring structure between two adjacent β strands, and a third disulfide bond that penetrates the ring [see for example, FIG. 1 in Muller et al., Structure 5:1325-1338 (1997)], similar to that found in other cysteine knot growth factors, e.g., transforming growth factor-β (TGF-β). The amino acid sequence of all known PDGF/VEGF proteins, with the exception of VEGF-E, contains the PDGF domain. The PDGF/VEGF family proteins are predominantly secreted glycoproteins that form either disulfide-linked or non-covalently bound homo- or heterodimers whose subunits are arranged in an anti-parallel manner [Stacker and Achen, Growth Factors 17:1-11 (1999); Muller et al., Structure 5:1325-1338 (1997)]. Binding constructs of the invention include those that bind VEGF/PDGF growth factor monomers, homodimers, and heterodimers.

The VEGF subfamily is composed of members that share a VEGF homology domain (VHD) characterized by the sequence: C—X(22-24)-P—[PSR]—C—V—X(3)—R—C-[GSTA]-G—C—C—X(6)-C—X(32-41)-C. (SEQ ID: 110) The VHD domain, determined through analysis of the VEGF subfamily members, comprises the PDGF motif but is more specific. The VEGF subfamily of growth factors and receptors regulate the development and growth of the vascular endothelial system. VEGF family members include, but are not limited to VEGF-A, VEGF-B, VEGF-C, VEGF-D and PlGF [Li, X. and U. Eriksson, "Novel VEGF Family Members: VEGF-B, VEGF-C and VEGF-D," Int. J. Biochem. Cell. Biol., 33(4):421-6 (2001))] Other VEGFs are bacterial or viral, the "VEGF-Es." Other VEGFs are derived from snake venom, the "NZ" series. [See e.g., Komori, et al. Biochemistry, 38(36):11796-803 (1999); Gasmi, et al., Biochem Biophys Res Commun, 268(1):69-72 (2002); Gasmi, et al., J Biol Chem; 277(33):29992-8 (2002); de Azevedo, et al., J. Biol. Chem., 276: 39836-39842 (2001)].

At least seven cell surface receptors that interact with PDGF/VEGF family members have been identified. These include PDGFR-α [See e.g., GenBank Acc. No. NM006206; Swiss Prot No. P16234], PDGFR-β [See e.g., GenBank Acc. No. NM002609; Swiss Prot. No. P09619], VEGFR-1/Flt-1 (fms-like tyrosine kinase-1; hereinafter "R-1") [GenBank Acc. No. X51602; De Vries, et al., Science 255:989-991 (1992)]; VEGFR-2/KDR/Flk-1 (kinase insert domain containing receptor/fetal liver kinase-1, hereinafter "R-2") [GenBank Acc. Nos. X59397 (Flk-1) and L04947 (KDR); Terman, et al., Biochem. Biophys. Res. Comm. 187:1579-1586 (1992); Matthews, et al., Proc. Natl. Acad. Sci. USA 88:9026-9030 (1991)]; VEGFR-3/Flt4 (fms-like tyrosine kinase 4; hereinafter "R-3") [U.S. Pat. No. 5,776,755 and GenBank Acc. No. X68203 and S66407; Pajusola et al., Oncogene 9:3545-3555 (1994); Hughes, et al., J. Mol. Evol. 52(2):77-79 (2001); Pajusola, et al., Oncogene 8(11):2931-37 (1993); Borg, et al., Oncogene 10(5):973-984 (1995), neuropilin-1 [Gen Bank Acc. No. NM003873], and neuropilin-2 [Gen Bank Acc. No. NM003872; SwissProt O60462]. The two PDGF receptors mediate signaling of PDGFs. Non-human VEGF and PDGF receptors may also be employed as part of the invention, e.g., chicken VEGFR-1 may be used alone or in hybrid form with human R-1 for improved expression.

VEGF121, VEGF165, VEGF-B, PlGF-1 and PlGF-2 bind VEGF-R1; VEGF121, VEGF145, VEGF165, (fully processed mature) VEGF-C, (fully processed mature) VEGF-D, VEGF-E, and NZ2 VEGF bind VEGF-R2; VEGF-C and VEGF-D bind VEGFR-3; VEGF165, VEGF-C, PlGF-2, and NZ2 VEGF bind neuropilin-1; and VEGF165 and VEGF-C binds neuropilin-2. [Neufeld, et al., FASEB. J. 13:9-22 (1999); Stacker and Achen, Growth Factors 17:1-11 (1999); Ortega, et al., Fron. Biosci. 4:141-152 (1999); Zachary, Intl. J. Biochem. Cell. Bio. 30:1169-1174 (1998); Petrova, et al., Exp. Cell. Res. 253:117-130 (1999); U.S. Pat. Appl. Pub. No. 20030113324]. Ligand, receptor interactions for the VEGFR subfamily are summarized in FIG. 1. PDGF-A, PDGF-B, and PDGF-C bind PDGFR-α. PDGF-B and PDGF-D bind PDGF-β.

Both the ligands and the receptors generally exist as dimers, including both homodimers and heterodimers. Such dimers can influence binding. For example, for the PDGFs, PDGF-AA binds PDGFR-α/α. PDGF-AB and PDGF-CC bind PDGFR-α/α and PDGFR-α/β. PDGFR-BB binds both of the homodimers and the heterodimeric PDGF receptor. PDGF-DD binds PDGF receptor heterodimers and beta receptor homodimers. [See, e.g., Pietras, et al., Cancer Cell, 3:439-443 (2003).] VEGF-A can heterodimerize with VEGF-B and PlGF. The VEGFs, PDGFs, and PlGFs, may exist as two or more isoforms, e.g., splice variants, and not all isoforms of a particular growth factor will share the same binding profile, or ability to dimerize with particular molecules. Certain isoforms of the same growth factor may also dimerize with each other. For example the 167 and 186 isoforms of VEGF-B can heterodimerize with each other.

Growth factor receptor tyrosine kinases generally comprise three principal domains: an extracellular domain, a transmembrane domain, and an intracellular domain. The extracellular domain binds ligands, the transmembrane domain anchors the receptor to a cell membrane, and the intracellular domain possesses one or more tyrosine kinase enzymatic domains and interacts with downstream signal transduction molecules. The vascular endothelial growth factor receptors (VEGFRs) and platelet derived growth factor receptors (PDGFRs) bind their ligand through their extracellular domains (ECDs), which are comprised of multiple immunoglobulin-like domains (Ig-domains). Ig-domains are identified herein using the designation "D#." For example "D1" refers to the first Ig-domain of a particular receptor ECD. "D1-3" refers to a construct containing at least the first three Ig-domains, and intervening sequence between domains 1 and 2 and 2 and 3, of a particular construct. Table 2 defines the boundaries of the Ig-domains for VEGFR-1, VEGFR-2, and VEGFR-3 of the invention. These boundaries are significant as the boundaries chosen can be used to form constructs, and so can influence the binding properties of the resulting constructs. This relationship is discussed in Example 1.

The complete ECD of PDGFRs and VEGFRs is not required for ligand (growth factor) binding. The ECD of VEGFR-1 (R-1) and VEGFR-2 (R-2) consists of seven Ig-like domains and the ECD of VEGFR-3 (R-3) has six intact Ig-like domains—D5 of R-3 is cleaved post-translationally into disulfide linked subunits leaving VEGFR-3. Veikkola, T., et al., Cancer Res. 60:203-212 (2000). In general, receptor fragments of at least the first three Ig-domains for this family are sufficient to bind ligand. The PDGFRs have five Ig-domains.

ally, Ferrara, J. Mol. Med. 77:527-543 (1999).] Two VEGF-β isoforms generated by alternative mRNA splicing exist, VEGF-B186 and VEGF-B167, with the first isoform accounting for about 80% of the total VEGF-B transcripts [Li, X., et al., Growth Factor, 19:49-59 (2001); Grimmond, et al., Genome Res., 6:124-131 (1996); Olofsson, et al., J. Biol. Chem., 271:19310-19317 (1996).] Three isoforms of PlGF produced by alternative mRNA splicing have been described [Hauser, et al., Growth Factors 9:259-268 (1993); Maglione, et al., Oncogene 8:925-931 (1993)]. PDGF-A and PDGF-B can homodimerize or heterodimerize to produce three different isoforms: PDGF-AA, PDGF-AB, or PDGF-BB.

The term "identity", as known in the art, refers to a relationship between the sequences of two or more polypeptide molecules or two or more nucleic acid molecules, as determined by comparing the sequences. In the art, "identity" also means the degree of sequence relatedness nucleic acid molecules or polypeptides sequences, as the case may be, as determined by the match between strings of two or more nucleotide or two or more amino acid sequences. "Identity" measures the percent of identical matches between the

TABLE 2

IMMUNOGLOBULIN-LIKE DOMAINS FOR VEGFR-1, VEGFR-2 AND VEGFR-3

| | R-1 SEQ ID NO: 1 positions | R-1 SEQ ID NO: 2 positions | R-2 SEQ ID NO: 3 positions | R-2 SEQ ID NO: 4 positions | R-3 SEQ ID NO: 5 positions | R-3 SEQ ID NO: 6 positions |
|---|---|---|---|---|---|---|
| D1 | 394-580 | 49-111 | 145-316 | 48-105 | 158-364 | 47-115 |
| D2 | 709-880 | 154-211 | 436-610 | 145-203 | 479-649 | 154-210 |
| D3 | 990-1192 | 248-315 | 724-931 | 241-310 | 761-961 | 248-314 |
| D4 | 1303-1474 | 352-409 | 1039-1204 | 346-401 | 1070-1228 | 351-403 |
| D5 | 1957-1864 | 450-539 | 1321-1600 | 440-533 | 1340-1633 | 441-538 |
| D6 | 1966-2167 | 573-640 | 1699-1936 | 566-645 | 1739-1990 | 574-657 |
| D7 | 2281-2452 | 678-735 | 2050-2221 | 683-740 | 2102-2275 | 695-752 |

In some embodiments, a binding unit of a binding construct comprises the ECD of a growth factor receptor. A binding unit may comprise at least one Ig-domain of a VEGFR as described in Table 2, to as many as seven. Ig-domain information for PDGFR-α and PDGFR-β is provided in Lokker, et al., J. Biol. Chem. 272: 33037-33044 (1997), which is incorporated by reference in its entirety. A binding unit may include sequence before the N-terminal most Ig-domain, may include sequence beyond the C-terminal most Ig-domain, and may include sequence between the Ig-domains as well. Binding units may also comprise variants, e.g., with one or more amino acid substitutions, additions, or deletions of an amino acid residue. Binding units also may comprise chimeras, e.g., combinations of Ig-domains from different receptors. In some embodiments, the first or second polypeptide comprises a receptor fragment comprising at least the first three Ig domains of a receptor tyrosine kinase.

The binding of a binding unit to a particular growth factor ligand refers to the ability to bind at least one natural isoform of at least one target growth factor, especially processed forms that are secreted from cells and circulate in vivo and/or bind heparin moieties. For example, "capable of binding VEGF-A" refers to the ability to bind at least one isoform of VEGF-A under physiological conditions. At least five human VEGF-A isoforms of 121, 145, 165, 189 or 206 amino acids in length (VEGF121-VEGF206), encoded by distinct mRNA splice variants, have been described, all of which are capable of stimulating mitogenesis in endothelial cells. [See genersmaller of two or more sequences with gap alignments (if any) addressed by particular a mathematical model of computer program (i.e., "algorithms"). Appropriate algorithms for determining the percent identities of the invention include BLASTP and BLASTN, using the most common and accepted default parameters.

1. VEGFR-1-Derived Binding Units

In some embodiments, a binding unit comprises a polypeptide similar or identical in amino acid sequence to a VEGFR-1 polypeptide or fragment thereof, preferably from the same species as the targeted growth factor(s). Thus, for binding to human growth factors, a binding unit preferably comprises a polypeptide that comprises an amino acid similar or identical to a fragment of SEQ ID NO: 2, wherein the fragment and the polypeptide binds one or more growth factors selected from the group consisting of VEGF-A, VEGF-B, and PlGF. The fragment minimally comprises enough of the VEGFR-1 sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated.

Preferred polypeptides may also be described as having an amino acid sequence encoded by a nucleic acid sequence at least 80% identical to a fragment of SEQ ID NO:1 encoding a ligand binding fragment of VEGFR-1. Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the R-1 receptor. For example, a preferred binding unit polypeptide comprises an amino acid sequence that binds one or more R-1 ligands and that is encoded by a nucleotide sequence that hybridizes to the complement of SEQ ID NO: 1 under moderately or highly stringent conditions discussed herein.

Exemplary R1 fragments for use as binding unit polypeptides (or for use as a starting point for designing R-1 analogs) have an amino terminal residue selected from the group consisting of positions 1 to 129 of SEQ ID NO: 2, and a carboxy terminal residue selected from the group consisting of positions 229 to 758 of SEQ ID NO: 2, wherein the VEGFR-1 fragment binds at least one of VEGF-A, VEGF-B, and PlGF.

2. VEGFR-2-Derived Binding Units

In some embodiments, a binding unit comprises a polypeptide similar or identical in amino acid sequence to a VEGFR-2 polypeptide or fragment thereof, preferably from the same species as the targeted growth factor(s). Thus, for binding to human growth factors, a binding unit preferably comprises a polypeptide that comprises an amino acid similar or identical to a fragment of SEQ ID NO: 4, wherein the fragment and the polypeptide binds one or more growth factors selected from the group consisting of VEGF-A, VEGF-C, VEGF-D, or VEGF-E. The fragment minimally comprises enough of the VEGFR-2 sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated.

Preferred polypeptides may also be described as having an amino acid sequence encoded by a nucleic acid sequence at least 80% identical to a fragment of SEQ ID NO:3 encoding a ligand binding fragment of VEGFR-2. Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the R-2 receptor. For example, a preferred binding unit polypeptide comprises an amino acid sequence that binds one or more R-2 ligands and that is encoded by a nucleotide sequence that hybridizes to the complement of SEQ ID NO: 3 under moderately or highly stringent conditions discussed herein.

Exemplary R2 fragments for use as binding unit polypeptides (or for use as a starting point for designing R-2 analogs) have an amino terminal residue selected from the group consisting of positions 1 to 118 of SEQ ID NO: 4, and a carboxy terminal residue selected from the group consisting of positions 326 to 764 of SEQ ID NO: 4, wherein VEGFR-2 fragment binds at least one of VEGF-A, VEGF-C, VEGF-D, and VEGF-E. Exemplary R2 fragments for use as binding unit polypeptides (or for use as a starting point for designing R-2 analogs) may alternatively have an amino terminal residue selected from the group consisting of positions 1 to 192 of SEQ ID NO: 4, and a carboxy terminal residue selected from the group consisting of positions 393 to 764 of SEQ ID NO: 4, wherein the VEGFR-2 fragment binds at least one of VEGF-A, VEGF-C, VEGF-D, and VEGF-E. Exemplary R2 fragments for use as binding unit polypeptides (or for use as a starting point for designing R-2 analogs) may also have an amino terminal residue selected from the group consisting of positions 1 to 48 of SEQ ID NO: 4, and a carboxy terminal residue selected from the group consisting of positions 214 to 764 of SEQ ID NO: 4, wherein the VEGFR-2 fragment binds at least one of VEGF-A, VEGF-C, VEGF-D, and VEGF-E.

In some embodiments, a binding unit of the binding construct comprises a fragment of R-2, SEQ ID NO: 4, selected from the group consisting of positions 24-326 (SEQ ID NO: 8), 118-326 (SEQ ID NO: 20), positions 118-220 (SEQ ID NO: 22), positions 118-226 (SEQ ID NO: 24), and positions 118-232 (SEQ ID NO: 26). In some embodiments, a binding unit of the binding construct comprises a fragment of R-2, SEQ ID NO: 4, selected from the group consisting of positions 106-240, positions 112-234, positions 114-220, positions 115-220, positions 116-222, positions 117-220, positions 118-221, positions 118-222, positions 118-223, positions 118-224, and positions 118-228. In some embodiments, a binding unit of the binding construct comprises a fragment of R-2, SEQ ID NO: 4, selected from the group consisting of positions 48-203, and 145-310 and 48-310. Exemplary embodiments are also discussed in Example 1.

3. VEGFR-3-Derived Binding Units

In some embodiments, a binding unit comprises a polypeptide similar or identical in amino acid sequence to a VEGFR-3 polypeptide or fragment thereof, preferably from the same species as the targeted growth factor(s). Thus, for binding to human growth factors, a binding unit preferably comprises a polypeptide that comprises an amino acid similar or identical to a fragment of SEQ ID NO: 6, where the fragment and the polypeptide binds one or more growth factors selected from the group consisting of VEGF-C and VEGF-D. The fragment minimally comprises enough of the VEGFR-3 sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the R-3 receptor.

Preferred polypeptides may also be described as having an amino acid sequence encoded by a nucleic acid sequence at least 80% identical to a fragment of SEQ ID NO:5 encoding a ligand binding fragment of VEGFR-3. Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. For example, a preferred binding unit polypeptide comprises an amino acid sequence that binds one or more R-3 ligands and that is encoded by a nucleotide sequence that hybridizes to the complement of SEQ ID NO: 5 under moderately or highly stringent conditions discussed herein.

Exemplary R-3 fragments for use as binding unit polypeptides (or for use as a starting point for designing R-3 analogs) have an amino terminal residue selected from the group consisting of positions 1 to 47 of SEQ ID NO: 6, and a carboxy terminal residue selected from the group consisting of positions 226 to 775 of SEQ ID NO: 6, wherein VEGFR-3 fragment binds at least one of VEGF-C and VEGF-D.

In some embodiments, a binding unit of the binding construct comprises a fragment of R-3, SEQ ID NO: 6, selected from the group consisting of positions 1-226 (SEQ ID NO: 38), positions 1-229 (SEQ ID NO: 36), and positions 1-329 (SEQ ID NO: 44). In some embodiments, a binding unit of the binding construct comprises a fragment of R-3, SEQ ID NO: 6, selected from the group consisting of positions 47-224, positions 47-225, positions 47-226, positions 47-227, positions 47-228, positions 47-229, positions 47-230, positions 47-231, positions 47-232, positions 47-236, positions 47-240, and positions 47-245. In some embodiments, a binding unit of the binding construct comprises a fragment of R-3, SEQ ID NO: 6, selected from the group consisting of positions 47-314, positions 47-210, and positions 47-247. Exemplary embodiments are also discussed in Example 1.

4. Neuropilin-1-Derived Binding Units

In some embodiments, a binding unit comprises a polypeptide similar or identical in amino acid sequence to a neuropilin-1 polypeptide or fragment thereof, preferably from the same species as the targeted growth factor(s). Thus, for binding to human growth factors, a binding unit preferably comprises a polypeptide that comprises an amino acid similar or identical to a fragment of SEQ ID NO: 113, where the fragment and the polypeptide binds one or more growth factors selected from the group consisting of VEGF-A, VEGF-B, VEGF-C, VEGF-E, and PlGF. The fragment minimally comprises enough of the neuropilin-1 sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated.

Preferred polypeptides may also be described as having an amino acid sequence encoded by a nucleic acid sequence at least 80% identical to a fragment of SEQ ID NO:112 encoding a ligand binding fragment of neuropilin-1. Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the neuropilin-1 receptor. For example, a preferred binding unit polypeptide comprises an amino acid sequence that binds one or more neuropilin-1 ligands and that is encoded by a nucleotide sequence that hybridizes to the complement of SEQ ID NO: 112 under moderately or highly stringent conditions discussed herein.

Exemplary neuropilin-1 fragments for use as binding unit polypeptides (or for use as a starting point for designing neuropilin-1 analogs) comprise a neuropilin-1 extracellular domain amino acid sequence comprising residues 22-856 of SEQ ID NO: 113, or a portion thereof; wherein the neuropilin-1 fragment and the binding unit bind at least one growth factor selected from the group consisting of VEGF-A, VEGF-B, VEGF-C, VEGF-E, and PlGF.

5. Neuropilin-2-Derived Binding Units

In some embodiments, a binding unit comprises a polypeptide similar or identical in amino acid sequence to a neuropilin-2 polypeptide or fragment thereof, preferably from the same species as the targeted growth factor(s). Thus, for binding to human growth factors, a binding unit preferably comprises a polypeptide that comprises an amino acid similar or identical to a fragment of SEQ ID NO: 115, wherein the fragment and the polypeptide binds one or more growth factors selected from the group consisting of VEGF-A, VEGF-C, and PlGF. The fragment minimally comprises enough of the neuropilin-2 sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated.

Preferred polypeptides may also be described as having an amino acid sequence encoded by a nucleic acid sequence at least 80% identical to a fragment of SEQ ID NO:114 encoding a ligand binding fragment of neuropilin-2. Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the neuropilin-2 receptor. For example, a preferred binding unit polypeptide comprises an amino acid sequence that binds one or more neuropilin-2 ligands and that is encoded by a nucleotide sequence that hybridizes to the complement of SEQ ID NO: 114 under moderately or highly stringent conditions discussed herein.

Exemplary neuropilin-2 fragments for use as binding unit polypeptides comprising residues 21-864 of SEQ ID NO: 115, or a portion thereof; wherein the neuropilin-2 fragment and the binding unit bind at least one growth factor selected from the group consisting of VEGF-A, VEGF-C, and PlGF.

Further neuropilin-1 and -2 species, isoforms, soluble fragments, etc., are provided in WO03/029814, U.S. application Ser. Nos. 10/262,538, 10/669,176, and 60/505,607, which are incorporated by reference in their entireties.

6. PDGFR-Alpha-Derived Binding Units

In some embodiments, a binding unit comprises a polypeptide similar or identical in amino acid sequence to a PDGFR-α polypeptide or fragment thereof, preferably from the same species as the targeted growth factor(s). Thus, for binding to human growth factors, a binding unit preferably comprises a polypeptide that comprises an amino acid similar or identical to a fragment of SEQ ID NO: 117, where the fragment and the polypeptide binds one or more growth factors selected from the group consisting of PDGF-A, PDGF-B, and PDGF-C. The fragment minimally comprises enough of the PDGFR-α sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the R-α receptor.

Preferred polypeptides may also be described as having an amino acid sequence encoded by a nucleic acid sequence at least 80% identical to a fragment of SEQ ID NO:116 encoding a ligand binding fragment of R-α Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. For example, a preferred binding unit polypeptide comprises an amino acid sequence that binds one or more R-α ligands and that is encoded by a nucleotide sequence that hybridizes to the complement of SEQ ID NO: 116 under moderately or highly stringent conditions discussed herein.

Exemplary R-α fragments for use as binding unit polypeptides (or for use as a starting point for designing R-α analogs) have an amino terminal residue selected from the group consisting of positions 1 to 123 of SEQ ID NO: 117, and a carboxy terminal residue selected from the group consisting of positions 313 to 524 of SEQ ID NO: 117, wherein the PDGFR-α fragment binds at least one of PDGF-A, PDGF-B, and PDGF-C.

7. PDGFR-Beta-Derived Binding Units

In some embodiments, a binding unit comprises a polypeptide similar or identical in amino acid sequence to a R-β polypeptide or fragment thereof, preferably from the same species as the targeted growth factor(s). Thus, for binding to human growth factors, a binding unit preferably comprises a polypeptide that comprises an amino acid similar or identical to a fragment of SEQ ID NO: 119, where the fragment and the polypeptide binds one or more growth factors selected from the group consisting of PDGF-B and PDGF-D. The fragment minimally comprises enough of the PDGFR-β sequence to bind the ligand, and may comprise the complete receptor. Extracellular domain fragments are preferred. Preferred polypeptides have an amino acid sequence at least 80% identical to a ligand binding fragment thereof. Fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. A genus of similar polypeptides can alternatively be defined by the ability of encoding polynucleotides to hybridize to the complement of a nucleotide sequence that corresponds to the cDNA sequence encoding the R-β receptor.

Preferred polypeptides may also be described as having an amino acid sequence encoded by a nucleic acid sequence at least 80% identical to a fragment of SEQ ID NO:118 encoding a ligand binding fragment of PDGFR-β. Nucleic acid fragments that are more similar, e.g., 85%, 90%, 91%, 92%, 93%, 94%, 95%, 96%, 97%, 98%, 99%, 99.5%, or 100% are highly preferred. Fragments that are 35%, 40%, 45%, 50%, 55%, 60%, 65%, 70%, and 75% are also contemplated. For example, a preferred binding unit polypeptide comprises an amino acid sequence that binds one or more R-β ligands and that is encoded by a nucleotide sequence that hybridizes to the complement of SEQ ID NO: 118 under moderately or highly stringent conditions discussed herein.

Exemplary R-β fragments for use as binding unit polypeptides (or for use as a starting point for designing R-β analogs) have an amino terminal residue selected from the group consisting of positions 1 to 124 of SEQ ID NO: 119, and a carboxy terminal residue selected from the group consisting of positions 314 to 531 of SEQ ID NO: 119, wherein PDGFR-β fragment binds at least one of PDGF-B and PDGF-D.

8. Other Binding Units

Although a binding unit may comprise a polypeptide similar or identical to an extracellular domain fragment of a growth factor receptor tyrosine kinase, other binding units are contemplated as well. In some embodiments, the binding unit is generated using phage display. In some embodiments, the binding unit comprises an antibody. In some embodiments, a binding unit comprises a polypeptide comprising an antibody (antigen binding) fragment, e.g., a domain antibody. Binding units, as well as binding constructs, need not comprise a polypeptide. In some embodiments, the binding construct comprises nucleic acid, e.g., DNA or RNA, such as an aptamer. In some embodiments, the binding construct comprises polysaccharides.

Growth factor binding molecules that have been described in the literature may be used as binding units to construct binding constructs of the inventory including molecules taught by the following: Veikkola, T., et al., *Cancer Res.* 60:203-212 (2000); Davis-Smyth, T., et al., *EMBO J.*, 15(18): 4919-27 (1996), U.S. Pat. Nos. 5,952,199; 6,100,071; 6,383,486; U.S. Pat. Appl. Nos. 20030092604; Niwa, et al., U.S. Pat. No. 6,348,333; Fairbrother, et al., *Biochemistry*, 37:17754-64 (1998); Starovasnik, M. et al., *J. Mol. Biol.*, 293: 531-44 (1999); Wiesmann, C., et al., *Cell*, 91:695-704 (1997); Fuh, et al., *J. Biol. Chem.*, 273(18): 11197-11204 (1998); Shinkai, A. et al., *J. Biol. Chem.*, 273(47):31283-88 (1998); Lu, et al., *J. Biol. Chem.*, 275(19): 14321-14330 (2000); Lu et al., *J. Immunological Methods*, 230:159-71 (1999); Lu, et al., *J. Biol. Chem.*, 278(44): 43496-43507 (2003); Makkinen, T., et al., *Nature Medicine*, 7(2), 199-205 (2001); Alitalo, et al., WO 02/060950; Karpanen, T., et al., *Cancer Research* 61:1786-90 (2001); Liu, et al., U.S. Pat. Appl. Publ. No. 2003/0064053; Kubo, H., et al., *Blood*, 96(2): 546-553 (2000); Rosen, *Hematol. Oncol. Clin. N. Am.*, 16:1173-1187 (2002); Kaplan, et al., *Growth Factors*, 14:243-256 (1997); Thomas, et al., U.S. Pat. No. 6,375,929; Kendall and Thomas, *PNAS, U.S.A.*, 90:10705-10709 (1993); Kovesdi, U.S. Pat. Appl. Publ. No. 2003/0053989, Daly, et al., U.S. Pat. Appl. Publ. No.: 2004/0014667; and Lokker, et al., J. Biol. Chem. 272: 33037-33044 (1997). These and other documents cited in this application are incorporated in their entireties. Molecules that have not previously been tested for their ability to bind to a particular growth factor may tested according to the assays provided herein. For example, some of the above documents teach a R-2 fragment that binds VEGF-A. That same molecule may be tested for its ability to bind VEGF-C.

Except as otherwise noted, descriptions supplied for receptors, also apply to receptor fragments and such fragments incorporated into binding constructs as described herein.

The growth factor receptors, from which binding units may be derived, include splice variants and naturally-occurring allelic variations. Allelic variants are well known in the art, and represent alternative forms or a nucleic acid sequence that comprise substitution, deletion or addition of one or more nucleotides, but which do not result in any substantial functional alteration of the encoded polypeptide. Standard methods can readily be used to generate such polypeptides including site-directed mutagenesis of polynucleotides, or specific enzymatic cleavage and ligation. Similarly, use of peptidomimetic compounds or compounds in which one or more amino acid residues are replaced by a non-naturally-occurring amino acid or an amino acid analog that retain binding activity is contemplated. Preferably, where amino acid substitution is used, the substitution is conservative, i.e. an amino acid is replaced by one of similar size and with similar charge properties. As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids that can be substituted for one another include asparagine, glutamine, serine and threonine. The term "conservative substitution" also includes the use of a substituted amino acid in place of an unsubstituted amino acid.

Alternatively, conservative amino acids can be grouped as described in Lehninger, (*Biochemistry*, Second Edition; Worth Publishers, Inc. NY:NY, pp. 71-77 (1975)) as set out in the following:

Non-polar (hydrophobic)
A. Aliphatic: A, L, I, V, P,
B. Aromatic: F, W,
C. Sulfur-containing: M,
D. Borderline: G.
Uncharged-polar
A. Hydroxyl: S, T, Y,
B. Amides: N, Q,
C. Sulfhydryl: C,
D. Borderline: G.
Positively Charged (Basic): K, R, H.
Negatively Charged (Acidic): D, E.
B. Linkers While binding units may be directly attached to one another (via a peptide, disulfide or other type of covalent bond), the binding constructs of the present invention may further comprise a (one or more) linker that connects together two or more different binding units, e.g., a receptor fragments with another receptor fragment, or even a copy of itself. A linker may also link a binding unit to other substituents described herein. The linker is generally a heterologous protein polypeptide. In some embodiments, the linker comprises a peptide that links the binding units to form a single continuous peptide that can be expressed as a single molecule. Linkers may be chosen such that they are less likely to induce an allergic reaction. Polysaccharides or other moieties also may be used to link binding units to form a binding construct.

More than one linker may be used per binding construct. The linker may be selected for optimal conformational (steric) freedom between the various ligand binding units to allow them to interact with each other if desired, e.g., to form dimers, or to allow them to interact with ligand. The linker may be linear such that consecutive binding units are linked in series, or the linker may serve as a scaffold to which various binding units are attached, e.g., a branched linker. A linker may also have multiple branches, e.g., as disclosed in Tam, J. Immunol. Methods 196:17 (1996). Binding units may be attached to each other or to the linker scaffold via N-terminal amino groups, C-terminal carboxyl groups, side chains, chemically modified groups, side chains, or other means.

Linker peptides may be designed to have sequences that permit desired characteristics. For example, the use of glycyl residues allow for a relatively large degree of conformational freedom, whereas a proline would tend to have the opposite effect. Peptide linkers may be chosen so that they achieve particular secondary and tertiary structures, e.g., alpha helices, beta sheets or beta barrels. Quaternary structure can also be utilized to create linkers that join two binding units together non-covalently. For example, fusing a protein domain with a hydrophobic face to each binding unit may permit the joining of the two binding units via the interaction between the hydrophobic interaction of the two molecules. In some embodiments, the linker may provide for polar interactions. For example, a leucine zipper domain of the proto-oncoproteins Myc and Max, respectively, may be used. Luscher and Larsson, *Ongogene* 18:2955-2966 (1999). In some embodiments, the linker allows for the formation of a salt bridge or disulfide bond. Linkers may comprise non-naturally occurring amino acids, as well as naturally occurring amino acids that are not naturally incorporated into a polypeptide. In some embodiments, the linker comprises a coordination complex between a metal or other ion and various residues from the multiple peptides joined thereby.

Linear peptide linkers of at least one amino acid residue are contemplated. In some embodiments the linker has more than 10,000 residues. In some embodiments the linker has from 1-10,000 residues. In some embodiments, the linker has from 1-1000 residues. In some embodiments, the linker has from 1-100 residues. In some embodiments, the linker has from 1-50 residues. In some embodiments the linker has 1-10 residues. In some embodiments, the linear peptide linker comprises residues with relatively inert side chains. Peptide linker amino acid residues need not be linked entirely or at all via alpha-carboxy and alpha-amino groups. That is, peptides may be linked via side chain groups of various residues.

The linker may affect whether the polypeptide(s) to which it is fused to is able to dimerize to each other or to another polypeptide. The linker serves a number of functions. Native receptor monomers restrained to the roughly two-dimensional plane of the cell membrane enjoy a relatively high local concentration and in the availability of co-receptors (binding units), increasing the probability of finding a partner. Receptors free in solution lacking such advantages may be aided by a linker that increases the effective concentration of the monomers.

In some embodiments, a binding construct may comprise more than one type of linker. Suitable linkers may also comprise the chemical modifications discussed below.

C. Substituents And Other Chemical Modifications

The binding constructs of the invention may be chemically modified with various substituents. Such modifications preferably does not substantially reduce the growth factor binding affinities or specificities of the binding construct. Rather, the chemical modifications impart additional desirable characteristics as discussed herein. Chemical modifications may take a number of different forms such as heterologous peptides, polysaccharides, lipids, radioisotopes, non-standard amino acid resides and nucleic acids, metal chelates, and various toxins.

The receptor fragments, binding constructs, and other peptide molecules of the present invention may be fused to heterologous peptides to confer various properties, e.g., increased solubility, modulation of clearance, targeting to particular cell or tissue types. In some embodiments, the receptor fragment is linked to a Fc domain of IgG or other immunoglobulin. In some embodiments, a receptor fragment is fused to alkaline phosphatase (AP). Methods for making Fc or AP fusion constructs are found in WO 02/060950. By fusing the ligand binding domain of VEGFR-2 or VEGFR-3 (or other receptors) with protein domains that have specific properties (e.g. half life, bioavailability, interaction partners) it is possible to confer these properties to the VEGFR binding domains (e.g., the receptor binding domain could be engineered to have a specific tissue distribution or specific biological half life). In some embodiments, binding construct may include a co-receptor and a VEGFR fragment.

The particular heterologous polypeptide used in a particular construct can influence whether or not a growth factor receptor fragment will dimerize, which in turn may affect ligand binding. Fc fusion all may permit dimers, whereas AP fusions may permit monomers, cited, which along with Ig-domain boundary differences as possible reasons for different results obtained by different groups for receptor fragments binging to ligands. [Lu, et al., *J. Biol. Chem.* 275(19): 14321-14330 (2000).]

For substituents such as an Fc region of human IgG, the fusion can be fused directly to a binding construct or fused through an intervening sequence. For example, a human IgG hinge, CH2 and CH3 region may be fused at either the N-terminus or C-terminus of a binding construct to attach the Fc region. The resulting Fc-fusion construct enables purification via a Protein A affinity column (Pierce, Rockford, Ill.). Peptide and proteins fused to an Fc region can exhibit a substantially greater half-life in vivo than the unfused counterpart. A fusion to an Fc region allows for dimerization/multimerization of the fusion polypeptide. The Fc region may be a naturally occurring Fc region, or may be modified for superior characteristics, e.g., therapeutic qualities, circulation time, reduced aggregation.

Polypeptides can be modified, for instance, by glycosylation, amidation, carboxylation, or phosphorylation, or by the creation of acid addition salts, amides, esters, in particular C-terminal esters, and N-acyl derivatives. The proteins also can be modified to create peptide derivatives by forming covalent or noncovalent complexes with other moieties. Covalently bound complexes can be prepared by linking the chemical moieties to functional groups on the side chains of amino acids comprising the peptides, or at the N- or C-terminus.

Polypeptides can be conjugated to a reporter group, including, but not limited to a radiolabel, a fluorescent label, an enzyme (e.g., that catalyzes a calorimetric or fluorometric reaction), a substrate, a solid matrix, or a carrier (e.g., biotin or avidin). Examples of analogs are described in WO 98/28621 and in Olofsson, et al., *Proc. Nat'l. Acad. Sci. USA*, 95:11709-11714 (1998), U.S. Pat. Nos. 5,512,545, and 5,474, 982; U.S. Patent Application Nos. 20020164687 and 20020164710.

Cysteinyl residues most commonly are reacted with haloacetates (and corresponding amines), such as chloroacetic acid or chloroacetamide, to give carboxymethyl or carbocyamidomethyl derivatives. Cysteinyl residues also are derivatized by reaction with bromotrifluoroacetone, α-bromo-β(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using 125I or 131I to prepare labeled proteins for use in radioimmunoassay.

Carboxyl side groups (aspartyl or glutamyl) are selectively modified by reaction with carbodiimides (R1) such as 1-cyclohexyl-3-(2-morpholinyl-(4-ethyl) carbodiimide or 1-ethyl-3 (4 azonia 4,4-dimethylpentyl)carbodiimide. Furthermore, aspartyl and glutamyl residues are converted to asparaginyl and glutaminyl residues by reaction with ammonium ions.

Derivatization with bifunctional agents is useful for crosslinking the binding construct to water-insoluble support matrixes. Such derivation may also provide the linker that may connect adjacent binding elements in a binding construct, or a binding elements to a heterologous peptide, e.g., a Fc fragment. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiiobis(succinimidylpropionate), and bifunctional maleimides such as bis-N-maleimido-1,8-octane. Derivatizing agents such as methyl-3-[(p-azidophenyl) dithio] propioimidate yield photoactivatable intermediates that are capable of forming cross links in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440, incorporated herein by reference, are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecule Properties*, W. H. Freeman & Co., San Francisco, pp. 79-86, 1983), acetylation of the N-terminal amine, and, in some instances, amidation of the C-terminal carboxyl groups. Such derivatives are chemically modified polypeptide compositions in which the binding construct polypeptide is linked to a polymer. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of the binding construct polypeptide polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water soluble polymer, some molecules will weigh more, some less, than the stated molecular weight). The average molecular weight of each polymer is between about 5 kDa and about 50 kDa, more preferably between about 12 kDa to about 40 kDa and most preferably between about 20 kDa to about 35 kDa.

Suitable water soluble polymers or mixtures thereof include, but are not limited to, N-linked or O-linked carbohydrates, sugars, phosphates, carbohydrates; sugars; phosphates; polyethylene glycol (PEG) (including the forms of PEG that have been used to derivatize proteins, including mono-(C1-C10) alkoxy- or aryloxy-polyethylene glycol); monomethoxy-polyethylene glycol; dextran (such as low molecular weight dextran, of, for example about 6 kD), cellulose; cellulose; other carbohydrate-based polymers, poly-(N-vinyl pyrrolidone)polyethylene glycol, propylene glycol homopolymers, a polypropylene oxide/ethylene oxide co-polymer, polyoxyethylated polyols (e.g., glycerol) and poly-vinyl alcohol. Also encompassed by the present invention are bifunctional crosslinking molecules which may be used to prepare covalently attached multimers.

In general, chemical derivatization may be performed under any suitable condition used to react a protein with an activated polymer molecule. Methods for preparing chemical derivatives of polypeptides will generally comprise the steps of (a) reacting the polypeptide with the activated polymer molecule (such as a reactive ester or aldehyde derivative of the polymer molecule) under conditions whereby the binding construct becomes attached to one or more polymer molecules, and (b) obtaining the reaction product(s). The optimal reaction conditions will be determined based on known parameters and the desired result. For example, the larger the ratio of polymer molecules:protein, the greater the amount of attached polymer molecule. In one embodiment, the binding construct polypeptide derivative may have a single polymer molecule moiety at the amino terminus. (See, e.g., U.S. Pat. No. 5,234,784).

A particularly preferred water-soluble polymer for use herein is polyethylene glycol (PEG). As used herein, polyethylene glycol is meant to encompass any of the forms of PEG that can be used to derivatize other proteins, such as mono-(C1-C10) alkoxy- or aryloxy-polyethylene glycol. PEG is a linear or branched neutral polyether, available in a broad range of molecular weights, and is soluble in water and most organic solvents. PEG is effective at excluding other polymers or peptides when present in water, primarily through its high dynamic chain mobility and hydrophibic nature, thus creating a water shell or hydration sphere when attached to other proteins or polymer surfaces. PEG is nontoxic, non-immunogenic, and approved by the Food and Drug Administration for internal consumption.

Proteins or enzymes when conjugated to PEG have demonstrated bioactivity, non-antigenic properties, and decreased clearance rates when administered in animals. F. M. Veronese et al., Preparation and Properties of Monomethoxypoly(ethylene glycol)-modified Enzymes for Therapeutic Applications, in J. M. Harris ed., *Poly(Ethylene Glycol) Chemistry—Biotechnical and Biomedical Applications*, 127-36, 1992, incorporated herein by reference. These phenomena are due to the exclusion properties of PEG in preventing recognition by the immune system. In addition, PEG has been widely used in surface modification procedures to decrease protein adsorption and improve blood compatibility. S. W. Kim et al., *Ann. N.Y. Acad. Sci.* 516: 116-30 1987; Jacobs et al., *Artif. Organs* 12: 500-501, 1988; Park et al., *J. Poly. Sci, Part A* 29:1725-31, 1991, incorporated herein by reference. Hydrophobic polymer surfaces, such as polyurethanes and polystyrene can be modified by the grafting of PEG (MW 3,400) and employed as nonthrombogenic surfaces. Surface properties (contact angle) can be more consistent with hydrophilic surfaces, due to the hydrating effect of PEG. More importantly, protein (albumin and other plasma proteins) adsorption can be greatly reduced, resulting from the high chain motility, hydration sphere, and protein exclusion properties of PEG.

PEG (MW 3,400) was determined as an optimal size in surface immobilization studies, Park et al., *J. Biomed. Mat. Res.* 26:739-45, 1992, while PEG (MW 5,000) was most beneficial in decreasing protein antigenicity. (F. M. Veronese et al., In J. M. Harris, et al., *Poly(Ethylene Glycol) Chemistry—Biotechnical and Biomedical Applications*, 127-36.)

Methods for preparing pegylated binding construct polypeptides will generally comprise the steps of (a) reacting the polypeptide with polyethylene glycol (such as a reactive ester or aldehyde derivative of PEG) under conditions whereby the binding construct polypeptide becomes attached to one or more PEG groups, and (b) obtaining the reaction product(s). In general, the optimal reaction conditions for the acylation reactions will be determined based on known parameters and the desired result. For example, the larger the ratio of PEG:protein, the greater the percentage of polypegylated product. In some embodiments, the binding construct will have a single PEG moiety at the N-terminus. See U.S. Pat. No. 8,234,784, herein incorporated by reference.

Derivatized binding constructs disclosed herein may have additional activities, enhanced or reduced biological activity, or other characteristics, such as increased or decreased half-life, as compared to the non-derivatized molecules.

II. POLYNUCLEOTIDES ENCODING BINDING CONSTRUCTS AND EXPRESSION SYSTEMS

The invention comprises not only the binding constructs, binding units, and polypeptides described herein, but also nucleic acids encoding such molecules, vectors comprising such molecules, and host cells comprising such vectors. Method employing any of the constructs, units, polypeptides, nucleic acids, vectors, and hosts cells are all considered aspects of the invention.

A. Nucleic Acids of the Invention

This invention also includes nucleic acid molecules whose sequence encode the polypeptides, binding units, and binding constructs of the invention. Nucleic acid molecules include those molecules which comprise nucleotide sequences which hybridize under moderately or highly stringent conditions as defined herein with the fully complementary sequence of the nucleic acid molecule of receptor tyrosine kinases described in Table 1A, or of a molecule encoding a polypeptide, which polypeptide comprises the receptor tyrosine kinase amino acids sequences described in Table 1A, or of a nucleic acid fragment as defined herein, or of a nucleic acid fragment encoding a polypeptide as defined herein.

Hybridization probes may be prepared using the sequences provided herein to screen cDNA, genomic or synthetic DNA libraries for related sequences. Regions of the DNA and/or amino acid sequence that exhibit significant identity to known sequences are readily determined using sequence alignment algorithms as described herein, and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, Molecular Cloning: A Laboratory Manual, 2nd Ed., Cold Spring Harbor Laboratory, (Cold Spring Harbor, N.Y. 1989); and Anderson et al., Nucleic Acid Hybridization: a Practical approach, Ch. 4, IRL Press Limited (Oxford, England). Limited, Oxford, England. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate (NaDodSO$_4$ or SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, 6.8-7.4; however, at typical ionic strength conditions, the rate of hybridization is nearly independent of pH. See Anderson et al., Nucleic Acid Hybridization: a Practical Approach, Ch. 4, IRL Press Limited (Oxford, England).

Factors affecting the stability of a DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$Tm(° C.)=81.5+16.6(\log [Na+])+0.41(\%G+C)-600/N-0.72(\% \text{ formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately" stringent conditions" " refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, a "moderately stringent" condition of 50° C. in 0.015 M sodium ion will allow about a 21% mismatch.

It will be appreciated by those skilled in the art that there is no absolute distinction between "highly" and "moderately" stringent conditions. For example, at 0.015M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

$$Tm=2° \text{ C. per } A\text{-}T \text{ base pair}+4° \text{ C. per } G\text{-}C \text{ base pair}$$

*The sodium ion concentration in 6× salt sodium citrate (SSC) is 1 M. See Suggs et al., Developmental Biology Using Purified Genes, p. 683, Brown and Fox (eds.) (1981).

High stringency washing conditions for oligonucleotides are usually at a temperature of 0-5° C. below the Tm of the oligonucleotide in 6×SSC, 0.1% SDS.

Differences in the nucleic acid sequence may result in conservative and/or non-conservative modifications of the amino acid sequence relative to the amino acid sequence. The invention is also directed to an isolated and/or purified DNA that corresponds to, or that hybridizes under stringent conditions with, any one of the foregoing DNA sequences.

B. Preparation of DNA Encoding Ligand, Receptor, and Binding Construct Polypeptides A nucleic acid molecule encoding all or part of a polypeptide of the invention such as a binding construct or binding unit of the invention can be made in a variety of ways, including, without limitation, chemical synthesis, cDNA or genomic library screening, expression library screening, and/or PCR amplification of cDNA or genomic DNA. These methods and others useful for isolating such DNA are set forth, for example, by Sambrook, et al., "Molecular Cloning: A Laboratory Manual," Cold Spring Harbor Laboratory Press, Cold Spring Harbor, N.Y. (1989), by Ausubel, et al., eds., "Current Protocols In Molecular Biology," Current Protocols Press (1994), and by Berger and Kimmel, "Methods In Enzymology: Guide To Molecular Cloning Techniques," vol. 152, Academic Press, Inc., San Diego, Calif. (1987). Preferred nucleic acid sequences are mammalian sequences, such as human, rat, and mouse.

Chemical synthesis of nucleic acid molecules can be accomplished using methods well known in the art, such as those set forth by Engels, et al., *Angew. Chem. Intl. Ed.*, 28:716-734 (1989). These methods include, inter alia, the phosphotriester, phosphoramidite and H-phosphonate methods of nucleic acid synthesis. Nucleic acids larger than about 100 nucleotides in length can be synthesized as several fragments, each fragment being up to about 100 nucleotides in length. The fragments can then be ligated together, as described below, to form the full length nucleic acid of interest. A preferred method is polymer-supported synthesis using standard phosphoramidite chemistry.

C. Preparation of a Vector for Expression

The term "vector" refers to a nucleic acid molecule amplification, replication, and/or expression vehicle, often derived from or in the form of a plasmid or viral DNA or RNA system, where the plasmid or viral DNA or RNA is functional in a selected host cell, such as bacterial, yeast, plant, invertebrate, and/or mammalian host cells. The vector may remain independent of host cell genomic DNA or may integrate in whole or in part with the genomic DNA. The vector will contain all necessary elements so as to be functional in any host cell it is compatible with. Such elements are set forth below.

Nucleic acid encoding a polypeptide or fragment thereof has been isolated, it is preferably inserted into an amplification and/or expression vector in order to increase the copy number of the gene and/or to express the encoded polypeptide in a suitable host cell and/or to transform cells in a target organism (to express the polypeptide in vivo). Numerous commercially available vectors are suitable, though "custom made" vectors may be used as well. The vector is selected to be functional in a particular host cell or host tissue (i.e., for replication and/or expression). The polypeptide or fragment thereof may be amplified/expressed in prokaryotic and/or eukaryotic host cells, e.g., yeast, insect (baculovirus systems), plant, and mammalian cells. Selection of the host cell will depend at least in part on whether the polypeptide or fragment thereof is to be glycosylated. If so, yeast, insect, or mammalian host cells are preferable; yeast and mammalian cells will glycosylate the polypeptide if a glycosylation site is present on the amino acid sequence.

Typically, the vectors used in any of the host cells will contain 5' flanking sequence and other regulatory elements such as an enhancer(s), a promoter, an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Optionally, the vector may contain a "tag" sequence, i.e., an oligonucleotide sequence located at the 5' or 3' end of the coding sequence that encodes polyHis (such as hexaHis) or another small immunogenic sequence. This tag will be expressed along with the protein, and can serve as an affinity tag for purification of the polypeptide from the host cell. Optionally, the tag can subsequently be removed from the purified polypeptide by various means such as using a selected peptidase.

The vector/expression construct may optionally contain elements such as a 5' flanking sequence, an origin of replication, a transcription termination sequence, a selectable marker sequence, a ribosome binding site, a signal sequence, and one or more intron sequences. The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native polypeptide 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

A transcription termination element is typically located 3' to the end of the polypeptide coding sequence and serves to terminate transcription of the polypeptide. Usually, the transcription termination element in prokaryotic cells is a G-C rich fragment followed by a poly T sequence. Such elements can be cloned from a library, purchased commercially as part of a vector, and readily synthesized.

Selectable marker genes encode proteins necessary for the survival and growth of a host cell in a selective culture medium. Typical selectable marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media.

A ribosome binding element, commonly called the Shine-Dalgarno sequence (prokaryotes) or the Kozak sequence (eukaryotes), is necessary for translation initiation of mRNA. The element is typically located 3' to the promoter and 5' to the coding sequence of the polypeptide to be synthesized. The Shine-Dalgarno sequence is varied but is typically a polypurine (i.e., having a high A-G content). Many Shine-Dalgarno sequences have been identified, each of which can be readily synthesized using methods set forth above.

All of the elements set forth above, as well as others useful in this invention, are well known to the skilled artisan and are described, for example, in Sambrook, et al., "Molecular Cloning: A Laboratory Manual," Cold Spring Harbor Laboratory Press, Cold Spring Harbor, N.Y. (1989) and Berger, et al., eds., "Guide To Molecular Cloning Techniques," Academic Press, Inc., San Diego, Calif. [1987].

For those embodiments of the invention where the recombinant polypeptide is to be secreted, a signal sequence is preferably included to direct secretion from the cell where it is synthesized. Typically, the polynucleotide encoding the signal sequence is positioned at the 5' end of the coding region. Many signal sequences have been identified, and any of them that are functional in a target cell or species may be used in conjunction with the transgene.

In many cases, gene transcription is increased by the presence of one or more introns on the vector. The intron may be naturally-occurring, especially where the transgene is a full length or a fragment of a genomic DNA sequence. The intron may be homologous or heterologous to the transgene and/or to the transgenic mammal into which the gene will be inserted. The position of the intron with respect to the promoter and the transgene is important, as the intron must be transcribed to be effective. A preferred position for an intron is 3' to the transcription start site, and 5' to the polyA transcription termination sequence. For cDNA transgenes, an intron is placed on one side or the other (i.e., 5' or 3') of the transgene coding sequence. Any intron from any source, including any viral, prokaryotic and eukaryotic (plant or animal) organisms, may be used to express the polypeptide, provided that it is compatible with the host cell(s) into which it is inserted. Also included herein are synthetic introns. Optionally, more than one intron may be used in the vector.

Preferred vectors for recombinant expression are those that are compatible with bacterial, insect, and mammalian host cells. Such vectors include, inter alia, pCRII (Invitrogen Company, San Diego, Calif.), pBSII (Stratagene Company, La Jolla, Calif.), and pETL (BlueBacII; Invitrogen).

After the vector has been constructed and a nucleic acid has been inserted into the proper site of the vector, the completed vector may be inserted into a suitable host cell for amplification and/or polypeptide expression. Commonly used include: Prokaryotic cells such as gram negative or gram positive bacteria, i.e., any strain of *E. coli, Bacillus, Streptomyces, Saccharomyces, Salmonella*, and the like; eukaryotic cells such as CHO (Chinese hamster ovary) cells; human kidney 293 cells; COS-7 cells; insect cells such as Sf4, Sf5, Sf9, and Sf21 and High 5 (all from the Invitrogen Company, San Diego, Calif.); plant cells and various yeast cells such as *Saccharomyces* and *Pichia*. Any transformable or transfectable cell or cell line derived from any organism such as bacteria, yeast, fungi, monocot and dicot plants, plant cells, and animals are suitable.

Insertion (also referred to as "transformation" or "transfection") of the vector into the selected host cell may be accomplished using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook, et al., supra.

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or binding assays.

D. Purification of Polypeptides

If the polypeptide has been designed to be secreted from the host cells, the majority of polypeptide will likely be found in the cell culture medium. If, however, the polypeptide is not secreted from the host cells, it will be present in the cytoplasm (for eukaryotic, gram positive bacteria, and insect host cells) or in the periplasm (for gram negative bacteria host cells).

For intracellular polypeptides, the host cells are first disrupted mechanically or osmotically to release the cytoplasmic contents into a buffered solution. The polypeptide is then isolated from this solution.

Purification of the polypeptide from solution can be accomplished using a variety of techniques. If the polypeptide has been synthesized such that it contains a tag such as hexahistidine or other small peptide at either its carboxyl or amino terminus, it may essentially be purified in a one-step process by passing the solution through an affinity column where the column matrix has a high affinity for the tag or for the polypeptide directly (i.e., a monoclonal antibody specifically recognizing the polypeptide). For example, polyhistidine binds with great affinity and specificity to nickel, thus an affinity column of nickel (such as the Qiagen nickel columns) can be used for purification of the His-tagged polypeptide. (See, for example, Ausubel, et al., eds., "Current Protocols In Molecular Biology," Section 10.11.8, John Wiley & Sons, New York (1993)).

The strong affinity a ligand for its receptor permits affinity purification of binding constructs, and binding constructs using an affinity matrix comprising a complementary binding partner. Affinity chromatography may be employed, e.g., using either natural binding partners (e.g. a ligand when purifying a binding construct with affinity for the same) or antibodies generated using standard procedures (e.g., immunizing a mouse, rabbit or other animal with an appropriate polypeptide). The peptides of the present invention may be used to generate such antibodies. Known antibodies or antibodies to known growth factor receptors may be employed when they share an epitope with a targeted binding construct.

In addition, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity. Preferred methods for purification include polyhistidine tagging and ion exchange chromatography in combination with preparative isoelectric focusing.

Polypeptide found in the periplasmic space of the bacteria or the cytoplasm of eukaryotic cells, the contents of the periplasm or cytoplasm, including inclusion bodies (bacteria) if the processed polypeptide has formed such complexes, can be extracted from the host cell using any standard technique known to the skilled artisan. For example, the host cells can be lysed to release the contents of the periplasm by French press, homogenization, and/or sonication. The homogenate can then be centrifuged.

If the polypeptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The solubilized polypeptide can then be analyzed using gel electrophoresis, immunoprecipitation or the like. If it is desired to isolate the polypeptide, isolation may be accomplished using standard methods such as those set forth below and in [Marston, et al., *Meth. Enz.*, 182:264-275 (1990).]

III. ANTI-LIGAND AND ANTI-RECEPTOR THERAPEUTIC COMPOUNDS

Anti-ligand or anti-receptor therapies as discussed below include, but are not limited to antibody, aptamer, antisense and interference RNA techniques and therapies. The following description makes specific reference to the production, testing, and use of particular anti-VEGFR-2 antibodies. However, the methods described may also be readily adapted for the production of other antibodies of the present invention, e.g., anti-growth factor ligand antibodies as binding units of the binding constructs. Such antibody-type binding units may form one binding unit of a binding construct. In some embodiments a binding construct has at least one binding unit that comprising a receptor fragment and at least one binding unit that comprises an antigen binding fragment. Antibodies directed against growth factors and receptors may also be used in combination with the binding constructs of the invention. Exemplary antibodies may be found in the co-owned, concurrently (Mar. 5, 2004) filed U.S. Provisional Patent Application Nos. 60/550,511: "Multivalent Antibody Materials And Methods For VEGF/PDGF Family Of Growth Factors," and related, co-filed International Patent Application No. PCT/US05/07742; and 60/550, 441: "Chimeric Anti-VEGF-D Antibodies And Humanized Anti-VEGF-D Antibodies And Methods Of Using Same," and related, co-filed International Patent Application No. PCT/US05/07283; all applications are incorporated by reference in their entireties.

A. Therapeutic Anti-VEGFR-2 Selective VEGF-A Antagonist Antibodies

Antibodies can be used for purification for VEGFR-2 constructs as described above or therapeutically where inhibition of VEGF-A binding by VEGFR-2 is desired (e.g., to achieve anti-neoplastic effects).

Polyclonal or monoclonal therapeutic anti-VEGFR-2 antibodies useful in practicing this invention may be prepared in laboratory animals or by recombinant DNA techniques using the following methods. Polyclonal antibodies to the VEGFR-2 molecule or a fragment thereof containing the target amino acid sequence generally are raised in animals by multiple subcutaneous (sc) or intraperitoneal (ip) injections of the VEGFR-2 molecule in combination with an adjuvant such as Freund's adjuvant (complete or incomplete). To enhance immunogenicity, it may be useful to first conjugate the VEGFR-2 molecule or a fragment containing the target amino acid sequence of a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl, or $R^1N=C=NR$, where R and $R^1$ are different alkyl groups. Alternatively, VEGF-2-immunogenic conjugates can be produced recombinantly as fusion proteins.

Animals are immunized against the immunogenic VEGFR-2 conjugates or derivatives (such as a fragment containing the target amino acid sequence) by combining about 1 mg or about 1 microgram of conjugate (for rabbits or mice, respectively) with about 3 volumes of Freund's complete adjuvant and injecting the solution intradermally at multiple sites. Approximately 7 to 14 days later, animals are bled and the serum is assayed for anti-VEGFR-2 titer. Animals are boosted with antigen repeatedly until the titer plateaus. Preferably, the animal is boosted with the same VEGFR-2 molecule or fragment thereof as was used for the initial immunization, but conjugated to a different protein and/or through a different cross-linking agent. In addition, aggregating agents such as alum are used in the injections to enhance the immune response.

Monoclonal antibodies may be prepared by recovering spleen cells from immunized animals and immortalizing the cells in conventional fashion, e.g. by fusion with myeloma cells. The clones are then screened for those expressing the desired antibody. The monoclonal antibody preferably does not cross-react with other VEGFR family members.

Preparation of antibodies using recombinant DNA methods such as the phagemid display method, may be accomplished using commercially available kits, as for example, the Recombinant Phagemid Antibody System available from Pharmacia (Uppsala, Sweden), or the SurfZAP™ phage display system (Stratagene Inc., La Jolla, Calif.).

One may increase the population of anti-VEGFR-2 antibodies that selectively block VEGF-A binding by using a Ig-domain 3 or other fragment as the immunogen, but that is not necessary. After antibodies are generated, they may be tested to ascertain their specific affinities. Competition studies may be performed that show that the antibody competes for binding to VEGFR-2 with VEGF-A, but not with VEGF-C.

One method comprises incubating VEGFR-2 expressing cells with either labeled-VEGF-A alone, the antibody being tested alone, or with both the VEGF-A and the antibody. A label on the antibody may be employed in addition to that on VEGF-A or instead of that label. The antibody may also be detected using a labeled secondary antibody. The first two groups acting as controls allow one to confirm that both the antibody and the VEGF-A ligand (or optionally VEGF-E) are able to bind to the receptor in the absence of the other. Those cell samples treated with both VEGF-A (or VEGF-E) and an antibody, that reveal binding of the antibody, but not VEGF-A (or VEGF-E) indicate that the antibody should be further tested. As described below, stoichiometric analysis can be used to ascertain that the ligand and antibody are competing for the same molecule.

This further testing may comprise binding studies that reveal that both VEGF-C (or VEGF-D) and the antibody are able to bind the receptor simultaneously. This testing also is designed to determine whether VEGF-C and the antibody are simultaneously binding to a single VEGFR-2 molecule as opposed to binding of VEGF-C and the antibody binding to different VEGFR-2 molecules. Comparative quantitative binding studies may accordingly be used. The VEGFR-2 cells are counted in each sample. VEGFR-2 samples, having been counted, are incubated with either labeled VEGF-C alone or labeled (or unlabelled using a secondary antibody for detection) antibody alone. The degree of binding is measured, quantitated, using suitable imaging procedures, e.g., if radiolabel is employed using a phosphoimager. The average number of VEGFR-2 receptors per cell are calculated by dividing the amount of bound molecules by the total number of cells. Whether the receptors are saturated with molecules may be achieved by repeating the assay with increasing amounts of the labeled molecule(s). The binding assay is repeated again with both ligand and antibody. If the quantification reveals that the number of antibodies and ligands bound is greater than the total number of receptors, then the antibody has the desired characteristics.

The described protocols may also be modified and used to produce antibodies against binding constructs and other constructs of the inventions to aid in purification of such constructs.

Preferably, antibodies for administration to humans, although prepared in a laboratory animal such as a mouse, will be "humanized", or chimeric, i.e. made to be compatible with the human immune system such that a human patient will not develop an immune response to the antibody. Even more preferably, human antibodies which can now be prepared using methods such as those described for example, in Lonberg, et al., *Nature Genetics,* 7:13-21 (1994) are preferred for therapeutic administration to patients. Fully human antibodies are highly preferred.

1. Humanization of Anti-VEGFR-2 Monoclonal Antibodies

Selective binding agents, including monoclonal antibodies, which selectively block VEGF-A without blocking VEGF-C (or VEGF-D) binding may be applied therapeutically. Following are protocols to improve the utility of anti-VEGFR-2 monoclonal antibodies as therapeutics in humans, by "humanizing" the monoclonal antibodies to improve their serum half-life and render them less immunogenic in human hosts (i.e., to prevent human antibody response to non-human anti-VEGFR-2 antibodies).

The principles of humanization have been described in the literature and are facilitated by the modular arrangement of antibody proteins. To minimize the possibility of binding complement, a humanized antibody of the IgG4 isotype is preferred.

For example, a level of humanization is achieved by generating chimeric antibodies comprising the variable domains of non-human antibody proteins of interest, such as the anti-VEGFR-2 monoclonal antibodies described herein, with the constant domains of human antibody molecules. (See, e.g., Morrison and Oi, *Adv. Immunol.,* 44:65-92 (1989).) The variable domains of VEGFR-2 neutralizing anti-VEGFR-2 antibodies are cloned from the genomic DNA of a B-cell hybridoma or from cDNA generated from mRNA isolated from the hybridoma of interest. The V region gene fragments are linked to exons encoding human antibody constant domains, and the resultant construct is expressed in suitable mammalian host cells (e.g., myeloma or CHO cells).

To achieve an even greater levels of humanization, only those portions of the variable region gene fragments that encode antigen-binding complementarity determining regions ("CDR") of the non-human monoclonal antibody genes are cloned into human antibody sequences. [See, e.g., Jones et al., *Nature,* 321:522-525 (1986); Riechmann et al., *Nature,* 332:323-327 (1988); Verhoeyen et al., *Science,* 239: 1534-36 (1988); and Tempest et al., *Bio/Technology,* 9:266-

71 (1991).] If necessary, the B-sheet framework of the human antibody surrounding the CDR3 regions also is modified to more closely mirror the three dimensional structure of the antigen-binding domain of the original monoclonal antibody. [(See Kettleborough et al., *Protein Engin.*, 4:773-783 (1991); and Foote et al., *J. Mol. Biol.*, 224:487-499 (1992).)]

In an alternative approach, the surface of a non-human monoclonal antibody of interest is humanized by altering selected surface residues of the non-human antibody, e.g., by site-directed mutagenesis, while retaining all of the interior and contacting residues of the non-human antibody. [See Padlan, *Molecular Immunol.*, 28(4/5):489-98 (1991).]

The foregoing approaches are employed using VEGFR-2-neutralizing anti-VEGFR-2 monoclonal antibodies and the hybridomas that produce them to generate humanized VEGFR-2-neutralizing antibodies useful as therapeutics to treat or palliate conditions wherein VEGFR-2 expression is detrimental and/or activation by VEGF-A. One therapeutic target is selective promotion of lymphangiogenesis while minimizing promotion of angiogenesis.

2. Human VEGFR-2-Neutralizing Antibodies from Phage Display

Human VEGFR-2-neutralizing antibodies are generated by phage display techniques such as those described in Aujame et al., *Human Antibodies*, 8(4):155-168 (1997); Hoogenboom, *TIBTECH*, 15:62-70 (1997); and Rader et al., *Curr. Opin. Biotechnol.*, 8:503-508 (1997), all of which are incorporated by reference. For example, antibody variable regions in the form of Fab fragments or linked single chain Fv fragments are fused to the amino terminus of filamentous phage minor coat protein pIII. Expression of the fusion protein and incorporation thereof into the mature phage coat results in phage particles that present an antibody on their surface and contain the genetic material encoding the antibody. A phage library comprising such constructs is expressed in bacteria, and the library is panned (screened) for VEGFR-2-specific phage-antibodies using labeled or immobilized VEGFR-2 as antigen-probe.

3. Human VEGFR-2-Neutralizing Antibodies from Transgenic Mice

Human VEGFR-2-neutralizing antibodies are generated in transgenic mice essentially as described in Bruggemann and Neuberger, *Immunol. Today*, 17(8):391-97 (1996) and Bruggemann and Taussig, *Curr. Opin. Biotechnol.*, 8:455-58 (1997). Transgenic mice carrying human V-gene segments in germline configuration and that express these transgenes in their lymphoid tissue are immunized with an VEGFR-2 composition using conventional immunization protocols. Hybridomas are generated using B cells from the immunized mice using conventional protocols and screened to identify hybridomas secreting anti-VEGFR-2 human antibodies (e.g., as described above).

4. Bispecific Antibodies

Bispecific antibodies that specifically bind to VEGFR-2 and that specifically bind to other antigens relevant to pathology and/or treatment are produced, isolated, and tested using standard procedures that have been described in the literature. See, e.g., Pluckthun & Pack, *Immunotechnology*, 3:83-105 (1997); Carter et al., *J. Hematotherapy*, 4: 463-470 (1995); Renner & Pfreundschuh, *Immunological Reviews*, 1995, No. 145, pp. 179-209; Pfreundschuh U.S. Pat. No. 5,643,759; Segal et al., *J. Hematotherapy*, 4: 377-382 (1995); Segal et al., *Immunobiology*, 185: 390-402 (1992); and Bolhuis et al., *Cancer Immunol. Immunother.*, 34: 1-8 (1991), all of which are incorporated herein by reference in their entireties. Bispecific antibodies that may be employed in combination with the binding constructs of the invention include those described in the co-owned, concurrently (Mar. 5, 2004) filed U.S. Provisional Patent Application No. 60/550,511: "Multivalent Antibody Materials And Methods For VEGF/PDGF Family Of Growth Factors,".

For example, bispecific antibodies (bscAb) are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. Bispecific fusion proteins are prepared in a similar manner. Bispecific single-chain antibodies and bispecific fusion proteins are antibody substances included within the scope of the present invention.

Antibody fragments that contain the antigen binding, or idiotype, of the molecule may be generated by known techniques. For example, such fragments include, but are not limited to, the $F(ab')_2$ fragment which may be produced by pepsin digestion of the antibody molecule; the Fab' fragments which may be generated by reducing the disulfide bridges of the $F(ab')_2$ fragment, and the two Fab' fragments which may be generated by treating the antibody molecule with papain and a reducing agent.

Chemically constructed bispecific antibodies may be prepared by chemically cross-linking heterologous Fab or $F(ab')_2$ fragments by means of chemicals such as heterobifunctional reagent succinimidyl-3-(2-pyridyldithiol)-propionate (SPDP, Pierce Chemicals, Rockford, Ill.). The Fab and $F(ab')_2$ fragments can be obtained from intact antibody by digesting it with papain or pepsin, respectively (Karpovsky et al., *J. Exp. Med.* 160:1686-701, 1984; Titus et al., *J. Immunol.*, 138:4018-22, 1987).

5. Humanization of Known Anti-VEGFR-2 Antibodies

Existing anti-VEGF-2 antibodies may also be employed in the various methods and compositions of the present invention, and, if not already humanized, may be humanized as discussed herein. Known anti-VEGFR-2 antibodies may be tested for the ability to selectively block VEGF-A binding using the methods discussed herein. Known anti-VEGFR-2 antibodies (anti-KDR antibodies) are taught for example in Lu et al., *J. Immunological Methods*, 230:159-71 (1999); Lu, et al., *J. Biol. Chem.*, 275(19): 14321-14330 (2000); and Lu, et al., *J. Biol. Chem.*, 278(44): 43496-43507 (2003).

6. Domain Antibodies

A domain antibody comprises a functional binding unit of an antibody, and can correspond to the variable regions of either the heavy ($V_H$) or light ($V_L$) chains of antibodies. A domain antibody can have a molecular weight of approximately 13 kDa, or approximately one-tenth of a full antibody. Domain antibodies may be derived from full antibodies such as those described herein.

B. Anti-Receptor and Anti-Ligand Aptamers

Recent advances in the field of combinatorial sciences have identified short polymer sequences with high affinity and specificity to a given target. For example, SELEX technology has been used to identify DNA and RNA aptamers with binding properties that rival mammalian antibodies, the field of immunology has generated and isolated antibodies or antibody fragments which bind to a myriad of compounds and phage display has been utilized to discover new peptide sequences with very favorable binding properties. Based on the success of these molecular evolution techniques, it is certain that molecules can be created which bind to any target molecule. A loop structure is often involved with providing the desired binding attributes as in the case of: aptamers which often utilize hairpin loops created from short regions without complimentary base pairing, naturally derived antibodies that utilize combinatorial arrangement of looped hyper-variable regions and new phage display libraries utilizing cyclic peptides that have shown improved results when compared to linear peptide phage display results. Thus, sufficient evidence has been generated to suggest that high affinity ligands can be created and identified by combinatorial molecular evolution techniques. For the present invention, molecular evolution techniques can be used to isolate binding constructs specific for ligands described herein. For more on aptamers, See generally, Gold, L., Singer, B., He, Y. Y., Brody. E., "Aptamers As Therapeutic And Diagnostic Agents," *J. Biotechnol.* 74:5-13 (2000). Relevant techniques for generating aptamers may be found in U.S. Pat. No. 6,699,843, which is incorporated by reference in its entirety.

In some embodiments, the aptamer may be generated by preparing a library of nucleic acids; contacting the library of nucleic acids with a growth factor, wherein nucleic acids having greater binding affinity for the growth factor (relative to other library nucleic acids) are selected and amplified to yield a mixture of nucleic acids enriched for nucleic acids with relatively higher affinity and specificity for binding to the growth factor. The processes may be repeated, and the selected nucleic acids mutated and rescreened, whereby a growth factor aptamer is be identified. Nucleic acids may be screened to select for molecules that bind to more than growth factor. Binding more than one growth factor can refer to binding more than one growth factor simultaneously or competitively. In some embodiments a binding construct will comprise at least one aptamer, wherein a first binding unit binds VEGF-A and a second binding unit binds VEGF-C. In some embodiments a binding construct will comprise at least one aptamer, wherein a first binding unit binds a VEGF growth factor subfamily member and a second binding unit binds a PDGF subfamily member.

C. Anti-Sense Molecules and Therapy

Another class of inhibitors that may be used in conjunction with the present invention is isolated antisense nucleic acid molecules that can hybridize to, or are complementary to, the nucleic acid molecule, nucleotide sequence, or fragments, analogs or derivatives thereof. An "antisense" nucleic acid comprises a nucleotide sequence that is complementary to a "sense" nucleic acid encoding a protein (e.g., complementary to the coding strand of a double-stranded cDNA molecule or complementary to an mRNA sequence). In specific embodiments, antisense nucleic acid molecules are provided that comprise a sequence complementary to at least about 10, 25, 50, 100, 250 or 500 nucleotides or an entire receptor or ligand coding strand, or to only a portion thereof. Nucleic acid molecules encoding fragments, homologs, derivatives and analogs of receptor or ligand or antisense nucleic acids complementary to a receptor or ligand nucleic acid sequence are additionally provided.

In one embodiment, an antisense nucleic acid molecule is antisense to a "coding region" of the coding strand of a nucleotide sequence encoding a receptor or ligand protein (or fragments or fragment combination thereof). The term "coding region" refers to the region of the nucleotide sequence comprising codons that are translated into amino acid residues. In another embodiment, the antisense nucleic acid molecule is antisense to a "conceding region" of the coding strand of a nucleotide sequence encoding the receptor or ligand protein. The term "conceding region" refers to 5' and 3' sequences that flank the coding region and that are not translated into amino acids (i.e., also referred to as 5' and 3' untranslated regions).

Given the coding strand sequences encoding the receptor or ligand protein disclosed herein, antisense nucleic acids of the invention can be designed according to the rules of Watson and Crick or Hoogsteen base pairing. The antisense nucleic acid molecule can be complementary to the entire coding region of a ligand or receptor mRNA, but more preferably is an oligonucleotide that is antisense to only a portion of the coding or noncoding region of receptor or ligand mRNA. For example, the antisense oligonucleotide can be complementary to the region surrounding the translation start site of receptor or ligand mRNA. An antisense oligonucleotide can be, for example, about 5, 10, 15, 20, 25, 30, 35, 40, 45, or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following section).

The antisense nucleic acid molecules of the invention are typically administered to a subject or generated in situ such that they hybridize with or bind to cellular mRNA and/or genomic DNA encoding a receptor or ligand to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an alpha-anomeric nucleic acid molecule. An alpha-anomeric nucleic acid molecule forms specific double-stranded hybrids with complementary RNA in which, contrary to the usual alpha-units, the strands run parallel to each other. See, e.g., Gaultier, et al., *Nucl. Acids Res.*, 15:6625-6641 (1987). The antisense nucleic acid molecule can also comprise a 2'-o-methylribonucleotide (see, e.g., Inoue, et al. *Nucl. Acids Res.*, 15:6131-6148 (1987)) or a chimeric RNA-DNA analogue (see, e.g., Inoue, et al., *FEBS Lett.*, 215:327-330 (1987)).

Production and delivery of antisense molecules are facilitated by providing a vector comprising an anti-sense nucleotide sequence complementary to at least a part of the Receptor or ligand DNA sequence. According to a yet further aspect of the invention such a vector comprising an anti-sense sequence may be used to inhibit, or at least mitigate, Receptor or ligand expression. The use of a vector of this type to inhibit Receptor or ligand expression is favored in instances where Receptor or ligand expression is associated with a particular disease state.

D. Anti-Ligand or Anti-Receptor RNA Interference

Use of RNA Interference to inactivate or modulate receptor or ligand expression is also contemplated by this invention. RNA interference is described in U.S. Patent Appl. No. 2002-0162126, and Hannon, G., *J. Nature*, 11:418:244-51 (2002). "RNA interference," "post-transcriptional gene silencing," "quelling"—these terms have all been used to describe similar effects that result from the overexpression or misexpression of transgenes, or from the deliberate introduction of double-stranded RNA into cells (reviewed in Fire, A., *Trends Genet.* 15:358-363 (1999); Sharp, P. A., *Genes Dev.*, 13:139-141 (1999); Hunter, C., *Curr. Biol.*, 9:R440-R442 (1999); Baulcombe, D. C., *Curr. Biol.* 9:R599-R601 (1999); Vaucheret, et al. *Plant J.* 16:651-659 (1998), all incorporated by reference. RNA interference, commonly referred to as RNAi, offers a way of specifically and potently inactivating a cloned gene.

IV. THERAPEUTIC FORMULATIONS AND ADMINISTRATION

A. Therapeutic Formulations

Binding constructs, or polynucleotides encoding the same, can be used directly to practice materials and methods of the invention, but in preferred embodiments, the compounds are formulated with pharmaceutically acceptable diluents, adjuvants, excipients, or carriers. The phrase "pharmaceutically or pharmacologically acceptable" refers to molecular entities and compositions that do not produce adverse, allergic, or other untoward reactions when administered to an animal or a human, e.g., orally, topically, transdermally, parenterally, by inhalation spray, vaginally, rectally, or by intracranial injection. (The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and/or surgical implantation at a particular site is contemplated as well.) Generally, this will also entail preparing compositions that are essentially free of pyrogens, as well as other impurities that could be harmful to humans or animals. The term "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art.

Therapeutic formulations of the compositions useful for practicing the invention such as polypeptides, polynucleotides, or antibodies may be prepared for storage by mixing the selected composition having the desired degree of purity with optional physiologically pharmaceutically-acceptable carriers, excipients, or stabilizers (*Remington's Pharmaceutical Sciences,* 18th edition, A. R. Gennaro, ed., Mack Publishing Company (1990)) in the form of a lyophilized cake or an aqueous solution. Pharmaceutical compositions may be produced by admixing with one or more suitable carriers or adjuvants such as water, mineral oil, polyethylene glycol, starch, talcum, lactose, thickeners, stabilizers, suspending agents, etc. Such compositions may be in the form of solutions, suspensions, tablets, capsules, creams, salves, ointments, or other conventional forms.

Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The composition to be used for in vivo administration should be sterile. This is readily accomplished by filtration through sterile filtration membranes, prior to or following lyophilization and reconstitution. Therapeutic compositions generally are placed into a container having a sterile access port, for example, an intravenous solution bag or vial having a stopper pierceable by a hypodermic injection needle. The route of administration of the composition is in accord with known methods, e.g. oral, injection or infusion by intravenous, intraperitoneal, intracerebral, intramuscular, intraocular, intraarterial, or intralesional routes, or by sustained release systems or implantation device. Where desired, the compositions may be administered continuously by infusion, bolus injection or by implantation device. The composition for parenteral administration ordinarily will be stored in lyophilized form or in solution.

The pharmaceutical forms suitable for injectable use include sterile aqueous solutions or dispersions and sterile powders for the extemporaneous preparation of sterile injectable solutions or dispersions. In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman, et al., *Biopolymers*, 22: 547-556 (1983)), poly(2-hydroxyethyl-methacrylate) (Langer, et al., *J. Biomed. Mater. Res.*, 15:167-277 (1981) and Langer, *Chem. Tech.*, 12:98-105 (1982)), ethylene vinyl acetate (Langer, et al., supra) or poly-D(–)-3-hydroxybutyric acid (EP 133,988). Sustained-release compositions also may include liposomes, which can be prepared by any of several methods known in the art (e.g., DE 3,218,121; Epstein, et al., *Proc. Natl. Acad. Sci. USA*, 82:3688-3692 (1985); Hwang, et al., *Proc. Natl. Acad. Sci. USA*, 77:4030-4034 (1980); EP 52,322; EP 36,676; EP 88,046; EP 143,949).

An effective amount of the compositions to be employed therapeutically will depend, for example, upon the therapeutic objectives, the route of administration, and the condition of the patient. A therapist can titer the dosage and modify the route of administration to obtain the optimal therapeutic effect. A typical daily dosage may range from about 1 µg/kg to up to 100 mg/kg or more, depending on the factors mentioned above. Typically, a clinician will administer the composition until a dosage is reached that achieves the desired effect. The progress of this therapy is easily monitored by conventional assays designed to evaluate the particular disease state being treated.

B. Kits and Unit Doses

In related variations of the preceding embodiments, a binding construct may be packaged or formulated together with another binding construct or other therapeutic (e.g., a chemotherapy agent), e.g., in a kit or package or unit dose, to permit co-administration, but these two components are not in admixture. In some embodiments, the two components to the kit/unit dose are packaged with instructions for administering the two compounds to a human subject for treatment of one of the disorders and diseases described herein.

C. Polynucleotide-Based Therapies

The present invention also includes gene therapy materials and methods. Specifically, polypeptides and binding constructions of the invention can be produced at therapeutic levels in vivo by administration of a gene therapy contrast that enters cells and is expressed in vivo to produce the polypeptides or binding constructs. For example, in some embodiments, the vasculature of a cancer cell or cancer cells may be contacted with an expression construct capable of providing a therapeutic peptide or binding constructs of the present invention. Expression of the polypeptide or binding construct causes a therapeutic outcome, for example, inhibition of growth factors and receptors in the vasculature of a tumor, an inhibition of angiogenesis, an inhibition of lymphangiogenesis, an ablation, regression or other inhibition of tumor growth, an induction of apoptosis of the blood or lymphatic vasculature of the tumor or indeed the tumor cells themselves.

For these embodiments, an exemplary expression construct comprises a virus or engineered construct derived from a viral genome. Such vectors and constructs are considered aspect of the invention. The expression construct generally comprises a nucleic acid encoding the gene or binding construct, including any nucleic acid molecule described herein, to be expressed and also additional regulatory regions that will effect the expression of the gene in the cell to which it is administered. Such regulatory regions include for example promoters, enhancers, polyadenylation signals and the like.

DNA may be introduced into a cell using a variety of viral vectors. In such embodiments, expression constructs comprising viral vectors containing the genes of interest may be adenoviral (see, for example, U.S. Pat. No. 5,824,544; U.S. Pat. No. 5,707,618; U.S. Pat. No. 5,693,509; U.S. Pat. No. 5,670,488; U.S. Pat. No. 5,585,362, each incorporated herein by reference), retroviral (see, for example, U.S. Pat. No. 5,888,502; U.S. Pat. No. 5,830,725; U.S. Pat. No. 5,770,414; U.S. Pat. No. 5,686,278; U.S. Pat. No. 4,861,719, each incorporated herein by reference), adeno-associated viral (see, for example, U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851,521; U.S. Pat. No. 5,252,479, each incorporated herein by reference), an adenoviral-adenoassociated viral hybrid (see, for example, U.S. Pat. No. 5,856,152 incorporated herein by reference) or a vaccinia viral or a herpesviral (see, for example, U.S. Pat. No. 5,879,934; U.S. Pat. No. 5,849,571; U.S. Pat. No. 5,830,727; U.S. Pat. No. 5,661,033; U.S. Pat. No. 5,328,688, each incorporated herein by reference) vector. Other vectors described herein may also be employed. Replication-deficient viral vectors are specifically contemplated.

In other embodiments, non-viral delivery is contemplated. These include calcium phosphate precipitation (Graham and Van Der Eb, *Virology*, 52:456-467 (1973); Chen and Okayama, *Mol. Cell. Biol.*, 7:2745-2752, (1987); Rippe, et al., *Mol. Cell. Biol.*, 10:689-695 (1990)), DEAE-dextran (Gopal, *Mol. Cell. Biol.*, 5:1188-1190 (1985)), electroporation (Tur-Kaspa, et al., *Mol. Cell. Biol.*, 6:716-718, (1986); Potter, et al., *Proc. Nat. Acad. Sci. USA*, 81:7161-7165, (1984)), direct microinjection (Harland and Weintraub, *J. Cell Biol.*, 101:1094-1099 (1985)), DNA-loaded liposomes (Nicolau and Sene, *Biochim. Biophys. Acta*, 721:185-190 (1982); Fraley, et al., *Proc. Natl. Acad. Sci. USA*, 76:3348-3352 (1979); Felgner, *Sci. Am.*, 276(6):102-6 (1997); Felgner, *Hum. Gene Ther.*, 7(15):1791-3, (1996)), cell sonication (Fechheimer, et al., *Proc. Natl. Acad. Sci. USA*, 84:8463-8467 (1987)), gene bombardment using high velocity microprojectiles (Yang, et al., *Proc. Natl. Acad. Sci. USA*, 87:9568-9572 (1990)), and receptor-mediated transfection (Wu and Wu, *J. Biol. Chem.*, 262:4429-4432 (1987); Wu and Wu, *Biochemistry*, 27:887-892 (1988); Wu and Wu, *Adv. Drug Delivery Rev.*, 12:159-167 (1993)).

In a particular embodiment of the invention, the expression construct (or indeed the peptides discussed above) may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, "In Liver Diseases, Targeted Diagnosis And Therapy Using Specific Receptors And Ligands," Wu, G., Wu, C., ed., New York: Marcel Dekker, pp. 87-104 (1991)). The addition of DNA to cationic liposomes causes a topological transition from liposomes to optically birefringent liquid-crystalline condensed globules (Radler, et al., *Science*, 275(5301):810-4, (1997)). These DNA-lipid complexes are potential non-viral vectors for use in gene therapy and delivery.

Liposome-mediated nucleic acid delivery and expression of foreign DNA in vitro has been very successful. Also contemplated in the present invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA (Kaneda, et al., *Science*, 243:375-378 (1989)). In other embodiments, the liposome may be complexed or employed in conjunction with nuclear nonhistone chromosomal proteins (HMG-1) (Kato, et al., *J. Biol. Chem.*, 266:3361-3364 (1991)). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu (1993), supra).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu (1987), supra) and transferrin (Wagner, et al., *Proc. Nat'l. Acad. Sci. USA*, 87(9):3410-3414 (1990)). Recently, a synthetic neoglycoprotein, which recognizes the same receptor as ASOR, has been used as a gene delivery vehicle (Ferkol, et al., *FASEB. J.*, 7:1081-1091 (1993); Perales, et al., *Proc. Natl. Acad. Sci., USA* 91:4086-4090 (1994)) and epidermal growth factor (EGF) has also been used to deliver genes to squamous carcinoma cells (Myers, EPO 0273085).

In other embodiments, the delivery vehicle may comprise a ligand and a liposome. For example, Nicolau, et al., *Methods Enzymol.*, 149:157-176 (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a particular cell type by any number of receptor-ligand systems with or without liposomes.

In another embodiment of the invention, the expression construct may simply consist of naked recombinant DNA or plasmids. Transfer of the construct may be performed by any of the methods mentioned above that physically or chemically permeabilize the cell membrane. This is applicable particularly for transfer in vitro, however, it may be applied for in vivo use as well. Dubensky, et al., *Proc. Nat. Acad. Sci. USA*, 81:7529-7533 (1984) successfully injected polyomavirus DNA in the form of $CaPO_4$ precipitates into liver and spleen of adult and newborn mice demonstrating active viral replication and acute infection. Benvenisty and Neshif, *Proc. Nat. Acad. Sci. USA*, 83:9551-9555 (1986) also demonstrated that direct intraperitoneal injection of $CaPO_4$ precipitated plasmids results in expression of the transfected genes.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein, et al., *Nature*, 327:70-73 (1987)). Several devices for accelerating small particles have been developed. One such device relies on a high voltage discharge to generate an electrical current, which in turn provides the motive force (Yang, et al., *Proc. Natl. Acad. Sci. USA*, 87:9568-9572 (1990)). The microprojectiles used have consisted of biologically inert substances such as tungsten or gold beads.

Those of skill in the art are well aware of how to apply gene delivery to in vivo and ex vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various cell types. For practically any cell, tissue or organ type, systemic delivery is contemplated. In other embodiments, a variety of direct, local and regional approaches may be taken. For example, the cell, tissue or organ may be directly injected with the expression vector or protein.

Promoters for gene therapy for use in this invention include cytomegalovirus (CMV) promoter/enhancer, long terminal repeat (LTR) of retroviruses, keratin 14 promoter, and a myosin heavy chain promoter.

In a different embodiment, ex vivo gene therapy is contemplated. In an ex vivo embodiment, cells from the patient are removed and maintained outside the body for at least some period of time. During this period, a therapy is delivered, after which the cells are reintroduced into the patient; preferably, any tumor cells in the sample have been killed.

The techniques, procedures and methods outlined herein are applicable to any and all of the polypeptides and binding constructs of the present invention.

D. Chemotherapy and Other Combination Therapies

Any one of the binding constructs of the present invention when used in a method of treating a disease, e.g. a neoplastic condition such as a tumor, may be employed alone, or in combination with other agents. In some embodiments, more than one binding construct may be administered. In some embodiments, a binding construct may be administered together with a chemotherapeutic agent.

Certain cancers or patients may lend themselves to a treatment of combined binding construct and chemotherapeutic agent to achieve an additive or even a synergistic effect compared to the use of any one therapy alone. The chemotherapeutic agents may include, but are not limited to, platinum coordination compounds, topoisomerase inhibitors, antibiotics, antimitotic alkaloids and difluoronucleosides, as described in U.S. Pat. No. 6,630,124. The binding construct and chemotherapeutic agent need not be administered simultaneously, nor must they be administered by the same means.

In some embodiments, the chemotherapeutic agent is a platinum coordination compound. The term "platinum coordination compound" refers to any tumor cell growth inhibiting platinum coordination compound that provides the platinum in the form of an ion. Preferred platinum coordination compounds include, but are not limited to, cis-diamminediaquoplatinum (II)-ion; chloro(diethylenetriamine)-platinum (II) chloride; dichloro(ethylenediamine)-platinum(II), diammine(1,1-cyclobutanedicarboxylato) platinum(I) (carboplatin); spiroplatin; iproplatin; diammine(2-ethylmalonato)-platinum(II); ethylenediaminemalonatoplatinum(II); aqua(1,2-diaminodyclohexane)-sulfatoplatinum(II); (1,2-diaminocyclohexane)malonatoplatinum(II); (4-caroxyphthalato)(1,2-diaminocyclohexane)platinum(II); (1,2-diaminocyclohexane)-(isocitrato)platinum(II); (1,2-diaminocyclohexane)cis(pyruvato)platinum(II); (1,2-diaminocyclohexane)oxalatoplatinum(II); ormaplatin; and tetraplatin.

In some embodiments, cisplatin is the preferred platinum coordination compound employed in the compositions and methods of the present invention. Cisplatin is commercially available under the name PLATINOL™ from Bristol Myers-Squibb Corporation and is available as a powder for constitution with water, sterile saline or other suitable vehicle. Other platinum coordination compounds suitable for use in the present invention are known and are available commercially and/or can be prepared by conventional techniques. Cisplatin, or cis-dichlorodiammineplatinum II, has been used successfully for many years as a chemotherapeutic agent in the treatment of various human solid malignant tumors. More recently, other diamino-platinum complexes have also shown efficacy as chemotherapeutic agents in the treatment of various human solid malignant tumors. Such diamino-platinum complexes include, but are not limited to, spiroplatinum and carboplatinum. Although cisplatin and other diamino-platinum complexes have been widely used as chemotherapeutic agents in humans, they have had to be delivered at high dosage levels that can lead to toxicity problems such as kidney damage.

Preferably, when cisplatin is used in combination with the binding constructs of the present invention, the results obtained are synergistic. That is to say, the effectiveness of the combination therapy of a binding construct and the platinum coordination compound is synergistic, i.e., the effectiveness is greater than the effectiveness expected from the additive individual effects of each. Therefore, the dosage of the platinum coordination compound can be reduced and thus, the risk of the toxicity problems and other side effects is concomitantly reduced.

In some embodiments, the chemotherapeutic agent of the present invention is a topoisomerase inhibitor. Topoisomerases are enzymes that are capable of altering DNA topology in eukaryotic cells. They are critical for cellular functions and cell proliferation. Generally, there are two classes of topoisomerases in eukaryotic cells, type I and type II. Topoisomerase I is a monomeric enzyme of approximately 100,000 molecular weight. The enzyme binds to DNA and introduces a transient single-strand break, unwinds the double helix (or allows it to unwind), and subsequently reseals the break before dissociating from the DNA strand. Various topoisomerase inhibitors have recently shown clinical efficacy in the treatment of humans afflicted with ovarian, cancer, esophageal cancer or non-small cell lung carcinoma.

One especially preferred topoisomerase inhibitor of the present invention is camptothecin and camptothecin analogs. Camptothecin is a water-insoluble, cytotoxic alkaloid produced by *Camptotheca accuminata* trees indigenous to China and *Nothapodytes foetida* trees indigenous to India. Camptothecin exhibits tumor cell growth inhibiting activity against a number of tumor cells. Compounds of the camptothecin analog class are typically specific inhibitors of DNA topoisomerase I. By the term "inhibitor of topoisomerase" is meant any tumor cell growth inhibiting compound that is structurally related to camptothecin. Compounds of the camptothecin analog class include, but are not limited to, topotecan, irinotecan and 9-amino-camptothecin.

In addition to the foregoing topoisomerase inhibitors, such compounds also include, but are not limited to, any tumor cell growth inhibiting camptothecin analog claimed or described in: U.S. Pat. No. 5,004,758, issued on Apr. 2, 1991 and European Patent Application Number 88311366.4, published on Jun. 21, 1989 as Publication Number EP 0 321 122; U.S. Pat. No. 4,604,463, issued on Aug. 5, 1986 and European Patent Application Publication Number EP 0 137 145, published on Apr. 17, 1985; U.S. Pat. No. 4,473,692, issued on Sep. 25, 1984 and European Patent Application Publication Number EP 0 074 256, published on Mar. 16, 1983; U.S. Pat. No. 4,545,880, issued on Oct. 8, 1985 and European Patent Application Publication Number EP 0 074 256, published on Mar. 16, 1983; European Patent Application Publication Number EP 0 088 642, published on Sep. 14, 1983; Wani et al, *J. Med. Chem.*, 29, 2358-2363 (1986); Nitta et al., *Proc. 14th International Congr. Chemotherapy*, Kyoto, 1985, Tokyo Press, Anticancer Section 1, p. 28-30, especially a compound called CPT-11. CPT-11 is a camptothecin analog with a 4-(piperidino)-piperidine side chain joined through a carbamate linkage at C-10 of 10-hydroxy-7-ethyl camptothecin. CPT-11 is currently undergoing human clinical trials and is also referred to as irinotecan; Wani et al, *J. Med. Chem.*, 23, 554 (1980); Wani et. al., *J. Med. Chem.*, 30, 1774 (1987); U.S. Pat. No. 4,342,776, issued on Aug. 3, 1982; U.S. patent application Ser. No. 581,916, filed on Sep. 13, 1990 and European Patent Application Publication Number EP 418 099, published on Mar. 20, 1991; U.S. Pat. No. 4,513,138, issued on Apr. 23, 1985 and European Patent Application Publication Number EP 0 074 770, published on Mar. 23, 1983; U.S. Pat. No. 4,399,276, issued on Aug. 16, 1983 and European Patent Application Publication Number 0 056 692, published on Jul. 28, 1982; the entire disclosure of each of which is hereby incorporated by reference. All of the above-listed compounds of the camptothecin analog class are available commercially and/or can be prepared by conventional techniques including those described in the above-listed references. The topoisomerase inhibitor may be selected from the group consisting of topotecan, irinotecan and 9-aminocamptothecin.

Preferably, when a topoisomerase inhibitor is used in combination with the binding constructs of the present invention, the results obtained are synergistic. That is, the effectiveness of the combination therapy of a binding construct and the topoisomerase inhibitor is synergistic, i.e., the effectiveness is greater than the effectiveness expected from the additive individual effects of each. Therefore, the dosage of the topoisomerase inhibitor can be reduced and thus, the risk of the toxicity problems and other side effects is concomitantly reduced.

The preparation of numerous compounds of the camptothecin analog class (including pharmaceutically acceptable salts, hydrates and solvates thereof) as well as the preparation of oral and parenteral pharmaceutical compositions comprising such a compounds of the camptothecin analog class and an inert, pharmaceutically acceptable carrier or diluent, is extensively described in U.S. Pat. No. 5,004,758, issued on Apr. 2, 1991 and European Patent Application Number 88311366.4, published on Jun. 21, 1989 as Publication Number EP 0 321 122, the teachings of which are incorporated herein by reference.

In still yet another embodiment of the present invention, the chemotherapeutic agent is an antibiotic compound. Suitable antibiotic include, but are not limited to, doxorubicin, mitomycin, bleomycin, daunorubicin and streptozocin.

Preferably, when an antibiotic is used in combination with the binding constructs of the present invention, the results obtained are synergistic. That is, the effectiveness of the combination therapy of a binding construct and the antibiotic compound is synergistic, i.e., the effectiveness is greater than the effectiveness expected from the additive individual effects of each. Therefore, the dosage of the antibiotic compound can be reduced and thus, the risk of the toxicity problems and other side effects is concomitantly reduced.

In some embodiments, the chemotherapeutic agent is an antimitotic alkaloid. In general, antimitotic alkaloids can be extracted from *Cantharanthus roseus*, and have been shown to be efficacious as anticancer chemotherapy agents. A great number of semi-synthetic derivatives have been studied both chemically and pharmacologically (see, O. Van Tellingen et al, Anticancer Research, 12, 1699-1716 (1992)). The antimitotic alkaloids of the present invention include, but are not limited to, vinblastine, vincristine, vindesine, Taxol and vinorelbine. The latter two antimitotic alkaloids are commercially available from Eli Lilly and Company, and Pierre Fabre Laboratories, respectively (see, U.S. Pat. No. 5,620,985). In a preferred aspect of the present invention, the antimitotic alkaloid is vinorelbine.

Preferably, when an antimitotic alkaloid is used in combination with the binding constructs of the present invention, the results obtained are synergistic. That is, the effectiveness of the combination therapy of a binding construct and an antimitotic alkaloids compound is synergistic, i.e., the effectiveness is greater than the effectiveness expected from the additive individual effects of each. Therefore, the dosage of the antimitotic alkaloid can be reduced and thus, the risk of the toxicity problems and other side effects is concomitantly reduced.

In another embodiment of the present invention, the chemotherapeutic agent is a difluoronucleoside. 2'-deoxy-2',2'-difluoronucleosides are known in the art as having antiviral activity. Such compounds are disclosed and taught in U.S. Pat. Nos. 4,526,988 and 4,808,614. European Patent Application Publication 184,365 discloses that these same difluoronucleosides have oncolytic activity. Preferably, the 2'-deoxy-2',2'-difluoronucleoside used in the compositions and methods of the present invention is 2'-deoxy-2',2'-difluorocytidine hydrochloride, also known as gemcitabine hydrochloride. Gemcitabine is commercially available or can be synthesized in a multi-step process as disclosed and taught in U.S. Pat. Nos. 4,526,988, 4,808,614 and 5,223,608, the teachings of which are incorporated herein by reference.

Preferably, when a difluoronucleoside is used in combination with the binding constructs of the present invention, the results obtained are synergistic. That is, the effectiveness of the combination therapy of a binding construct and a difluoronucleoside compound is synergistic, i.e., the effectiveness is greater than the effectiveness expected from the additive individual effects of each. Therefore, the dosage of the difluoronucleoside can be reduced and thus, the risk of the toxicity problems and other side effects is concomitantly reduced.

E. Disease Targets

1. Neoplasms

Neoplasms treatable by the present invention include solid tumors, for example, carcinomas and sarcomas. Carcinomas include malignant neoplasms derived from epithelial cells which infiltrate, for example, invade, surrounding tissues and give rise to metastases. Adenocarcinomas are carcinomas derived from glandular tissue, or from tissues that form recognizable glandular structures. Another broad category of cancers includes sarcomas and fibrosarcomas, which are tumors whose cells are embedded in a fibrillar or homogeneous substance, such as embryonic connective tissue. The invention also provides methods of treatment of cancers of myeloid or lymphoid systems, including leukemias, lymphomas, and other cancers that typically are not present as a tumor mass, but are distributed in the vascular or lymphoreticular systems. Further contemplated are methods for treatment of adult and pediatric oncology, growth of solid tumors/malignancies, myxoid and round cell carcinoma, locally advanced tumors, cancer metastases, including lymphatic metastases. The cancers listed herein are not intended to be limiting. Both age (child and adult), sex (male and female), primary and secondary, pre- and post-metastatic, acute and chronic, benign and malignant, anatomical location cancer embodiments and variations are contemplated targets. Cancers are grouped by embryonic origin (e.g., carcinoma, lymphomas, and sarcomas), by organ or physiological system, and by miscellaneous grouping. Particular cancers may overlap in their classification, and their listing in one group does not exclude them from another.

Carcinomas that may targeted include adrenocortical, acinar, acinic cell, acinous, adenocystic, adenoid cystic, adenoid squamous cell, cancer adenomatosum, adenosquamous, adnexel, cancer of adrenal cortex, adrenocortical, aldosterone-producing, aldosterone-secreting, alveolar, alveolar cell, ameloblastic, ampullary, anaplastic cancer of thyroid gland, apocrine, basal cell, basal cell, alveolar, comedo basal cell, cystic basal cell, morphea-like basal cell, multicentric basal cell, nodulo-ulcerative basal cell, pigmented basal cell, sclerosing basal cell, superficial basal cell, basaloid, basosquamous cell, bile duct, extrahepatic bile duct, intrahepatic bile duct, bronchioalveolar, bronchiolar, bronchioloalveolar, bronchoalveolar, bronchoalveolar cell, bronchogenic, cerebriform, cholangiocelluarl, chorionic, choroids plexus, clear cell, cloacogenic anal, colloid, comedo, corpus, cancer of corpus uteri, cortisol-producing, cribriform, cylindrical, cylindrical cell, duct, ductal, ductal cancer of the prostate, ductal cancer in situ (DCIS), eccrine, embryonal, cancer en cuirasse, endometrial, cancer of endometrium, endometroid, epidermoid, cancer ex mixed tumor, cancer ex pleomorphic adenoma, exophytic, fibrolamellar, cancer fibro'sum, follicular cancer of thyroid gland, gastric, gelatinform, gelatinous, giant cell, giant cell cancer of thyroid gland, cancer gigantocellula're, glandular, granulose cell, hepatocellular, Hürthle cell, hypemephroid, infantile embryonal, islet cell carcinoma, inflammatory cancer of the breast, cancer in si'tu, intraductal, intraepidermal, intraepithelial, juvenile embryonal, Kulchitsky-cell, large cell, leptomeningeal, lobular, infiltrating lobular, invasive lobular, lobular cancer in situ (LCIS), lymphoepithelial, cancer medullare, medullary, medullary cancer of thyroid gland, medullary thyroid, melanotic, meningeal, Merkel cell, metatypical cell, micropapillary, cancer mol'le, mucinous, cancer muci'parum, cancer mucocellula're, mucoepidermoid, cancer muco'sum, mucous, nasopharyngeal, neuroendocrine cancer of the skin, noninfiltrating, non-small cell, non-small cell lung cancer (NSCLC), oat cell, cancer ossi'ficans, osteoid, Paget's, papillary, papillary cancer of thyroid gland, periampullary, preinvasive, prickle cell, primary intrasseous, renal cell, scar, schistosomal bladder, Schneiderian, scirrhous, sebaceous, signet-ring cell, cancer sim'plex, small cell, small cell lung cancer (SCLC), spindle cell, cancer spongio'sum, squamous, squamous cell, terminal duct, anaplastic thyroid, follicular thyroid, medullary thyroid, papillary thyroid, trabecular cancer of the skin, transitional cell, tubular, undifferentiated cancer of thyroid gland, uterine corpus, verrucous, villous, cancer villo'sum, yolk sac, squamous cell particularly of the head and neck, esophageal squamous cell, and oral cancers and carcinomas.

Sarcomas that may be targeted include adipose, alveolar soft part, ameloblastic, avian, botryoid, sarcoma botryoi'des, chicken, chloromatous, chondroblastic, clear cell sarcoma of kidney, embryonal, endometrial stromal, epithelioid, Ewing's, fascial, fibroblastic, fowl, giant cell, granulocytic, hemangioendothelial, Hodgkin's, idiopathic multiple pigmented hemorrhagic, immunoblastic sarcoma of B cells, immunoblastic sarcoma of T cells, Jensen's, Kaposi's, kupffer cell, leukocytic, lymphatic, melanotic, mixed cell, multiple, lymphangio, idiopathic hemorrhagic, multipotential primary sarcoma of bone, osteoblastic, osteogenic, parosteal, polymorphous, pseudo-kaposi, reticulum cell, reticulum cell sarcoma of the brain, rhabdomyosarcoma, rous, soft tissue, spindle cell, synovial, telangiectatic, sarcoma (osteosarcoma)/malignant fibrous histiocytoma of bone, and soft tissue sarcomas.

Lymphomas that may targeted include AIDS-related, non-Hodgkin's, Hodgkin's, T-cell, T-cell leukemia/lymphoma, African, B-cell, B-cell monocytoid, bovine malignant, Burkitt's, centrocytic, lymphoma cu'tis, diffuse, diffuse, large cell, diffuse, mixed small and large cell, diffuse, small cleaved cell, follicular, follicular center cell, follicular, mixed small cleaved and large cell, follicular, predominantly large cell, follicular, predominantly small cleaved cell, giant follicle, giant follicular, granulomatous, histiocytic, large cell, immunoblastic, large cleaved cell, large nocleaved cell, Lennert's, lymphoblastic, lymphocytic, intermediate; lymphocytic, intermediately differentiated, plasmacytoid; poorly differentiated lymphocytic, small lymphocytic, well differentiated lymphocytic, lymphoma of cattle; MALT, mantle cell, mantle zone, marginal zone, Mediterranean lymphoma mixed lymphocytic-histiocytic, nodular, plasmacytoid, pleomorphic, primary central nervous system, primary effusion, small b-cell, small cleaved cell, small concleaved cell, T-cell lymphomas; convoluted T-cell, cutaneous t-cell, small lymphocytic T-cell, undefined lymphoma, u-cell, undifferentiated, aids-related, central nervous system, cutaneous T-cell, effusion (body cavity based), thymic lymphoma, and cutaneous T cell lymphomas.

Leukemias and other blood cell malignancies that may be targeted include acute lymphoblastic, acute myeloid, lymphocytic, chronic myelogenous, hairy cell, lymphoblastic, myeloid, lymphocytic, myelogenous, leukemia, hairy cell, T-cell, monocytic, myeloblastic, granulocytic, gross, hand mirror-cell, basophilic, hemoblastic, histiocytic, leukopenic, lymphatic, Schilling's, stem cell, myelomonocyic, prolyniphocytic, micromyeloblastic, megakaryoblastic, megakaryoctyic, rieder cell, bovine, aleukemic, mast cell, myelocytic, plamsa cell, subleukemic, multiple myeloma, nonlymphocytic, and chronic myelocytic leukemias.

Brain and central nervous system (CNS) cancers and tumors that may be targeted include astrocytomas (including cerebellar and cerebral), brain stem glioma, brain tumors, malignant gliomas, ependymoma, glioblastoma, medulloblastoma, supratentorial primitive neuroectodermal tumors, visual pathway and hypothalamic gliomas, primary central nervous system lymphoma, ependymoma, brain stem glioma, visual pathway and hypothalamic glioma, extracranial germ cell tumor, medulloblastoma, myelodysplastic syndromes, oligodendroglioma, myelodysplastic/myeloproliferative diseases, myelogenous leukemia, myeloid leukemia, multiple myeloma, myeloproliferative disorders, neuroblastoma, plasma cell neoplasm/multiple myeloma, central nervous system lymphoma, intrinsic brain tumors, astrocytic brain tumors, gliomas, and metastatic tumor cell invasion in the central nervous system.

Gastrointestinal cancers that may be targeted include extrahepatic bile duct cancer, colon cancer, colon and rectum cancer, colorectal cancer, gallbladder cancer, gastric (stomach) cancer, gastrointestinal carcinoid tumor, gastrointestinal carcinoid tumors, gastrointestinal stromal tumors, bladder cancers, islet cell carcinoma (endocrine pancreas), pancreatic cancer, islet cell pancreatic cancer, prostate cancer rectal cancer, salivary gland cancer, small intestine cancer, colon cancer, and polyps associated with colorectal neoplasia.

Bone cancers that may be targeted include osteosarcoma and malignant fibrous histiocytomas, bone marrow cancers, bone metastases, osteosarcoma/malignant fibrous histiocytoma of bone, and osteomas and osteosarcomas. Breast cancers that may be targeted include small cell carcinoma and ductal carcinoma.

Lung and respiratory cancers that may be targeted include bronchial adenomas/carcinoids, esophagus cancer esophageal cancer, esophageal cancer, hypopharyngeal cancer, laryngeal cancer, hypopharyngeal cancer, lung carcinoid tumor, non-small cell lung cancer, small cell lung cancer, small cell carcinoma of the lungs, mesothelioma, nasal cavity and paranasal sinus cancer, nasopharyngeal cancer, nasopharyngeal cancer, oral cancer, oral cavity and lip cancer, oropharyngeal cancer; paranasal sinus and nasal cavity cancer, and pleuropulmonary blastoma.

Urinary tract and reproductive cancers that may be targeted include cervical cancer, endometrial cancer, ovarian epithelial cancer, extragonadal germ cell tumor, extracranial germ cell tumor, extragonadal germ cell tumor, ovarian germ cell tumor, gestational trophoblastic tumor, spleen, kidney cancer, ovarian cancer, ovarian epithelial cancer, ovarian germ cell tumor, ovarian low malignant potential tumor, penile cancer, renal cell cancer (including carcinomas), renal cell cancer, renal pelvis and ureter (transitional cell cancer), transitional cell cancer of the renal pelvis and ureter, gestational trophoblastic tumor, testicular cancer, ureter and renal pelvis, transitional cell cancer, urethral cancer, endometrial uterine cancer, uterine sarcoma, vaginal cancer, vulvar cancer, ovarian carcinoma, primary peritoneal epithelial neoplasms, cervical carcinoma, uterine cancer and solid tumors in the ovarian follicle), superficial bladder tumors, invasive transitional cell carcinoma of the bladder, and muscle-invasive bladder cancer.

Skin cancers and melanomas (as well as non-melanomas) that may be targeted include cutaneous t-cell lymphoma, intraocular melanoma, tumor progression of human skin keratinocytes, basal cell carcinoma, and squamous cell cancer. Liver cancers that may be targeted include extrahepatic bile duct cancer, and hepatocellular cancers. Eye cancers that may be targeted include intraocular melanoma, retinoblastoma, and intraocular melanoma Hormonal cancers that may be targeted include: parathyroid cancer, pineal and supratentorial primitive neuroectodermal tumors, pituitary tumor, thymoma and thymic carcinoma, thymoma, thymus cancer, thyroid cancer, cancer of the adrenal cortex, and ACTH-producing tumors.

Miscellaneous other cancers that may be targeted include advanced cancers, AIDS-related, anal cancer adrenal cortical, aplastic anemia, aniline, betel, buyo cheek, cerebriform, chimney-sweeps, clay pipe, colloid, contact, cystic, dendritic, cancer a deux, duct, dye workers, encephaloid, cancer en cuirasse, endometrial, endothelial, epithelial, glandular, cancer in situ, kang, kangri, latent, medullary, melanotic, mule-spinners', non-small cell lung, occult cancer, paraffin, pitch workers', scar, schistosomal bladder, scirrhous, lymph node, small cell lung, soft, soot, spindle cell, swamp, tar, and tubular cancers.

Miscellaneous other cancers that may be targeted also include carcinoid (gastrointestinal and bronchal) Castleman's disease chronic myeloproliferative disorders, clear cell sarcoma of tendon sheaths, Ewing's family of tumors, head and neck cancer, lip and oral cavity cancer, Waldenström's macroglobulinemia, metastatic squamous neck cancer with occult primary, multiple endocrine neoplasia syndrome, multiple myeloma/plasma cell neoplasm, Wilms' tumor, mycosis fungoides, pheochromocytoma, sezary syndrome, supratentorial primitive neuroectodermal tumors, unknown primary site, peritoneal effusion, malignant pleural effusion, trophoblastic neo-plasms, and hemangiopericytoma.

2. Other Disease Targets

Neoplasms are not the only diseases that may be targeted using the binding constructs of the invention. The binding constructs of the invention may also be used to treat such diseases as rheumatoid arthritis, edemas (and other types of plasma leakage), cancer associated disorders such as cancer-associated ascites formation, diabetes, and inflammatory diseases such as psoriasis. The binding constructs may be used as therapeutics for any disease associated with abnormally high levels of growth factor expression.

V. NON-EXCLUSIVE EXAMPLES OF THE INVENTION

The invention may be more readily understood by reference to the following examples, which are given to illustrate the invention and not in any way to limit its scope. These examples primarily make reference to binding constructs that bind particular growth factors of the VEGF subfamily, but they may also be adapted for use of binding constructs that bind other VEGF subfamily members, as well as for binding constructs that bind PDGF subfamily members. Similarly, binding constructs comprising other VEFGR receptor fragments, PDGFR receptor fragments, and neuropilin receptor fragments may also be employed in variations of these examples.

Example 1

VEGFR-2 and VEGFR-3 Fragments that Bind VEGF-A or VEGF-C

To determine the portion of a receptor's extracellular domain (ECD) that was sufficient for ligand binding, fragments of the ECDs of VEGFR-2 (R-2) and VEGFR-3 (R-3) were used to make various soluble constructs. The constructs included Fc domain human IgG fragments fused to the C-terminus of the receptor fragments. As indicated in Tables 3 and 4, some constructs were made using a heterologous (N-terminal) signal peptide derived from CD33.

Construction of Fragments and Plasmids
R-2 Constructs
To construct the VEGFR-2/IgG expression plasmid, the construct, R-2 A, comprising the first three Ig-domains (D1-3) of VEGFR-2 was amplified by PCR using primers 5'-GCGGATCCTTGCCTAGTGTTTCTCTTGATC-3' (SEQ ID NO: 72), and 5'-CCAGTCACCTGCTCCGGATCTTCATGGACCCTGACAAATG-3' (SEQ ID NO: 73), and cloned into the Signal pIgplus vector (Novagen, Madison, Wis.). The resulting plasmid was digested with BamHI and KpnI, treated with T4 polymerase and back-ligated. To assemble other VEGFR-2/IgG constructs, PCRs were performed using the D1-3 construct as the template, T7 forward primer and the following reverse primers:

```
5'-GCTGGATCTTGAACATAGACATAAATG-3' (R-2 F),,        (SEQ ID NO: 59)

5'-CTAGGATCCCCTACAACGACAACTATG-3' (R-2 B),,        (SEQ ID NO: 60)

5'-CTAGGATCCACATCATAAATCCTATAC-3' (R-2 C),,        (SEQ ID NO: 61)

5'-GCATGGTCTCGGATCATGAGAAGACGGACTCAGAAC-3' (R-2 D),,  (SEQ ID NO: 62)

5'-CTAGGATCCTTTTCTCCAACAGATAG-3' (R-2 E);          (SEQ ID NO: 63)
``` forward primer 5'-AGCGCTAGCGTTCAAGATTACAGATCTCC-3' (SEQ ID NO: 64), and the following reverse primers:

```
5'-ATGTGTGAGGTTTTGCACAAG-3' (R-2 G),,              (SEQ ID NO: 65)

5'-CTAGGATCCCCTACAACGACAACTATG-3' (R-2 H),,        (SEQ ID NO: 66)

5'-CTAGGATCCACATCATAAATCCTATAC-3' (R-2 I),,        (SEQ ID NO: 67)

5'-GCATGGTCTCGGATCATGAGAAGACGGACTCAGAAC-3' (R-2 J),,  (SEQ ID NO: 68)

5'-CTAGGATCCTTTTCTCCAACAGATAG-3' (R-2 K),,         (SEQ ID NO: 69)
``` forward primer 5'-AGCGCTAGCTATAGGATTTATGATGTG-3' (SEQ ID NO: 70), and reverse primer

```
                                                    (SEQ ID NO: 71)
5'-ATGTGTGAGGTTTTGCACAAG-3'(R-2 L),.
```

The PCR products were digested with NheI and BstYI (R-2 F and L constructs), NheI and BamHI (R-2 E, and H-K constructs), BamHI (R-2 linker B and C constructs), BamHI and BsaI (R-2 D construct), or NheI and BsmBI (R-2 G construct), and cloned into the Signal pIgplus vector. In order to repair frame-shifts in constructs containing nucleotide sequence coding for domain 1 of VEGFR-2, the vectors were cut with restriction enzyme NotI, blunted with Klenow enzyme, cut with EcoRV and back-ligated.

R-3 Constructs
A series of R-3 constructs with N-termini between Ig domains 2 and 3 of VEGFR-3 (R-3 C through F constructs) was created by PCR using the expression plasmid comprising the R-3 D1-3 transcript (e.g., the R-3 G construct, SEQ ID NO: 43) as template, T7 as forward primer and the following reverse primers:

```
5'-TCAGGATCCGCGAGCTCGTTGCCTG-3',    (SEQ ID NO: 74)

5'-TACAGGATCCCCTGTGATGTGCACCAG-3',  (SEQ ID NO: 75)

5'-TCAGGATCCGCGTGCACCAGGAAGG-3',    (SEQ ID NO: 76)
and

5'-TCAGGATCCGCGAAGGGGTTGGAAAG-3'.   (SEQ ID NO: 77)
```

The Ig homology domain 1 was deleted from the D1-3 expression plasmid (R-3 G construct) by site-directed mutagenesis using primers
5'CCTTGAACATCACGGAGGAGTCACACGTCAGAGACTTTGA GCAGCCATTCATCAACAAGC-3' (SEQ ID NO: 78) and
5'AGCTGCTGGTAGGGGAGAAGGATCCTGAACTGCACCGTGT GG-3' (SEQ ID NO: 79), and excision of the BamH I fragment from the resulting plasmid. That procedure combined with the described truncation primers, for R-3 C through F constructs, allows for the production of the R-3 constructs (e.g., C, D, E, F, J, K, L, and M). The plasmid coding for domains 2 and 3 of VEGFR-3 (R-3 I) was made by transfer of the Sph I fragment from the original expression R-3 D1-3 plasmid into the plasmid encoding only domain 2 of VEGFR-3 (R-3 J). The sequence derived from a particular receptor is listed in Table 2. Expression was performed using standard calcium phosphate-mediated transfection into 293T cells.

The binding assays utilized minimal VEGF-A (SEQ ID NOS: 106 and 107) and VEGF-C (SEQ ID NOS: 108 and 109) fragments with 109 residues each (called VEGF-A 109 and VEGF-C 109). These constructs are not naturally occurring, but are effective for binding assays. Other growth factor constructs, either natural or artificial, may also be used for performing these assays.

Either Tritiated VEGF-A 109 or VEGF-C 109 was used in a given binding experiment. Ligand in solution was precipitated by mixing 175 µl of ligand solution with 100 µl binding mix at 4° C. overnight, with agitation. The ligand solution may be the supernatant of metabolically labeled 293T cells. The binding mixes used for the receptor binding analysis were as follows: for VEGFR-1 binding assays, the binding mix was phosphate buffered saline (PBS) containing 1.5% BSA, 0.06% Tween 20, 3 µg/ml heparin and 400 ng/ml VEGFR-1-Fc fusion protein (100 µl of this binding mix was added to 200 µl of ligand solution). For VEGFR-2 binding assays, the binding mix was 82% conditioned cell supernatant from 293T cells transiently expressing VEGFR-2-Fc fusion protein in mixture with 18% of a PBS solution that contained 5% BSA, 0.2% Tween 20, and 10 µg/ml heparin (250 µl of binding mix was added to 200 µl of ligand solution). For VEGFR-3 binding assays, the binding mix was 82% conditioned cell supernatant from 293T cells transiently expressing VEGFR-3-Fc fusion protein, 18% of PBS containing 5% BSA, 0.2% Tween 20, and 10 µg/ml heparin (250 µl of binding mix was added to 200 µl of ligand solution). To collect precipitated ligand, 50 µl of a 30% protein A sepharose (PAS, Pharmacia) slurry in PBS was added and incubated under agitation for at least 1.5 hr at 4° C. Standard buffer was added to each immunoprecipitation sample and boiled for 5 minutes at 95° C. during which the immunopreciptated proteins become dissociated from the protein A sepharose. After centrifugation, 10 µl of each sample was analyzed on 15% SDS-PAGE under reducing conditions. The gels were dried and exposed for either 12 hours on phosphorimager plates or 4 weeks on X-ray film.

Figure 2:
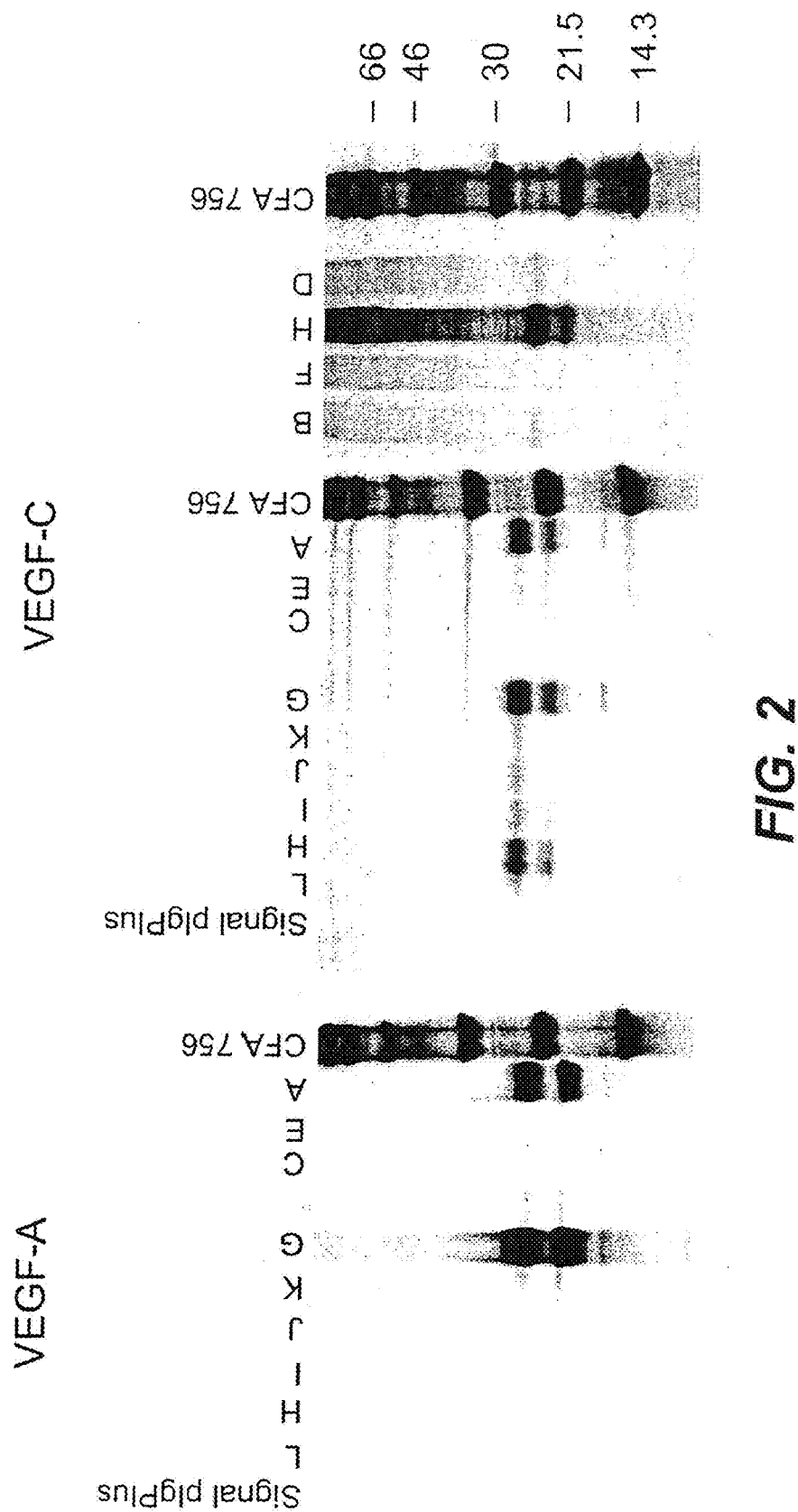
FIG. 2 is an autoradiograph of a PAGE from binding assays of VEGFR-2 fragment binding constructs using either radiolabeled VEGF-A or VEGF-C constructs.
Figure 3:
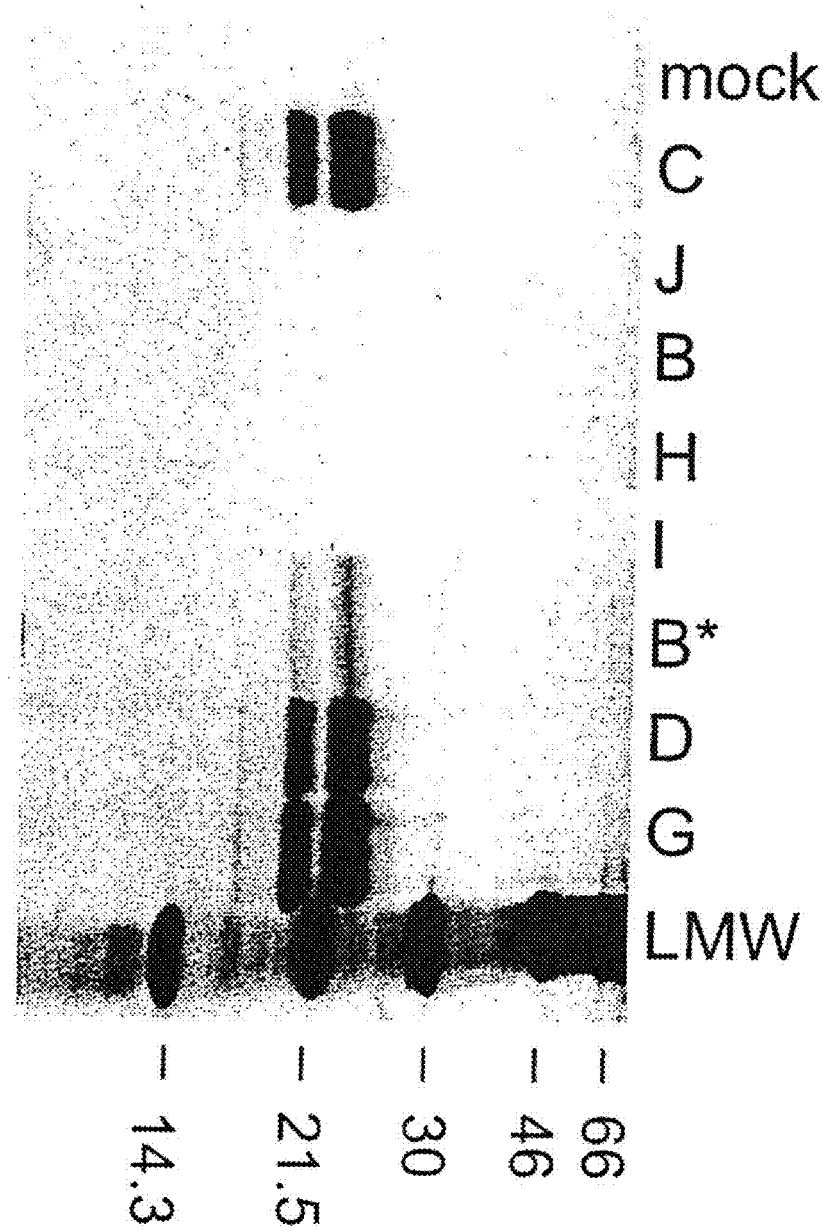
FIG. 3 is an autoradiograph of a PAGE from binding assays of VEGFR-3 fragment binding constructs using a radiolabeled VEGF-C construct.

Tables 3 and 4 identify constructs by name, a DNA and deduced amino acid sequence from the sequence listing, the portion of VEGFR-2 (SEQ ID NO: 4) or VEGFR-3 (SEQ ID NO: 6) amino acid sequence that was included in the constructs, whether the constructs expressed, and, if tested, whether constructs bound ligand. The table data is compiled from the PAGE gels shown in FIGS. 2 and 3. The asterisk adjacent to the "B*" indicates a "spill-over" from the adjacent lane, as the origin of the bands seen in the "B" lane. A failure to express under the particular experimental conditions used in this instance should not be interpreted as a failure to bind. The experiments can be repeated using different receptor fragments, binding constructs, ligands, or combinations thereof.

TABLE 3

| Fc Fusion Constructs | SEQ ID NOS: | SEQ ID NO: 4 | Expression | Binds VEGF-A | Binds VEGF-C |
|---|---|---|---|---|---|
| R-2 A with CD33 Signal Peptide | SEQ ID NOS: 7 and 8 | 24-326 | Yes | Yes | Yes |
| R-2 B with CD33 Signal Peptide | SEQ ID NOS: 9 and 10 | 24-220 | Yes | No | No |
| R-2 C with CD33 Signal Peptide | SEQ ID NOS: 11 and 12 | 24-226 | Yes | No | No |
| R-2 D with CD33 Signal Peptide | SEQ ID NOS: 13 and 14 | 24-232 | Yes | No | No |
| R-2 E with CD33 Signal Peptide | SEQ ID NOS: 15 and 16 | 24-241 | Yes | No | No |
| R-2 F with CD33 Signal Peptide | SEQ ID NOS: 17 and 18 | 24-122 | Yes | No | No |
| R-2 G with CD33 Signal Peptide | SEQ ID NOS: 19 and 20 | 118-326 | Yes | Yes | Yes |
| R-2 H with CD33 Signal Peptide | SEQ ID NOS: 21 and 22 | 118-220 | Yes | No | Yes |
| R-2 I with CD33 Signal Peptide | SEQ ID NOS: 23 and 24 | 118-226 | Yes | No | Weak |
| R-2 J with CD33 Signal Peptide | SEQ ID NOS: 25 and 26 | 118-232 | Yes | No | Very Weak |
| R-2 K with CD33 Signal Peptide | SEQ ID NOS: 27 and 28 | 118-241 | Yes | No | No |
| R-2 L with CD33 Signal Peptide | SEQ ID NOS: 29 and 30 | 220-326 | Yes | No | No |

TABLE 4

VEGFR-3 CONSTRUCTS

| Fc Fusion Constructs | Sequence ID Nos. | SEQ ID NO: 6 | Expression | Binds VEGF-C |
|---|---|---|---|---|
| R-3 A with CD33 Signal Peptide | SEQ ID NOS: 31 and 32 | 138-329 | No | — |
| R-3 B with CD33 Signal Peptide | SEQ ID NOS: 33 and 34 | 138-226 | Yes | No |
| R-3 C | SEQ ID NOS: 35 and 36 | 1-229 | Yes | Yes |
| R-3 D | SEQ ID NOS: 37 and 38 | 1-226 | Yes | Yes |
| R-3 E | SEQ ID NOS: 39 and 40 | 1-223 | No | — |
| R-3 F | SEQ ID NOS: 41 and 42 | 1-220 | No | — |
| R-3 G | SEQ ID NOS: 43 and 44 | 1-329 | Yes | Yes |
| R-3 H | SEQ ID NOS: 45 and 46 | 1-134 | Yes | No |
| R-3 I | SEQ ID NOS: 47 and 48 | 1-39, 132-329 | Yes | No |
| R-3 J | SEQ ID NOS: 49 and 50 | 1-39, 132-247 | Yes | No |
| R-3 K | SEQ ID NOS: 51 and 52 | 1-39, 132-229 | Yes | No |
| R-3 L | SEQ ID NOS: 53 and 54 | 1-39, 132-226 | No | — |
| R-3 M | SEQ ID NOS: 55 and 56 | 1-39, 132-223 | No | — |
| R-3 N | SEQ ID NOS: 57 and 58 | 1-40, 226-329 | — | — |

The results of these assays demonstrate that novel receptor fragments are capable of binding ligands that the receptor as a whole may bind. In addition to providing a clearer picture as to what regions of the ECD are necessary for ligand binding, the binding data identifies receptor fragments useful as therapeutics.

The present data show that the R-2H fragment of R-2 of approximately 100 residues and spanning D2 of R-2 is sufficient for VEGF-C binding. For R-3, a larger fragment is required for VEGF-C binding, e.g., the R-3 D construct in table 4, which spans D1-2 of R-3.

Three-dimensional modeling based on the structure of VEGFR-1 complexed with VEGF-A was used to predict that a groove in VEGF-C might accommodate the region between Ig-like domains 2 and 3 of VEGFR-3 (Flt4). WO 01/62942. The present data shows for the first time that sequence intermediate between the second and third Ig domains of R-3 is important for ligand binding.

For R-1 and R-2, the first Ig-domain has been described as inhibitory for VEGF-A binding. Lu, et al, *J. Biol. Chem.*, 275(19): 14321-14330 (2000); Shinkai, A. et al., *J. Biol. Chem.*, 273(47):31283-88 (1998). For VEGF-C binding, the present data show that the inhibitory role of the first Ig-domain appears to apply to R-2 fragments, but not R-3 fragments.

The data also provides novel information regarding R-2 fragments and VEGF-A binding. Conflicting reports exist for constructs comprising the second and third Ig-domains of R-2 and VEGF-A binding. Fuh, et al., *J. Biol. Chem.*, 273(18): 11197-11204 (1998); Niwa, et al., U.S. Pat. No. 6,348,333; Shinkai, A. et al., *J. Biol. Chem.*, 273(47):31283-88 (1998). Fuh reported that only domains 2 and 3 were needed. Niwa taught that only 1 and 2 were needed. Shinkai stressed the importance of domain 4 of R-2. The issue is further confused because different reports have defined the boundaries of the Ig-domains in different ways, i.e., different start and stop points, a practice that has been recognized as potentially affecting whether fragments bind ligands, and with what degree of affinity. Shinkai, A. et al., *J. Biol. Chem.*, 273(47): 31283-88 (1998).

Example 2

Ligand Binding Assays Involving Binding Constructs with More than One Binding Element The assays as performed in Example 1 are repeated, substituting a binding construct with multiple binding units. For example, one employs a binding construct comprising a binding unit that binds VEGF-A and a binding unit that binds VEGF-C. One looks for the ability of such a binding construct to bind both VEGF-A and VEGF-C. This information may be obtained by using different radio- or other labels, e.g., fluorescent labels for fluorescence resonance energy transfer (FRET), on each type of ligand or use of labels on the binding construct and or ligands, to determine whether a given binding construct molecules are binding a molecule of VEGF-A and VEGF-C. Constructs that are shown to bind more than one growth factor ligand, as well as those described in Example 1 and elsewhere herein, have an indication for anti-neoplastic therapies where multiple growth factors contribute to neoplastic cell growth.

Example 3

Chimeric VEGFR Binding Constructs which Bind Multiple Ligands

As stated above, constructs that bind more than one growth factor ligand have an indication as anti-neoplastic therapies where multiple growth factors contribute to neoplastic cell growth. In order to determine the efficacy of a binding construct designed to bind more than one growth factor, two chimeric binding constructs were generated and their ability of each to bind to two growth factors was measured.

The binding constructs were designed as immunoblobulin fusion proteins as described above. To construct chimeric VEGF receptor/hIgG1Fc fusion proteins, the pIgPlus vector was used to build a construct comprising the first immunoglobulin-like domain of VEGFR-3 and the second and third Ig-like domains of VEGFR-2. The construct is designated R-3D1-R2D2+3/hIgG1Fc. To clone the R-3D1-R2D2+3/hIgG1Fc construct, PCR was performed with CMV forward primer (18782, 5' TACTTGGCAGTACATCTACGTATT-AGTCATCGC-3') (SEQ ID NO: 122) and reverse primer v360 (5'-CGGAGATCTGTAGTCTTGCACGTACACG-TAGGAGCTGGC-3') (SEQ ID NO: 123) using plgPlus-hVEGFR-3D1-3-IgG1Fc as a template. The PCR-product was cut with SnaBI and BglII. The 718 bp D1-R2D2+3/hIgG1Fc insert was ligated into the SnaBI- and partially BglII-cut vector plgPlus-hVEGFR-2D1-3-IgG1Fc described above. The presence and sequence of the correct insert was confirmed by sequencing a representative isolated hVEGFR-3D1-R2D2+3/hIgG1Fc clone (clone #2). (SEQ ID NO: 124 and SEQ ID NO: 125).

In addition to the above chimeric construct, a chimeric VEGF receptor/hIgG1Fc fusion protein was constructed having the first Ig-like domain of VEGFR-3, the second Ig-like domain of VEGFR-2 and the third Ig-like domain of VEGFR-1. The construct is designated R-3D1-R2D2-R1D3/hIgG1Fc.

To clone the pIgPlus-hVEGFR-3D1-R2D2-R1D3/hIgG1Fc construct, PCR was performed using pIgPlus-hVEGFR-3D1-R2D2+3/hIgG1Fc as a template and the T7 forward and reverse primer v362 (5'-TACAATTGAGGA-CAAGCGTATGTCCACGAAGTAGTT-TAACTGGACGAGGC GTGCTTATTTGCACATCAT-AAATCCTATACC-3') (SEQ ID NO: 126). The PCR-product was cut with HindIII and MfeI/MunI. The 787 bp VEGFR-3D1-R2D2+3/hIgG1Fc insert was ligated into the HindIII- and partially MfeI-cut vector plgPlus-hVEGFR-1D1-3-IgG1Fc. The presence and sequence of the correct chimeric insert was confirmed by sequencing the a representative hVEGFR-3D1-R2D2-R1D3/hIgG1Fc clone (clone #6) (SEQ ID NO: 127 and SEQ ID NO: 128).

Expression of Chimeric VEGFR/hIgG1Fc Fusions:

For expression analysis, the two new chimeric VEGF receptors and control constructs expressing R-1D1-3/hIgG1Fc, R-2D1-3/hIgG1Fc, R-3D1-3/hIgG1Fc, mature VEGF-C and VEGF-$A_{165}$ were transiently transfected into 293T cells using JetPEI (QBioGene/MP Biomedicals, Irvine, Calif.). Metabolic labeling with $^{35}$S-methionine and $^{35}$S-cysteine was carried out at 48 hours post-transfection and labeling maintained for 24 hours. The serum-free conditioned medium was then immunoprecipitated using Protein A sepharose and either: a) specific antiserum against human mature VEGF-C; b) goat polyclonal antibody against human VEGF-A (R&D systems, Minneapolis, Minn.); or, c) serum-free medium of 293T cells taken 48 to 72 hours post-transient transfection with VEGF receptor/hIgG1Fc proteins (control proteins, R-1D1-3, R-2D1-3, R-3D1-3; chimeric proteins, R-3D1-R2D2+3 and R-3D1-R2D2-R1D3).

The immunoprecipitated fractions were analyzed on 17% SDS-PAGE and the dried gels were exposed for 12 hours on phosphoimager plates or 36 hours on X-ray films. Expression analysis demonstrated that the chimeric receptor fusion proteins exhibited high expression levels in transfected 293 T cells.

Analysis of Binding Properties of Chimeric VEGF Receptor/hIgG1Fc Fusions:

Ligand binding analysis was performed as described for the VEGF-C/VEGF-A hybrid growth factors in Example 1. Briefly, the unlabeled conditioned medium of transiently transfected 293T cells expressing the chimeric VEGFR/IgG1Fc fusion proteins was used to precipitate the $^{35}$S metabolically labeled mature VEGF-C, full-length VEGF-C, and VEGF-$A_{165}$. SDS-PAGE of ligands immunoprecipitated with chimeric and control VEGFR/IgFc showed that the R-3D1-R2D2-R1D3/Ig chimeric protein strongly bound both VEGF-A and VEGF-C, as predicted based on the VEGFR2 and R1 immunoglobulin domains. In one experiment, the chimeric construct R-3D1-R2D2+3/Ig exhibited binding to VEGF-C and not VEGF-A. A second experiment with the R-3D-R2D2+3 μg construct showed only weak binding to VEGF-A.

These results demonstrate that the ligand binding constructs generated herein are useful in developing compositions that bind multiple growth factors involved in numerous cell activities. These constructs provide promising therapy for diseases such as cancer and other proliferative diseases wherein multiple growth factors mediate the condition or disease state.

Example 4

Assay for Neutralization of Growth Factor Activity

The following protocol provides an assay to determine whether a binding construct neutralizes one or more PDGF/VEGF growth factors by preventing the growth factor(s) from stimulating phosphorylation of its receptor.

Cells such as NIH 3T3 cells are transformed or transfected with a cDNA encoding a PDGFR/VEGFR receptor, such as VEGFR-3, and cultured under conditions where the encoded receptor is expressed on the surface of the cells. Transfected cells are cultured with either 1) plain growth medium; 2) growth medium supplemented with 50 ng/ml of one or more ligands for the recombinant receptor, such as fully processed VEGF-C and/or VEGF-D, which are ligands for VEGFR-3; 3) growth medium supplemented with 50 ng/ml of growth factor that does not bind the recombinant receptor (e.g., VEGF-A in the case of VEGFR-3), to serve as a control; or any of (1), (2), or (3) that is first pre-incubated with varying concentrations of a binding construct to be tested.

After culturing with the culture mediums described above in the presence or absence of the binding construct, the cells are lysed, immunoprecipitated using anti-receptor (e.g., anti-VEGFR-3) antiserum, and analyzed by Western blotting using anti-phosphotyrosine antibodies. Cells stimulated with the appropriate growth factor ligand (VEGF-C/D) stimulate VEGFR-3 autophosphorylation, which is detected with the anti-phosphotyrosine antibodies. Binding constructs that reduce or eliminate the ligand-mediated stimulation of receptor phosphorylation (e.g., in a dose-dependent manner) are considered neutralizing binding constructs.

Example 5

EPO Chimera Survival/Proliferation Blocking Assay

A binding construct is tested for the ability to block the binding of the growth factor(s) to their receptors, using bioassays of receptor binding and cross-linking. These assays involve the use of Ba/F3 pre-B cells which have been transfected with plasmid constructs encoding chimeric receptors consisting of the extracellular domain of growth factor receptors and the cytoplasmic domain of the erythropoietin receptor (Stacker, S A. et al., J. Biol. Chem. 274:34884-34892, 1999; Achen, M G. et al., Eur. J. Biochem. 267:2505-2515, 2000). These cells are routinely passaged in interleukin-3 (IL-3) and will die in the absence of IL-3. However, if signaling is induced from the cytoplasmic domain of the chimeric receptors, these cells survive and proliferate in the absence of IL-3. Such signaling is induced by ligands which bind and cross-link the extracellular domains of the chimeric receptors. Therefore binding of a growth factor ligand to the extracellular domains of the chimeric receptors causes the cells to survive and proliferate in the absence of IL-3. Addition of binding constructs that block the binding of growth factor to the extracellular domains will cause cell death in the absence of IL-3. An alternative Ba/F3 cell line which expresses a chimeric receptor containing the extracellular domain of the Tie2 receptor (that does not bind VEGF family members) is not induced by the relevant growth factors to proliferate and is used, in the presence of IL-3, as a control to test for non-specific effects of potential inhibitors.

In an exemplary assay, a binding construct that can bind VEGF-A and VEGF-C is tested. Samples of purified VEGF-A and VEGF-C are incubated with varying amounts of the binding construct for one hour at 4° C. in PBS before dilution of the mixtures 1:10 with IL-3-deficient cell culture medium. Ba/F3 cell lines expressing receptor(s) capable of binding the growth factors are then incubated in the media for 48 hours at 37° C. To measure DNA synthesis in the cells, 1 μCi of 3H-thymidine is added and the cells are incubated for 4 hours prior to harvesting. Incorporated 3H-thymidine is measured using a cell harvester (Tomtec®) and beta counting. The ability of the binding construct to block growth factor-mediated cell growth and survival (as measured by DNA synthesis) is analyzed relative to the control Tie2 cell line in the presence of IL-3. Growth inhibition in the experimental group relative to the control group demonstrates that the binding construct blocks cell growth, presumably by blocking the binding and cross-linking of receptors by growth factor ligands at the cell surface.

Example 6

Effect of Binding Constructs on BCE Migration

Solutions containing growth factors pre-incubated alone or with varying concentrations of a binding construct are placed in wells made in collagen gel and used to stimulate the migration of bovine capillary endothelial (BCE) cells in the gel as follows. A further control comprising neither growth factor ligand nor binding construct may also be employed, as may a control with just binding construct. Binding constructs that cause a decrease in migration (relative to when growth factor alone is employed) have an indication as therapeutics to prevent or retard angiogenesis.

BCE cells (Folkman et al., Proc. Natl. Acad. Sci. (USA), 76:5217-5221 (1979)) are cultured as described in Pertovaara et al., J. Biol. Chem., 269:6271-74 (1994). These or other cells employed may be transformed with growth factor receptor if not already expressed. For testing of VEGF-A/VEGF-C binding constructs, cells would be transformed with both VEGFR-2 and/or VEGFR-3. The collagen gels are prepared by mixing type I collagen stock solution (5 mg/ml in 1 mM HCl) with an equal volume of 2×MEM and 2 volumes of MEM containing 10% newborn calf serum to give a final collagen concentration of 1.25 mg/ml. The tissue culture plates (5 cm diameter) are coated with about 1 mm thick layer of the solution, which is allowed to polymerize at 37° C. BCE cells were seeded on top of this layer. For the migration assays, the cells are allowed to attach inside a plastic ring (1 cm diameter) placed on top of the first collagen layer. After 30 minutes, the ring is removed and unattached cells are rinsed away. A second layer of collagen and a layer of growth medium (5% newborn calf serum (NCS)), solidified by 0.75% low melting point agar (FMC BioProducts, Rockland, Me.), are added. A well (3 mm diameter) is punched through all the layers on both sides of the cell spot at a distance of 4 mm, and the sample or control solutions are pipetted daily into the wells. Photomicrographs of the cells migrating out from the spot edge are taken after six days through an Olympus CK 2 inverted microscope equipped with phase-contrast optics. The migrating cells are counted after nuclear staining with the fluorescent dye bisbenzimide (1 mg/ml, Hoechst 33258, Sigma).

The number of cells migrating at different distances from the original area of attachment towards wells containing sample solutions are determined 6 days after addition of the media. The number of cells migrating out from the original ring of attachment is counted in five adjacent 0.5 mm×0.5 mm squares using a microscope ocular lens grid and 10× magnification with a fluorescence microscope. Cells migrating further than 0.5 mm are counted in a similar way by moving the grid in 0.5 mm steps. The experiments are carried out twice with similar results. Daily addition of 1 ng of FGF2 into the wells may be employed as a positive control for cell migration.

Example 7

Soluble VEGFR-1, VEGFR-2, and/or VEGFR-3 Containing Constructs Inhibitory Effect on VEGF-C Mediated Tumor Growth and Metastasis To demonstrate the ability of polypeptides and binding constructs of the invention employed to inhibit tumor growth and/or metastasis, any accepted tumor model may be employed. Exemplary models include animals predisposed to developing various types of cancers, animals injected with tumors or tumor cells or tumor cell lines from the same or different species, including optionally cells transformed to recombinantly overexpress one or more growth factors such as VEGF-A, VEGF-B, VEGF-C, VEGF-D, or VEGF-E, or PDGF-A, or PDGF-B, or PDGF-C, or PDGF-D or PlGF. To provide a model for tumors in vivo in which multiple growth factors are detectable, it is possible to transform tumor cell lines with exogenous DNA to cause expression of multiple growth factors.

Polypeptide binding constructs may be administered directly, e.g., in protein form by i.v. transfusion or by implanted micropumps, or in nucleic acid form as part of a gene therapy regimen. Subjects are preferably grouped by sex, weight, age, and medical history to help minimize variations amongst subjects.

Efficacy is measured by a decrease in tumor, size (volume) and weight. One may also examine the nature of the effect on tumor size, spreads (metastases) and number of tumors. For example, use of specific cell markers can be used to show the effect on angiogenesis relative to lymphangiogenesis, a VEGF-A binding construct expected to have a greater effect on the former, and a VEGF-C binding construct expected to have a greater effect on the latter. Animals may be looked at as a whole for survival time and changes in weight. Tumors and specimens are examined for evidence of angiogenesis, lymphangiogenesis, and/or necrosis.

SCID mice may be used as subjects for the ability of the soluble binding constructs of the present invention to inhibit or prevent the growth of tumors. The binding construct used in the therapy is generally chosen such that it binds to a growth factor ligand expressed by the tumor cell, especially growth factors that are overexpressed by the tumor cell relative to non-neoplastic cells in the subject. In the SCID model, tumor cells, e.g., MCF-7 cells, may be transfected with a virus encoding a particular growth factor under the control of a promoter or other expression control sequence that provides for overexpression of the growth factor as described in WO 02/060950. Alternatively, other cell lines may be employed, e.g., HT-1080, as described in U.S. Pat. No. 6,375,929. One may transfect the tumor cells with as may growth factor ligands as one desires to overexpress, or a tumor cell line may be chosen that already overexpresses one or more growth factor ligands of interest. One group of subjects is implanted with cells that have been mock-transfected, i.e., with a vector lacking a growth factor ligand insert.

Either before, concurrently with, or after the tumor implantation of the above-described cells, subjects are treated with a particular binding construct. There are a number of different ways of administering the construct. In vivo and/or ex vivo gene therapy may be employed. For example, cells may be transfected with a adenovirus, or other vector, that encodes the construct and implanted with the tumor cells expressing the growth factor(s), the cells transfected with the binding construct may be the same as those transformed with growth factor(s) (or already overexpressing the growth factor(s)). In some embodiments, an adenovirus that encodes that binding construct is injected in vivo, e.g., intravenously. In some embodiments, the binding construct itself (e.g., in protein form) is administered either systematically or locally, e.g., using a micropump. When testing the efficacy of a particular binding construct, at least one control is normally employed. For example, in the case of a vector-based therapy, a vector with an empty insert or LacZ is employed, or the insert may be a construct comprising a complete ECD of a growth factor receptor capable of binding the growth factor(s) of interest, such a control may employ more than one ECD construct if necessary (e.g., for binding multiple ligands if binding constructs with multiple ligand binding affinities are employed).

Exemplary Procedures

A. Preparation of Plasmid Expression Vectors, Transfection of Cells, and Testing of the Same A cDNA encoding VEGF-A, VEGF-B, VEGF-C, VEGF-D, PlGF, PDGF-A, PDGF-B, PDGF-C, PDGF-D, or combinations thereof introduced into a pEBS7 plasmid (Peterson and Legerski, *Gene*, 107: 279-84, 1991). This same vector may be used for the expression of the soluble binding constructs.

The MCF-7S1 subclone of the human MCF-7 breast carcinoma cell line is transfected with the plasmid DNA by electroporation and stable cell pools are selected and cultured as previously described (Egeblad and Jaattela, *Int. J. Cancer*, 86: 617-25, 2000). The cells are metabolically labeled in methionine and cysteine free MEM (Gibco) supplemented with 100 μCi/ml [35S]-methionine and [35S]-cysteine (Redivue Pro-Mix, Amersham Pharmacia Biotech). The labeled growth factors are immunoprecipitated from the conditioned medium using antibodies against the expressed growth factor(s). The immunocomplexes and the binding complexes are precipitated using protein A sepharose (Amersham Pharmacia Biotech), washed twice in 0.5% BSA, 0.02% Tween 20 in PBS and once in PBS and analyzed in SDS-PAGE under reducing conditions.

B. Subject Preparation and Treatment

Cells (20,000/well) are plated in quadruplicate in 24-wells, trypsinized on replicate plates after 1, 4, 6, or 8 days and counted using a hemocytometer. Fresh medium is provided after 4 and 6 days. For the tumorgenesis assay, sub-confluent cultures are harvested by trypsination, washed twice and $10^7$ cells in PBS are inoculated into the fat pads of the second (axillar) mammary gland of ovariectomized SCID mice, carrying subcutaneous 60-day slow-release pellets containing 0.72 mg 17β-estradiol (Innovative Research of America). The ovarectomy and implantation of the pellets are performed 4-8 days before tumor cell inoculation.

The cDNA coding for the binding construct(s) is subcloned into the pAdBglII plasmid and the adenoviruses produced as previously described (Laitinen et al., *Hum. Gene Ther.*, 9: 1481-6, 1998). The binding construct(s) or LacZ control (Laitinen et al., *Hum. Gene Ther.*, 9: 1481-6, 1998) adenoviruses, $10^9$ pfu/mouse, are injected intravenously into the SCID mice 3 hours before the tumor cell inoculation.

C. Analysis of Treatment Efficacy

Tumor length and width are measured twice weekly in a blinded manner, and the tumor volume are calculated as the length×width×depth×0.5, assuming that the tumor is a hemi-ellipsoid and the depth is the same as the width (Benz et al., *Breast Cancer Res. Treat.*, 24: 85-95, 1993).

The tumors are excised, fixed in 4% paraformaldehyde (pH 7.0) for 24 hours, and embedded in paraffin. Sections (7 μm) are immunostained with monoclonal antibodies against, for example, PECAM-1 (Pharmingen), VEGFR-1, VEGFR-2, VEGFR-3 (Kubo et al., *Blood*, 96: 546-553, 2000) or PCNA (Zymed Laboratories), PDGFR-α, PDGFR-β or polyclonal antibodies against LYVE-1 (Banerji et al., J Cell Biol, 144: 789-801, 1999), VEGF-C (Joukov et al., *EMBO J.*, 16: 3898-911, 1997), laminin according to published protocols (Partanen et al., *Cancer*, 86: 2406-12, 1999), or any of the growth factors. The average of the number of the PECAM-1 positive vessels are determined from three areas (60× magnification) of the highest vascular density (vascular hot spots) in a section. All histological analyses are performed using blinded tumor samples.

Three weeks after injection of adenovirus constructs and/or protein therapy, four mice from each group are narcotized, the ventral skin is opened and a few microliters 3% Evan's blue dye (Sigma) in PBS is injected into the tumor. The drainage of the dye from the tumor is followed macroscopically.

Imagining and monitoring of blood and blood proteins to provide indication of the health of subjects and the extent of tumor vasculature may also be performed.

Example 8

Effects on Tumor Progression in Subjects Using a Combined Therapy of a Binding Construct and a Chemotherapeutic Agent This study is carried out to test the efficacy of using the binding constructs of the invention in combination with other anti-cancer therapies and/or using multiple binding constructs of the invention. Such therapies include chemotherapy, radiation therapy, anti-sense therapy, RNA interference, and monoclonal antibodies directed to cancer targets. The combinatorial effect may be additive, but it is preferably synergistic in its anti-cancer effects, e.g., prevention, suppression, regression, and elimination of cancers, prolongation of life, and/or reduction in side-effects.

Subjects are divided into groups with one group receiving a chemotherapeutic agent, one group receiving a binding construct, and one group receiving both a chemotherapeutic agent and a binding construct at regular periodic intervals, e.g., daily, weekly or monthly. In human studies, the subjects are generally grouped by sex, weight, age, and medical history to help minimize variations among subjects. Ideally, the subjects have been diagnosed with the same type of cancer. In human or non-human subjects, progress can be followed by measuring tumor size, metastases, weight gain/loss, vascularization in tumors, and white blood cells counts.

Biopsies of tumors are taken at regular intervals both before and after beginning treatment. For example, biopsies are taken just prior to treatment, at one week, and then at one month intervals, thereafter, or whenever possible, e.g., as tumors are excised. One examines the biopsies for cell markers, and overall cell and tissue morphology to assess the effectiveness of the treatment. In addition, or in the alternative, imagining techniques may be employed.

For non-human animal studies, an additional placebo control may be employed. Animal studies, performed in accordance with NIH guidelines, also provide the advantage of the insertion of relatively uniform cancer cell population, and tumors that selectively overproduce the one or more growth factors targeted by the binding construct. Tumors may be excised and analyzed as described in any one of Examples 2-5.

Example 9

Animal Models to Demonstrate the Efficacy of Anti-VEGFR-2 Therapies for Treatment of Diseases by Inhibition of VEGF-A Mediated Effects While Preserving VEGF-C Binding An acceptable animal model is used, e.g., mice or rats. In some embodiments, animals with tumors are treated with selective VEGF-A antagonist anti-VEGFR-2 antibodies or a control. At various time points, before, during, and after treatment, tumors are excised from the two groups. The tumors are then examined for VEGF-A and VEGF-C mediated characteristics to determine whether VEGF-A mediated characteristic have been diminished relative to VEGF-C mediated characteristics. These characteristics may be assessed using cell surface markers indicative of angiogenesis and markers indicative of lymphangiogenesis.

The foregoing description and examples have been set forth merely to illustrate the invention and are not intended to be limiting. Because modifications of the disclosed embodiments incorporating the spirit and substance of the invention may occur to persons skilled in the art, the invention should be construed to include everything within the scope of the appended claims and equivalents thereof. The patents, patent application publications and other publications (e.g., Journal articles, and web/Internet materials) referenced herein are incorporated in their entirety.

Although the applicant(s) invented the full scope of the claims appended hereto, the claims are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

What is claimed is:

1. A method of inhibiting endothelial cell proliferation comprising steps of:
   (a) screening a mammal to identify a neoplastic disorder characterized by endothelial cell proliferation, and an elevated level of VEGF-C in serum or in a tissue sample from a tumor; and
   (b) administering a composition to the mammal identified according to step (a) as having a neoplastic disorder characterized by endothelial cell proliferation and the elevated level of VEGF-C, wherein said composition comprises a fusion protein comprising a first binding unit polypeptide connected to a heterologous peptide, in an amount effective to inhibit endothelial or smooth muscle cell proliferation in said mammal, wherein the amino acid sequence of the first binding unit polypeptide consists of an amino acid sequence at least 95% identical to a VEGFR-3 fragment consisting of a portion of SEQ ID NO: 6, wherein the amino-terminal amino acid of the VEGFR-3 fragment is selected from the group consisting of positions 1-47 of SEQ ID NO: 6, wherein the carboxy-terminal residue of the VEGFR-3 fragment is selected from the group consisting of positions 211 to 247 of SEQ ID NO: 6, and wherein the VEGFR-3 fragment and the purified fusion protein bind human VEGF-C.

2. A method of inhibiting endothelial cell proliferation in a mammal, comprising administering to a mammal a composition, said composition comprising a fusion protein comprising a first binding unit polypeptide connected to a heterologous peptide, in an amount effective to inhibit endothelial cell proliferation in the mammal, wherein the amino acid sequence of the first binding unit polypeptide consists of an amino acid sequence at least 95% identical to a VEGFR-3 fragment consisting of a portion of SEQ ID NO: 6, wherein the amino-terminal amino acid of the VEGFR-3 fragment is selected from the group consisting of positions 1-47 of SEQ ID NO: 6, wherein the carboxy-terminal residue of the VEGFR-3 fragment is selected from the group consisting of positions 211 to 247 of SEQ ID NO: 6, and wherein the VEGFR-3 fragment and the purified fusion protein bind human VEGF-C.

3. The method of claim 1 or 2, wherein the heterologous peptide comprises an immunoglobulin constant domain fragment.

4. The method of claim 1 or 2, wherein the amino acid sequence that is at least 95% identical to the VEGFR-3 fragment is selected from the group consisting of SEQ ID NOS: 36 and 38.

5. The method of claim 1 or 2 wherein the fusion protein further comprises a signal peptide.

6. The method of claim 5, wherein the signal peptide directs secretion of the fusion protein from a cell that expresses the fusion protein.

7. The method of claim 1 or 2, wherein the VEGFR-3 fragment has an amino acid sequence selected from the group consisting of positions 1-226 and 1-229 of SEQ ID NO: 6.

8. The method of claim 1 or 2, wherein the fusion protein comprises an amino acid sequence of a VEGFR-3 fragment connected to a heterologous peptide, said VEGFR-3 fragment consisting of a portion of SEQ ID NO: 6, wherein the amino-terminal residue of the VEGFR-3 fragment is selected from the group consisting of positions 1 to 47 of SEQ ID NO: 6, wherein the carboxy-terminal residue of the VEGFR-3 fragment is selected from the group consisting of positions 211 to 247 of SEQ ID NO: 6, and wherein the VEGFR-3 fragment and the purified fusion protein bind human VEGF-C.

9. The method of claim 8, wherein the VEGFR-3 fragment has a carboxy-terminal amino acid selected from the group consisting of positions 226 and 229 of SEQ ID NO: 6.

10. The method of claim 1 or 2 wherein the composition comprises a binding construct comprising the fusion protein is operatively connected with a second binding unit that binds at least one growth factor selected from the group consisting of VEGF-A, VEGF-B, VEGF-C, VEGF-D, VEGF-E, PlGF, PDGF-A, PDGF-B, PDGF-C, and PDGF-D, wherein the second binding unit is selected from the group consisting of a polypeptide comprising a vascular endothelial growth factor receptor extracellular domain fragment, a platelet derived growth factor receptor extracellular domain fragment, and a polypeptide comprising an antigen binding fragment of an antibody that immunoreacts with the at least one of said growth factors.

11. The method of claim 10, further comprising a linker connecting the first and second binding units.

12. The method of claim 11, wherein the linker comprises a peptide that links the first and second polypeptides to form a single polypeptide.

* * * * *